United States Patent
Hashimoto et al.

(10) Patent No.: US 11,764,479 B2
(45) Date of Patent: Sep. 19, 2023

(54) ANTENNA, BICYCLE, DISPLAY APPARATUS, AND UNMANNED AIRCRAFT

(71) Applicant: KYOCERA Corporation, Kyoto (JP)

(72) Inventors: Sunao Hashimoto, Yokohama (JP); Nobuki Hiramatsu, Yokohama (JP); Hiroshi Uchimura, Kagoshima (JP); Yasuhiko Fukuoka, Yokohama (JP); Masato Fujishiro, Yokohama (JP); Toi Kanda, Tokyo (JP)

(73) Assignee: KYOCERA CORPORATION, Kyoto (JP)

( * ) Notice: Subject to any disclaimer, the term of this patent is extended or adjusted under 35 U.S.C. 154(b) by 358 days.

(21) Appl. No.: 16/964,179

(22) PCT Filed: Jan. 7, 2019

(86) PCT No.: PCT/JP2019/000108
§ 371 (c)(1),
(2) Date: Jul. 22, 2020

(87) PCT Pub. No.: WO2019/142676
PCT Pub. Date: Jul. 25, 2019

(65) Prior Publication Data
US 2021/0036400 A1    Feb. 4, 2021

(30) Foreign Application Priority Data

Jan. 22, 2018  (JP) .................................. 2018-008411
Jan. 22, 2018  (JP) .................................. 2018-008415
Jan. 22, 2018  (JP) .................................. 2018-008416

(51) Int. Cl.
*H01Q 1/22*    (2006.01)
*H01Q 1/32*    (2006.01)
(Continued)

(52) U.S. Cl.
CPC ............ *H01Q 15/006* (2013.01); *B62J 45/20* (2020.02); *B62J 45/41* (2020.02); *B62J 45/416* (2020.02);
(Continued)

(58) Field of Classification Search
CPC .......... H01Q 1/22; H01Q 1/2241; H01Q 1/32; H01Q 9/0414; B62J 50/20; B62J 50/22
See application file for complete search history.

(56) References Cited

U.S. PATENT DOCUMENTS 10,828,532 B2 *  11/2020  Izuru ...................... A63B 69/16
11,015,705 B2      5/2021  Ho
(Continued)

FOREIGN PATENT DOCUMENTS

CN    205652331 U    10/2016
CN    206885325 U    1/2018
(Continued)

OTHER PUBLICATIONS

Yasutaka Murakami et al., Low-Profile Design and Bandwidth Characteristics of Artificial Magnetic Conductor with Dielectric Substrate, 2015, pp. 172-179, vol. J98-B, No. 2, IEEE, Japan, 9pp.
(Continued)

*Primary Examiner* — Jason Crawford
(74) *Attorney, Agent, or Firm* — HAUPTMAN HAM, LLP

(57) ABSTRACT

Provided are a new antenna, a bicycle including the new antenna, a display apparatus including the new antenna, and an unmanned aircraft including the new antenna. An antenna includes a first conductor, a second conductor facing the first conductor in a first direction, a third conductor, a fourth conductor, and a feeding line electromagnetically connected to the third conductor. The third conductor is located between the first conductor and the second conductor, apart
(Continued)

from the first conductor and the second conductor, and extends in the first direction. The fourth conductor is connected to the first conductor and the second conductor and extends in the first direction. The first conductor and the second conductor are capacitively connected via the third conductor. The antenna is disposed in a bicycle component of a bicycle such that the fourth conductor faces the bicycle component.

11 Claims, 101 Drawing Sheets

(51) Int. Cl.
*B62J 50/22* (2020.01)
*B62J 45/20* (2020.01)
*B62J 45/41* (2020.01)
*H01Q 9/04* (2006.01)
*H01Q 15/00* (2006.01)
*B62J 45/416* (2020.01)
*H01Q 1/28* (2006.01)
*B62K 3/02* (2006.01)

(52) U.S. Cl.
CPC ............... *B62J 50/22* (2020.02); *H01Q 1/22* (2013.01); *H01Q 1/28* (2013.01); *H01Q 1/32* (2013.01); *H01Q 1/3233* (2013.01); *H01Q 9/0414* (2013.01); *B62K 3/02* (2013.01)

(56) References Cited

U.S. PATENT DOCUMENTS

| | | | |
|---|---|---|---|
| 11,155,319 B2 | 10/2021 | Luman et al. | |
| 11,459,061 B2 | 10/2022 | Ho et al. | |
| 11,483,029 B2* | 10/2022 | Uchimura | H01Q 1/2216 |
| 11,502,387 B2* | 11/2022 | Isoyama | H01Q 15/14 |
| 2010/0024590 A1* | 2/2010 | O'Neill | G01L 3/242 |
| | | | 702/41 |
| 2013/0150028 A1* | 6/2013 | Akins | H04W 4/029 |
| | | | 455/456.3 |
| 2015/0130673 A1 | 5/2015 | Ng et al. | |
| 2015/0345925 A1* | 12/2015 | Smit | G01L 5/00 |
| | | | 702/150 |
| 2017/0025744 A1 | 1/2017 | Becze et al. | |
| 2017/0115660 A1 | 4/2017 | Caubel et al. | |
| 2018/0233810 A1 | 8/2018 | Sun | |
| 2018/0268668 A1* | 9/2018 | Tetsuka | G01D 5/14 |
| 2020/0262510 A1 | 8/2020 | Hahn et al. | |
| 2020/0346714 A1 | 11/2020 | Hahn | |
| 2021/0036400 A1* | 2/2021 | Hashimoto | H01Q 21/065 |
| 2021/0036736 A1* | 2/2021 | Uchimura | H01Q 15/0026 |
| 2021/0057809 A1* | 2/2021 | Yoshikawa | H01Q 15/14 |
| 2022/0355901 A1* | 11/2022 | Nekozuka | H01Q 1/325 |

FOREIGN PATENT DOCUMENTS

| | | |
|---|---|---|
| CN | 206907920 U | 1/2018 |
| CN | 116133968 A | 5/2023 |
| EP | 3159254 A1 | 4/2017 |
| EP | 3173796 A1 | 5/2017 |
| GB | 2067842 A | 7/1981 |
| JP | 200095181 A | 4/2000 |
| JP | 2000131090 A | 5/2000 |
| JP | 2001188998 A | 7/2001 |
| JP | 2007059966 A * | 3/2007 |
| JP | 2007230340 A | 9/2007 |
| JP | 2011116324 A | 6/2011 |
| JP | 201752313 A | 3/2017 |
| JP | 2017124814 A | 7/2017 |
| JP | 7041690 B2 | 3/2022 |
| WO | 2017111612 A1 | 6/2017 |

OTHER PUBLICATIONS

Yasutaka Murakami et al., Optimum Configuration of Reflector for Dipole Antenna with AMC Reflector, 2015, pp. 1212-1220, vol. 98-B, No. 11, IEEE, 10pp.

* cited by examiner

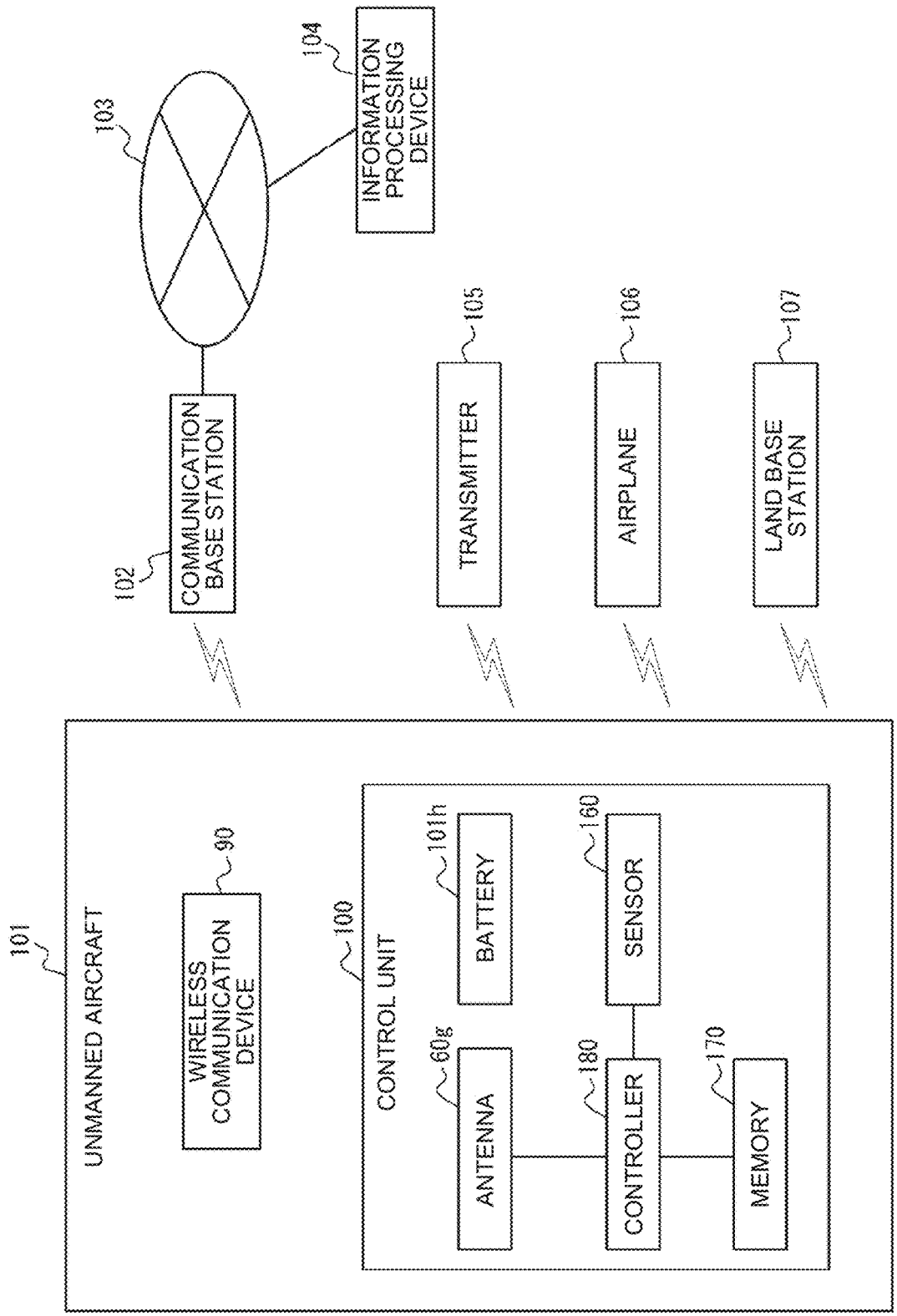

ANTENNA, BICYCLE, DISPLAY APPARATUS, AND UNMANNED AIRCRAFT

CROSS-REFERENCE TO RELATED APPLICATIONS

This application is a National Stage of PCT international application Ser. No. PCT/JP2019/000108 filed on Jan. 7, 2019 which designates the United States, incorporated herein by reference, and which is based upon and claims the benefit of priority from Japanese Patent Application No. 2018-008411 filed on Jan. 22, 2018, Japanese Patent Application No. 2018-008415 filed on Jan. 22, 2018, and Japanese Patent Application No. 2018-008416 filed on Jan. 22, 2018, the entire disclosures of which are incorporated herein for reference.

BACKGROUND

1. Technical Field

The present disclosure relates to an antenna, a bicycle, a display apparatus, and an unmanned aircraft.

2. Description of the Related Art

An electromagnetic wave emitted from an antenna is reflected by a metal conductor. The electromagnetic wave reflected by the metal conductor has a phase shift of 180°. The reflected electromagnetic wave is combined with an electromagnetic wave radiated from the antenna. The electromagnetic wave radiated from the antenna may have small amplitude due to the combination thereof with an electromagnetic wave having a phase shift. As a result, the amplitude of the electromagnetic wave radiated from the antenna is reduced. Setting the distance between the antenna and the metal conductor to be ¼ of a wavelength λ of an electromagnetic wave to be radiated reduces the influence of the reflected wave.

Meanwhile, there has been proposed a technology for reducing the influence of a reflected wave by using an artificial magnetic wall. This technology is described, for example, in Non Patent Literature 1 and Non Patent Literature 2.

Non Patent Literature

Non Patent Literature 1: Murakami et al., "Low Attitude Design and a Band Characteristic of an Artificial Magnetic Conductor using a Dielectric Substrate" Trans. Inst. Electron. Inform. Communi. Engnr. Jpn. (B), Vol. J98-B No. 2, pp. 172-179

Non Patent Literature 2: Murakami et al., "An Optimum Configuration of a Reflector for a Dipole Antenna with an AMC reflector" Trans. Inst. Electron. Inform. Communi. Engnr. Jpn. (B), Vol. J98-B No. 11, pp. 1212-1220

SUMMARY

An antenna according to an aspect of the present disclosure includes a first conductor, a second conductor that faces the first conductor in a first direction, a third conductor, a fourth conductor, and a feeding line that is electromagnetically connected to the third conductor. The third conductor is located between the first conductor and the second conductor, apart from the first conductor and the second conductor, and extends in the first direction. The fourth conductor is connected to the first conductor and the second conductor and extends in the first direction. The first conductor and the second conductor are capacitively connected via the third conductor. The antenna is disposed in a bicycle component of a bicycle such that the fourth conductor faces the bicycle component.

An antenna according to another aspect of the present disclosure includes a first conductor, a second conductor that faces the first conductor in a first direction, a third conductor, a fourth conductor, and a feeding line that is electromagnetically connected to the third conductor. The third conductor is located between the first conductor and the second conductor, apart from the first conductor and the second conductor, and extends in the first direction. The fourth conductor is connected to the first conductor and the second conductor and extends in the first direction. The first conductor and the second conductor are capacitively connected via the third conductor. The antenna is disposed in a conductive long portion included in a frame of a bicycle such that the first direction is along the long portion.

A bicycle according to another aspect of the present disclosure includes an antenna and a bicycle component. The antenna includes a first conductor, a second conductor that faces the first conductor in a first direction, a third conductor, a fourth conductor, and a feeding line that is electromagnetically connected to the third conductor. The third conductor is located between the first conductor and the second conductor, apart from the first conductor and the second conductor, and extends in the first direction. The fourth conductor is connected to the first conductor and the second conductor and extends in the first direction. The first conductor and the second conductor are capacitively connected via the third conductor. The antenna is disposed in the bicycle component of the bicycle such that the fourth conductor faces the bicycle component.

A bicycle according to another aspect of the present disclosure includes an antenna and a frame including at least one conductive long portion. The antenna includes a first conductor, a second conductor that faces the first conductor in a first direction, a third conductor, a fourth conductor, and a feeding line that is electromagnetically connected to the third conductor. The third conductor is located between the first conductor and the second conductor, apart from the first conductor and the second conductor, and extends in the first direction. The fourth conductor is connected to the first conductor and the second conductor and extends in the first direction. The first conductor and the second conductor are capacitively connected via the third conductor. The antenna is disposed in the long portion such that the first direction is along the long portion.

A display apparatus according to another aspect of the present disclosure includes an antenna and a display device. The antenna includes a first conductor, a second conductor that faces the first conductor in a first direction, a third conductor, a fourth conductor, and a feeding line that is electromagnetically connected to the third conductor. The third conductor is located between the first conductor and the second conductor, apart from the first conductor and the second conductor, and extends in the first direction. The fourth conductor is connected to the first conductor and the second conductor and extends in the first direction. The first conductor and the second conductor are capacitively connected via the third conductor. The antenna is disposed in a bicycle component of a bicycle such that the fourth conductor faces the bicycle component or disposed in a conductive long portion included in a frame of the bicycle such that the first direction is along the long portion.

An antenna according to another aspect of the present disclosure includes a first conductor and a second conductor that face each other in a first direction, one or a plurality of third conductors, a fourth conductor, and a feeding line that is electromagnetically connected to the third conductor. The third conductors are located between the first conductor and the second conductor and extend in the first direction. The fourth conductor is connected to the first conductor and the second conductor and extends in the first direction. The first conductor and the second conductor are capacitively connected via the third conductor. The antenna is disposed in an unmanned aircraft.

In an unmanned aircraft according to another aspect of the present disclosure, an antenna is disposed. The antenna includes a first conductor and a second conductor that face each other in a first direction, one or a plurality of third conductors, a fourth conductor, and a feeding line that is electromagnetically connected to the third conductor. The third conductor is located between the first conductor and the second conductor and extends in the first direction. The fourth conductor is connected to the first conductor and the second conductor and extends in the first direction. The first conductor and the second conductor are capacitively connected via the third conductor.

BRIEF DESCRIPTION OF THE DRAWINGS

FIG. 99 is a functional block diagram of the unmanned aircraft illustrated in FIG. 96.

DETAILED DESCRIPTION

Figure 1:
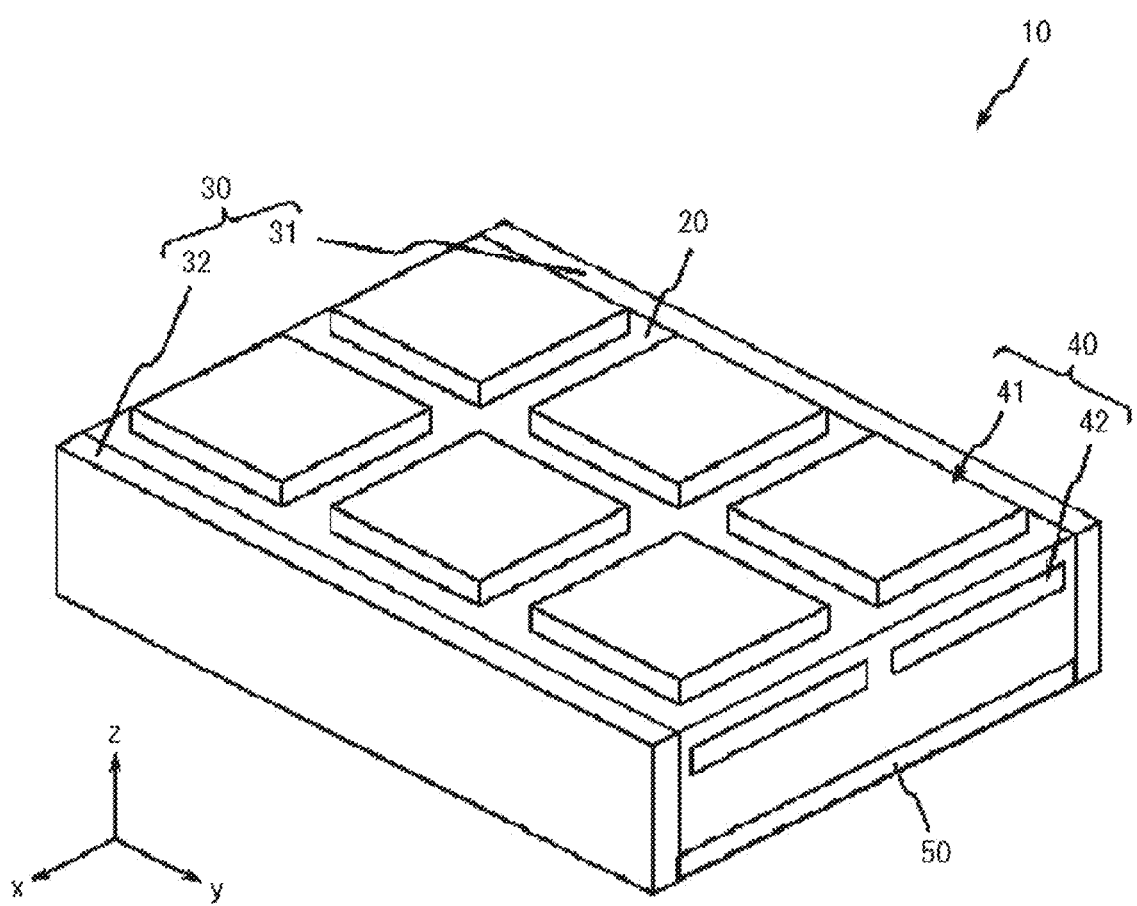
FIG. 1 is a perspective view illustrating an embodiment of a resonator.

An object of the present disclosure is to provide a new antenna, a bicycle including the new antenna, a display apparatus including the new antenna, and an unmanned aircraft including the new antenna. According to the present disclosure, there are provided the new antenna, the bicycle including the new antenna, the display apparatus including the new antenna, and the unmanned aircraft including the new antenna.

A plurality of embodiments according to the present disclosure will be described below. The resonant structure can include a resonator. The resonance structure includes the resonator and another member such that the resonator and the other member can be integrated with each other. A resonator 10 illustrated in FIGS. 1 to 62 includes a base 20, pair conductors 30, a third conductor 40, and a fourth conductor 50. The base 20 makes contact with the pair conductors 30, the third conductor 40, and the fourth conductor 50. In the resonator 10, the pair conductors 30, the third conductor 40, and the fourth conductor 50 each function as a resonator. The resonator 10 can resonate at a plurality of resonant frequencies. One resonant frequency of the resonant frequencies of the resonator 10 is defined as a first frequency $f_1$. The wavelength of the first frequency $f_1$ is $\lambda_1$. The resonator 10 can have at least one of the plurality of resonant frequencies as an operating frequency. The first frequency $f_1$ of the resonator 10 is used as the operating frequency.

The base 20 can include either a ceramic material or a resin material as a composition. The ceramic material includes a sintered aluminum oxide, sintered aluminum nitride, mullite refractory, sintered glass ceramic, crystallized glass obtained by depositing a crystal component in a glass base material, and sintered microcrystal of mica, aluminum titanate, or the like. The resin material includes a material obtained by curing an uncured material such as an epoxy resin, a polyester resin, a polyimide resin, a polyamide-imide resin, a polyetherimide resin, and a liquid crystal polymer.

Each of the air conductors 30, the third conductor 40, and the fourth conductor 50 can include, as a composition, any of a metal material, an alloy of the metal material, hardened metal paste, and a conductive polymer. All of the pair conductors 30, the third conductor 40, and the fourth conductor 50 may include the same material. All of the pair conductors 30, the third conductor 40, and the fourth conductor 50 may include different materials. Any combination of the pair conductors 30, the third conductor 40, and the fourth conductor 50 may include the same material. The metal material includes copper, silver, palladium, gold, platinum, aluminum, chromium, nickel, cadmium, lead, selenium, manganese, tin, vanadium, lithium, cobalt, titanium, and the like. The alloy includes a plurality of metal materials. The metal paste agent includes a powdered metal material that is kneaded together with an organic solvent and a binder. The binder includes an epoxy resin, a polyester resin, a polyimide resin, a polyamide-imide resin, and a polyetherimide resin. The conductive polymer includes a polythiophene polymer, a polyacethylene polymer, a polyaniline polymer, a polypyrrole polymer, and the like.

The resonator 10 includes two pair conductors 30. The pair conductors 30 include a plurality of conductive members. The pair conductors 30 include a first conductor 31 and a second conductor 32. The pair conductors 30 can include three or more conductive members. Each conductor of the pair conductors 30 is separated from the other conductor in a first direction. In the conductors of the pair conductors 30, one conductor can be paired with the other conductor. The conductors of the pair conductors 30 can appear as an electric wall, in relation to the resonator between the pair conductors. The first conductor 31 is positioned apart from the second conductor 32 in the first direction. The conductors 31 and 32 extend along a second plane intersecting the first direction.

In the present disclosure, the first direction (first axis) is represented as an x-direction. In the present disclosure, a third direction (third axis) is represented as a y-direction. In the present disclosure, a second direction (second axis) is represented as a z-direction. In the present disclosure, a first plane is represented as an xy surface. In the present disclosure, the second plane is represented as a yz surface. In the present disclosure, a third plane is represented as a zx surface. These planes are planes in a coordinate space and do not represent a specific plate or a specific surface. In the present disclosure, an area (surface integral) in an xy plane may be referred to as a first area. In the present disclosure, an area in a yz plane may be referred to as a second area. In the present disclosure, an area in a zx plane may be referred to as a third area. The area (surface integral) is measured in units of square meters or the like. In the present disclosure, a length in the x-direction may be simply referred to as a "length". In the present disclosure, a length in the y-direction may be simply referred to as a "width". In the present disclosure, a length in the z-direction may be simply referred to as a "height".

In an example, the conductors 31 and 32 are located at either end of the base 20 in the x-direction. Each of the conductors 31 and 32 can partially face outside the base 20. Each of the conductors 31 and 32 can have a portion that is located inside the base 20 and another portion that is located outside the base 20. Each of the conductors 31 and 32 can be located within the base 20.

The third conductor 40 functions as a resonator. The third conductor 40 can include at least one of a line resonator, patch resonator, and slot resonator. In an example, the third conductor 40 is located on the base 20. In an example, the third conductor 40 is located at an end of the base 20 in the z-direction. In an example, the third conductor 40 can be located within the base 20. The third conductor 40 can have a portion that is located inside the base 20 and another portion that is located outside the base 20. The third conductor 40 can have a surface that partially faces outside the base 20.

The third conductor 40 includes at least one conductive member. The third conductor 40 can include a plurality of conductive members. When the third conductor 40 includes the plurality of conductive members, the third conductor 40 can be referred to as a third conductor group. The third conductor 40 includes at least one conductive layer. The third conductor 40 includes at least one conductive member in one conductive layer. The third conductor 40 can include a plurality of conductive layers. For example, the third conductor 40 can include three or more conductive layers. The third conductor 40 includes at least one conductive member in each of the plurality of conductive layers. The third conductor 40 extends in the xy plane. The xy plane includes the x-direction. Each of the conductive layers of the third conductor 40 extends along the xy plane.

In an example of the plurality of embodiments, the third conductor 40 includes a first conductive layer 41 and a second conductive layer 42. The first conductive layer 41 extends along the xy plane. The first conductive layer 41 can be located on the base 20. The second conductive layer 42 extends along the xy plane. The second conductive layer 42 can be capacitively coupled to the first conductive layer 41. The second conductive layer 42 can be electrically connected to the first conductive layer 41. The two conductive layers capacitively coupled can face each other in the y-direction. The two conductive layers capacitively coupled can face each other in the x-direction. The two conductive layers capacitively coupled can face each other in the first plane. The two conductive layers facing each other in the first plane can also be said that two conductive members are located in one conductive layer. The second conductive layer 42 can be located so as to at least partially overlap the first conductive layer 41 in the z-direction. The second conductive layer 42 can be located within the base 20.

The fourth conductor 50 is located apart from the third conductor 40. The fourth conductor 50 is electrically connected to the conductors 31 and 32 of the pair conductors 30. The fourth conductor 50 is electrically connected to the first conductor 31 and the second conductor 32. The fourth conductor 50 extends along the third conductor 40. The fourth conductor 50 extends along the first plane. The fourth conductor 50 expands from the first conductor 31 to the second conductor 32. The fourth conductor 50 is located on the base 20. The fourth conductor 50 can be located within the base 20. The fourth conductor 50 can have a portion that is located inside the base 20 and another portion that is located outside the base 20. The fourth conductor 50 can have a surface that partially faces outside the base 20.

In an example of the plurality of embodiments, the fourth conductor 50 can function as a ground conductor in the resonator 10. The potential of the fourth conductor 50 can be a reference potential of the resonator 10. The fourth conductor 50 can be connected to the ground of a device including the resonator 10.

In an example of the plurality of embodiments, the resonator 10 can include the fourth conductor 50 and a reference potential layer 51. The reference potential layer 51 is located apart from the fourth conductor 50 in the z-direction. The reference potential layer 51 is electrically insulated from the fourth conductor 50. The potential of the reference potential layer 51 can be a reference potential of the resonator 10. The reference potential layer 51 can be electrically connected to the ground of a device including the resonator 10. The fourth conductor 50 can be electrically separated from the ground of a device including the resonator 10. The reference potential layer 51 faces either the third conductor 40 or the fourth conductor 50 in the z-direction.

In an example of the plurality of embodiments, the reference potential layer 51 faces the third conductor 40 via the fourth conductor 50. The fourth conductor 50 is located between the third conductor 40 and the reference potential layer 51. The distance between the reference potential layer 51 and the fourth conductor 50 is smaller than the distance between the third conductor 40 and the fourth conductor 50.

In the resonator 10 including the reference potential layer 51, the fourth conductor 50 can include one or a plurality of conductive members. In the resonator 10 including the reference potential layer 51, the fourth conductor 50 can include one or a plurality of conductive members, and the third conductor 40 can include one conductive member that is connected to the pair conductors 30. In the resonator 10 including the reference potential layer 51, each of the third conductor 40 and the fourth conductor 50 can include at least one resonator.

In the resonator 10 including the reference potential layer 51, the fourth conductor 50 can include a plurality of conductive layers. For example, the fourth conductor 50 can include a third conductive layer 52 and a fourth conductive layer 53. The third conductive layer 52 can be capacitively coupled to the fourth conductive layer 53. The third conductive layer 52 can be electrically connected to the first conductive layer 41. The two conductive layers capacitively coupled can face each other in the y-direction. The two conductive layers capacitively coupled can face each other in the x-direction. The two conductive layers capacitively coupled can face each other in the xy plane.

The distance between the two conductive layers capacitively coupled with facing each other in the z-direction is smaller than the distance between the conductor group and the reference potential layer 51. For example, the distance between the first conductive layer 41 and the second conductive layer 42 is smaller than the distance between the third conductor 40 and the reference potential layer 51. For example, the distance between the third conductive layer 52 and the fourth conductive layer 53 is shorter than the distance between the fourth conductor 50 and the reference potential layer 51.

Each of the first conductor 31 and the second conductor 32 can include one or a plurality of conductive members. Each of the first conductor 31 and the second conductor 32 can include one conductive member. Each of the first conductor 31 and the second conductor 32 can include a plurality of conductive members. Each of the first conductor 31 and the second conductor 32 can include at least one fifth conductive layer 301 and a plurality of fifth conductors 302.

The pair conductors 30 include at least one fifth conductive layer 301 and a plurality of fifth conductors 302.

The fifth conductive layer 301 extends in the y-direction. The fifth conductive layer 301 extends along the xy plane. The fifth conductive layer 301 is a layered conductive member. The fifth conductive layer 301 can be located on the base 20. The fifth conductive layer 301 can be located within the base 20. A plurality of the fifth conductive layers 301 is separated from each other in the z-direction. The plurality of the fifth conductive layers 301 is aligned in the z-direction. The plurality of the fifth conductive layers 301 partially overlaps each other in the z-direction. Each of the fifth conductive layers 301 electrically connects the plurality of fifth conductors 302. The fifth conductive layer 301 serves as a connecting conductor that connects the plurality of fifth conductors 302. The fifth conductive layer 301 can be electrically connected to any conductive layer of the third conductor 40. In an embodiment, the fifth conductive layer 301 is electrically connected to the second conductive layer 42. The fifth conductive layer 301 can be integrated with the second conductive layer 42. In an embodiment, the fifth conductive layer 301 can be electrically connected to the fourth conductor 50. The fifth conductive layer 301 can be integrated with the fourth conductor 50.

Each of the fifth conductors 302 extends in the z-direction. The plurality of fifth conductors 302 is separated from each other in the y-direction. The distance between the fifth conductors 302 is equal to or less than ½ of the wavelength $\lambda_1$. When the distance between fifth conductors 302 electrically connected is equal to or less than ½ of the wavelength $\lambda_1$, each of the first conductors 31 and second conductors 32 can reduce leakage of an electromagnetic wave in a resonant frequency band from between the fifth conductors 302. Since leakage of the electromagnetic wave in the resonant frequency band from the pair conductors 30 is small, the pair conductors 30 appear as an electric wall due to the unit structure. At least part of the plurality of fifth conductors 302 are electrically connected to the fourth conductor 50. In an embodiment, part of the plurality of fifth conductors 302 can electrically connect the fourth conductor 50 and fifth conductive layers 301. In an embodiment, the plurality of fifth conductors 302 can be electrically connected to the fourth conductor 50 via the fifth conductive layers 301. Part of the plurality of fifth conductors 302 can electrically connect one fifth conductive layer 301 to another fifth conductive layer 301. Each of the fifth conductors 302 can employ a via conductor and a through-hole conductor.

The resonator 10 includes the third conductor 40 that functions as a resonator. The third conductor 40 can function as an artificial magnetic wall (artificial magnetic conductor; AMC). The artificial magnetic conductor can also be called as a reactive impedance surface (RIS).

The resonator 10 includes the third conductor 40 that functions as a resonator, between two pair conductors 30 facing each other in the x-direction. The two pair conductors 30 appear as the electric wall (electric conductor) extending in the yz plane from the third conductor 40. The resonator 10 is electrically open at an end in the y-direction. The resonator 10 has high impedance in zx planes at both ends in the y-direction. The zx planes at both ends of the resonator 10 in the y-direction appear as a magnetic wall (magnetic conductor) from the third conductor 40. The resonator 10 is surrounded by two electric walls and two high-impedance surfaces (magnetic walls), and the resonator of the third conductor 40 has an artificial magnetic conductor character in the z-direction. The resonator of the third conductor 40 surrounded by the two electric walls and two high-impedance surfaces has a finite number of artificial magnetic conductor characters.

The "artificial magnetic conductor character" exhibits a phase difference of 0 degree between an incident wave and a reflected wave at an operating frequency. In the resonator 10, the phase difference between an incident wave and a reflected wave at the first frequency $f_1$ is 0 degree. In the "artificial magnetic conductor character", the phase difference between an incident wave and a reflected wave is −90 degrees to +90 degrees in an operating frequency band. The operating frequency band is a frequency band between a second frequency $f_2$ and a third frequency $f_3$. The second frequency $f_2$ is a frequency at which a phase difference between an incident wave and a reflected wave is +90 degrees. The third frequency $f_3$ is a frequency at which a phase difference between an incident wave and a reflected wave is −90 degrees. The width of the operating frequency band determined on the basis of the second and third frequencies may be, for example, not less than 100 MHz when the operating frequency is approximately 2.5 GHz. The width of the operating frequency band may be, for example, not less than 5 MHz when the operating frequency is approximately 400 MHz.

The operating frequency of the resonator 10 can be different from a resonant frequency of a resonator of each third conductor 40. The operating frequency of the resonator 10 can be changed depending on the lengths, sizes, shapes, materials, or the like of the base 20, the pair conductors 30, the third conductor 40, and the fourth conductor 50.

In an example of the plurality of embodiments, the third conductor 40 can include at least one unit resonator 40X. The third conductor 40 can include one unit resonator 40X. The third conductor 40 can include a plurality of unit resonators 40X. The unit resonators 40X are located so as to overlap the fourth conductor 50 in the z-direction. The unit resonator 40X faces the fourth conductor 50. The unit resonator 40X can function as a frequency selective surface (FSS). The plurality of unit resonators 40X is arranged along the xy plane. The plurality of unit resonators 40X can be regularly arranged in the xy plane. The unit resonators 40X can be arranged in the form of a square grid, oblique grid, rectangular grid, or hexagonal grid.

The third conductor 40 can include a plurality of conductive layers that is arranged in the z-direction. Each of the plurality of conductive layers of the third conductor 40 includes at least one-equivalent unit resonator. For example, the third conductor 40 includes the first conductive layer 41 and the second conductive layer 42.

The first conductive layer 41 includes at least one-equivalent first unit resonator 41X. The first conductive layer 41 can include one first unit resonator 41X. The first conductive layer 41 can include a plurality of first divisional resonators 41Y that is obtained by dividing one first unit resonator 41X. The plurality of first divisional resonators 41Y can be formed into at least one-equivalent first unit resonator 41X by adjacent unit structures 10X. The plurality of first divisional resonators 41Y is located at the ends of the first conductive layer 41. The first unit resonator 41X and the first divisional resonator 41Y can be called a third conductor.

The second conductive layer 42 includes at least one-equivalent second unit resonator 42X. The second conductive layer 42 can include one second unit resonator 42X. The second conductive layer 42 can include a plurality of second divisional resonators 42Y that is obtained by dividing one second unit resonator 42X. The plurality of second divisional resonators 42Y can be formed into at least one-equivalent second unit resonator 42X by adjacent unit structures 10X. The plurality of second divisional resonators 42Y is located at the ends of the second conductive layer 42. The second unit resonator 42X and the second divisional resonator 42Y can be called a third conductor.

The second unit resonator 42X and the second divisional resonators 42Y are located so as to at least partially overlap the first unit resonator 41X and the first divisional resonators 41Y in the Z-direction. In the third conductor 40, at least part of the unit resonators and partial resonators of the respective layers overlap in the Z-direction to form one unit resonator 40X. The unit resonator 40X includes at least one-equivalent resonator in each layer.

When the first unit resonator 41X includes a line or patch resonator, the first conductive layer 41 includes at least one first unit conductor 411. The first unit conductor 411 can function as the first unit resonator 41X or the first divisional resonator 41Y. The first conductive layer 41 includes a plurality of first unit conductors 411 that is arranged in n rows and m columns in the x and y directions. In the above, n and m are each independently a natural number of 1 or more. In an example illustrated in FIGS. 1 to 9 and the like, the first conductive layer 41 includes six first unit conductors 411 that are arranged in a grid of two rows and three columns. The first unit conductors 411 can be arranged in the form of a square grid, oblique grid, rectangular grid, or hexagonal grid. A first unit conductors 411 corresponding to a first divisional resonator 41Y is located at an end of the first conductive layer 41 in the xy plane.

In a case where the first unit resonator 41X uses a slot resonator, the first conductive layer 41 has at least one conductive layer extending in the x and y directions. The first conductive layer 41 includes at least one first unit slot 412. The first unit slot 412 can function as the first unit resonator 41X or the first divisional resonator 41Y. The first conductive layer 41 can include a plurality of first unit slots 412 that is arranged in n rows and m columns in the x and y directions. In the above, n and m are each independently a natural number of 1 or more. In an example illustrated in FIGS. 6 to 9 and the like, the first conductive layer 41 includes six first unit slots 412 that are arranged in a grid of two rows and three columns. The first unit slots 412 can be arranged in the form of a square grid, oblique grid, rectangular grid, or hexagonal grid. A first unit slot 412 corresponding to a first divisional resonator 41Y is located at an end of the first conductive layer 41 in the xy plane.

In a case where the second unit resonator 42X uses a line or patch resonator, the second conductive layer 42 includes at least one second unit conductor 421. The second conductive layer 42 can include a plurality of second unit conductors 421 that is arranged in the x and y directions. The second unit conductors 421 can be arranged in the form of a square grid, oblique grid, rectangular grid, or hexagonal grid. The second unit conductor 421 can function as the second unit resonator 42X or the second divisional resonator 42Y. A second unit conductor 421 corresponding to a second divisional resonator 42Y is located at an end of the second conductive layer 42 in the xy plane.

The second unit conductor 421 at least partially overlaps at least one of the first unit resonator 41X and the first divisional resonator 41Y in the z-direction. The second unit conductor 421 can overlap a plurality of first unit resonators 41X. The second unit conductor 421 can overlap a plurality of first divisional resonators 41Y. The second unit conductor 421 can overlap one first unit resonator 41X and four first divisional resonators 41Y. The second unit conductor 421 can only overlap one first unit resonator 41X. The center of gravity of the second unit conductor 421 can coincide with that of one first unit conductor 411. The center of gravity of the second unit conductor 421 can be located between a plurality of first unit conductors 411 and first divisional resonators 41Y. The center of gravity of the second unit conductor 421 can be located between two first unit resonators 41X arranged in the x-direction or y-direction.

The second unit conductor 421 can at least partially overlap two first unit conductors 411. The second unit conductor 421 can overlap only one first unit conductor 411. The center of gravity of the second unit conductor 421 can be located between two first unit conductors 411. The center of gravity of the second unit conductor 421 can coincide with that of one first unit conductor 411. The second unit conductor 421 can at least partially overlap a first unit slot 412. The second unit conductor 421 can overlap only one first unit slot 412. The center of gravity of the second unit conductor 421 can be located between two first unit slots 412 arranged in the x-direction or y-direction. The center of gravity of second unit conductors 421 can coincide with that of one first unit slot 412.

In a case where the second unit resonator 42X uses a slot resonator, the second conductive layer 42 has at least one conductive layer extending along the xy plane. The second conductive layer 42 includes at least one second unit slot 422. The second unit slot 422 can function as the second unit resonator 42X or the second divisional resonator 42Y. The second conductive layer 42 can include a plurality of second unit slots 422 that is arranged in the xy plane. The second unit slots 422 can be arranged in the form of a square grid, oblique grid, rectangular grid, or hexagonal grid. The second unit slot 422 corresponding to the second divisional resonator 42Y is located at an end of the second conductive layer 42 in the xy plane.

The second unit slot 422 at least partially overlaps at least one of the first unit resonator 41X and the first divisional resonator 41Y in the y-direction. The second unit slot 422 can overlap a plurality of first unit resonators 41X. The second unit slot 422 can overlap a plurality of first divisional resonators 41Y. The second unit slot 422 can overlap one first unit resonator 41X and four first divisional resonators 41Y. The second unit slot 422 can overlap only one first unit resonator 41X. The center of gravity of the second unit slot 422 can coincide with that of one first unit conductor 41X. The center of gravity of the second unit slot 422 can be located between a plurality of first unit conductors 41X. The center of gravity of the second unit slot 422 can be located between two first unit resonators 41X and two first divisional resonators 41Y arranged in the x-direction or y-direction.

The second unit slot 422 can at least partially overlap two first unit conductors 411. The second unit slot 422 can overlap only one first unit conductor 411. The center of gravity of the second unit slot 422 can be located between two first unit conductors 411. The center of gravity of second unit slot 422 can coincide with that of one first unit conductor 411. The second unit slot 422 can at least partially overlap a first unit slot 412. The second unit slot 422 can overlap only one first unit slot 412. The center of gravity of the second unit slot 422 can be located between two first unit slots 412 arranged in the x-direction or y-direction. The center of gravity of the second unit slot 422 can overlap one first unit slot 412.

The unit resonator 40X includes at least one-equivalent first unit resonator 41X and at least one-equivalent second unit resonator 42X. The unit resonator 40X can include one first unit resonator 41X. The unit resonator 40X can include a plurality of first unit resonators 41X. The unit resonator 40X can include one first divisional resonator 41Y. The unit resonator 40X can include a plurality of first divisional resonators 41Y. The unit resonator 40X can include a portion of a first unit resonator 41X. The unit resonator 40X can include one or a plurality of partial first unit resonators 41X. The unit resonator 40X includes a plurality of partial resonators that includes one or a plurality of partial first unit resonators 41X and one or a plurality of first divisional resonators 41Y. The plurality of partial resonators included in the unit resonator 40X is combined into at least one-equivalent first unit resonator 41X. The unit resonator 40X can include a plurality of first divisional resonators 41Y without including the first unit resonator 41X. The unit resonator 40X can include, for example, four first divisional resonators 41Y. The unit resonator 40X can include only a plurality of partial first unit resonators 41X. The unit resonator 40X can include one or a plurality of partial first unit resonators 41X and one or a plurality of first divisional resonators 41Y. The unit resonator 40X can include, for example, two partial first unit resonators 41X and two first divisional resonators 41Y. The unit resonator 40X can include, at both ends in the x-direction, first conductive layers 41 that are substantially the same in mirror image. The unit resonator 40X can include first conductive layers 41 that are substantially symmetric about a center line extending in the z-direction.

The unit resonator 40X can include one second unit resonator 42X. The unit resonator 40X can include a plurality of second unit resonators 42X. The unit resonator 40X can include one second divisional resonator 42Y. The unit resonator 40X can include a plurality of second divisional resonators 42Y. The unit resonator 40X can include a portion of a second unit resonator 42X. The unit resonator 40X can include one or a plurality of partial second unit resonators 42X. The unit resonator 40X includes a plurality of partial resonators that includes one or a plurality of partial second unit resonators 42X and one or a plurality of second divisional resonators 42Y. The plurality of partial resonators included in the unit resonator 40X is combined into at least one-equivalent second unit resonator 42X. The unit resonator 40X can include a plurality of second divisional resonators 42Y without including the second unit resonator 42X. The unit resonator 40X can include, for example, four second divisional resonators 42Y. The unit resonator 40X can include only a plurality of partial second unit resonators 42X. The unit resonator 40X can include one or a plurality of partial second unit resonators 42X and one or a plurality of second divisional resonators 42Y. The unit resonator 40X can include, for example, two partial second unit resonators 42X and two second divisional resonators 42Y. The unit resonator 40X can include, at both ends in the x-direction, second conductive layers 42 that are substantially the same in mirror image. The unit resonator 40X can include second conductive layers 42 that are substantially symmetric about a center line extending in the y-direction.

In an example of the plurality of embodiments, the unit resonator 40X includes one first unit resonator 41X and a plurality of partial second unit resonators 42X. For example, the unit resonator 40X includes one first unit resonator 41X and four halves of second unit resonators 42X. The unit resonator 40X includes one-equivalent first unit resonator 41X and two-equivalent second unit resonators 42X. The configuration of the unit resonator 40X is not limited to this example.

The resonator 10 can include at least one unit structure 10X. The resonator 10 can include a plurality of unit structures 10X. The plurality of unit structures 10X can be arranged in the xy plane. The plurality of unit structures 10X can be arranged in the form of a square grid, oblique grid, rectangular grid, or hexagonal grid. The unit structure 10X includes any of repeated units of square grid, oblique grid, rectangular grid, and hexagonal grid. The unit structures 10X arranged infinitely along the xy plane can function as an artificial magnetic conductor (AMC).

The unit structure 10X can include at least part of the base 20, at least part of the third conductor 40, and at least part of the fourth conductor 50. The portions of the base 20, third conductor 40, and fourth conductor 50 that are included in the unit structure 10X overlap in the z-direction. The unit structure 10X includes the unit resonator 40X, part of the base 20 that overlaps the unit resonator 40X in the z-direction, and the fourth conductor 50 that overlaps the unit resonator 40X in the z-direction. The resonator 10 can include, for example, six unit structures 10X that are arranged in two rows and three columns.

The resonator 10 can include at least one unit structure 10X between two pair conductors 30 facing each other in the x-direction. The two pair conductors 30 appear as electric walls extending in the yz plane from the unit structure 10X. The unit structure 10X is electrically open at an end in the y-direction. The unit structure 10X has high impedance in zx planes at both ends in the y-direction. In the unit structure 10X, the zx planes at both ends in the y-direction appear as magnetic walls. The unit structures 10X can be arranged repeatedly so as to be line-symmetric in the z-direction. The unit structure 10X surrounded by two electric walls and two high impedance surfaces (magnetic walls) has an artificial magnetic conductor character in the z-direction. The unit structure 10X surrounded by two electric walls and two high-impedance surfaces (magnetic walls) has a finite number of artificial magnetic conductor characters.

The operating frequency of the resonator 10 can be different from the operating frequency of the first unit resonator 41X. The operating frequency of the resonator 10 can be different from the operating frequency of the second unit resonator 42X. The operating frequency of the resonator 10 can be changed by the coupling of the first unit resonator 41X and the second unit resonator 42X that form the unit resonator 40X.

The third conductor 40 can include the first conductive layer 41 and the second conductive layer 42. The first conductive layer 41 includes at least one first unit conductor 411. The first unit conductor 411 includes a first connecting conductor 413 and a first floating conductor 414. The first connecting conductor 413 is connected to any of the pair conductors 30. The first floating conductor 414 is not connected to the pair conductors 30. The second conductive layer 42 includes at least one second unit conductor 421. The second unit conductor 421 includes a second connecting conductor 423 and a second floating conductor 424. The second connecting conductor 423 is connected to any of the pair conductors 30. The second floating conductor 424 is not connected to the pair conductors 30. The third conductor 40 can include a first unit conductor 411 and the second unit conductor 421.

The first connecting conductor 413 can have a larger length than the first floating conductor 414 in the x-direction. The first connecting conductor 413 can have a smaller length than the first floating conductor 414 in the x-direction. The first connecting conductor 413 can have a length that is half of that of the first floating conductor 414, in the x-direction. The second connecting conductor 423 can have a larger length than the second floating conductor 424 in the x-direction. The second connecting conductor 423 can have a smaller length than the second floating conductor 424 in the x-direction. The second connecting conductor 423 can have a length that is half of that of the second floating conductor 424, in the x-direction.

The third conductor 40 can include a current path 401 that serves as a current path between the first conductor 31 and the second conductor 32 when the resonator 10 resonates. The current path 401 can be connected to the first conductor 31 and the second conductor 32. The current path 401 has capacitance between the first conductor 31 and the second conductor 32. The capacitance of the current path 401 is electrically connected in series between the first conductor 31 and the second conductor 32. In the current path 401, conductive members are separated between the first conductor 31 and the second conductor 32. The current path 401 can include a conductive member connected to the first conductor 31 and a conductive member connected to the second conductor 32.

In the plurality of embodiments, in the current path 401, the first unit conductor 411 and the second unit conductor 421 partially face each other in the z-direction. In the current path 401, the first unit conductor 411 and the second unit conductor 421 are capacitively coupled. The first unit conductor 411 has a capacitance component at an end in the x-direction. The first unit conductor 411 can have a capacitance component at an end in the y-direction that faces the second unit conductor 421 in the z-direction. The first unit conductor 411 can have a capacitance component at an end in the x-direction and at an end in the y-direction that face the second unit conductor 421 in the z-direction. The second unit conductor 421 has a capacitance component at an end in the x-direction. The second unit conductor 421 can have a capacitance component at an end in the y-direction that faces the first unit conductor 411 in the z-direction. The second unit conductor 421 can have a capacitive component at an end in the x-direction and at an end in the y-direction that face the first unit conductor 411 in the z-direction.

The resonator 10 can reduce a resonant frequency by increasing the capacitive coupling in the current path 401. In achieving a desired operating frequency, the resonator 10 can reduce the length in the x-direction by increasing the capacitive coupling in the current path 401. In the third conductor 40, the first unit conductor 411 and the second unit conductor 421 face each other in a stacking direction of the base 20 and are capacitively coupled. The third conductor 40 can adjust the capacitance between the first unit conductor 411 and the second unit conductor 421 by the area of a portion where the first unit conductor 411 and the second unit conductor 421 face each other.

In the plurality of embodiments, the length of the first unit conductor 411 in the y-direction is different from the length of the second unit conductor 421 in the y-direction. In the resonator 10, when a relative position between the first unit conductor 411 and the second unit conductor 421 is displaced from an ideal position along the xy plane, different lengths in a third direction between the first unit conductor 411 and the second unit conductor 421 can reduce a change in magnitude of the capacitance.

In the plurality of embodiments, the current path 401 includes one conductive member that is spatially separated from the first conductor 31 and the second conductor 32 and is capacitively coupled to the first conductor 31 and the second conductor 32.

In the plurality of embodiments, the current path 401 includes the first conductive layer 41 and the second conductive layer 42. The current path 401 includes at least one first unit conductor 411 and at least one second unit conductor 421. The current path 401 includes two first connecting conductors 413 and two second connecting conductors 423 or one first connecting conductor 413 and one second connecting conductor 423. In the current path 401, the first unit conductors 411 and the second unit conductors 421 can be arranged alternately in a first direction.

In the plurality of embodiments, the current path 401 includes the first connecting conductor 413 and the second connecting conductor 423. The current path 401 includes at least one first connecting conductor 413 and at least one second connecting conductor 423. In the current path 401, the third conductor 40 has capacitance between the first connecting conductor 413 and the second connecting conductor 423. In an example of the embodiments, the first connecting conductor 413 can face the second connecting conductor 423 to have capacitance. In an example of the embodiment, the first connecting conductor 413 can be capacitively connected to the second connecting conductor 423 via another conductive member.

In the plurality of embodiments, the current path 401 includes the first connecting conductor 413 and the second floating conductor 424. The current path 401 includes two first connecting conductors 413. In the current path 401, the third conductor 40 has capacitance between the two first connecting conductors 413. In an example of the embodiments, the two first connecting conductors 413 can be capacitively connected via at least one second floating conductor 424. In an example of the embodiment, the two first connecting conductors 413 can be capacitively connected via at least one first floating conductor 414 and a plurality of second floating conductors 424.

In the plurality of embodiments, the current path 401 includes the first floating conductor 414 and the second connecting conductor 423. The current path 401 includes two second connecting conductors 423. In the current path 401, the third conductor 40 has capacitance between the two second connecting conductors 423. In an example of the embodiments, the two second connecting conductors 423 can be capacitively connected via at least one first floating conductor 414. In an example of the embodiment, the two second connecting conductors 423 can be capacitively connected via a plurality of first floating conductors 414 and at least one second floating conductor 424.

In the plurality of embodiments, each of the first connecting conductor 413 and the second connecting conductor 423 can have a length that is one quarter of a wavelength λ of a resonant frequency. Each of the first connecting conductor 413 and the second connecting conductor 423 can function as a resonator that has a length one half of the wavelength λ. Each of the first connecting conductor 413 and the second connecting conductor 423 can be capacitively coupled to a resonator so as to oscillate in an odd mode or an even mode. The resonator 10 can use a resonant frequency in the even mode after capacitive coupling as the operating frequency.

The current path 401 can be connected to the first conductor 31 at a plurality of points. The current path 401 can be connected to the second conductor 32 at a plurality of points. The current path 401 can include a plurality of conductive paths that independently conducts current from the first conductor 31 to the second conductor 32.

In the second floating conductor 424 capacitively coupled to the first connecting conductor 413, an end of the second floating conductor 424 that is capacitively coupled to the first connecting conductor 413 has a smaller distance from the first connecting conductor 413 compared with distances from the pair conductors 30. In the first floating conductor 414 capacitively coupled to the second connecting conductor 423, an end of the first floating conductor 414 that is capacitively coupled to the second connecting conductor 423 has a smaller distance from the second connecting conductor 423 compared with distances from the pair conductors 30.

In the resonators 10 according to the plurality of embodiments, the conductive layers of the third conductors 40 can have different lengths in y-directions. A conductive layer of the third conductor 40 is capacitively coupled to another conductive layer in the z-direction. In the resonator 10, when conductive layers have different lengths in y-directions, a change in capacitance is reduced even if the conductive layers are displaced in the y-directions. In the resonator 10, the different lengths of the conductive layers in the y-directions can increase the acceptable range of displacement of the conductive layers in the y-direction.

In the resonators 10 according to the plurality of embodiments, the third conductors 40 have capacitance due to capacitive coupling between conductive layers. A plurality of capacitive portions having the capacitance can be arranged in the y-direction. The plurality of capacitive portions arranged in the y-direction can have an electromagnetically parallel relationship. The resonator 10, a plurality of capacitive portions electrically arranged in parallel can mutually complement individual capacitive errors.

When the resonator 10 is in a resonant state, current flows through the pair conductors 30, the third conductor 40, and the fourth conductor 50 in a loop. When the resonator 10 is in the resonant state, alternating current is flowing in the resonator 10. In the resonator 10, current flowing through the third conductor 40 is defined as first current, and current flowing through the fourth conductor 50 is defined as second current. When the resonator 10 is in the resonant state, a direction in which the first current flows is different from a direction in which the second current flows, in the x-direction. For example, when the first current flows in a +x-direction, the second current flows in a −x-direction. For example, when the first current flows in the −x-direction, the second current flows in the +x-direction. That is, when the resonator 10 is in the resonant state, the loop current alternately flows in the +x-direction and the −x-direction. The resonator 10 radiates an electromagnetic wave by repeating reversal of the loop current that generates a magnetic field.

In the plurality of embodiments, the third conductor 40 includes the first conductive layer 41 and the second conductive layer 42. In the third conductor 40, since the first conductive layer 41 and the second conductive layer 42 are capacitively coupled to each other, current globally appears to flow in one direction in the resonant state. In the plurality of embodiments, current flowing through each conductor has a high density at an end in the y-direction.

In the resonator 10, the first current and the second current flow in a loop via the pair conductors 30. In the resonator 10, the first conductor 31, the second conductor 32, the third conductor 40, and the fourth conductor 50 form a resonance circuit. The resonant frequency of the resonator 10 is the resonant frequency of each unit resonator. When the resonator 10 includes one unit resonator or when the resonator 10 includes part of a unit resonator, the resonant frequency of the resonator 10 changes depending on the base 20, pair conductors 30, third conductor 40, and fourth conductor 50 as well as electromagnetic coupling between the resonator 10 and the surroundings. For example, when the third conductor 40 has poor periodicity, the resonator 10 becomes one unit resonator as a whole or becomes part of one unit resonator as a whole. For example, the resonant frequency of the resonator 10 changes depending on the lengths of the first conductor 31 and second conductor 32 in the z-direction, the lengths of the third conductor 40 and the fourth conductor 50 in the x-direction, and the capacitance of the third conductor 40 and fourth conductor 50. For example, when the resonator 10 has a large capacitance between the first unit conductor 411 and the second unit conductor 421, the lengths of the first conductor 31 and second conductor 32 in the z-direction and the lengths of the third conductor 40 and fourth conductor 50 in the x-direction are reduced, simultaneously enabling reduction of the resonant frequency.

In the plurality of embodiments, in the resonator 10, the first conductive layer 41 serves as an effective electromagnetic wave radiation surface in the z-direction. In the plurality of embodiments, in the resonator 10, a first area of the first conductive layer 41 is larger than a first area of the other conductive layers. The resonator 10 can increase the first area of the first conductive layer 41 to increase the radiation of the electromagnetic wave.

In the plurality of embodiments, the resonator 10 can include one or a plurality of impedance elements 45. Each of the impedance elements 45 has an impedance value between a plurality of terminals. The impedance element 45 changes the resonant frequency of the resonator 10. The impedance element 45 can include a register, a capacitor, and an inductor. The impedance element 45 can include a variable element whose impedance value can be changed. The variable element can change the impedance value with an electric signal. The variable element can change the impedance value with a physical mechanism.

The impedance element 45 can be connected to two unit conductors of the third conductor 40 arranged in the x-direction. The impedance element 45 can be connected to two first unit conductors 411 that are arranged in the x-direction. The impedance element 45 can be connected to a first connecting conductor 413 and the first floating conductor 414, that are arranged in the x-direction. The impedance element 45 can be connected to the first conductor 31 and the first floating conductor 414. The impedance element 45 is connected to a unit conductor of the third conductor 40 at the center in the y-direction. The impedance element 45 is connected to the centers of the two first unit conductors 411 in the y-direction.

The impedance element 45 is electrically connected in series between two conductive members that are arranged in the x-direction in the xy plane. The impedance element 45 can be electrically connected in series between two first unit conductors 411 that are arranged in the x-direction. The impedance element 45 can be electrically connected in series between a first connecting conductor 413 and the first floating conductor 414 that are arranged in the x-direction. The impedance element 45 can be electrically connected in series between the first conductor 31 and the first floating conductor 414.

The impedance element 45 can be electrically connected in parallel to two first unit conductors 411 and two second unit conductors 421 that overlap in the z-direction and have capacitance. The impedance element 45 can be electrically connected in parallel to the second connecting conductor 423 and the first floating conductor 414 that overlap in the z-direction and have capacitance.

The resonator 10 can reduce the resonant frequency by adding a capacitor as the impedance element 45. The resonator 10 can increase the resonant frequency by adding an inductor as the impedance element 45. The resonator 10 can include impedance elements 45 having different impedance values. The resonator 10 can include capacitors having different electric capacitances as the impedance elements 45. The resonator 10 can include inductors having different inductances as the impedance elements 45. In the resonator 10, addition of the impedance elements 45 having different impedance values increases an adjustment range of the resonant frequency. The resonator 10 can simultaneously include a capacitor and an inductor as the impedance elements 45. In the resonator 10, simultaneous addition of the capacitor and the inductor as the impedance elements 45 increases the adjustment range of the resonant frequency. Since the resonator 10 includes the impedance element 45, the resonator 10 can be one unit resonator as a whole or be part of one unit resonator as a whole.

Figure 2:
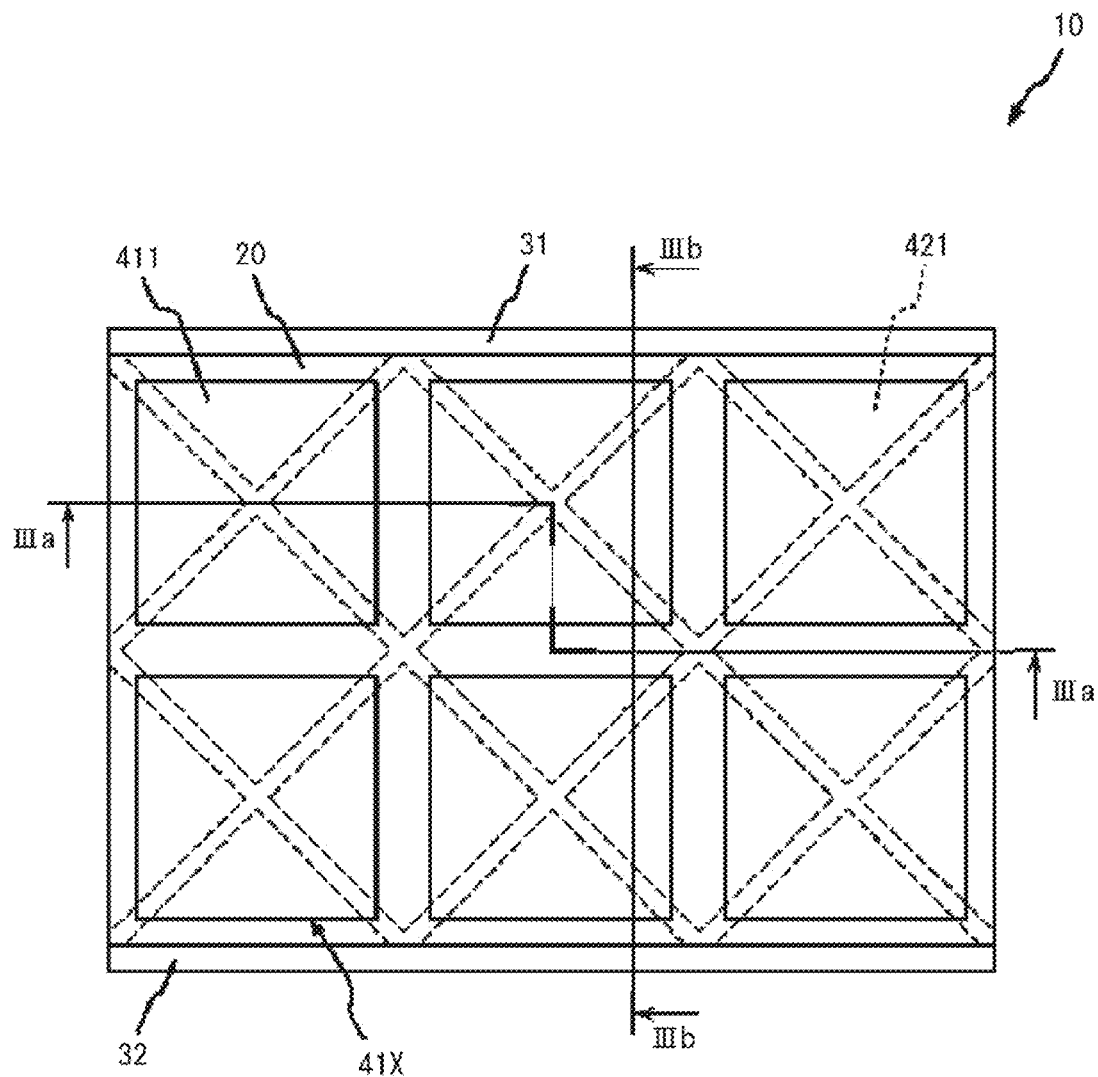
FIG. 2 is a plan view of the resonator illustrated in FIG. 1.
Figure 2:
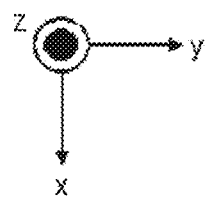
Figure 3A:
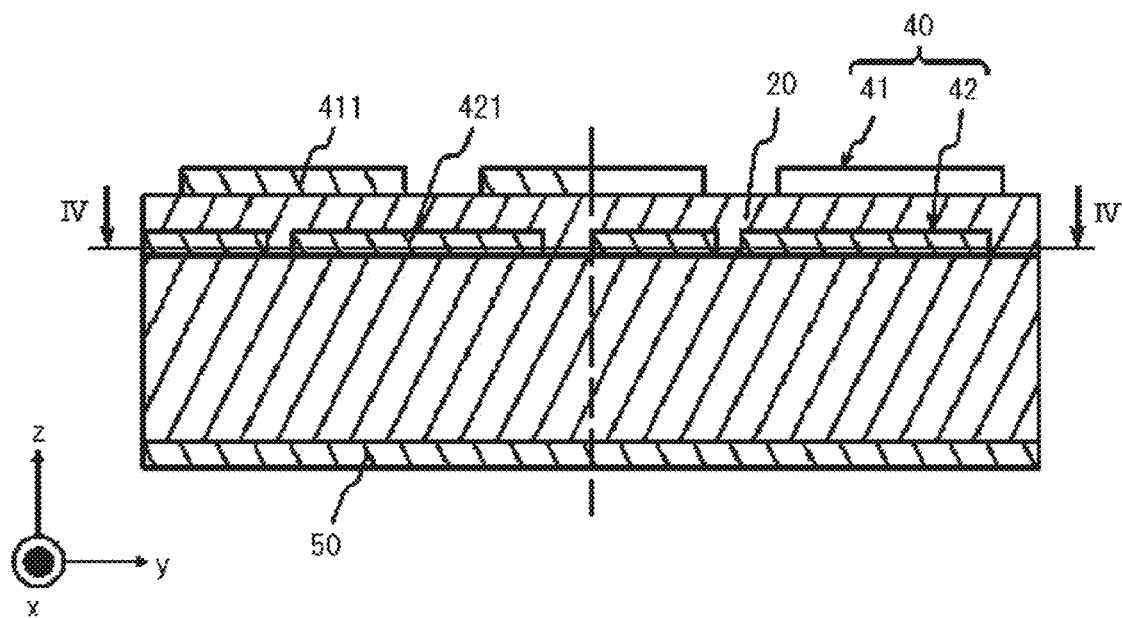
FIG. 3A is a sectional view of an example of the resonator illustrated in FIG. 1.
Figure 3B:
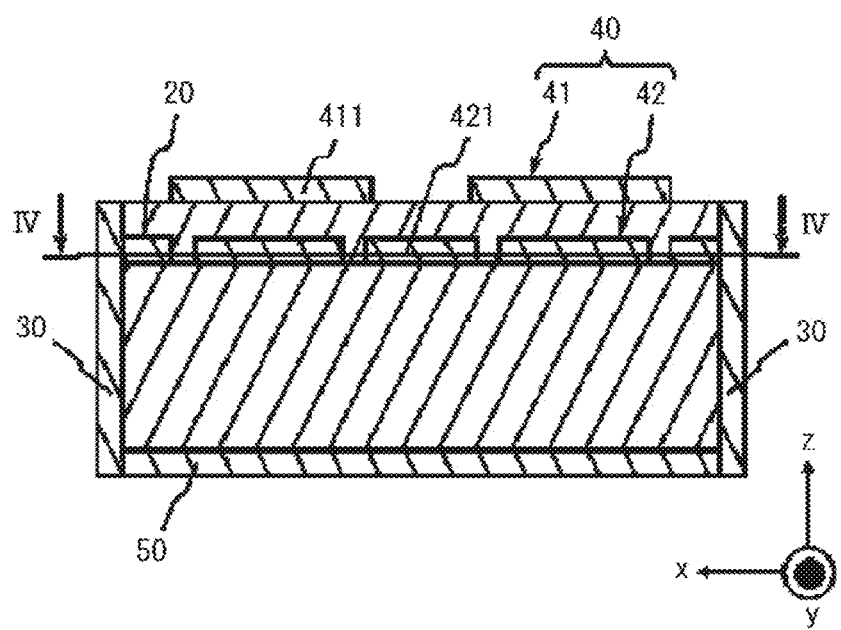
FIG. 3B is a sectional view of another example of the resonator illustrated in FIG. 1.
Figure 4:
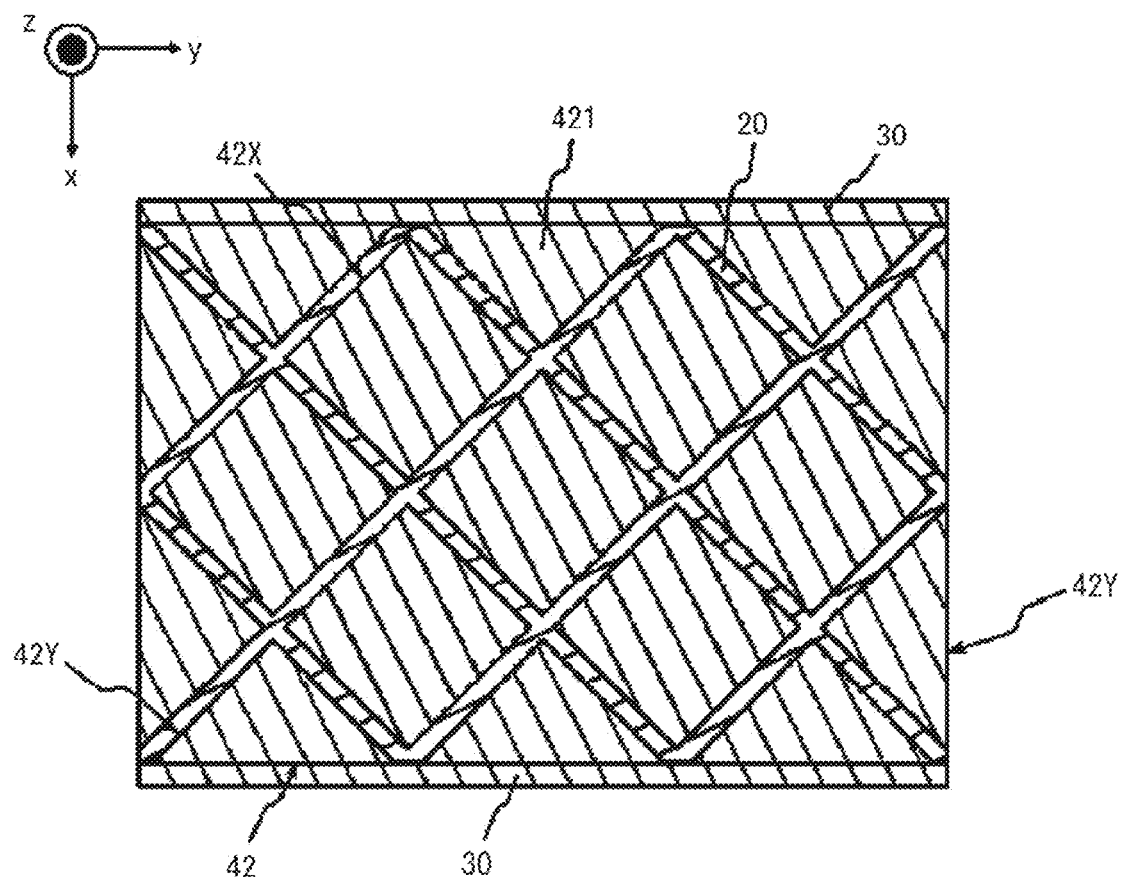
FIG. 4 is a sectional view of the resonator illustrated in FIG. 1.
Figure 5:
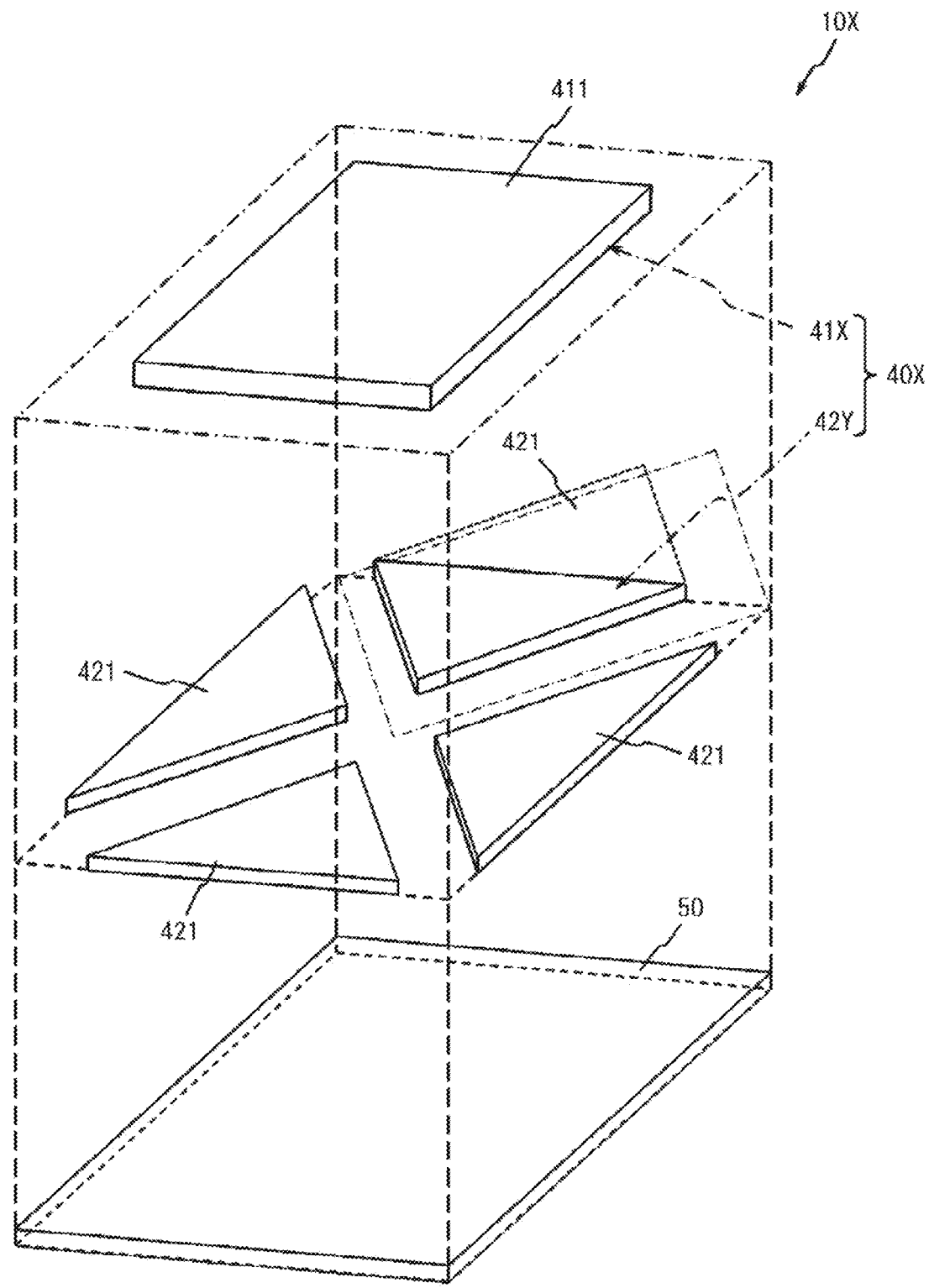
FIG. 5 is a conceptual view illustrating a unit structure of the resonator illustrated in FIG. 1.

FIGS. 1 to 5 are diagrams illustrating a resonator 10, which is an example of the plurality of embodiments. FIG. 1 is a schematic diagram of the resonator 10. FIG. 2 is a plan view of the xy plane, as viewed in the z-direction. FIG. 3A is a cross-sectional view taken along line IIIa-IIIa illustrated in FIG. 2. FIG. 3B is a cross-sectional view taken along line IIIb-IIIb illustrated in FIG. 2. FIG. 4 is a cross-sectional view taken along line IV-IV illustrated in FIG. 3. FIG. 5 is a conceptual diagram illustrating the unit structure 10X, which is an example of the plurality of embodiments.

In the resonator 10 illustrated in FIGS. 1 to 5, the first conductive layer 41 includes a patch resonator that serves as the first unit resonator 41X. The second conductive layer 42 includes a patch resonator that serves as the second unit resonator 42X. The unit resonator 40X includes one first unit resonator 41X and four second divisional resonators 42Y. The unit structure 10X includes the unit resonator 40X, part of the base 20 that overlaps the unit resonator 40X in the z-direction, and part of the fourth conductor 50.

Figure 6:
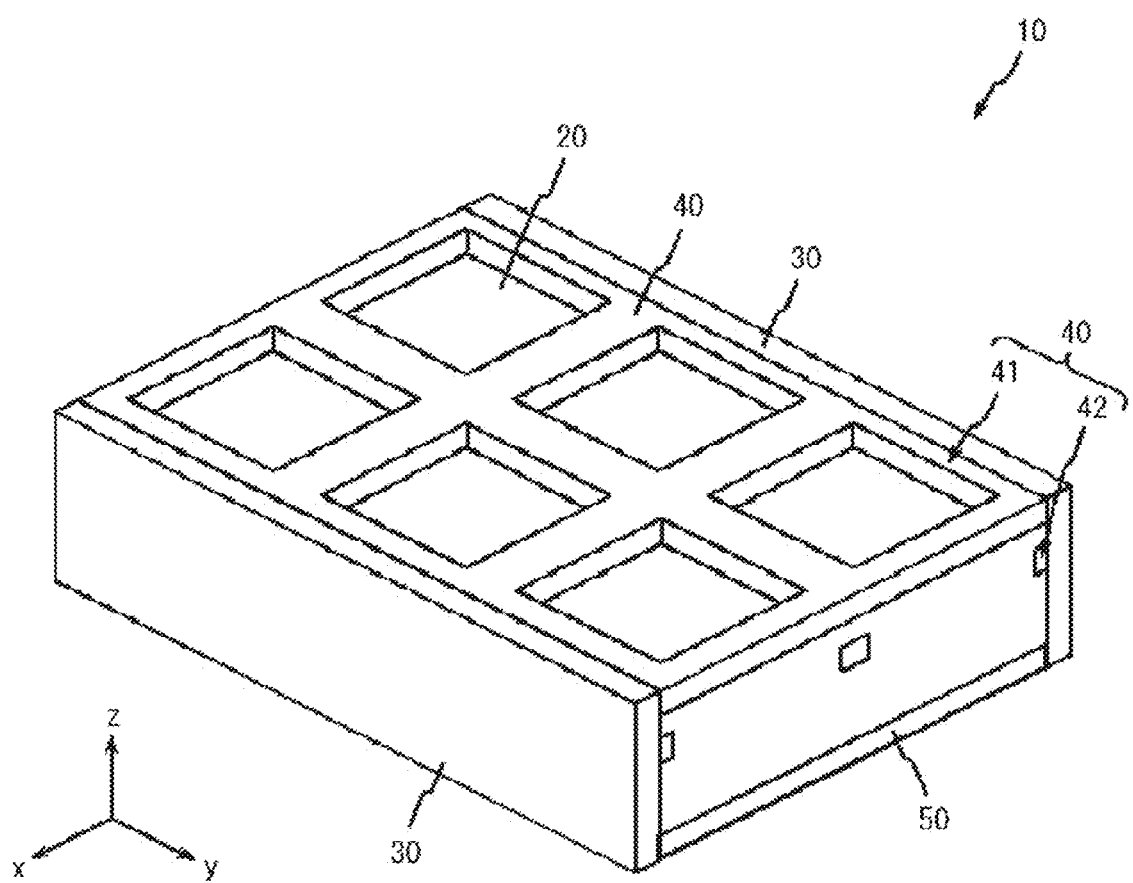
FIG. 6 is a perspective view illustrating an embodiment of the resonator.
Figure 7:
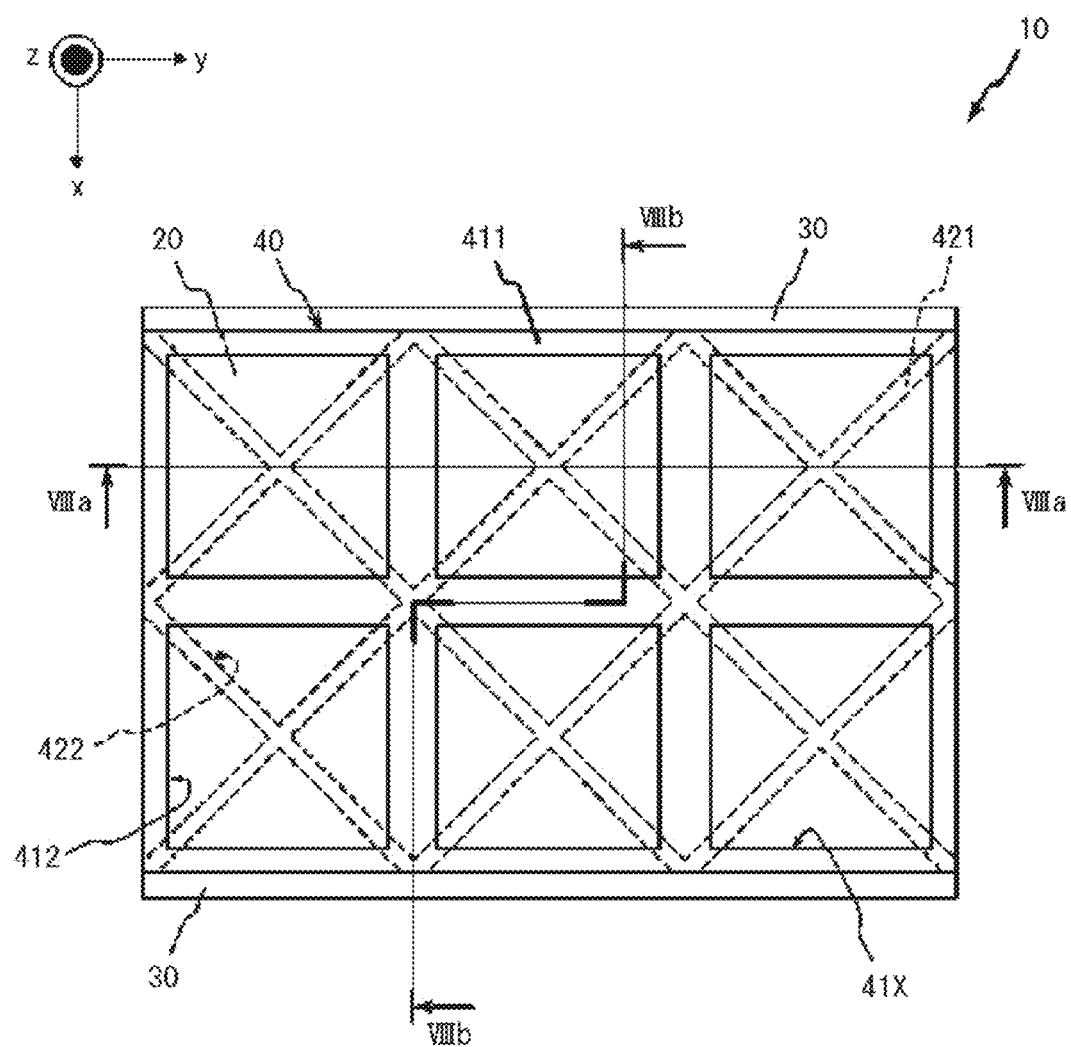
FIG. 7 is a plan view of the resonator illustrated in FIG. 6.
Figure 8A:
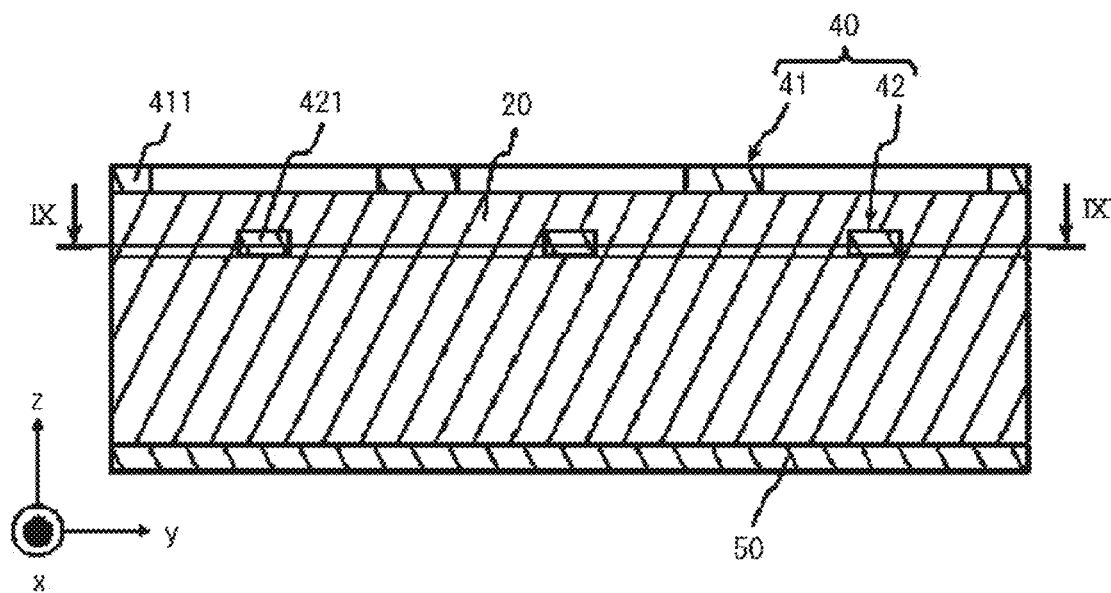
FIG. 8A is a sectional view of an example of the resonator illustrated in FIG. 6.
Figure 8B:
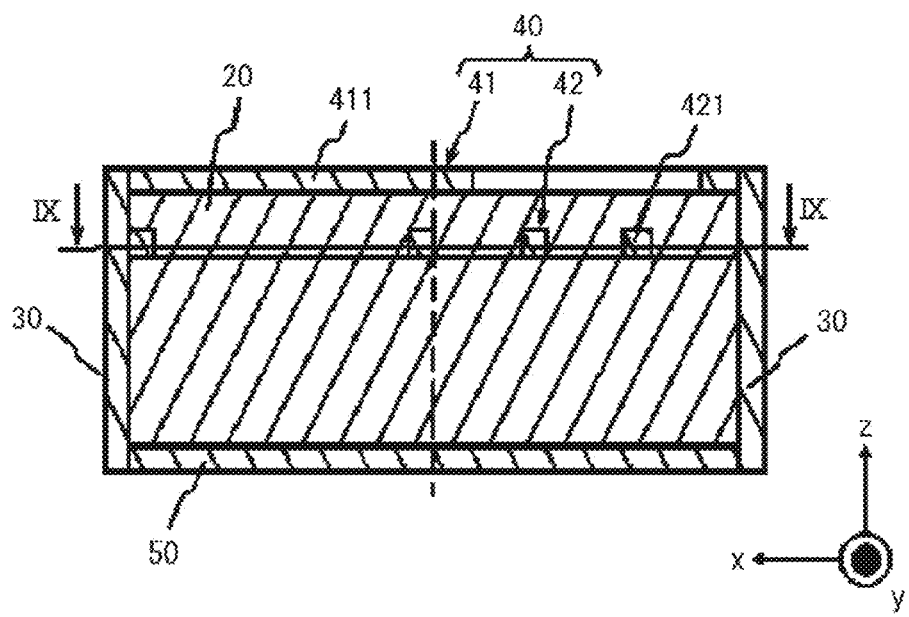
FIG. 8B is a sectional view of another example of the resonator illustrated in FIG. 6.
Figure 9:
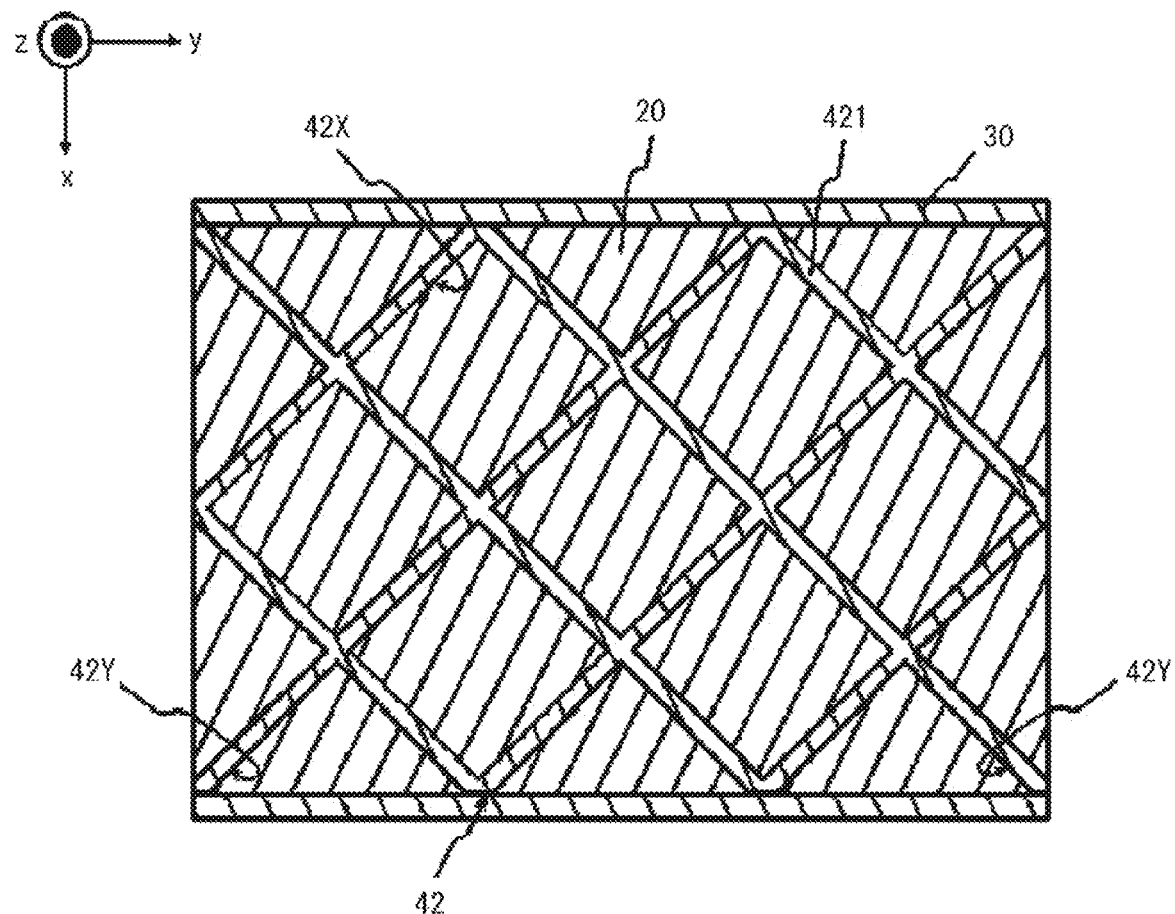
FIG. 9 is a sectional view of the resonator illustrated in FIG. 6.

FIGS. 6 to 9 are diagrams illustrating a resonator 10, which is an example of the plurality of embodiments. FIG. 6 is a schematic diagram of the resonator 10. FIG. 7 is a plan view of the xy plane, as viewed in the z-direction. FIG. 8A is a cross-sectional view taken along line VIIIa-VIIIa illustrated in FIG. 7. FIG. 8B is a cross-sectional view taken along line VIIIb-VIIIb illustrated in FIG. 7. FIG. 9 is a cross-sectional view taken along line IX-IX illustrated in FIG. 8.

In the resonator 10 illustrated in FIGS. 6 to 9, the first conductive layer 41 includes a slot resonator that serves as the first unit resonator 41X. The second conductive layer 42 includes a slot resonator that serves as the second unit resonator 42X. The unit resonator 40X includes one first unit resonator 41X and four second divisional resonators 42Y. The unit structure 10X includes the unit resonator 40X, part of the base 20 that overlaps the unit resonator 40X in the z-direction, and part of the fourth conductor 50.

Figure 10:
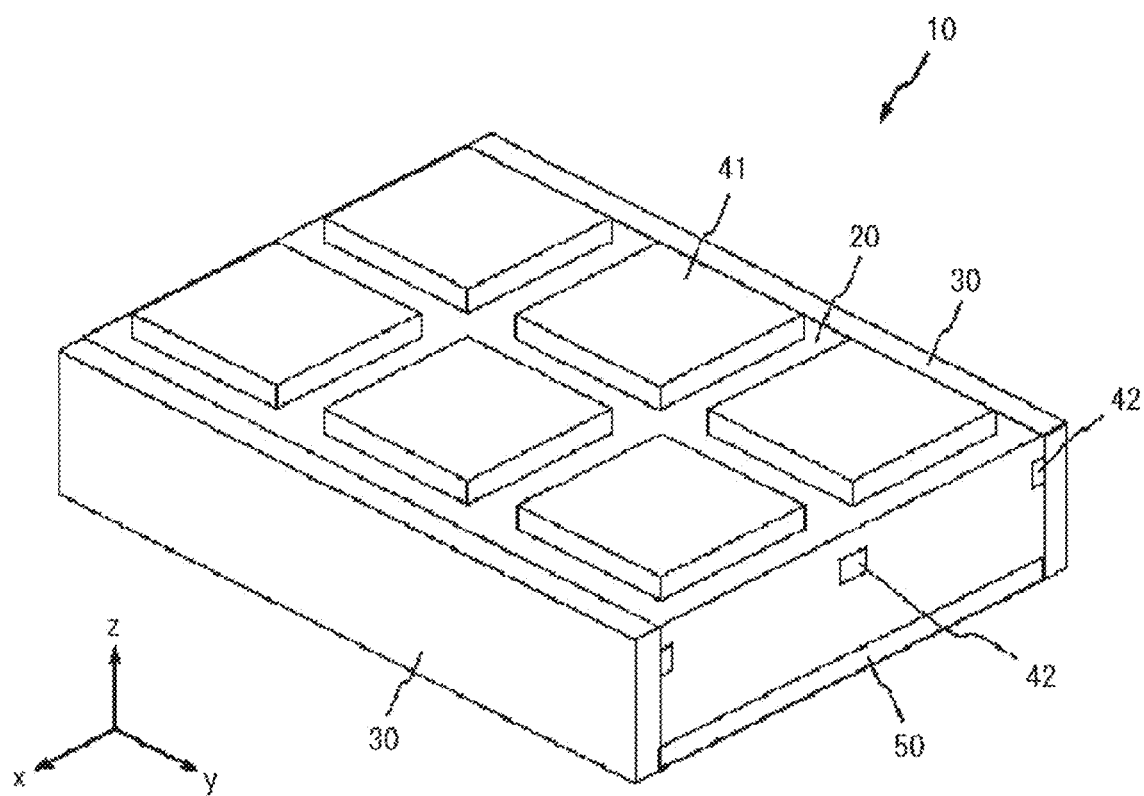
FIG. 10 is a perspective view illustrating an embodiment of the resonator.
Figure 11:
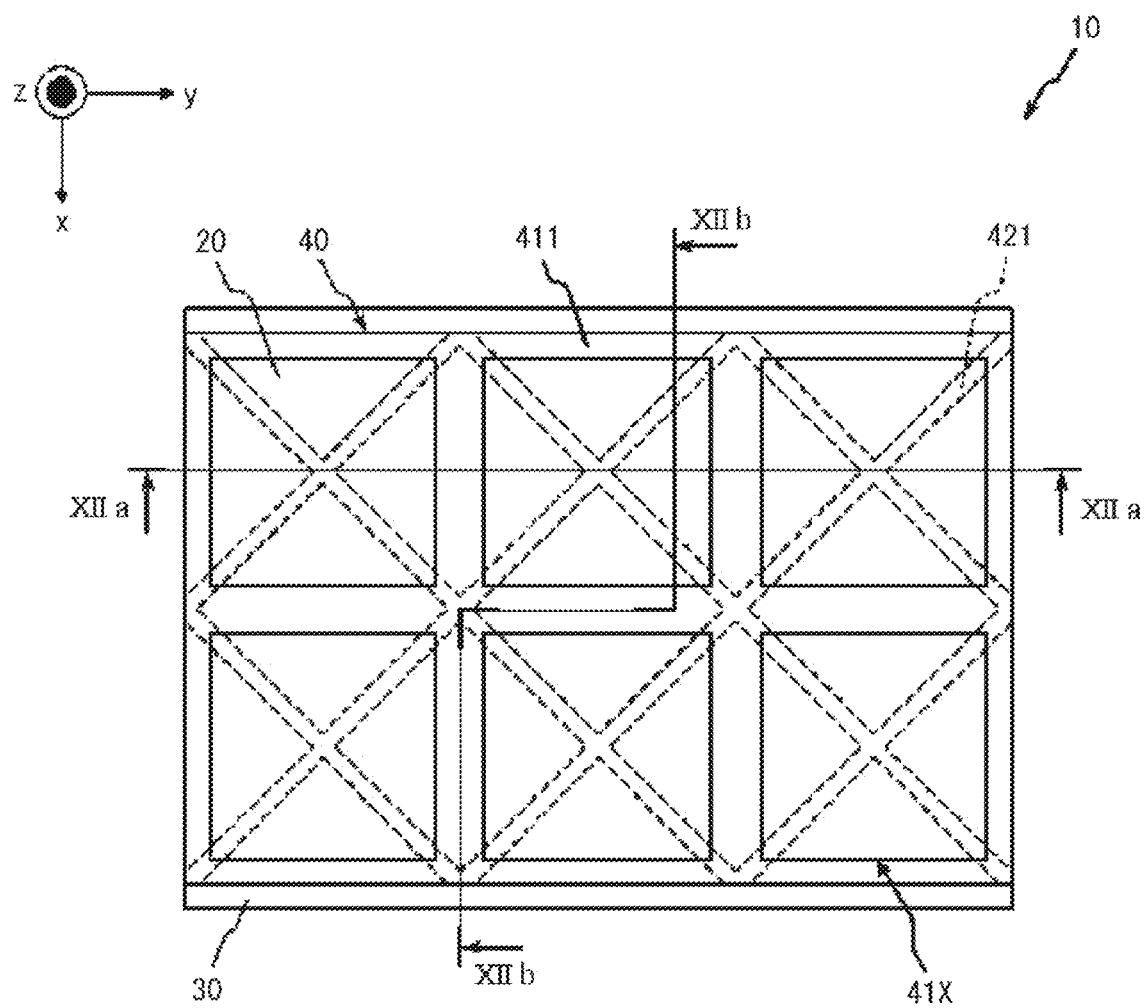
FIG. 11 is a plan view of the resonator illustrated in FIG. 10.
Figure 12A:
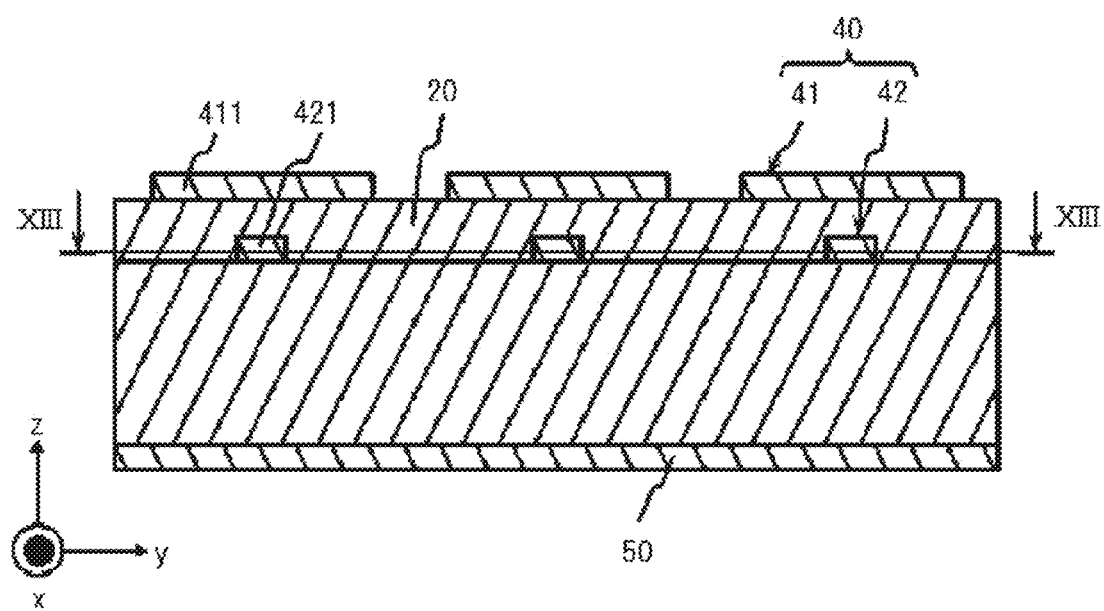
FIG. 12A is a sectional view of an example of the resonator illustrated in FIG. 10.
Figure 12B:
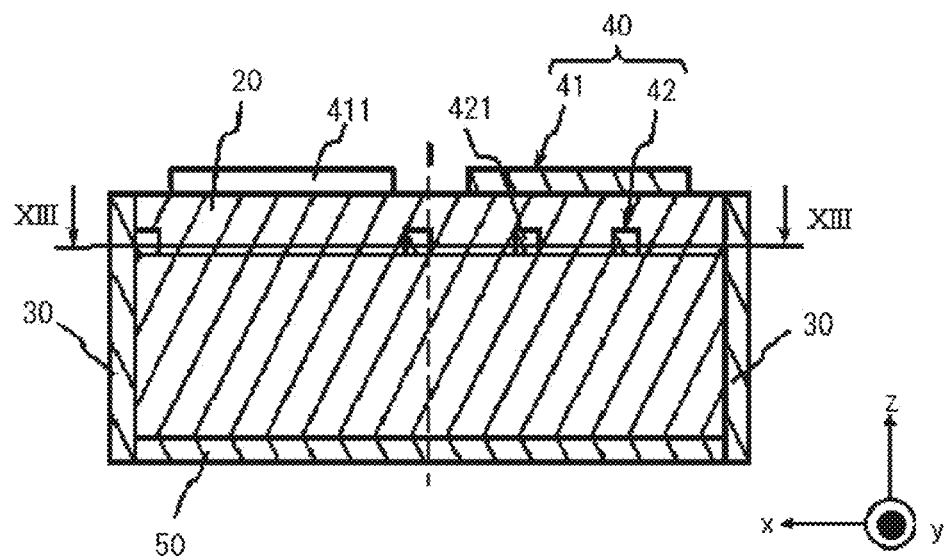
FIG. 12B is a sectional view of another example of the resonator illustrated in FIG. 10.
Figure 13:
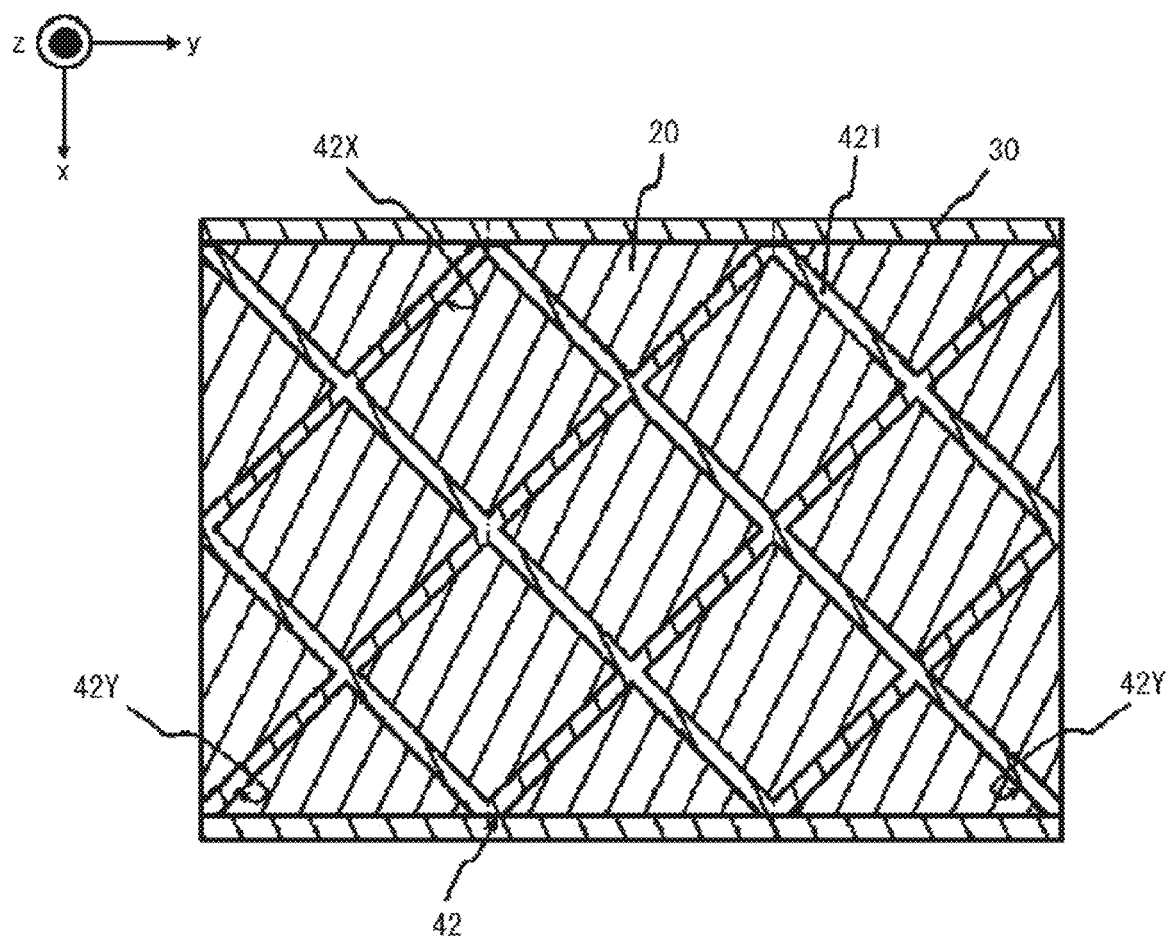
FIG. 13 is a sectional view of the resonator illustrated in FIG. 10.

FIGS. 10 to 13 are diagrams illustrating a resonator 10, which is an example of the plurality of embodiments. FIG. 10 is a schematic diagram of the resonator 10. FIG. 11 is a plan view of the xy plane, as viewed in the z-direction. FIG. 12A is a cross-sectional view taken along line XIIa-XIIa illustrated in FIG. 11. FIG. 12B is a cross-sectional view taken along line XIIb-XIIb illustrated in FIG. 11. FIG. 13 is a cross-sectional view taken along line XIII-XIII illustrated in FIG. 12.

In the resonator 10 illustrated in FIGS. 10 to 13, the first conductive layer 41 includes a patch resonator that serves as the first unit resonator 41X. The second conductive layer 42 includes a slot resonator that serves as the second unit resonator 42X. The unit resonator 40X includes one first unit resonator 41X and four second divisional resonators 42Y.

The unit structure 10X includes the unit resonator 40X, part of the base 20 that overlaps the unit resonator 40X in the z-direction, and part of the fourth conductor 50.

Figure 14:
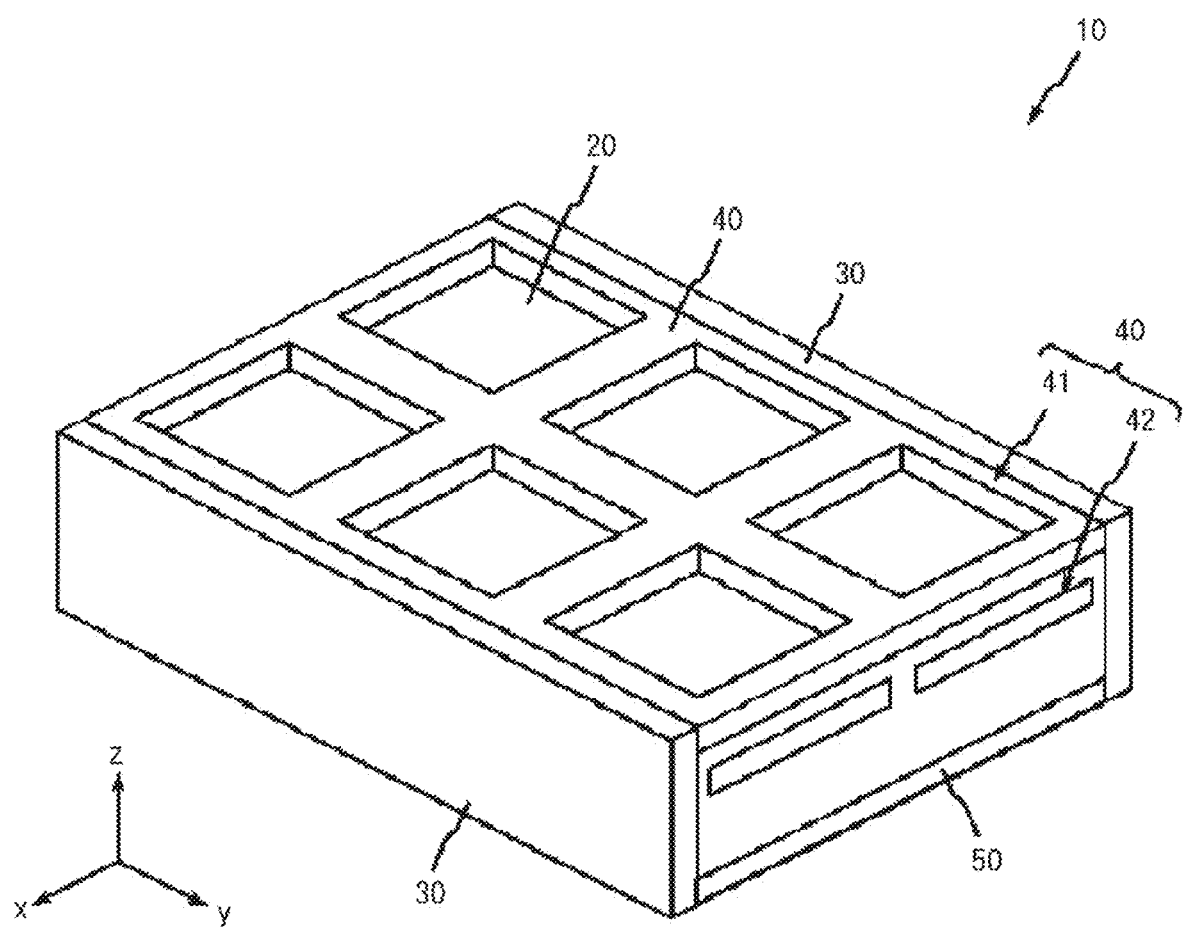
FIG. 14 is a perspective view illustrating an embodiment of the resonator.
Figure 15:
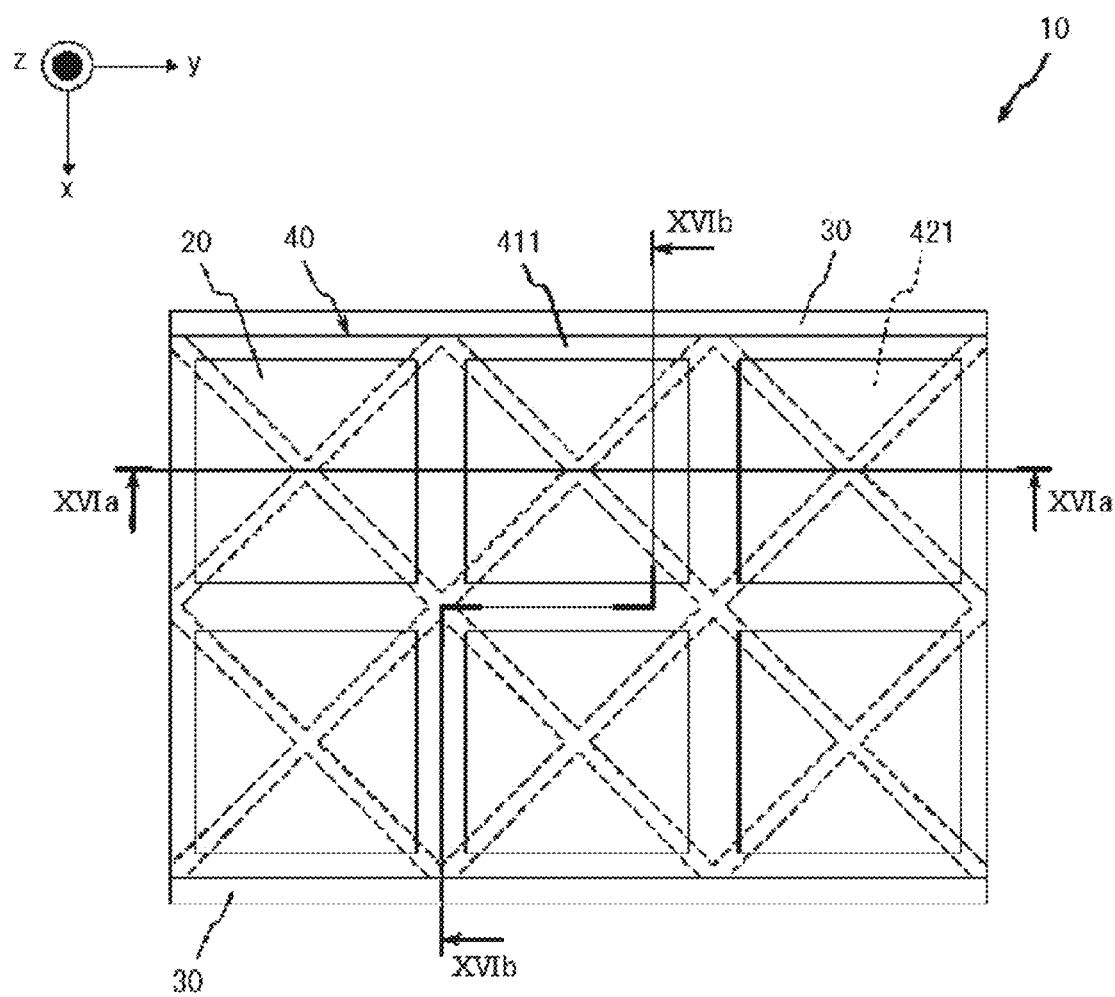
FIG. 15 is a plan view of the resonator illustrated in FIG. 14.
Figure 16A:
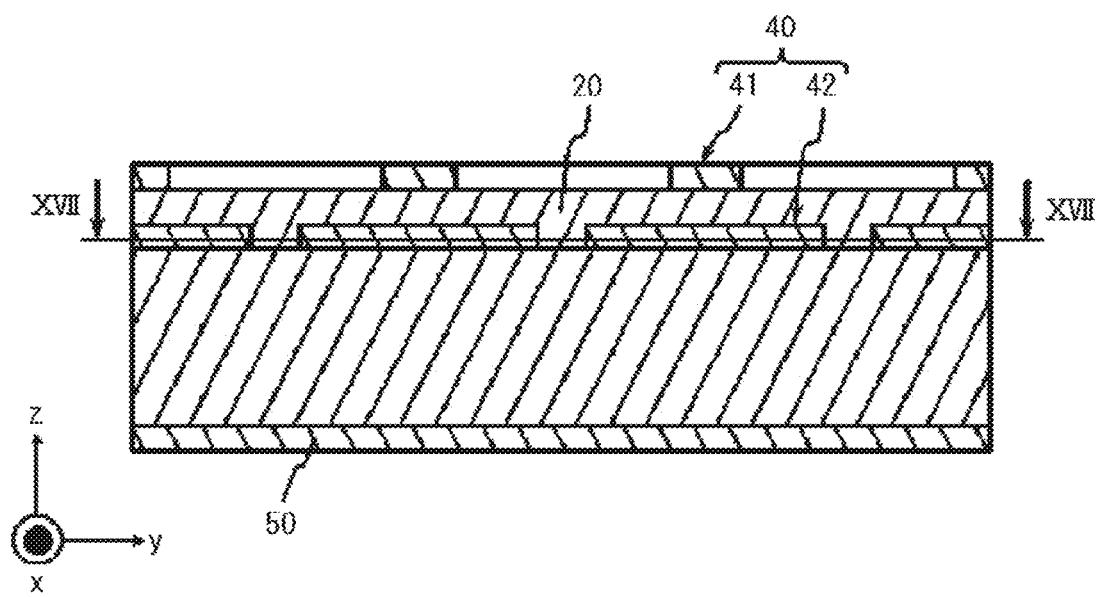
FIG. 16A is a sectional view of an example of the resonator illustrated in FIG. 14.
Figure 16B:
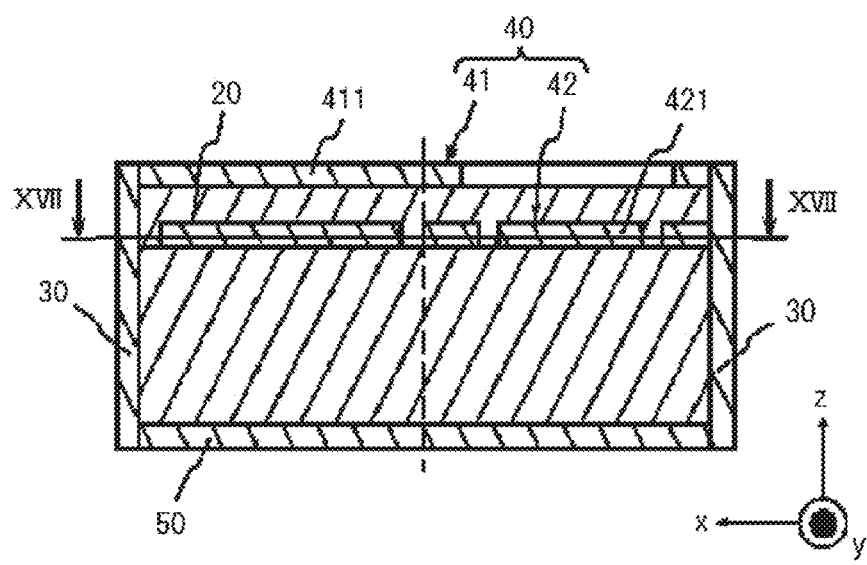
FIG. 16B is a sectional view of another example of the resonator illustrated in FIG. 14.
Figure 17:
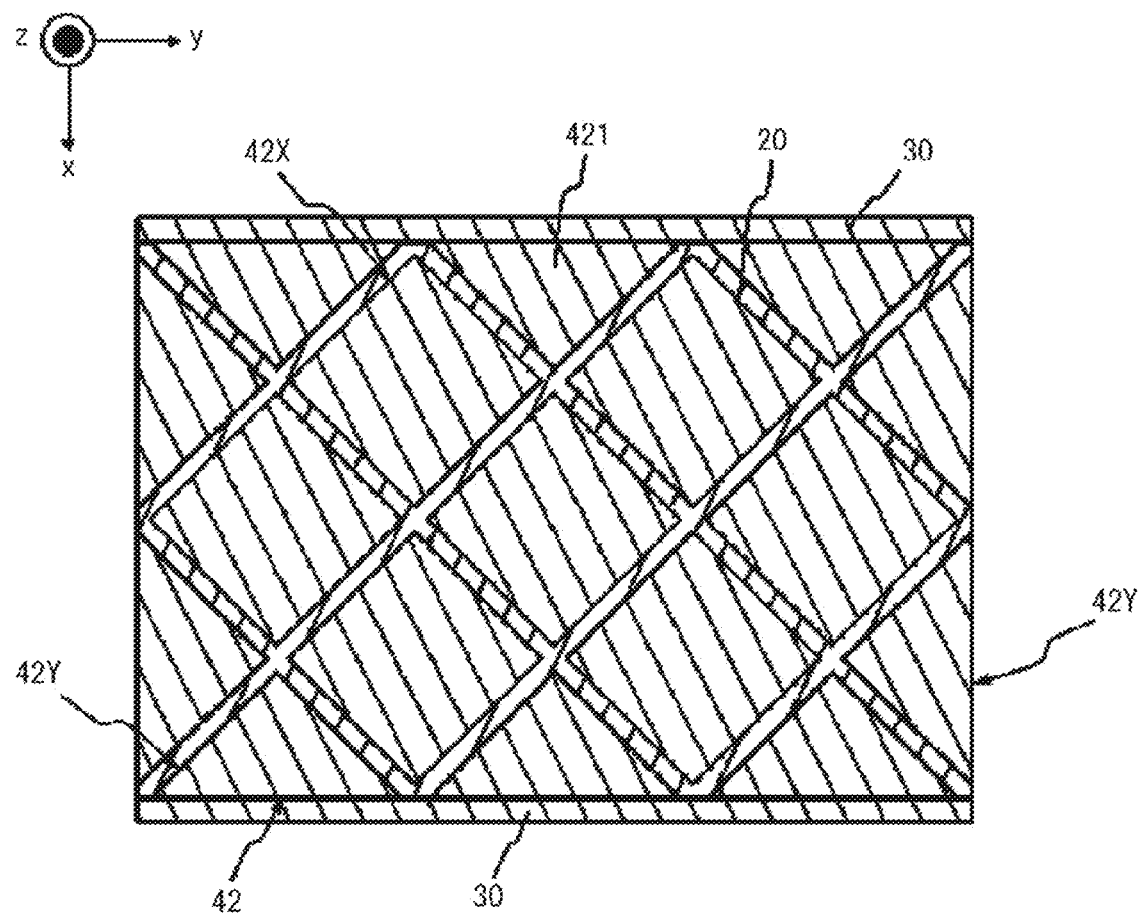
FIG. 17 is a sectional view of the resonator illustrated in FIG. 14.

FIGS. 14 to 17 are diagrams illustrating a resonator 10, which is an example of the plurality of embodiments. FIG. 14 is a schematic diagram of the resonator 10. FIG. 15 is a plan view of the xy plane, as viewed in the z-direction. FIG. 16A is a cross-sectional view taken along line XVIa-XVIa illustrated in FIG. 15. FIG. 16B is a cross-sectional view taken along line XVIb-XVIb illustrated in FIG. 15. FIG. 17 is a cross-sectional view taken along line XVII-XVII illustrated in FIG. 16.

In the resonator 10 illustrated in FIGS. 14 to 17, the first conductive layer 41 includes a slot resonator that serves as the first unit resonator 41X. The second conductive layer 42 includes a patch resonator that serves as the second unit resonator 42X. The unit resonator 40X includes one first unit resonator 41X and four second divisional resonators 42Y. The unit structure 10X includes the unit resonator 40X, part of the base 20 that overlaps the unit resonator 40X in the z-direction, and part of the fourth conductor 50.

Figure 18:
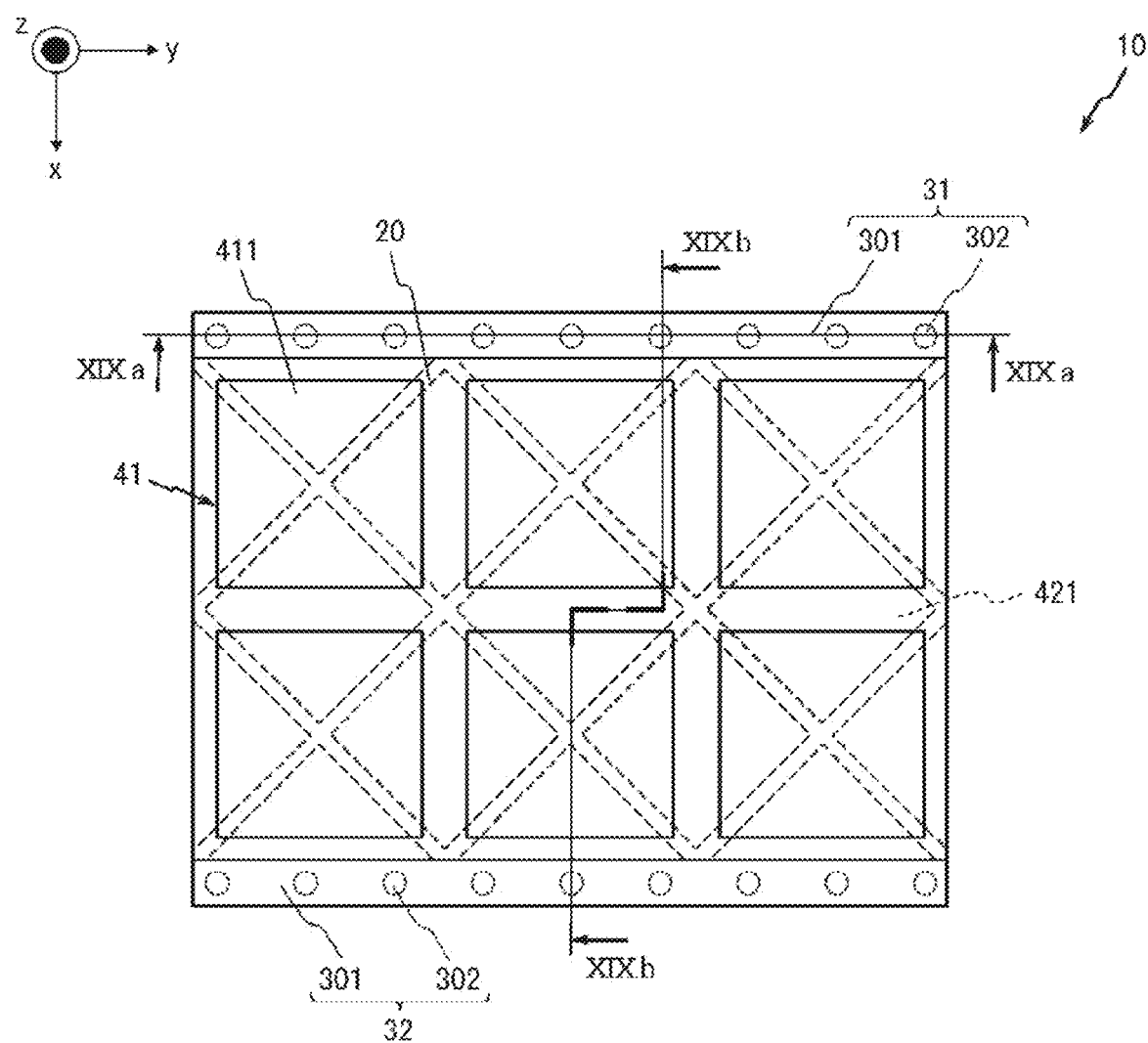
FIG. 18 is a plan view illustrating an embodiment of the resonator.
Figure 19A:
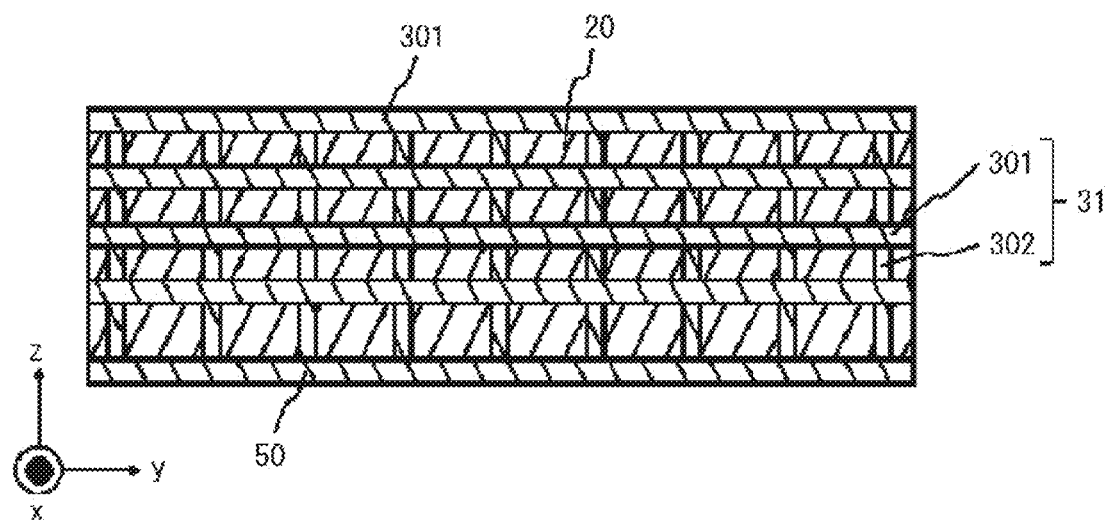
FIG. 19A is a sectional view of an example of the resonator illustrated in FIG. 18.
Figure 19B:
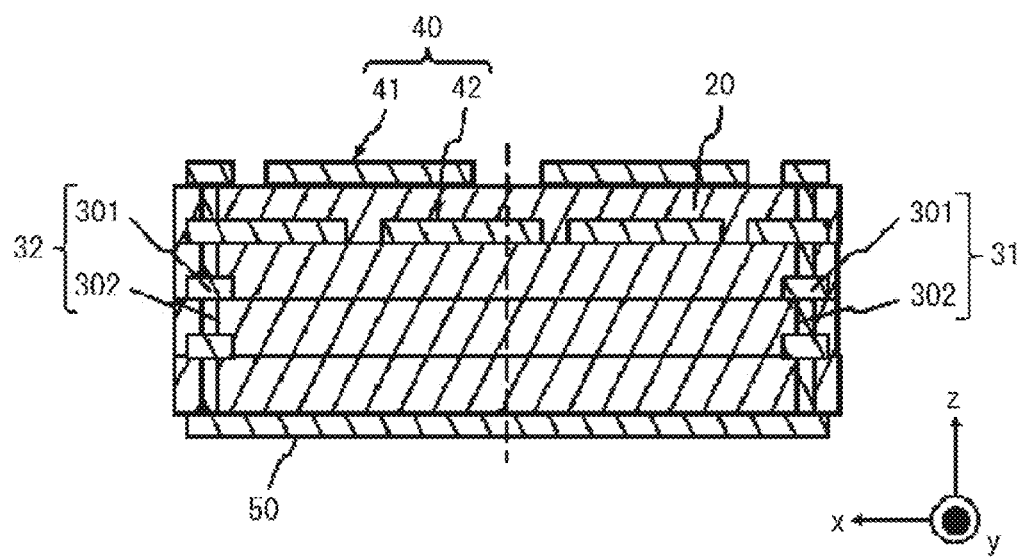
FIG. 19B is a sectional view of another example of the resonator illustrated in FIG. 18.

FIGS. 1 to 17 are diagrams each illustrating the resonator 10 as an example. The configuration of the resonator 10 is not limited to the structures illustrated in FIGS. 1 to 17. FIG. 18 is a diagram illustrating the resonator 10 including the pair conductors 30 having another configuration. FIG. 19A is a cross-sectional view taken along line XIXa-XIXa illustrated in FIG. 18. FIG. 19B is a cross-sectional view taken along line XIXb-XIXb illustrated in FIG. 18.

Figure 20:
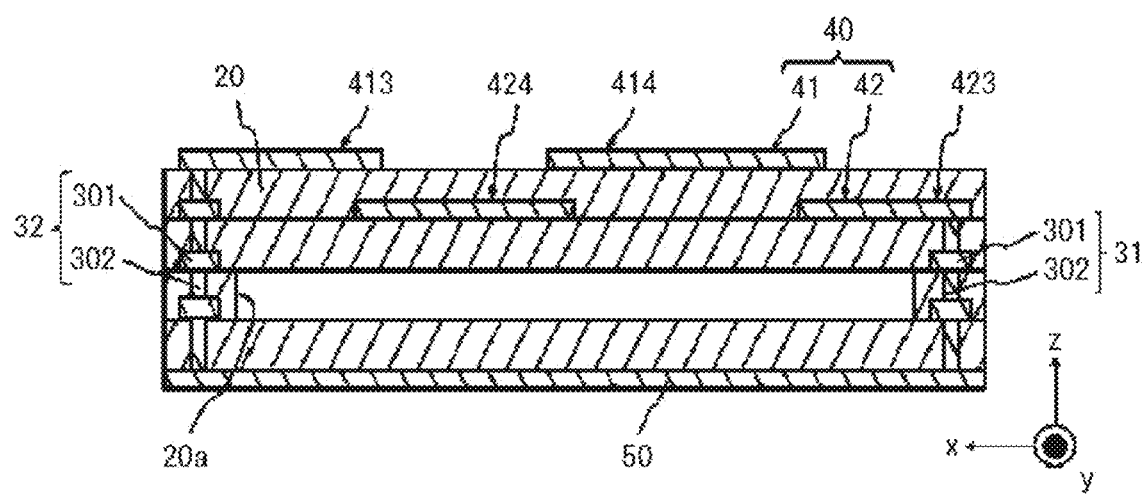
FIG. 20 is a sectional view illustrating an embodiment of the resonator.

FIGS. 1 to 19 are diagrams each illustrating the base 20 as an example. The configuration of the base 20 is not limited to the configurations illustrated in FIGS. 1 to 19. The base 20 can internally include a cavity 20a, as illustrated in FIG. 20. The cavity 20a is located between the third conductor 40 and the fourth conductor 50 in the z-direction. A dielectric constant of the cavity 20a is lower than a dielectric constant of the base 20. The base 20 including the cavity 20a can reduce an electromagnetic distance between the third conductor 40 and the fourth conductor 50.

Figure 21:
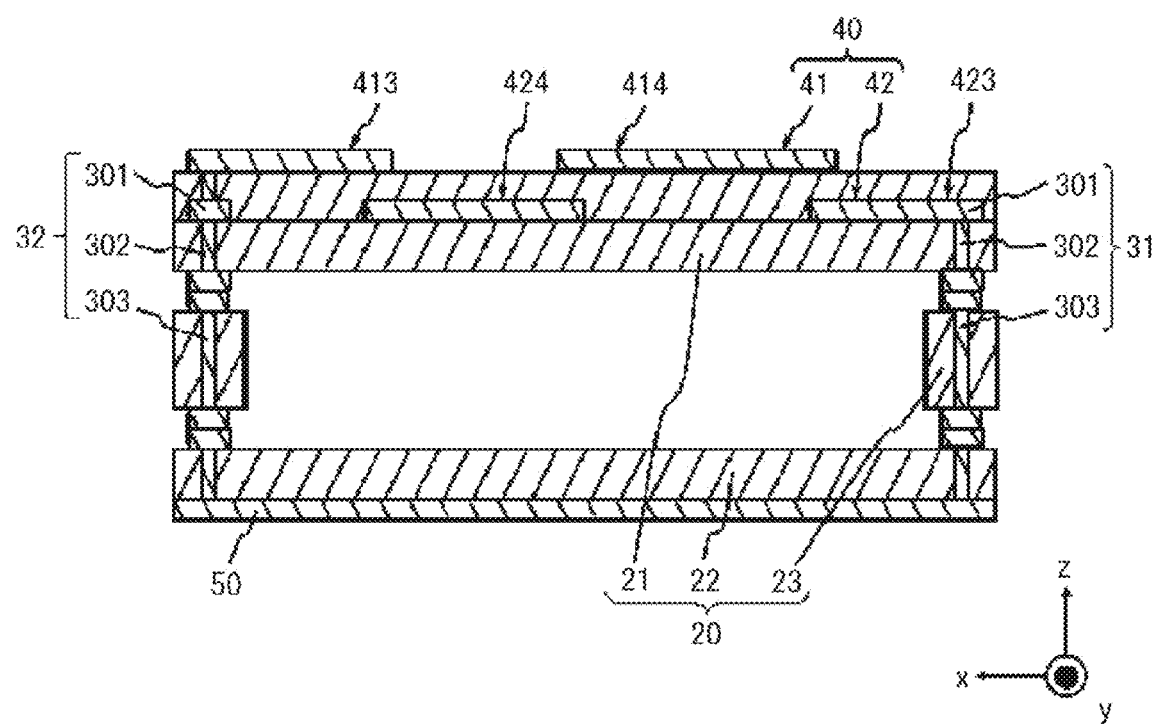
FIG. 21 is a plan view of an embodiment of the resonator.

The base 20 can include a plurality of members, as illustrated in FIG. 21. The base 20 can include a first base 21, a second base 22, and a connector 23. The first base 21 and the second base 22 can be mechanically connected via the connector 23. The connector 23 can internally include a sixth conductor 303. The sixth conductor 303 is electrically connected to a fifth conductive layer 301 or a fifth conductor 302. The sixth conductor 303 is formed as the first conductor 31 or the second conductor 32 together with the fifth conductive layer 301 and the fifth conductor 302.

Figure 22A:
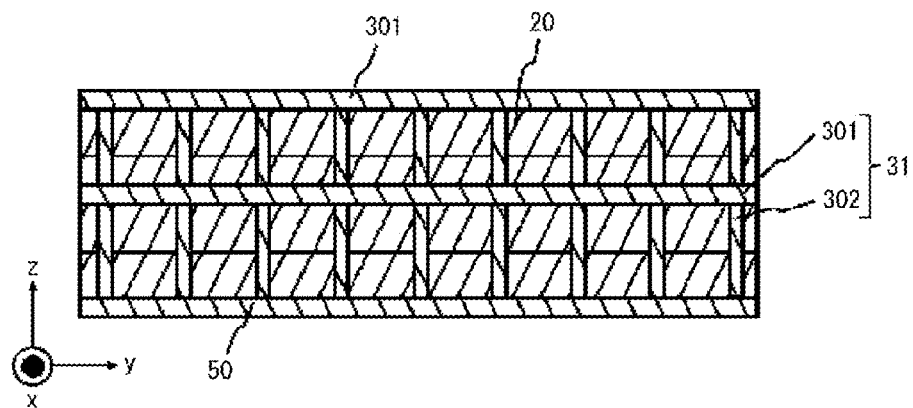
FIG. 22A is a sectional view illustrating an embodiment of the resonator.
Figure 22B:
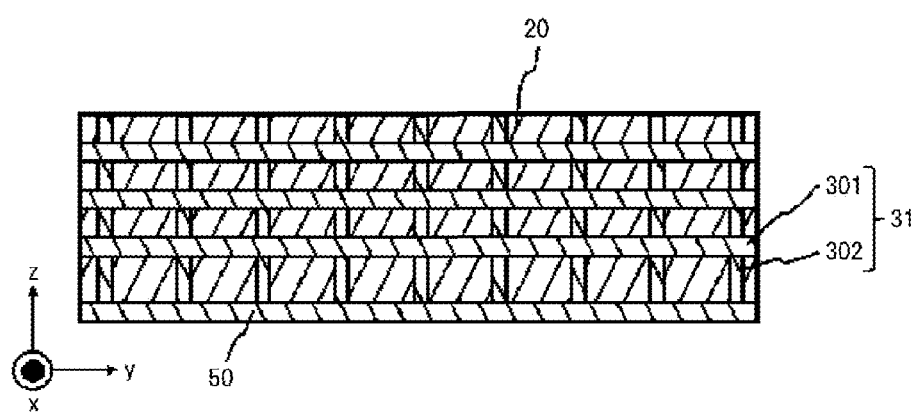
FIG. 22B is a sectional view illustrating an embodiment of the resonator.
Figure 22C:
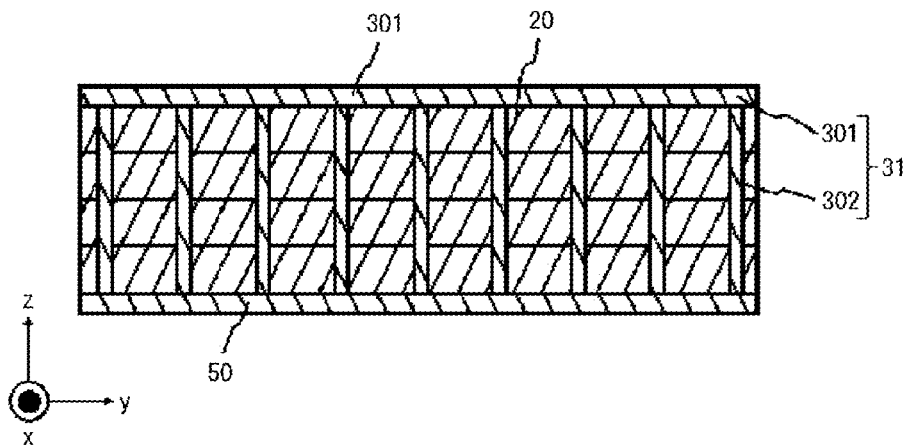
FIG. 22C is a sectional view illustrating an embodiment of the resonator.

FIGS. 1 to 21 are diagrams each illustrating the pair conductors 30 as an example. The configuration of the pair conductors 30 is not limited to the configurations illustrated in FIGS. 1 to 21. FIGS. 22 to 28 are diagrams illustrating resonators 10 which includes other pair conductors 30 having other configurations. FIG. 22 is a cross-sectional view corresponding to FIG. 19A. As illustrated in FIG. 22A, the number of the fifth conductive layers 301 can be changed as appropriate. As illustrated in FIG. 22B, the fifth conductive layer 301 may not be located on the base 20. As illustrated in FIG. 22C, the fifth conductive layer 301 may not be located within the base 20.

Figure 23:
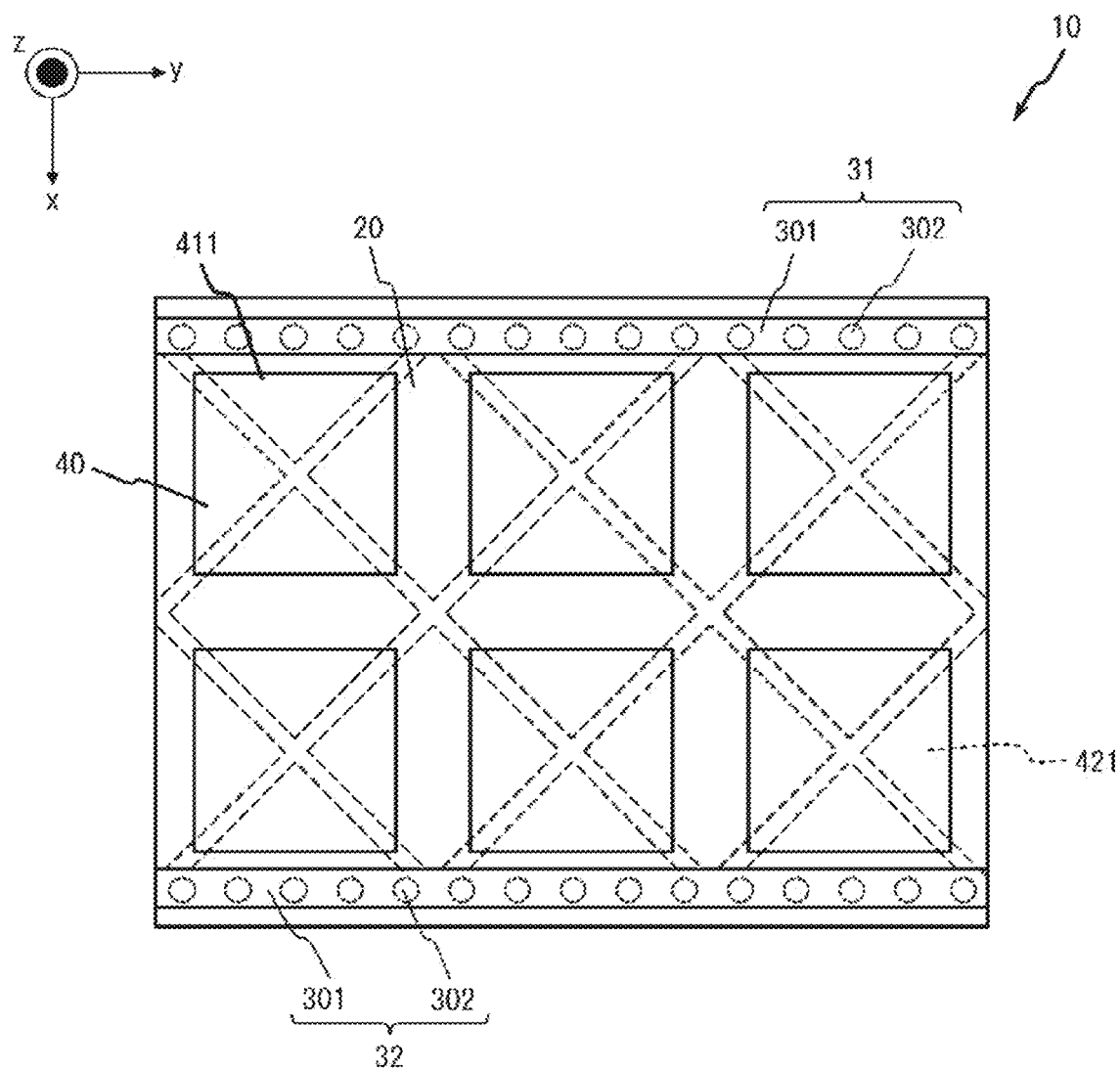
FIG. 23 is a plan view of an embodiment of the resonator.
Figure 24:
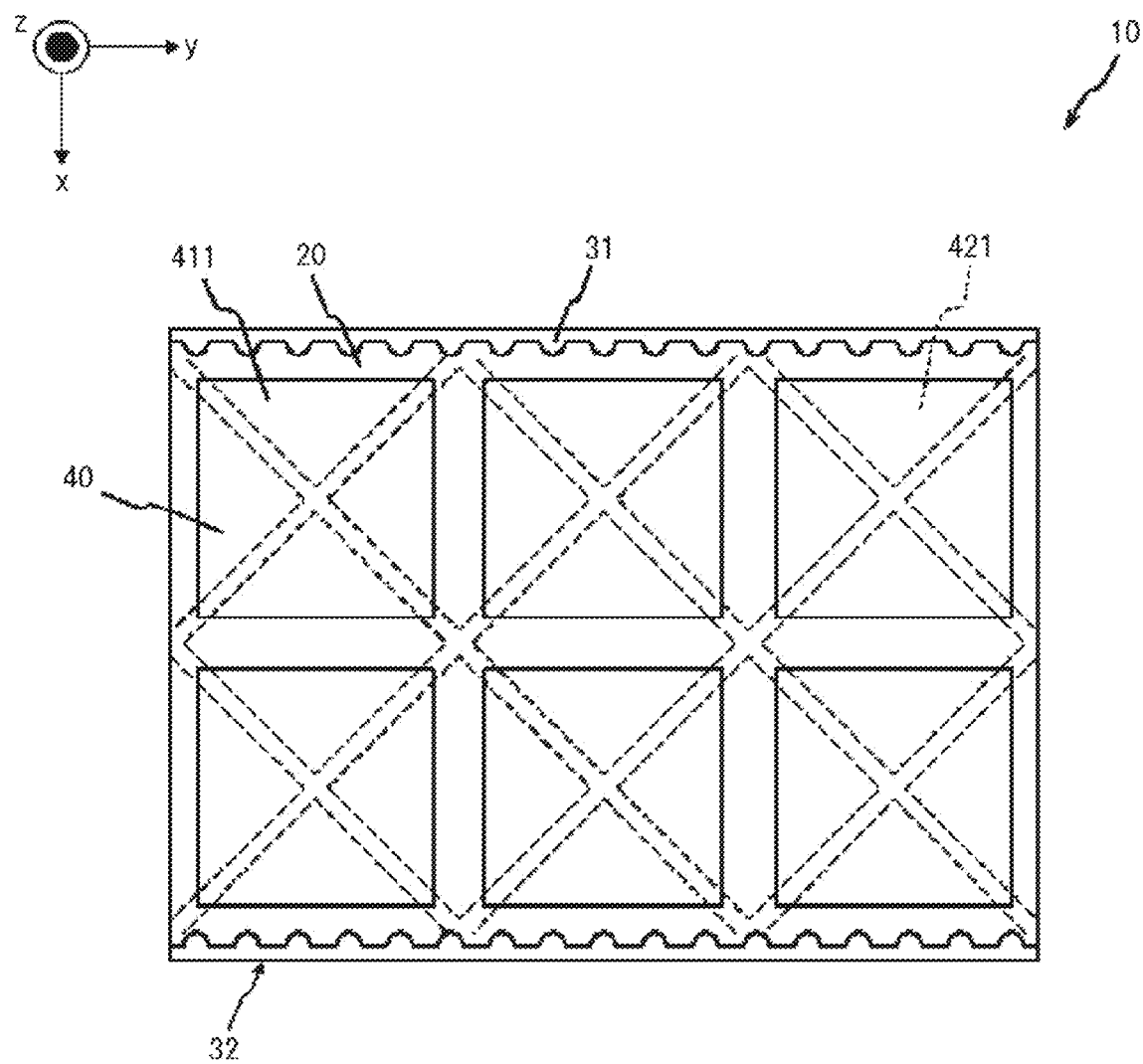
FIG. 24 is a plan view of an embodiment of the resonator.

FIG. 23 is a plan view corresponding to FIG. 18. As illustrated in FIG. 23, in the resonator 10, the fifth conductor 302 can be separated from the boundary of the unit resonator 40X. FIG. 24 is a plan view corresponding to FIG. 18. As illustrated in FIG. 24, two pair conductors 30 each can include protrusions that protrude toward the other of the pair conductors 30. Such a resonator 10 can be formed, for example, by applying metal paste to the base 20 having recesses and curing the metal paste.

Figure 25:
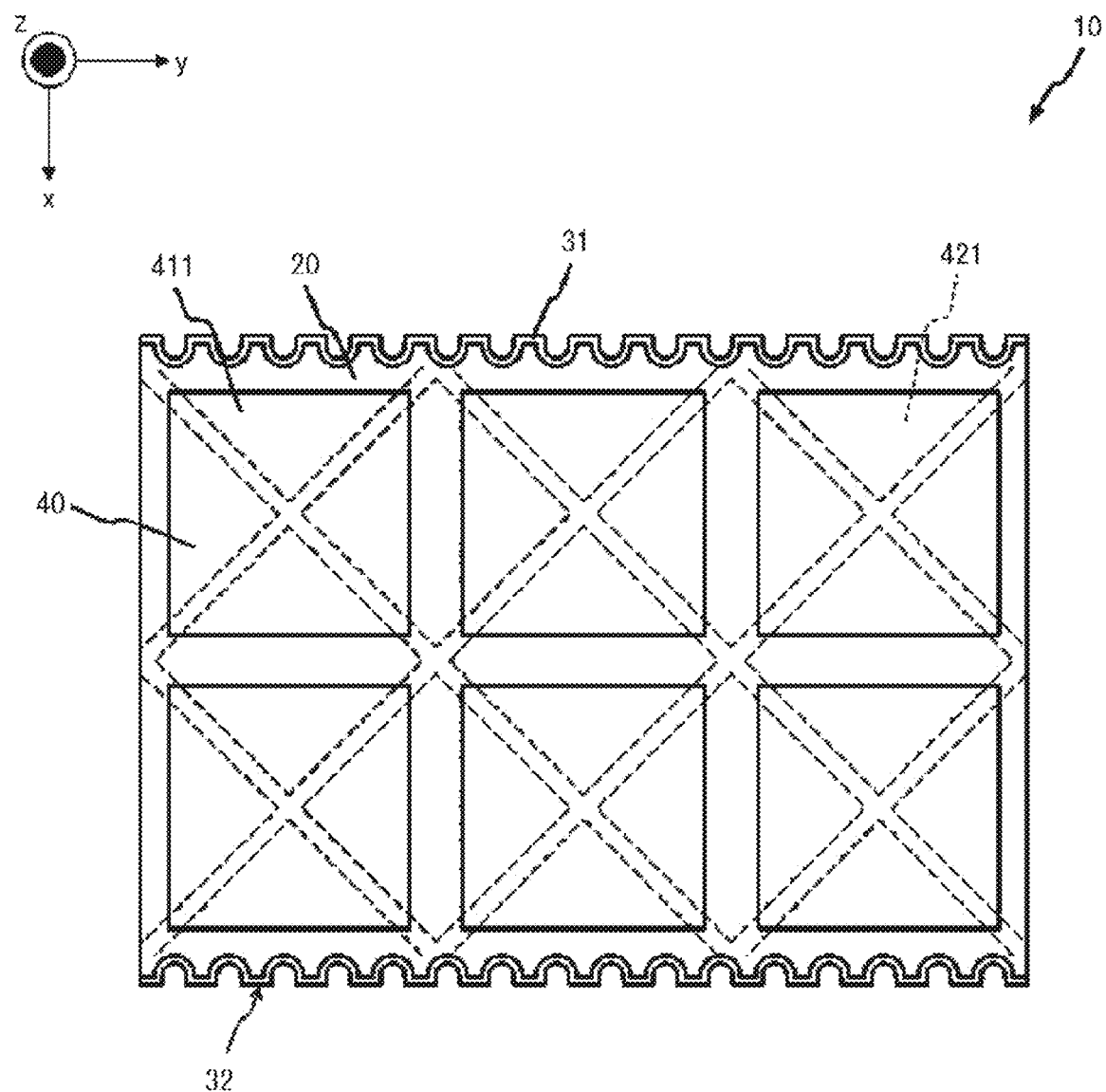
FIG. 25 is a plan view of an embodiment of the resonator.

FIG. 25 is a plan view corresponding to FIG. 18. As illustrated in FIG. 25, the base 20 can have recesses. As illustrated in FIG. 25, the pair conductors 30 each have recesses that are recessed inward in the x-direction from an outer surface. As illustrated in FIG. 25, the pair conductors 30 each extend along a surface of the base 20. Such a resonator 10 can be formed, for example, by spraying a fine metal material onto the base 20 having recesses.

Figure 26:
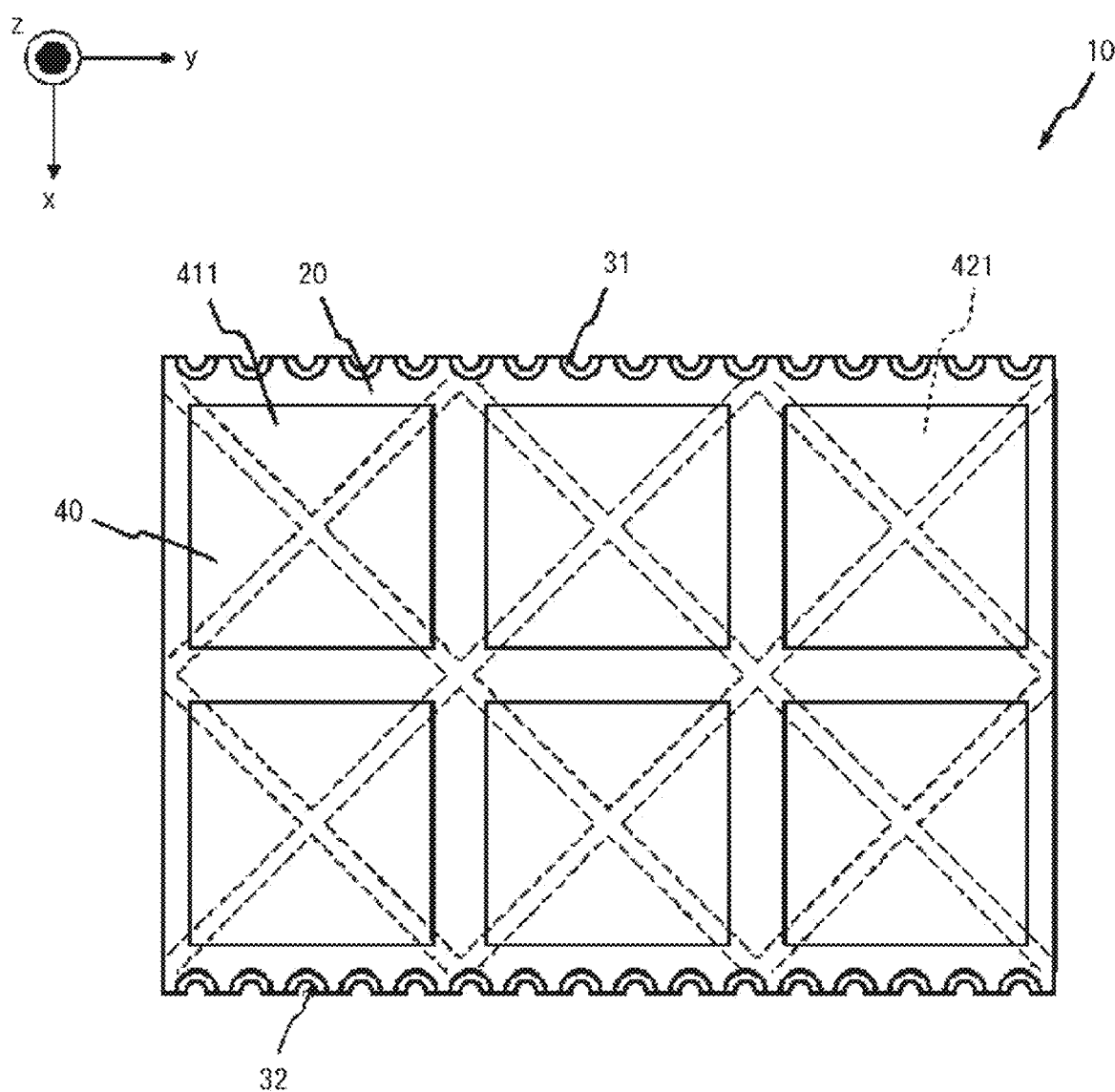
FIG. 26 is a plan view of an embodiment of the resonator.

FIG. 26 is a plan view corresponding to FIG. 18. As illustrated in FIG. 26, the base 20 can have recesses. As illustrated in FIG. 26, the pair conductors 30 each have recesses that are recessed inward in the x-direction from an outer surface. As illustrated in FIG. 26, the pair conductors 30 each extend along the recesses of the base 20. Such a resonator 10 can be manufactured, for example, by dividing a mother substrate along an array of through-hole conductors. Such pair conductors 30 can be referred to as an end surface through-hole or the like.

Figure 27:
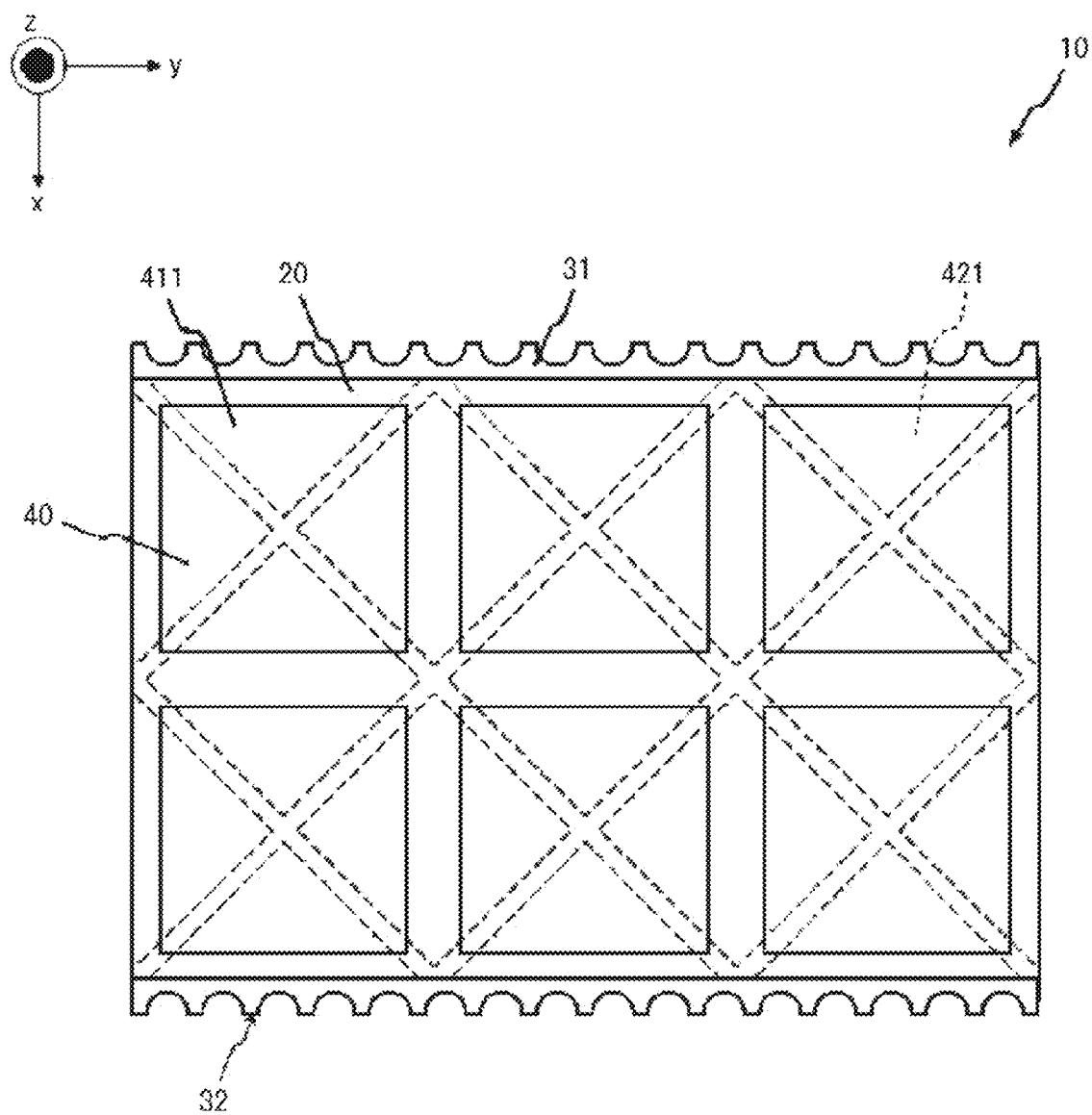
FIG. 27 is a plan view of an embodiment of the resonator.

FIG. 27 is a plan view corresponding to FIG. 18. As illustrated in FIG. 27, the base 20 can have recesses. As illustrated in FIG. 27, the pair conductors 30 each have recesses that are recessed inward in the x-direction from an outer surface. Such a resonator 10 can be manufactured, for example, by dividing a mother substrate along an array of through-hole conductors. Such pair conductors 30 can be referred to as an end surface through-hole or the like.

Figure 28:
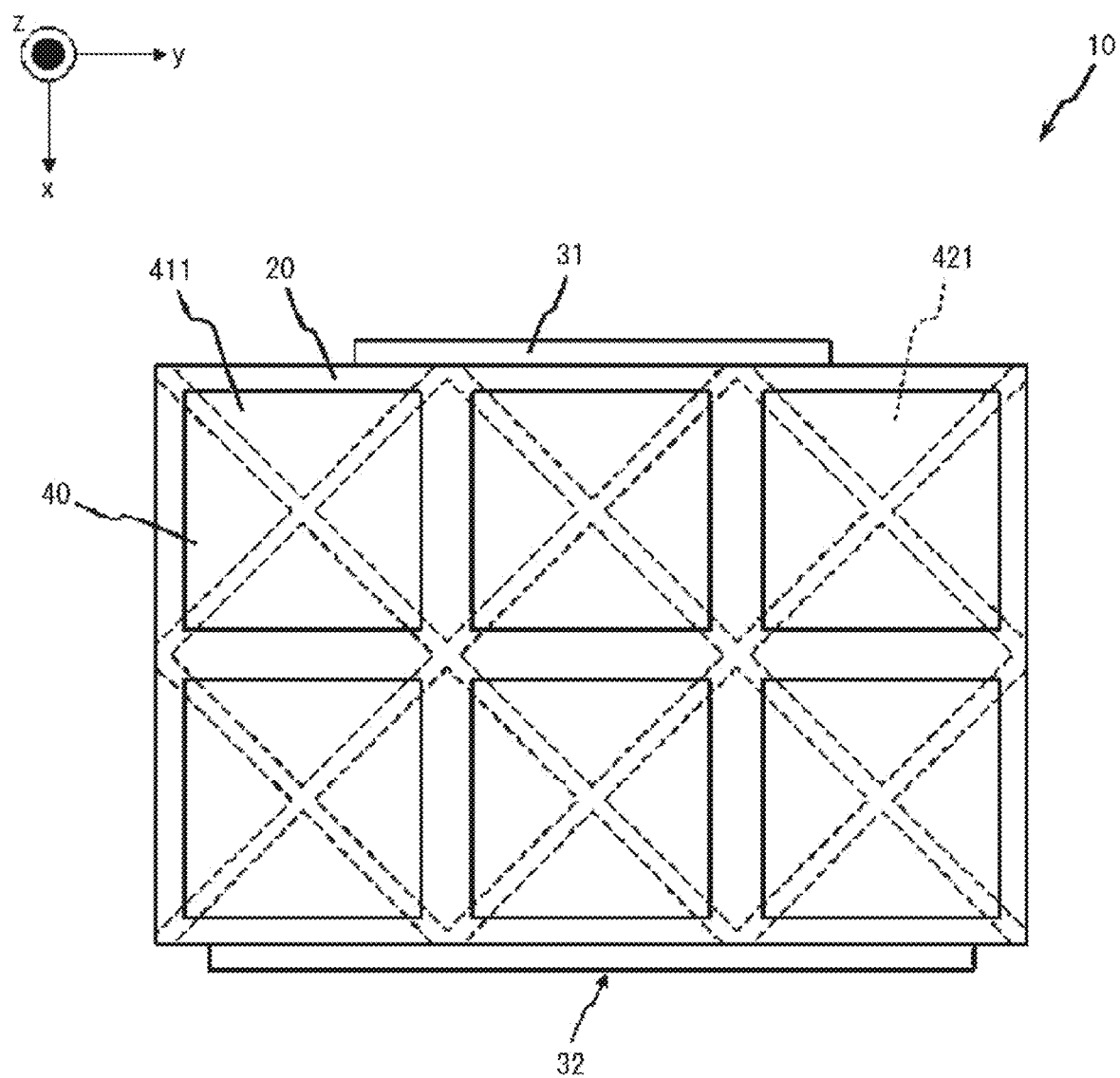
FIG. 28 is a plan view of an embodiment of the resonator.

FIG. 28 is a plan view corresponding to FIG. 18. As illustrated in FIG. 28, pair conductors 30 each may have a smaller length in the x-direction than the base 20. The configuration of the pair conductors 30 is not limited to these configurations. Two pair conductors 30 can have different configurations. For example, one of the pair conductors 30 may include the fifth conductive layer 301 and the fifth conductor 302, and the other of the pair conductors 30 may include an end surface through-hole.

Figure 29A:
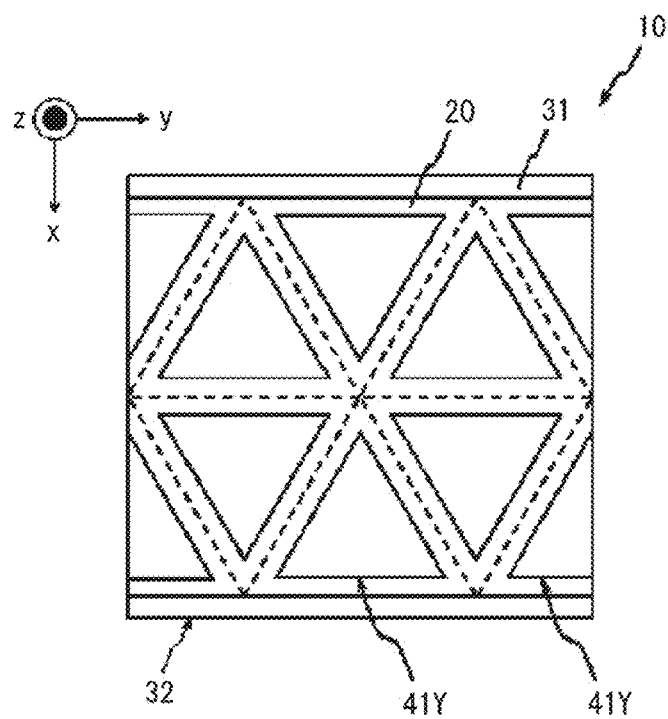
FIG. 29A is a plan view of an embodiment of the resonator.
Figure 29B:
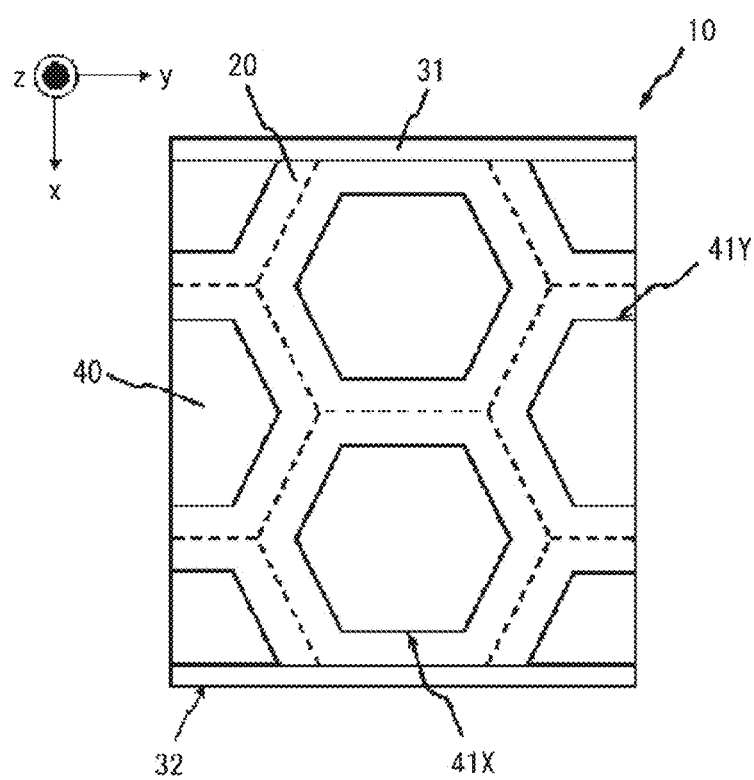
FIG. 29B is a plan view of an embodiment of the resonator.
Figure 30:
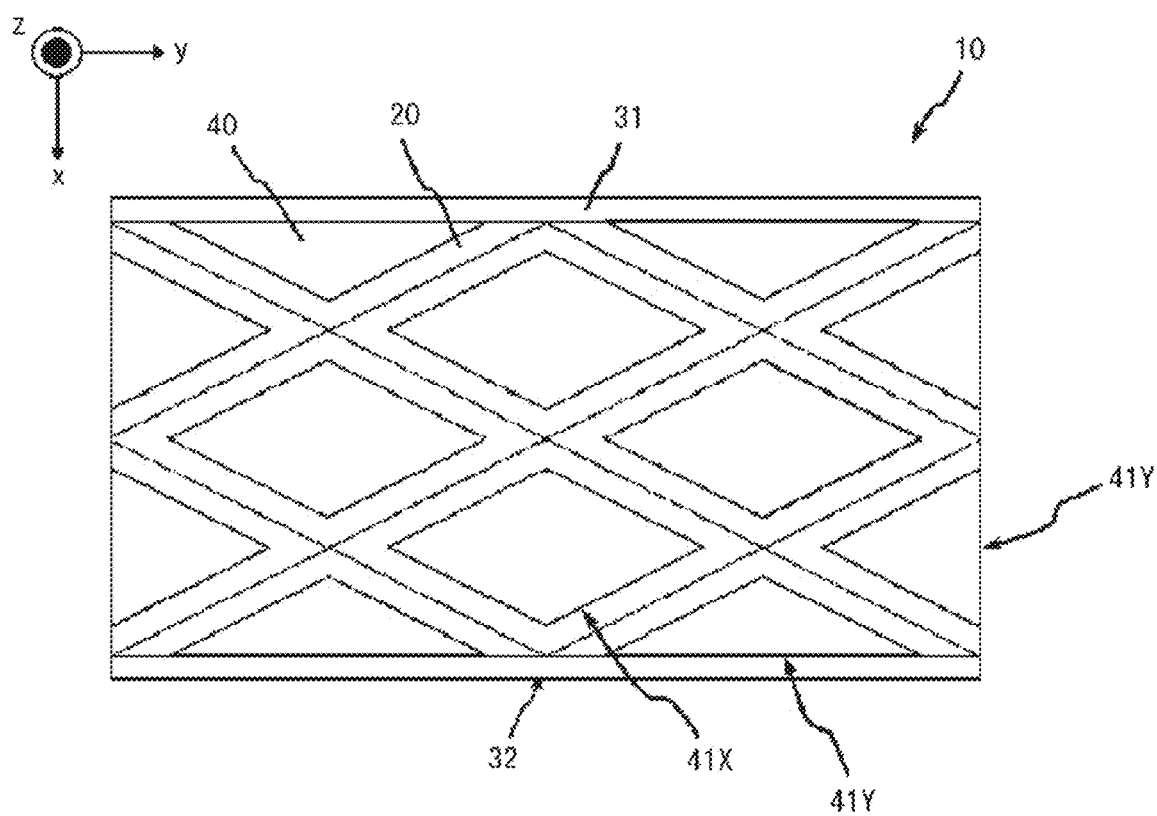
FIG. 30 is a plan view of an embodiment of the resonator.

FIGS. 1 to 28 are diagrams each illustrating the third conductor 40 as an example. The configuration of the third conductor 40 is not limited to the configurations illustrated in FIGS. 1 to 28. The unit resonator 40X, the first unit resonator 41X, and the second unit resonator 42X are not limited to the square shape. The unit resonator 40X, the first unit resonator 41X, and the second unit resonator 42X can be referred to as the unit resonator 40X and the like. For example, the unit resonators 40X and the like may have a triangular shape as illustrated in FIG. 29A and may have a hexagonal shape as illustrated in FIG. 29B. As illustrated in FIG. 30, each side of the unit resonator 40X and the like can extend in a direction different from the x-direction and the y-direction. In the third conductor 40, the second conductive layer 42 can be located on the base 20 and the first conductive layer 41 can be located within the base 20. In the third conductor 40, the second conductive layer 42 can be located farther from the fourth conductor 50 than the first conductive layer 41.

Figure 31A:
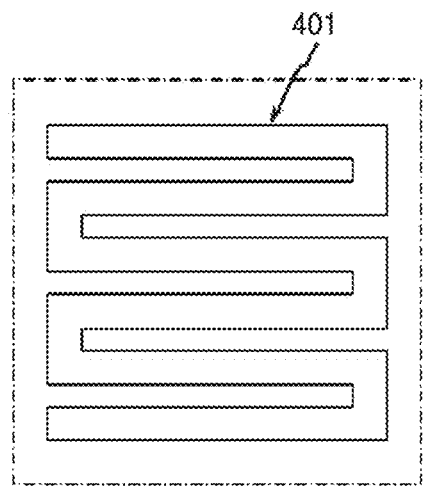
FIG. 31A is a schematic view illustrating an example of the resonator.
Figure 31B:
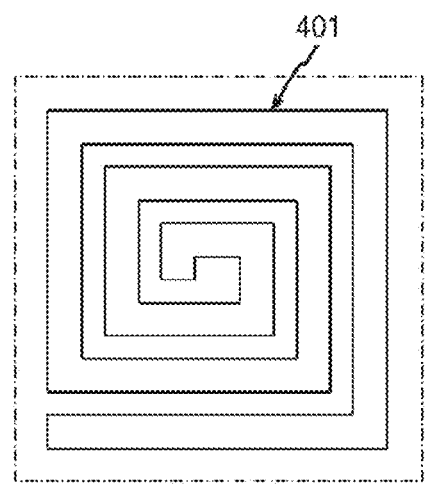
FIG. 31B is a schematic view illustrating an example of the resonator.
Figure 31C:
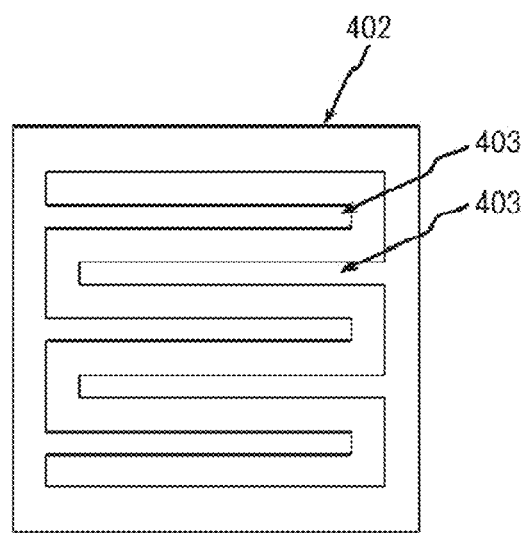
FIG. 31C is a schematic view illustrating an example of the resonator.
Figure 31D:
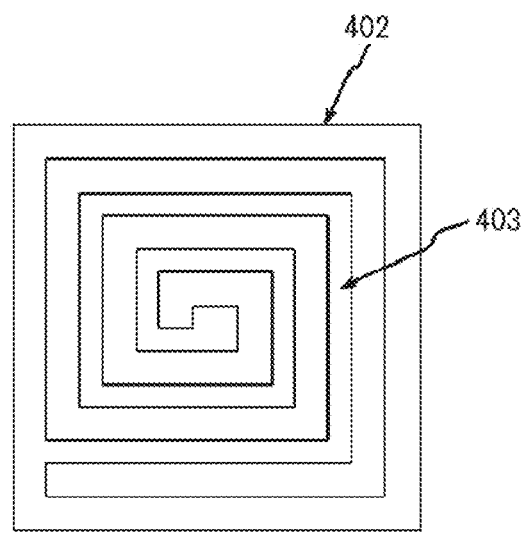
FIG. 31D is a schematic view illustrating an example of the resonator.
Figure 32A:
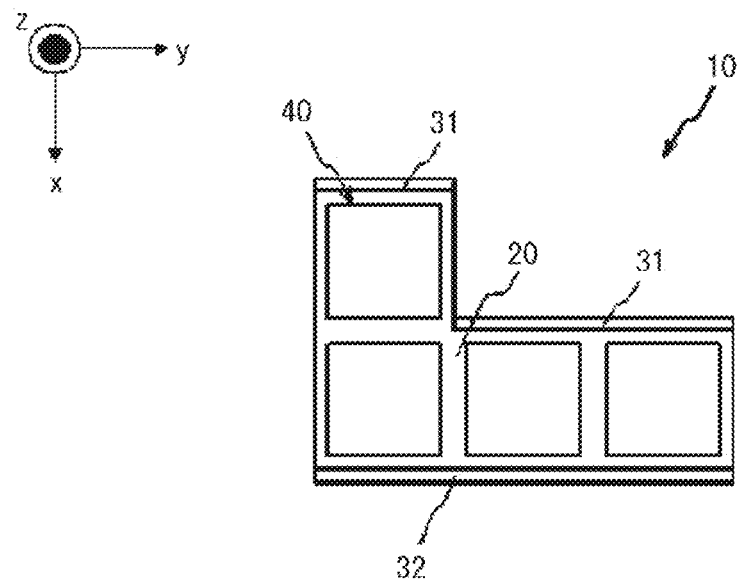
FIG. 32A is a plan view of an embodiment of the resonator.
Figure 32B:
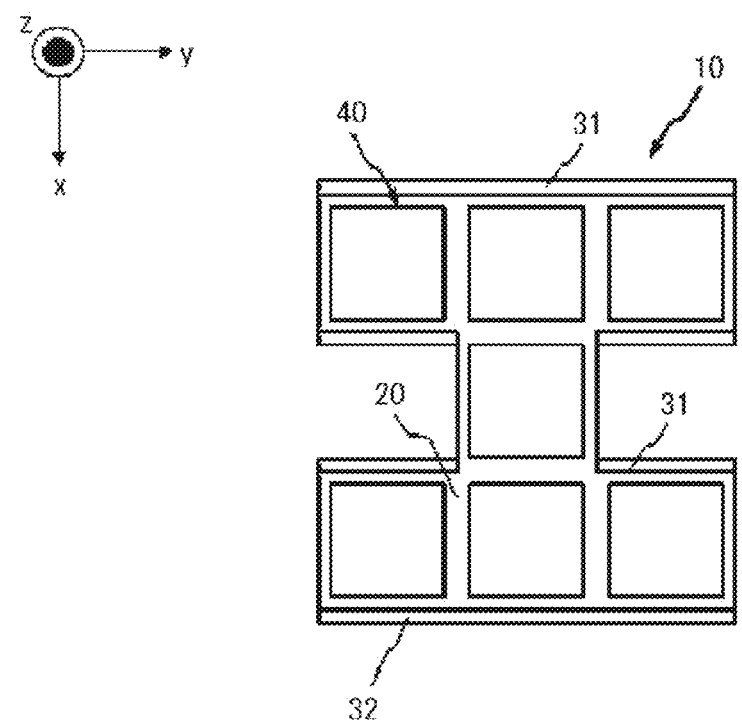
FIG. 32B is a plan view of an embodiment of the resonator.
Figure 32C:
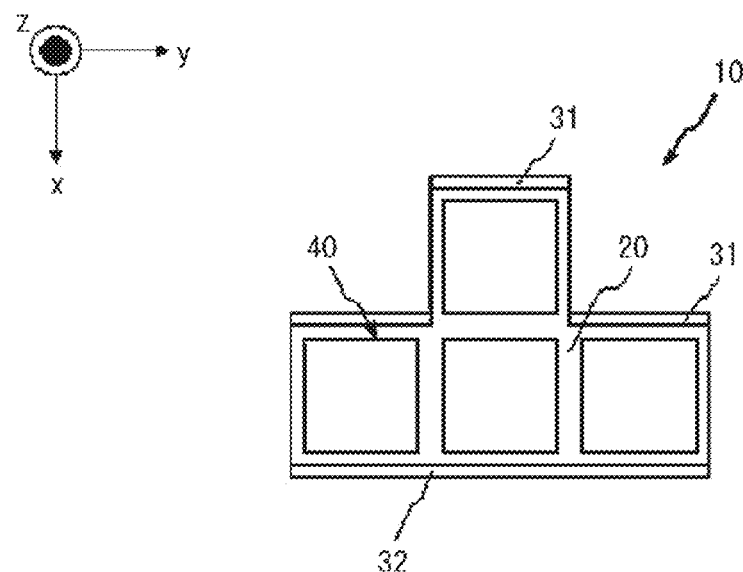
FIG. 32C is a plan view of an embodiment of the resonator.
Figure 32D:
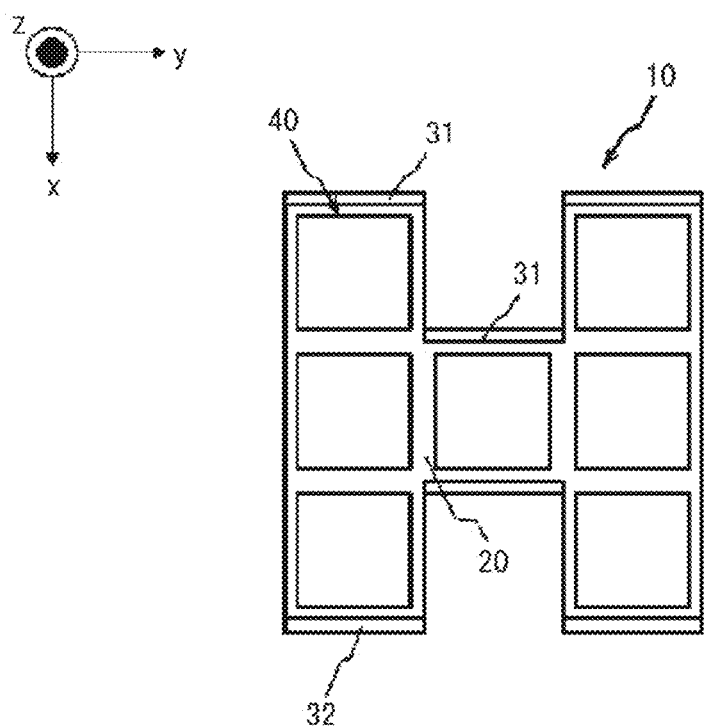
FIG. 32D is a plan view of an embodiment of the resonator.
Figure 33A:
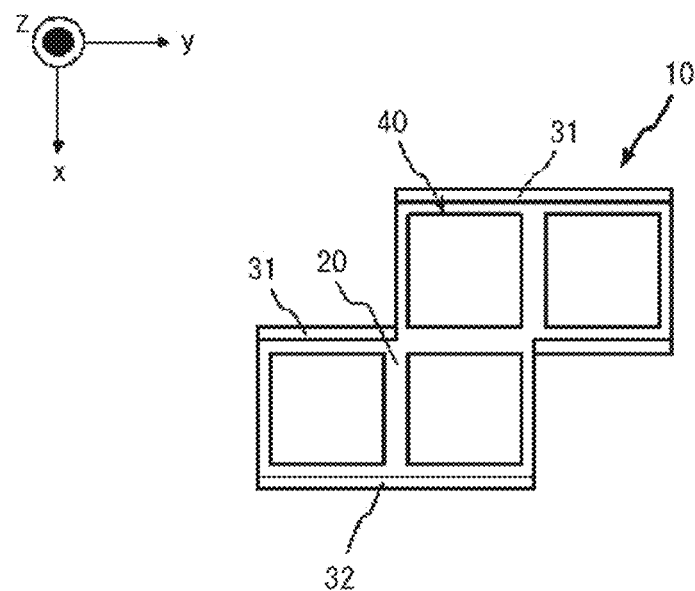
FIG. 33A is a plan view of an embodiment of the resonator.
Figure 33B:
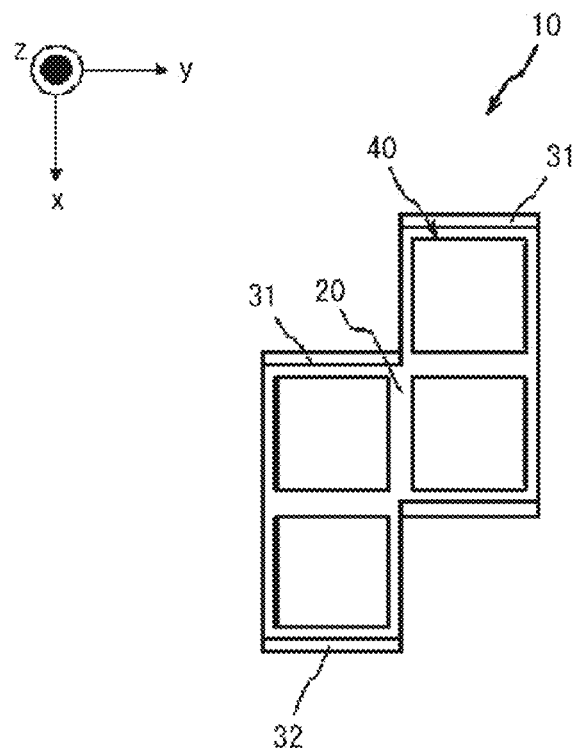
FIG. 33B is a plan view of an embodiment of the resonator.
Figure 33C:
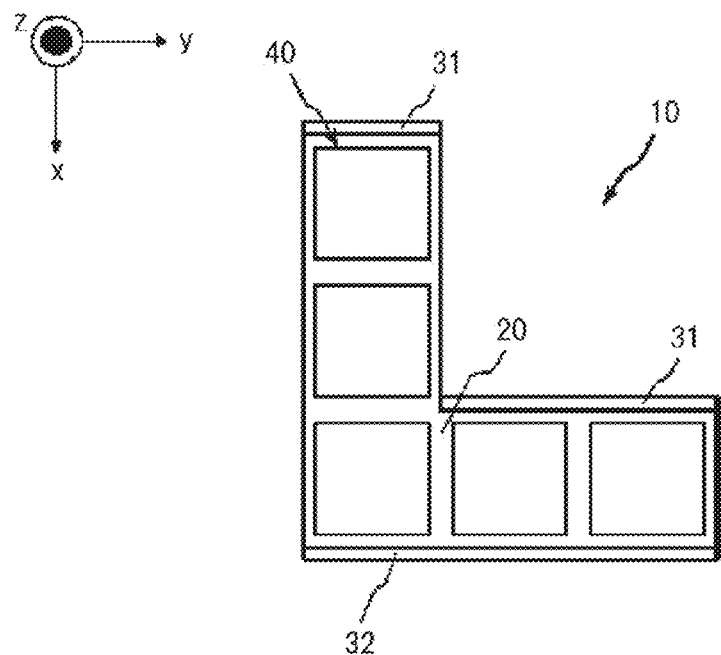
FIG. 33C is a plan view of an embodiment of the resonator.
Figure 33D:
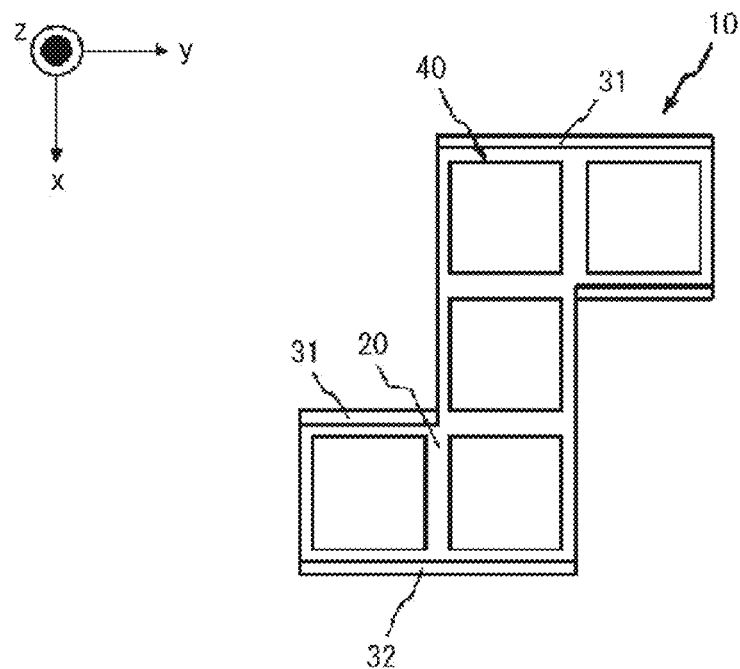
FIG. 33D is a plan view of an embodiment of the resonator.
Figure 34A:
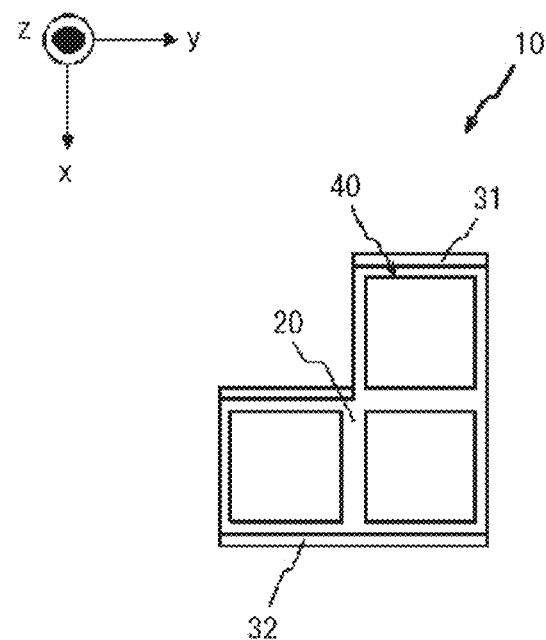
FIG. 34A is a plan view of an embodiment of the resonator.
Figure 34B:
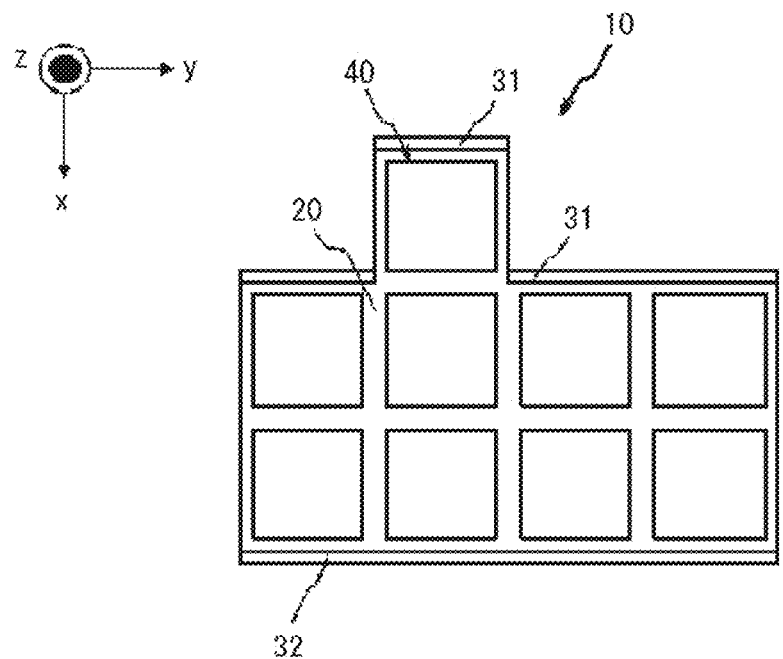
FIG. 34B is a plan view of an embodiment of the resonator.
Figure 34C:
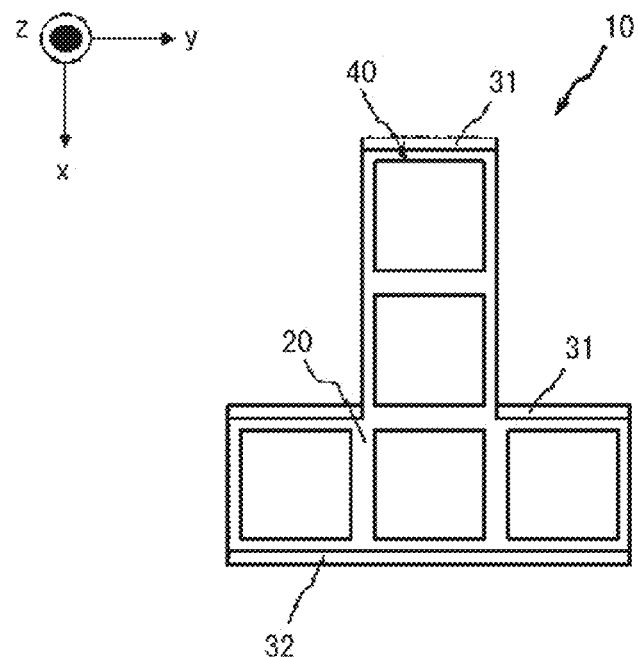
FIG. 34C is a plan view of an embodiment of the resonator.
Figure 34D:
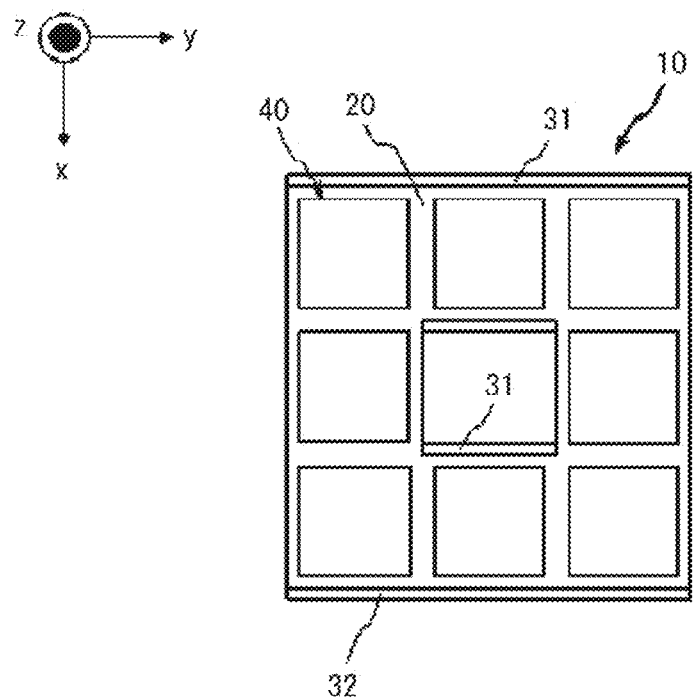
FIG. 34D is a plan view of an embodiment of the resonator.

FIGS. 1 to 30 are diagrams each illustrating the third conductor 40 as an example. The configuration of the third conductor 40 is not limited to the configurations illustrated in FIGS. 1 to 30. The resonator including the third conductor 40 may be a linear resonator 401. FIG. 31A illustrates a meander-line resonator 401. FIG. 31B illustrates a spiral resonator 401. The resonator including the third conductor 40 may be a slot resonator 402. The slot resonator 402 can have one or a plurality of seventh conductors 403 in an opening. The seventh conductors 403 in the opening has one end that is opened and the other end that is electrically connected to a conductor defining the opening. In a unit slot illustrated in FIG. 31C, five seventh conductors 403 are located in an opening. In the unit slot, the seventh conductors 403 form a shape corresponding to a meander line. In a unit slot illustrated in FIG. 31D, one seventh conductor 403 is located in an opening. In the unit slot, the seventh conductor 403 forms a shape corresponding to a spiral.

FIGS. 1 to 31 are diagrams each illustrating a configuration of the resonator 10 as an example. The configuration of the resonator 10 is not limited to the configurations illustrated in FIGS. 1 to 31. For example, the resonator 10 can include three or more pair conductors 30. For example, one of the pair conductors 30 can face two pair conductors 30 in the x-direction. The two pair conductors 30 have different distances from the one of the pair conductors 30. For example, the resonator 10 can include two pairs of pair conductors 30. In the two pairs of pair conductors 30, the distances between the respective pairs and the lengths of the respective pairs are different. The resonator 10 can include five or more first conductors. The resonator 10 includes the unit structure 10X that can be aligned with another unit structure 10X in the y-direction. The unit structure 10X of the resonator 10 can be aligned with another unit structure 10X in the x-direction without through the pair conductors 30. FIGS. 32 to 34 are diagrams illustrating examples of the resonators 10. In the resonators 10 illustrated in FIGS. 32 to 34, the unit resonator 40X of the unit structure 10X is represented as a square, but the unit resonator 40X is not limited to this shape.

Figure 35:
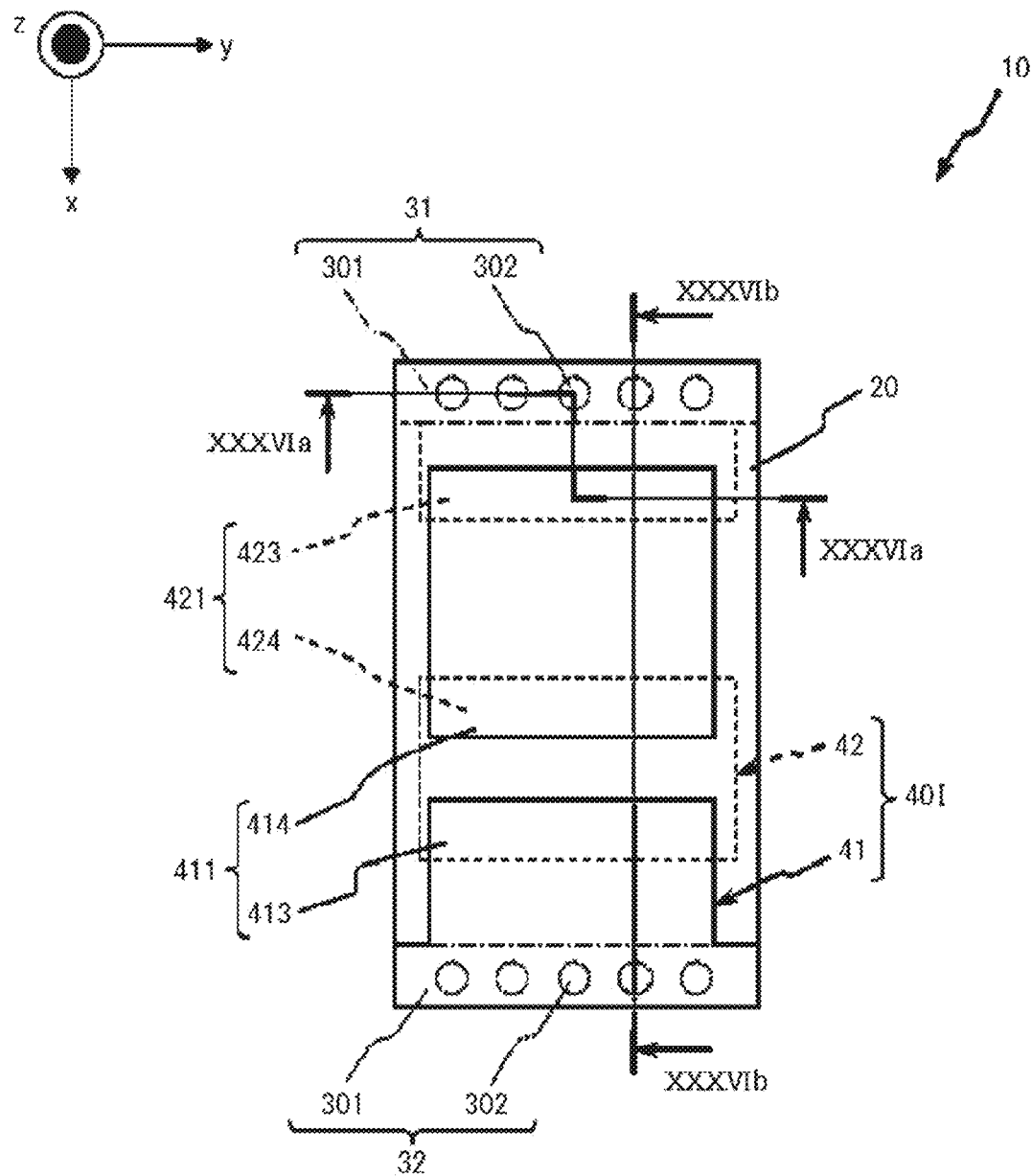
FIG. 35 is a plan view of an embodiment of the resonator.
Figure 36A:
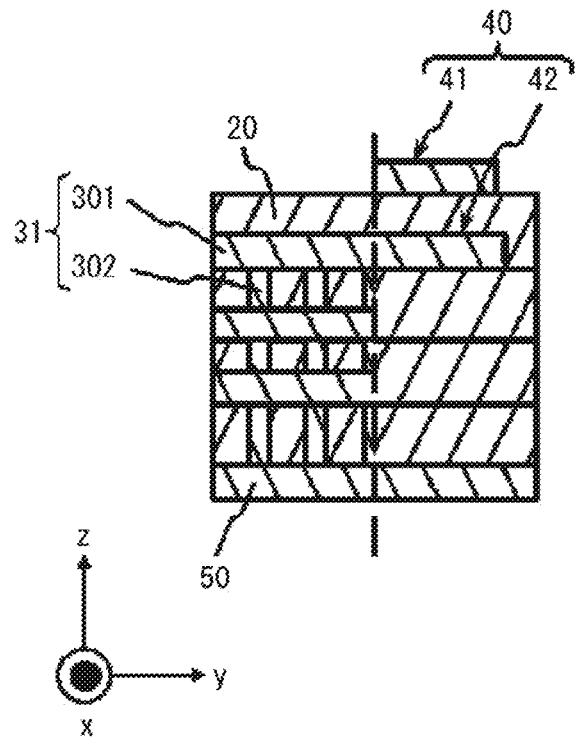
FIG. 36A is a sectional view illustrating an embodiment of the resonator.
Figure 36B:
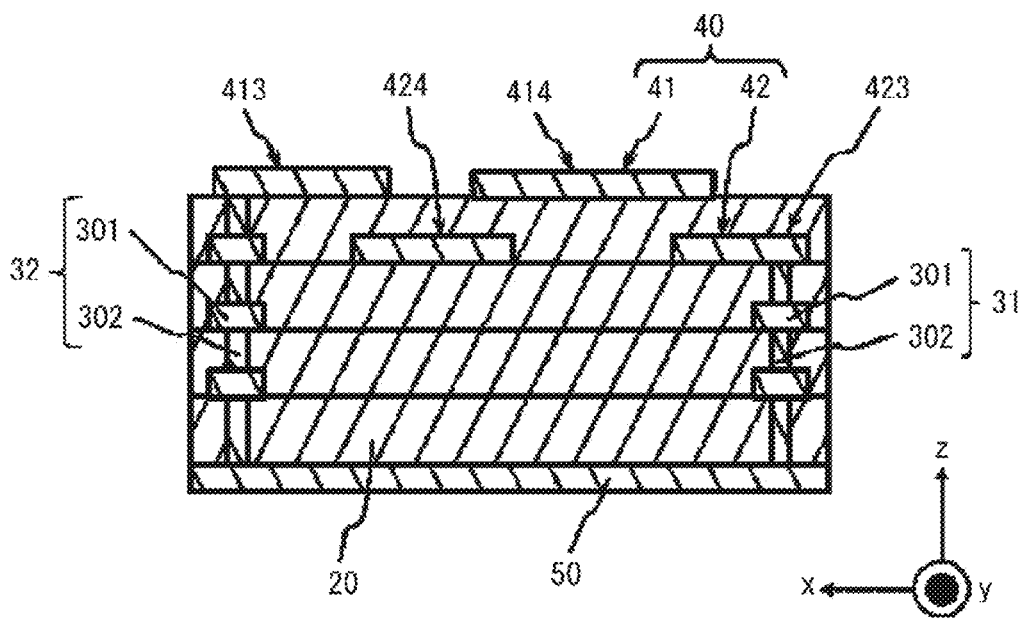
FIG. 36B is a sectional view illustrating an embodiment of the resonator.

FIGS. 1 to 34 are diagrams each illustrating a configuration of the resonator 10 as an example. The configuration of the resonator 10 are not limited to the configurations illustrated in FIGS. 1 to 34. FIG. 35 is a plan view of the xy plane, as viewed in the z-direction. FIG. 36A is a cross-sectional view taken along line XXXVIa-XXXVIa illustrated in FIG. 35 FIG. 36B is a cross-sectional view taken along line XXXVIb-XXXVIb illustrated in FIG. 35.

In the resonator 10 illustrated in FIGS. 35 to 36, the first conductive layer 41 includes half of a patch resonator as the first unit resonator 41X. The second conductive layer 42 includes half of a patch resonator as the second unit resonator 42X. The unit resonator 40X includes one first divisional resonator 41Y and one second divisional resonator 42Y. The unit structure 10X includes the unit resonator 40X, part of the base 20 overlapping the unit resonator 40X in the z-direction, and part of the fourth conductor 50. In the resonator 10 illustrated in FIG. 35, three unit resonators 40X are arranged in the x-direction. The first unit conductor 411 and the second unit conductor 421 included in the three unit resonators 40X form one current path 401.

Figure 37:
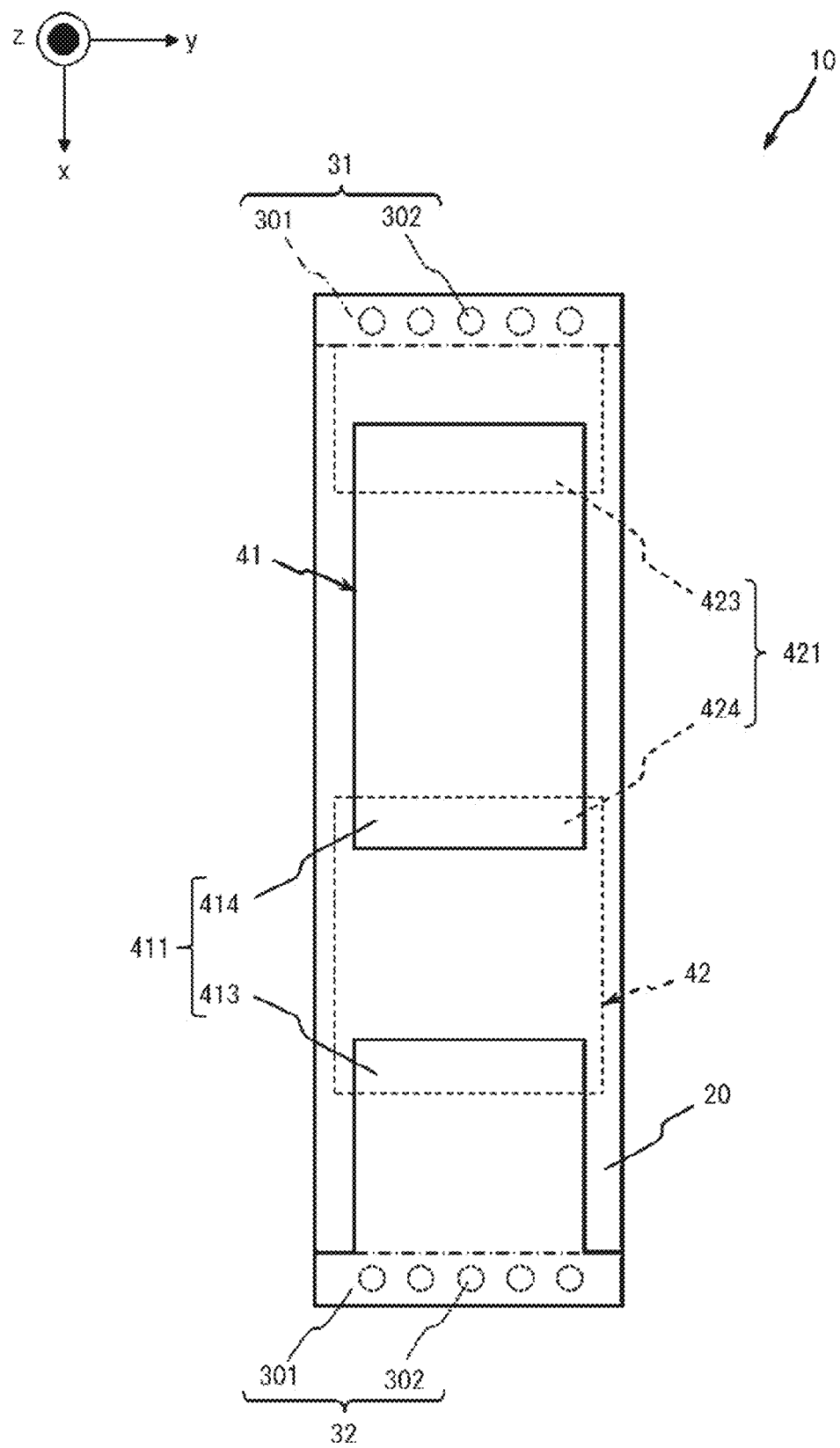
FIG. 37 is a plan view of an embodiment of the resonator.
Figure 38:
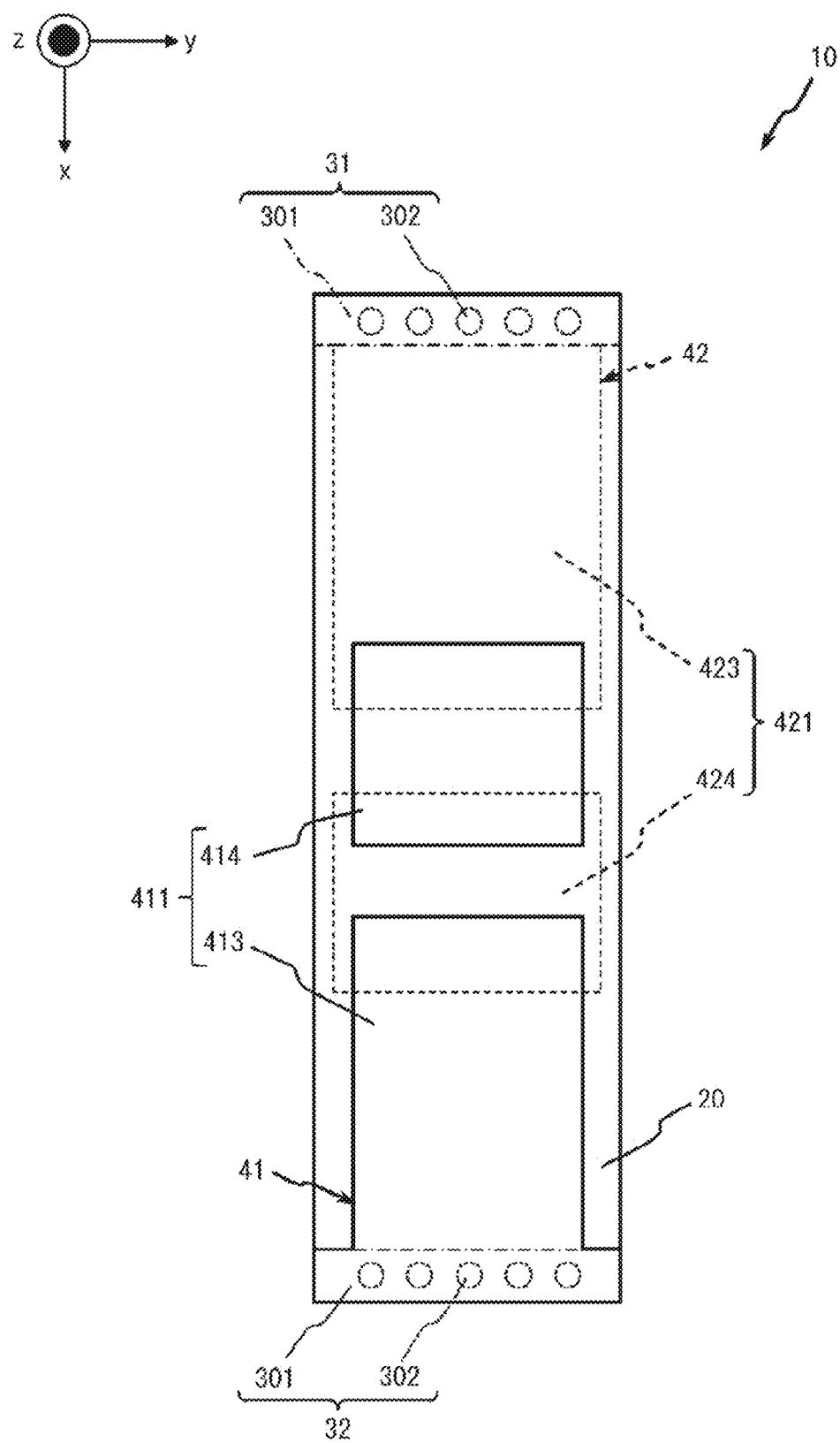
FIG. 38 is a plan view of an embodiment of the resonator.

FIG. 37 illustrates another example of the resonator 10 illustrated in FIG. 35. The resonator 10 illustrated in FIG. 37 has a length larger in the x-direction than the resonator 10 illustrated in FIG. 35. The size of the resonator 10 is not limited to the resonator 10 illustrated in FIG. 37 and can be changed as appropriate. In the resonator 10 of FIG. 37, the first connecting conductor 413 has a length in the x-direction that is different from the first floating conductor 414. In the resonator 10 of FIG. 37, the length of the first connecting conductor 413 in the x-direction is smaller than that of the first floating conductor 414. FIG. 38 illustrates another example of the resonator 10 illustrated in FIG. 35. In the resonator 10 illustrated in FIG. 38, the third conductor 40 has different lengths in the x-direction. In the resonator 10 of FIG. 38, the length of the first connecting conductor 413 in the x-direction is larger than that of the first floating conductor 414.

Figure 39:
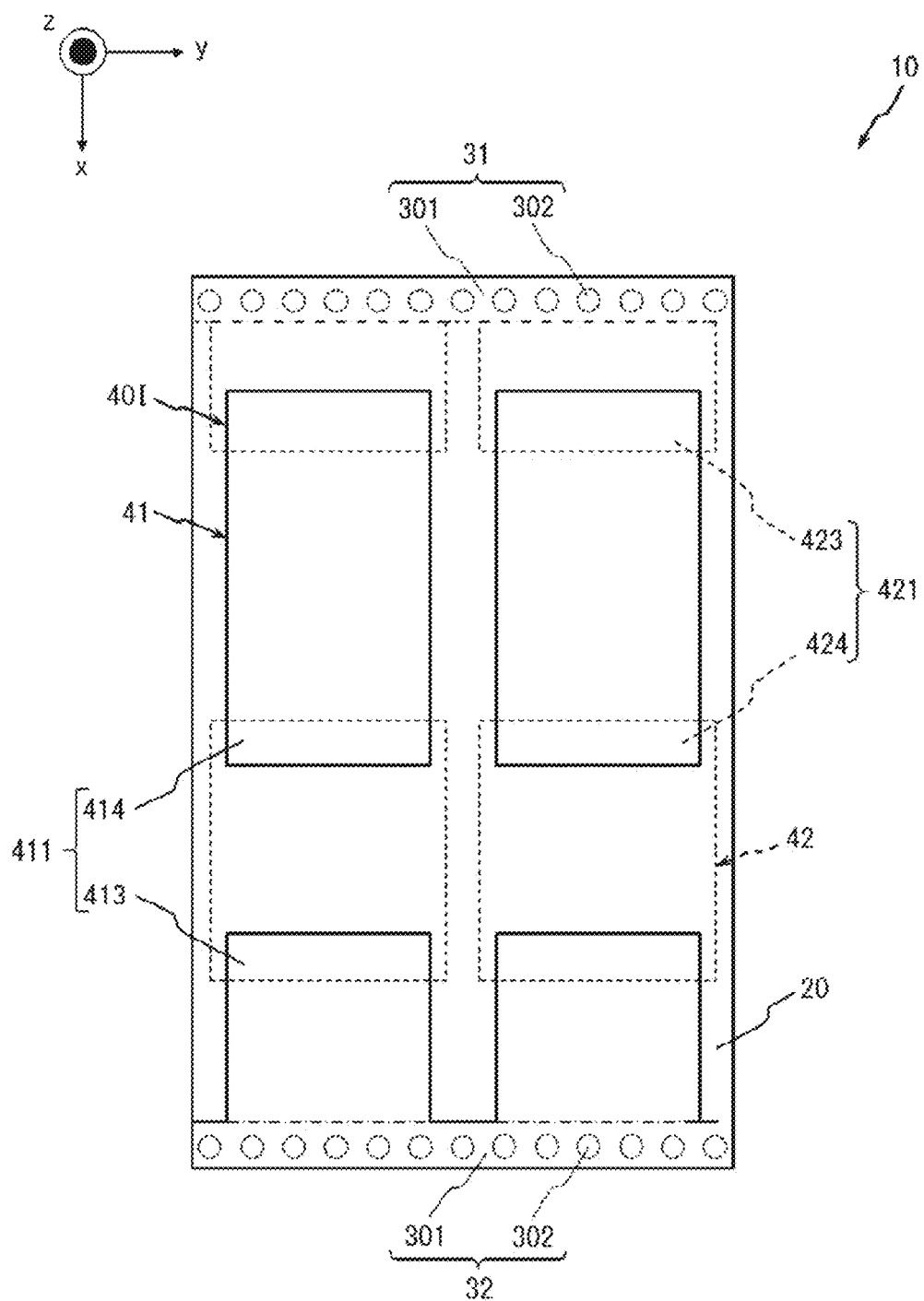
FIG. 39 is a plan view of an embodiment of the resonator.

FIG. 39 illustrates another example of the resonator 10. FIG. 39 illustrates another example of the resonator 10 illustrated in FIG. 37. In the plurality of embodiments, in the resonator 10, a plurality of first unit conductors 411 and second unit conductors 421 arranged in the x-direction are capacitively coupled. In the resonator 10, two current paths 401 can be arranged in y-directions in which no current flows from one side to the other side.

Figure 40:
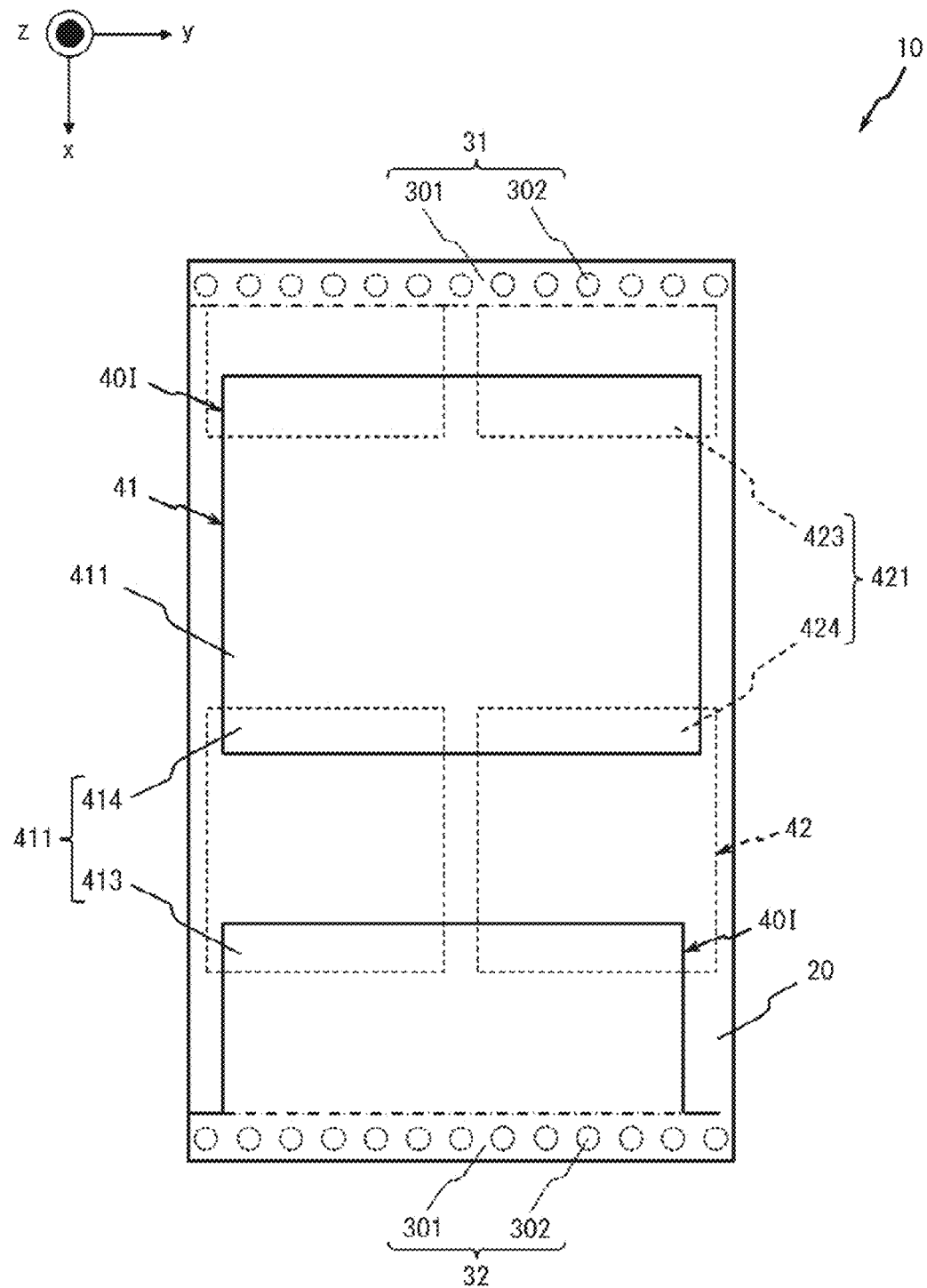
FIG. 40 is a plan view of an embodiment of the resonator.

FIG. 40 illustrates another example of the resonator 10. FIG. 40 illustrates another example of the resonator 10 illustrated in FIG. 39. In the plurality of embodiments, the resonator 10 can be configured such that the number of conductive members connected to the first conductor 31 and the number of conductive members connected to the second conductor 32 are different in number. In the resonator 10 of FIG. 40, one first connecting conductor 413 is capacitively coupled to two second floating conductors 424. In the resonator 10 of FIG. 40, the two second connecting conductors 423 are capacitively coupled to one first floating conductor 414. In the plurality of embodiments, the number of first unit conductors 411 can be different from the number of second unit conductors 421 capacitively coupled to the first unit conductors 411.

Figure 41:
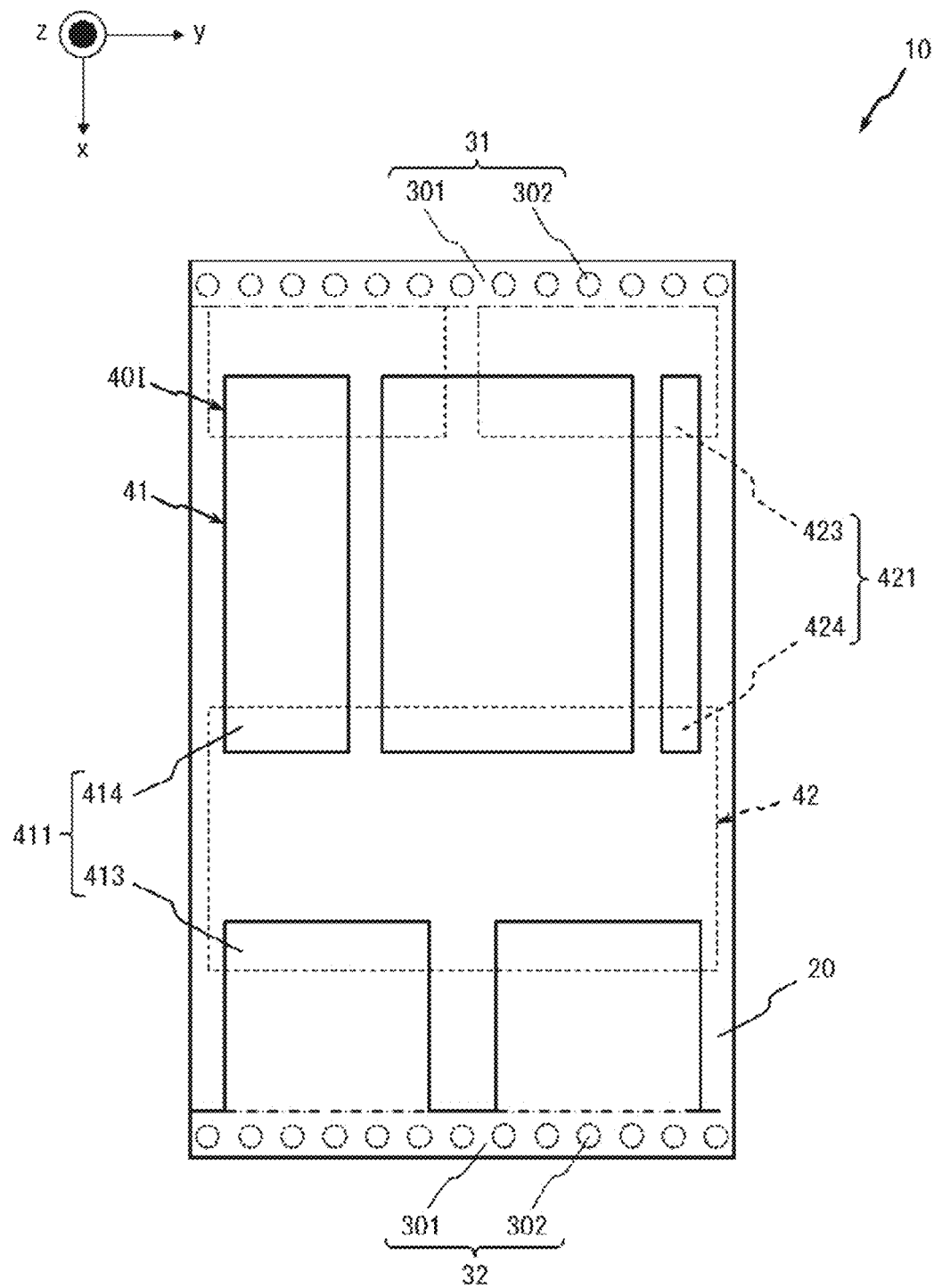
FIG. 41 is a plan view of an embodiment of the resonator.

FIG. 41 illustrates another example of the resonator 10 illustrated in FIG. 39. In the plurality of embodiments, the first unit conductor 411 can be configured such that the number of second unit conductors 421 capacitively coupled at a first end in the x-direction and the number of second unit conductors 421 capacitively coupled at a second end in the x-direction are different. In the resonator 10 of FIG. 41, one second floating conductor 424 has a first end in the x-direction to which two first connecting conductors 413 are capacitively coupled and a second end to which three second floating conductors 424 are capacitively coupled. In the plurality of embodiments, a plurality of conductive members arranged in the y-direction can have different lengths in the y-direction. In the resonator 10 of FIG. 41, the three first floating conductors 414 arranged in the y-direction have different lengths in the y-direction.

Figure 42:
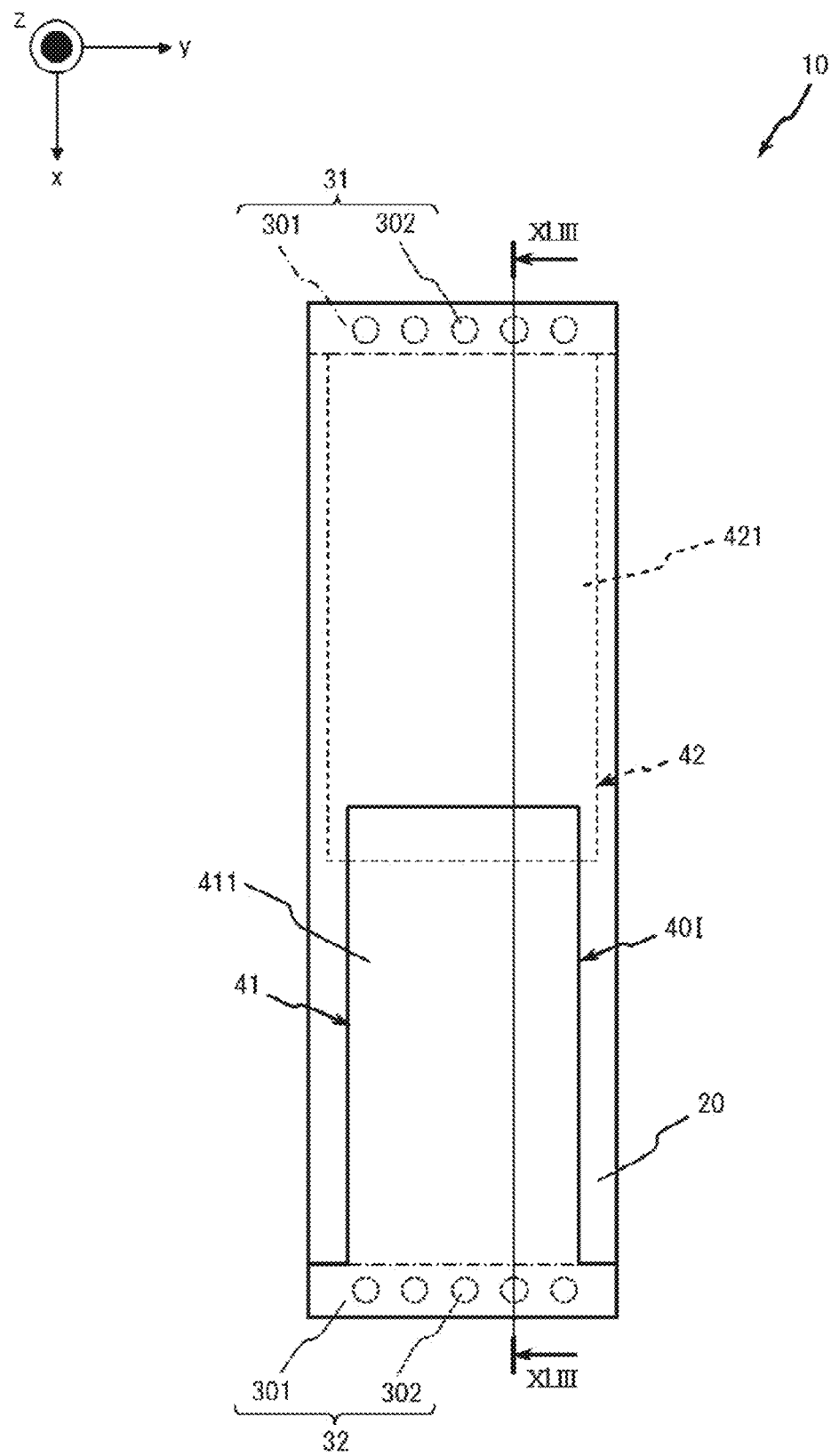
FIG. 42 is a plan view of an embodiment of the resonator.
Figure 43:
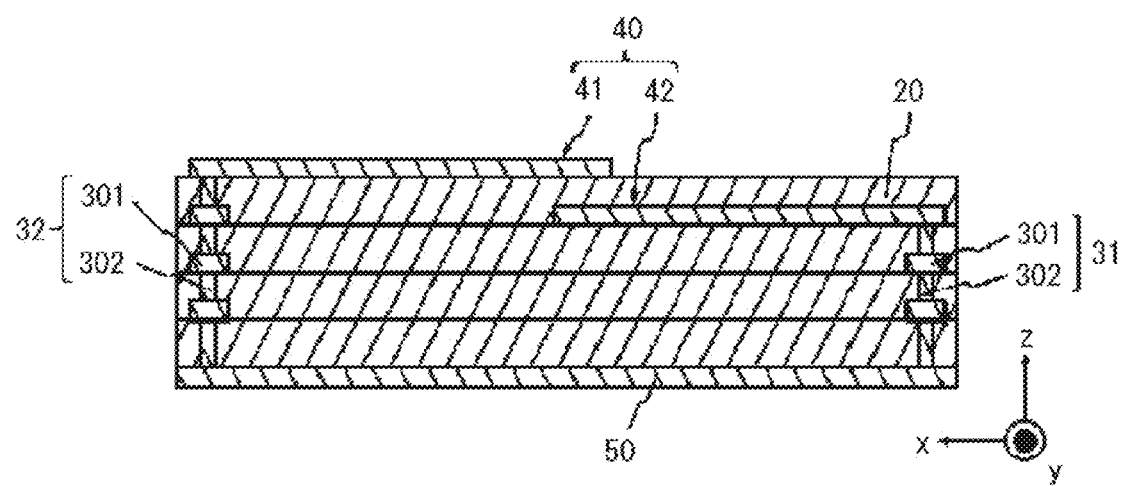
FIG. 43 is a sectional view illustrating an embodiment of the resonator.

FIG. 42 illustrates another example of the resonator 10. FIG. 43 is a cross-sectional view taken along line XLIII-XLIII illustrated in FIG. 42. In the resonator 10 illustrated in FIGS. 42 and 43, the first conductive layer 41 includes half of a patch resonator as the first unit resonator 41X. The second conductive layer 42 includes half of a patch resonator as the second unit resonator 42X. The unit resonator 40X includes one first divisional resonator 41Y and one second divisional resonator 42Y. The unit structure 10X includes the unit resonator 40X, part of the base 20 that overlaps the unit resonator 40X in the z-direction, and part of the fourth conductor 50. In the resonator 10 illustrated in FIG. 42, one unit resonator 40X extends in the x-direction.

Figure 44:
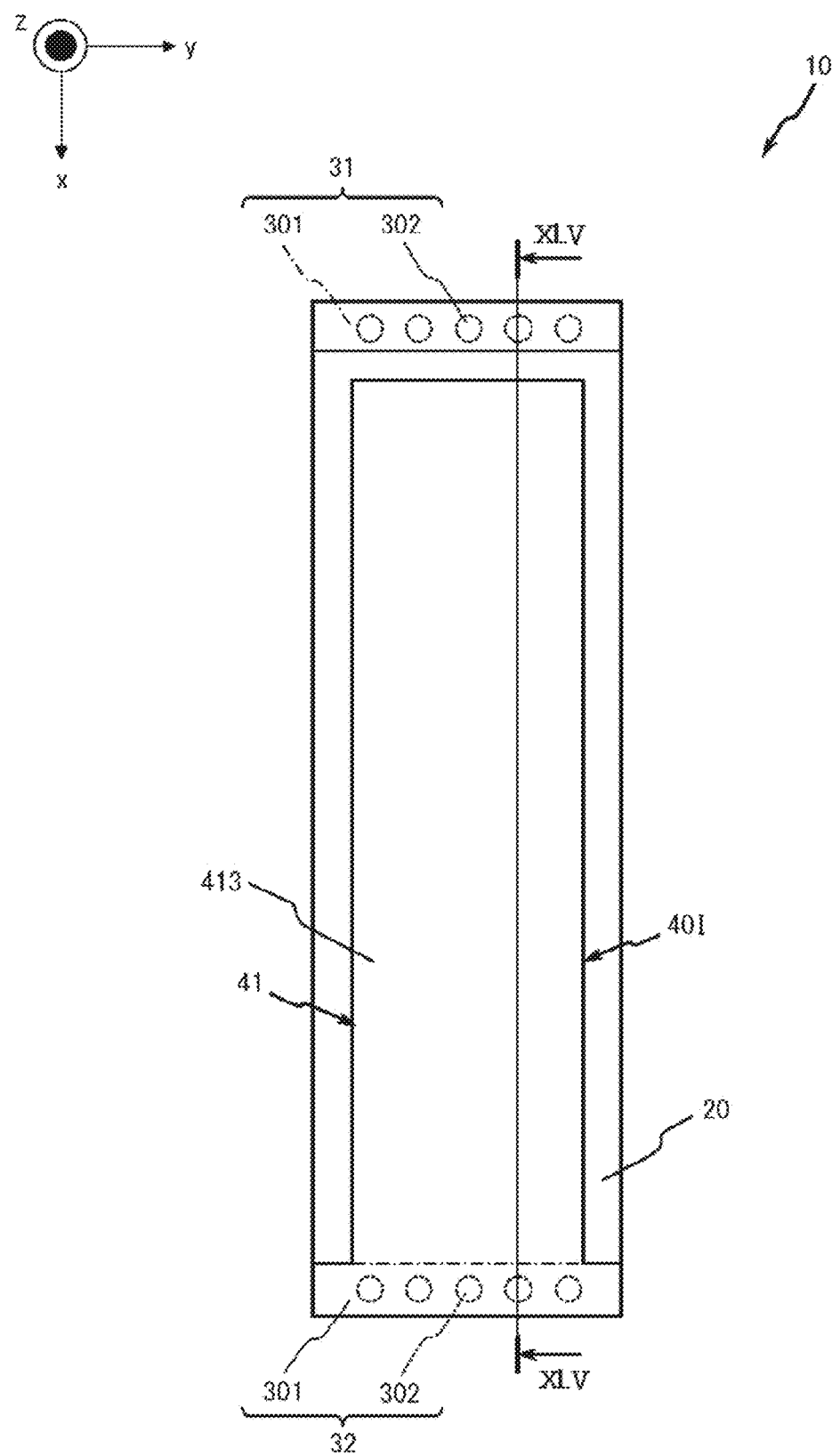
FIG. 44 is a plan view of an embodiment of the resonator.
Figure 45:
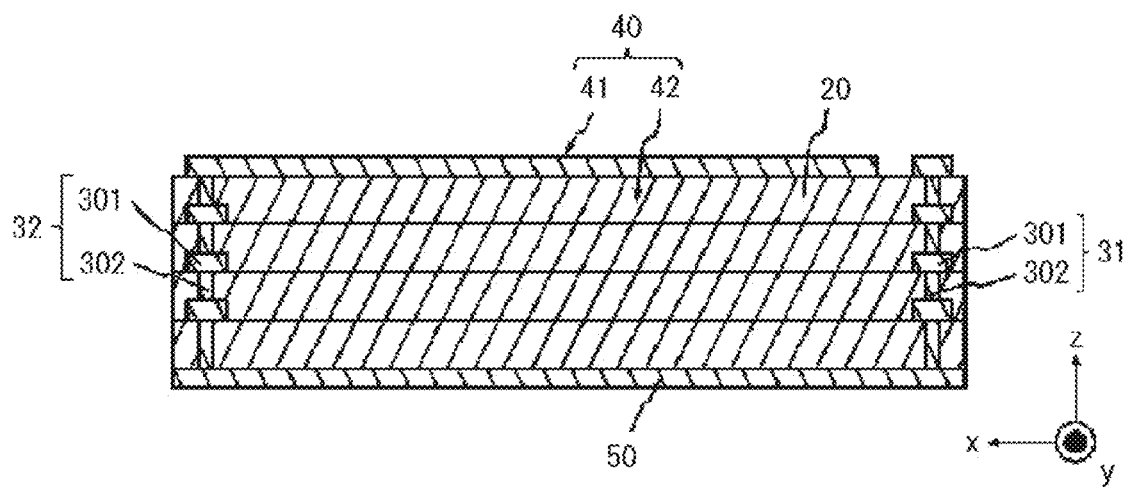
FIG. 45 is a sectional view illustrating an embodiment of the resonator.

FIG. 44 illustrates another example of the resonator 10. FIG. 45 is a cross-sectional view taken along line XLV-XLV illustrated in FIG. 44 In the resonator 10 illustrated in FIGS. 44 and 45, the third conductor 40 includes only the first connecting conductor 413. The first connecting conductor 413 faces the first conductor 31 in the xy plane. The first connecting conductor 413 is capacitively coupled to the first conductor 31.

Figure 46:
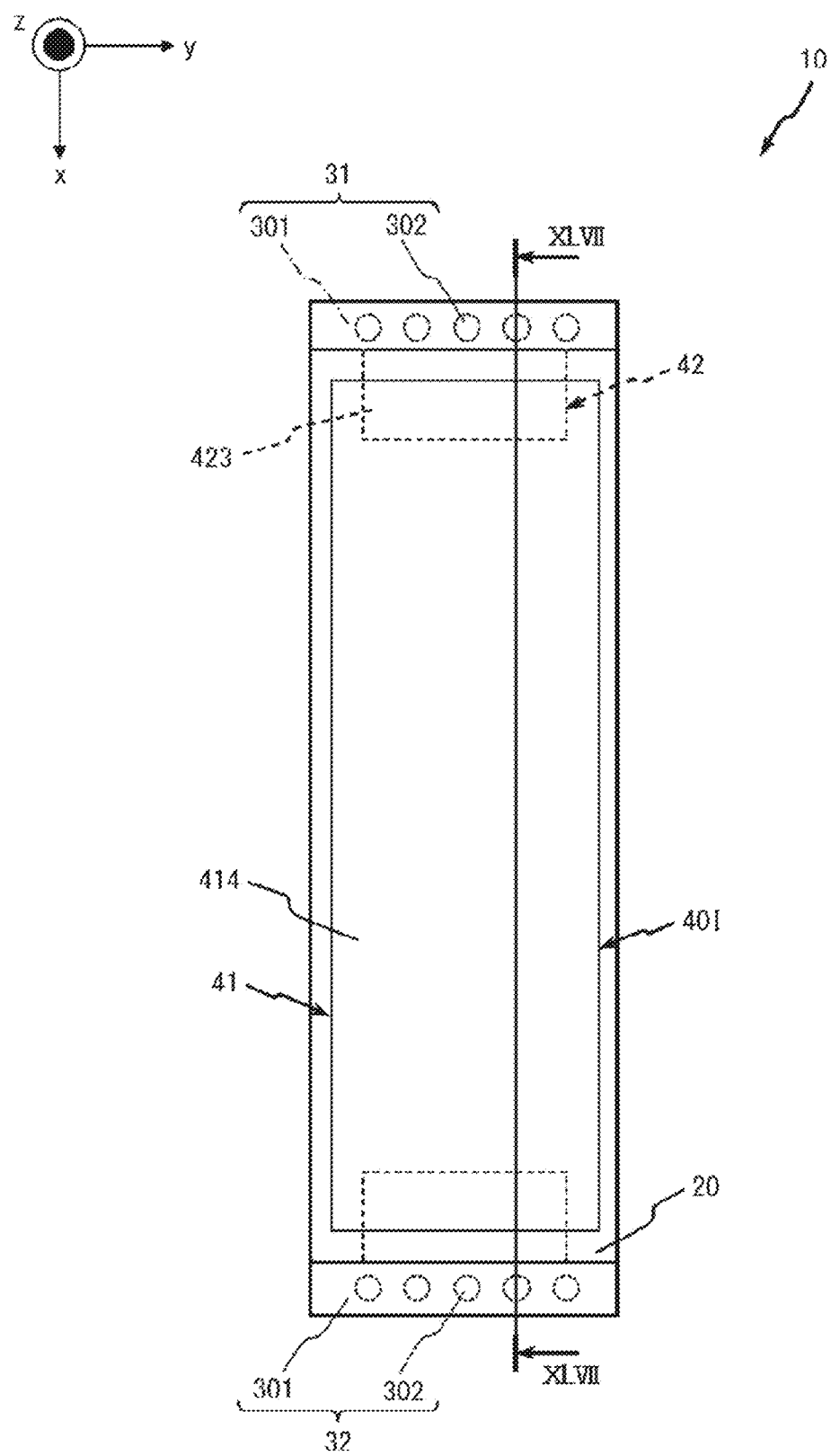
FIG. 46 is a plan view of an embodiment of the resonator.
Figure 47:
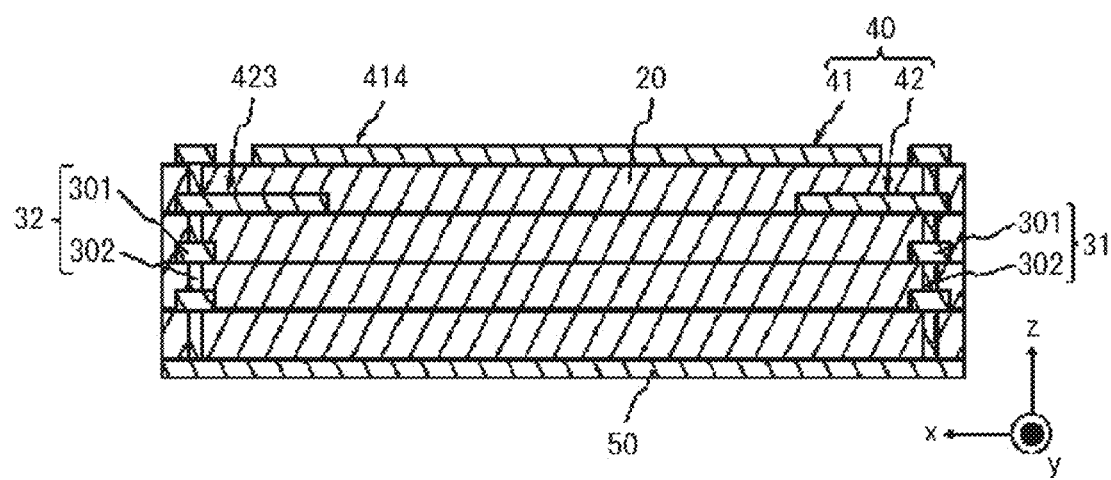
FIG. 47 is a sectional view illustrating an embodiment of the resonator.

FIG. 46 illustrates another example of the resonator 10. FIG. 47 is a cross-sectional view taken along line XLVII-XLVII illustrated in FIG. 46. In the resonator 10 illustrated in FIGS. 46 and 47, the third conductor 40 includes the first conductive layer 41 and the second conductive layer 42. The first conductive layer 41 includes one first floating conductor 414. The second conductive layer 42 includes two second connecting conductors 423. The first conductive layer 41 faces the pair conductors 30 in the xy plane. The two second connecting conductors 423 overlap the one first floating conductor 414 in the z-direction. The one first floating conductor 414 is capacitively coupled to the two second connecting conductors 423.

Figure 48:
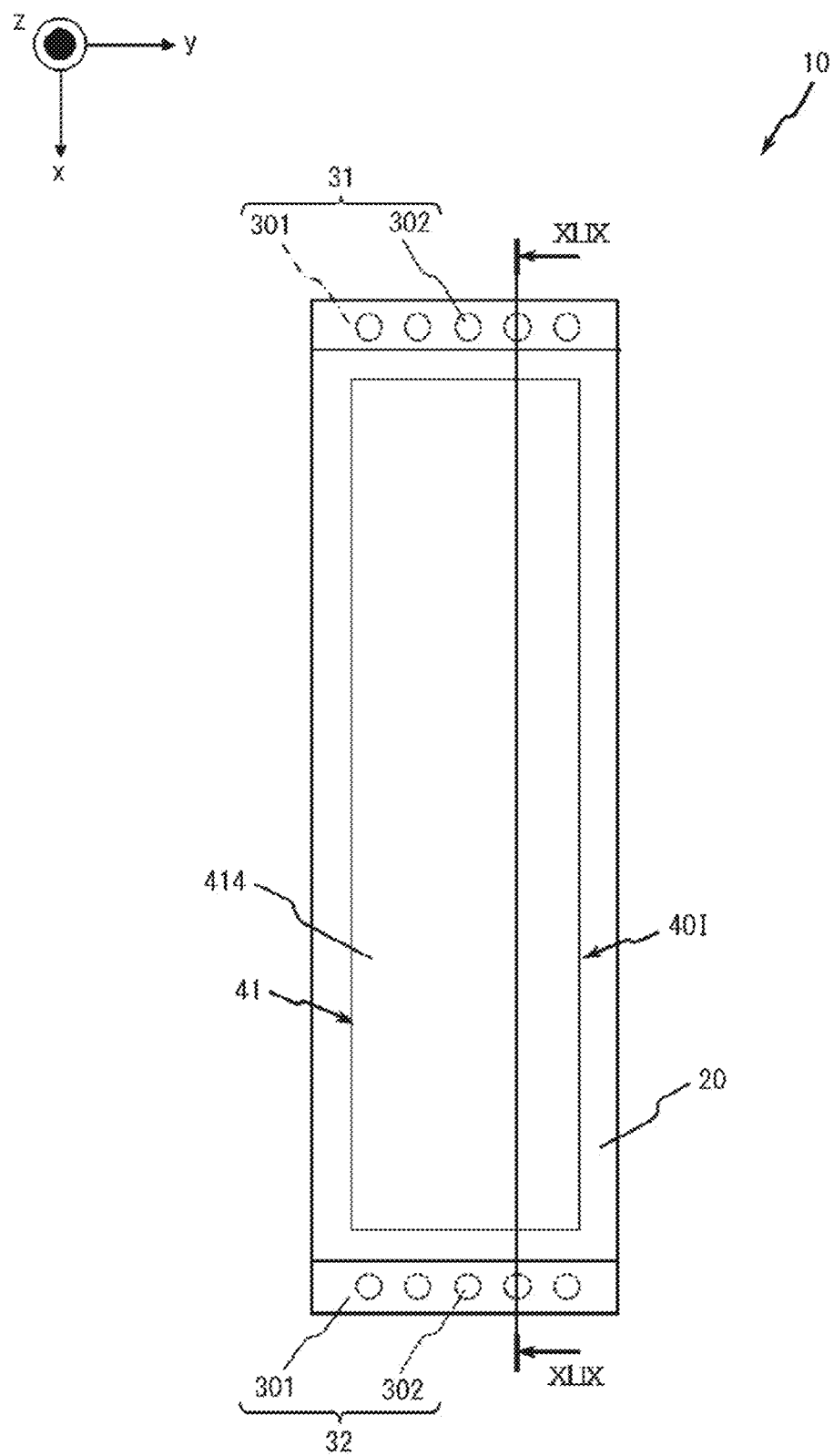
FIG. 48 is a plan view of an embodiment of the resonator.
Figure 49:
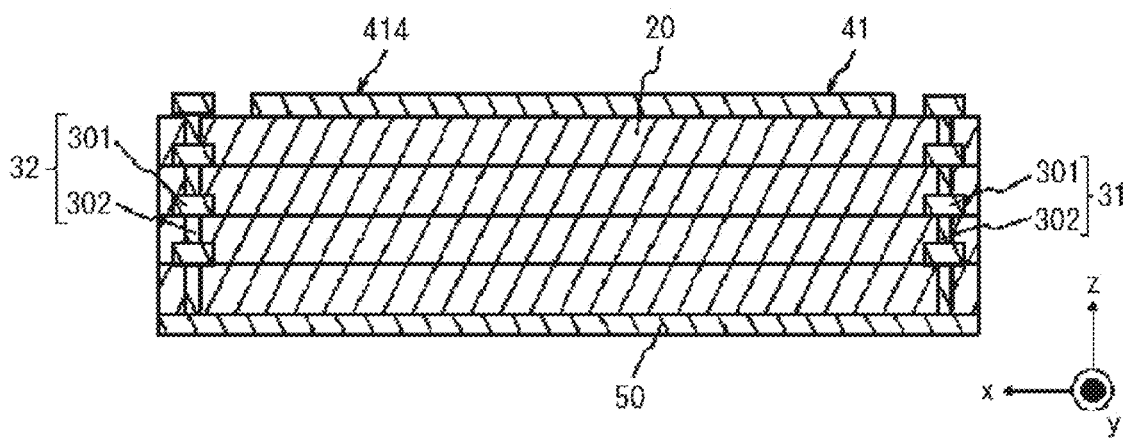
FIG. 49 is a sectional view illustrating an embodiment of the resonator.

FIG. 48 illustrates another example of the resonator 10. FIG. 49 is a cross-sectional view taken along line XLIX-XLIX illustrated in FIG. 48. In the resonator 10 illustrated in FIGS. 48 and 49, the third conductor 40 includes only the first floating conductor 414. The first floating conductor 414 faces the pair conductors 30 in the xy plane. The first connecting conductor 413 is capacitively coupled to the pair conductors 30.

Figure 50:
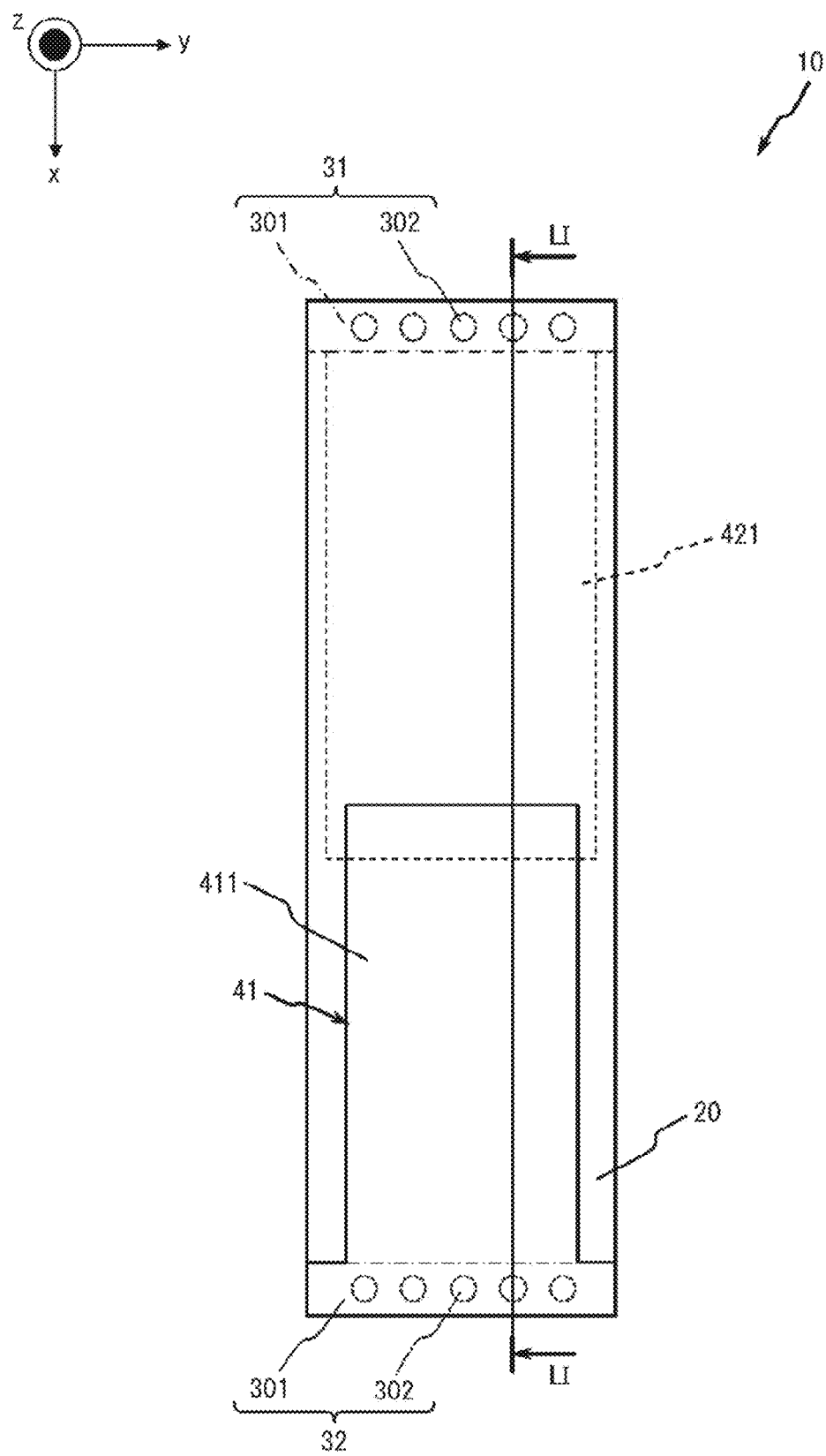
FIG. 50 is a plan view of an embodiment of the resonator.
Figure 51:
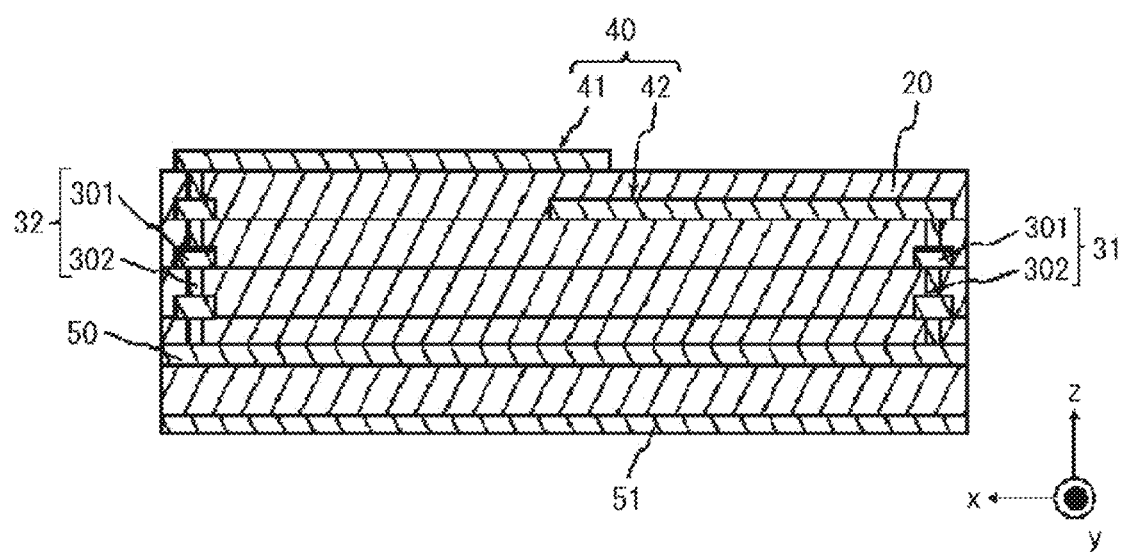
FIG. 51 is a sectional view illustrating an embodiment of the resonator.

FIG. 50 illustrates another example of the resonator 10. FIG. 51 is a cross-sectional view taken along line LI-LI illustrated in FIG. 50. The resonator 10 illustrated in FIGS. 50 and 51 is different from the resonator 10 illustrated in FIGS. 42 and 43 in the configuration of the fourth conductor 50. The resonator 10 illustrated in FIGS. 50 and 51 includes the fourth conductor 50 and the reference potential layer 51. The reference potential layer 51 is electrically connected to the ground of a device including the resonator 10. The reference potential layer 51 faces the third conductor 40 via the fourth conductor 50. The fourth conductor 50 is located between the third conductor 40 and the reference potential layer 51. The distance between the reference potential layer 51 and the fourth conductor 50 is smaller than the distance between the third conductor 40 and the fourth conductor 50.

Figure 52:
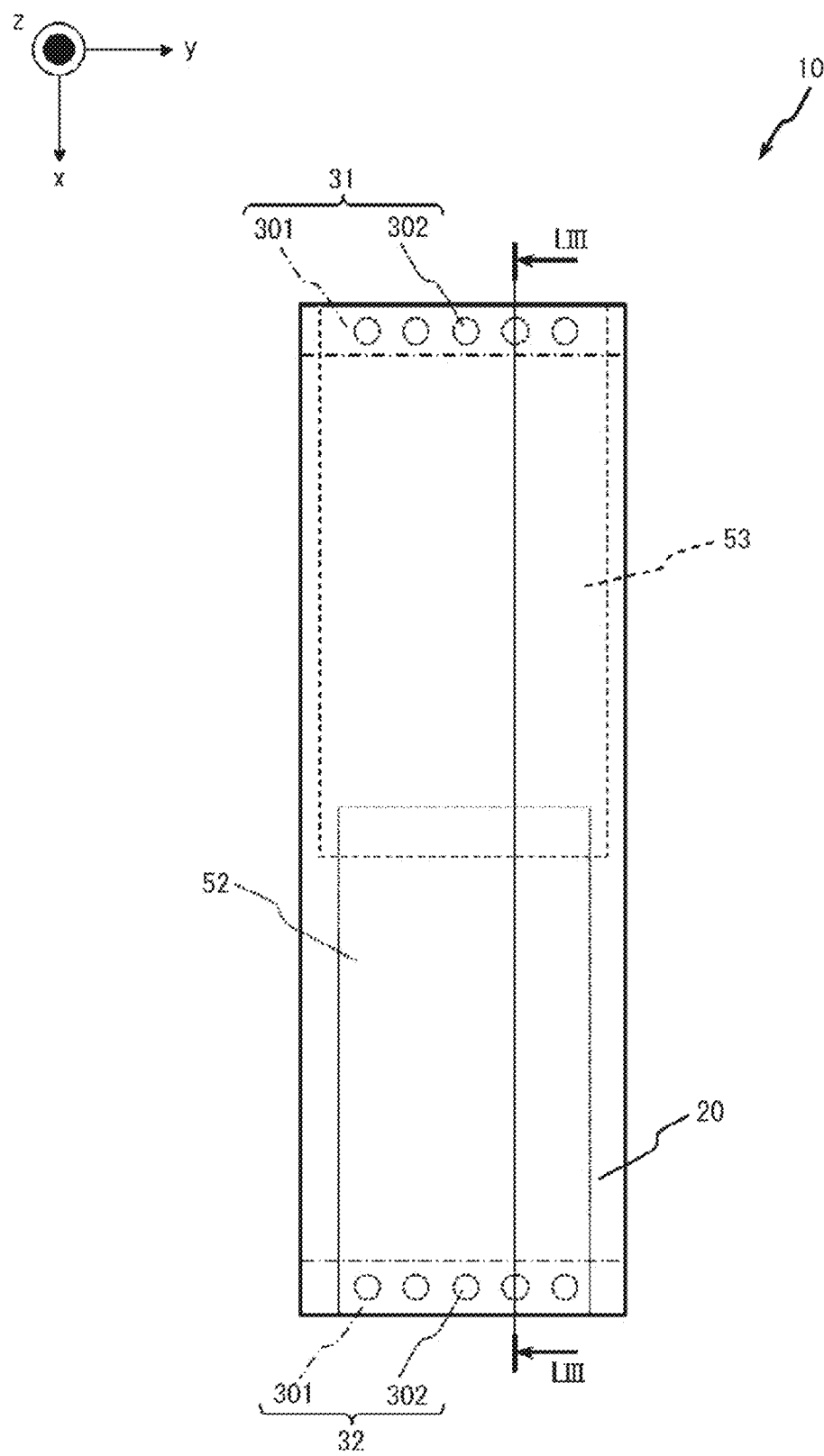
FIG. 52 is a plan view of an embodiment of the resonator.
Figure 53:
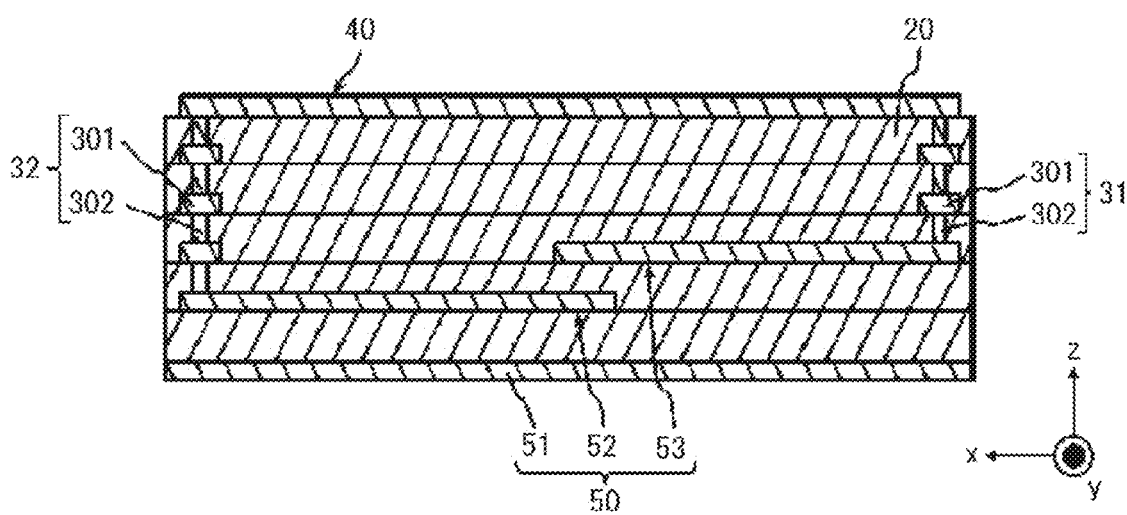
FIG. 53 is a sectional view illustrating an embodiment of the resonator.

FIG. 52 illustrates another example of the resonator 10. FIG. 53 is a cross-sectional view taken along line LIII-LIII illustrated in FIG. 52. The resonator 10 includes the fourth conductor 50 and the reference potential layer 51. The reference potential layer 51 is electrically connected to the ground of a device including the resonator 10. The fourth conductor 50 includes a resonator. The fourth conductor 50 includes the third conductive layer 52 and the fourth conductive layer 53. The third conductive layer 52 and the fourth conductive layer 53 are capacitively coupled. The third conductive layer 52 and the fourth conductive layer 53 face each other in the z-direction. The distance between the third conductive layer 52 and the fourth conductive layer 53 is smaller than the distance between the fourth conductive layer 53 and the reference potential layer 51. The distance between the third conductive layer 52 and the fourth conductive layer 53 is shorter than the distance between the fourth conductor 50 and the reference potential layer 51. The third conductor 40 is formed into one conductive layer.

Figure 54:
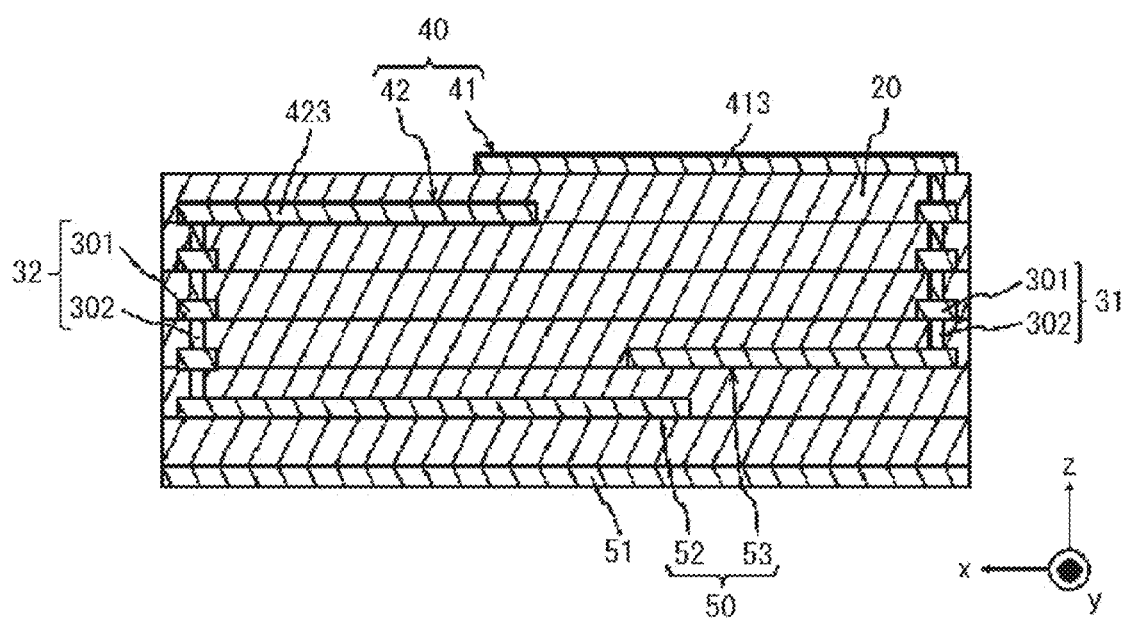
FIG. 54 is a sectional view illustrating an embodiment of the resonator.

FIG. 54 illustrates another example of the resonator 10 illustrated in FIG. 53. The resonator 10 includes the third conductor 40, the fourth conductor 50, and the reference potential layer 51. The third conductor 40 includes the first conductive layer 41 and the second conductive layer 42. The first conductive layer 41 includes the first connecting conductor 413. The second conductive layer 42 includes the second connecting conductor 423. The first connecting conductor 413 is capacitively coupled to the second connecting conductor 423. The reference potential layer 51 is electrically connected to the ground of a device including the resonator 10. The fourth conductor 50 includes the third conductive layer 52 and the fourth conductive layer 53. The third conductive layer 52 and the fourth conductive layer 53 are capacitively coupled. The third conductive layer 52 and the fourth conductive layer 53 face each other in the z-direction. The distance between the third conductive layer 52 and the fourth conductive layer 53 is smaller than the distance between the fourth conductive layer 53 and the reference potential layer 51. The distance between the third conductive layer 52 and the fourth conductive layer 53 is shorter than the distance between the fourth conductor 50 and the reference potential layer 51.

Figure 55:
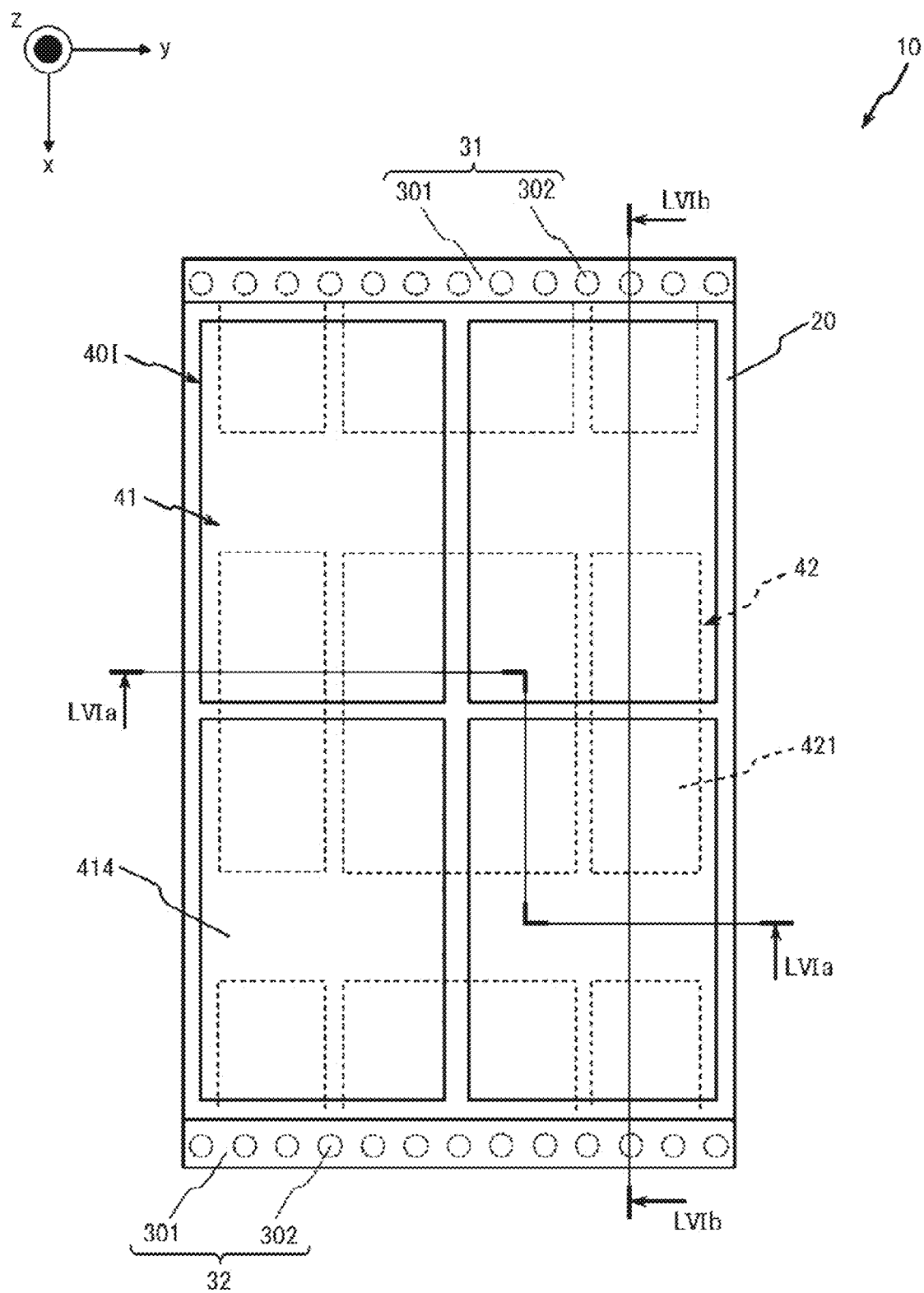
FIG. 55 is a plan view of an embodiment of the resonator.
Figure 56A:
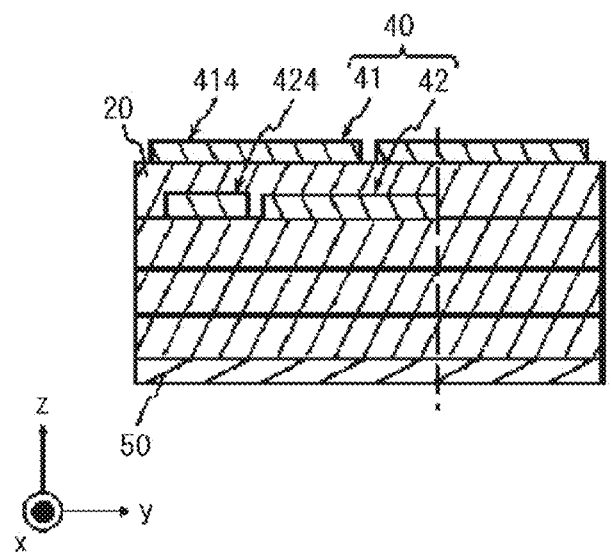
FIG. 56A is a sectional view illustrating an embodiment of the resonator.
Figure 56B:
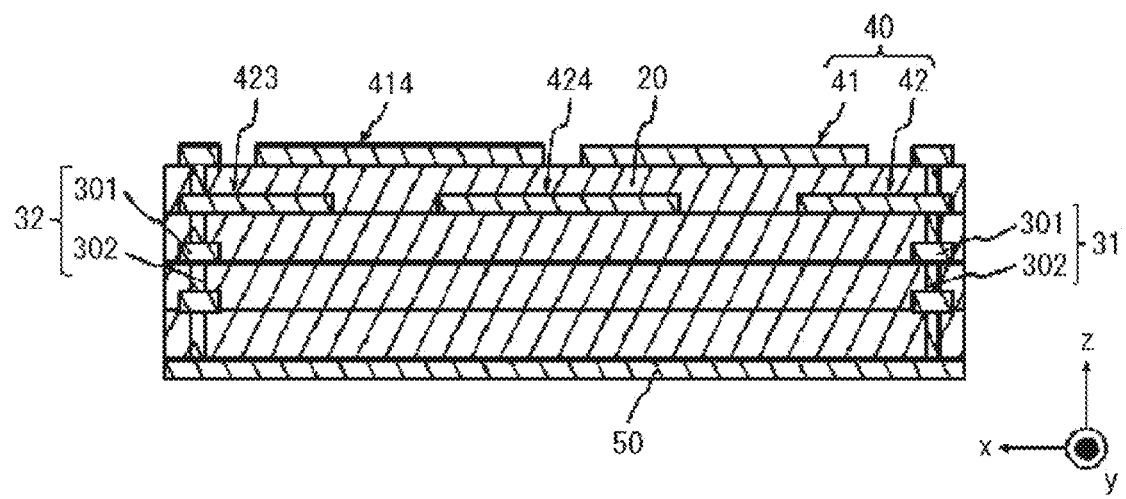
FIG. 56B is a sectional view illustrating an embodiment of the resonator.

FIG. 55 illustrates another example of the resonator 10. FIG. 56A is a cross-sectional view taken along line LVIa-LVIa illustrated in FIG. 55. FIG. 56B is a cross-sectional view taken along line LVIb-LVIb illustrated in FIG. 55. In the resonator 10 illustrated in FIG. 55, the first conductive layer 41 includes four first floating conductors 414. The first conductive layer 41 illustrated in FIG. 55 does not include the first connecting conductor 413. In the resonator 10 illustrated in FIG. 55, the second conductive layer 42 includes six second connecting conductors 423 and three second floating conductors 424. Two of the second connecting conductors 423 are each capacitively coupled to two of the first floating conductors 414. One of the second floating conductors 424 is capacitively coupled to four first floating conductors 414. Two of the second floating conductors 424 are capacitively coupled to two first floating conductors 414.

Figure 57:
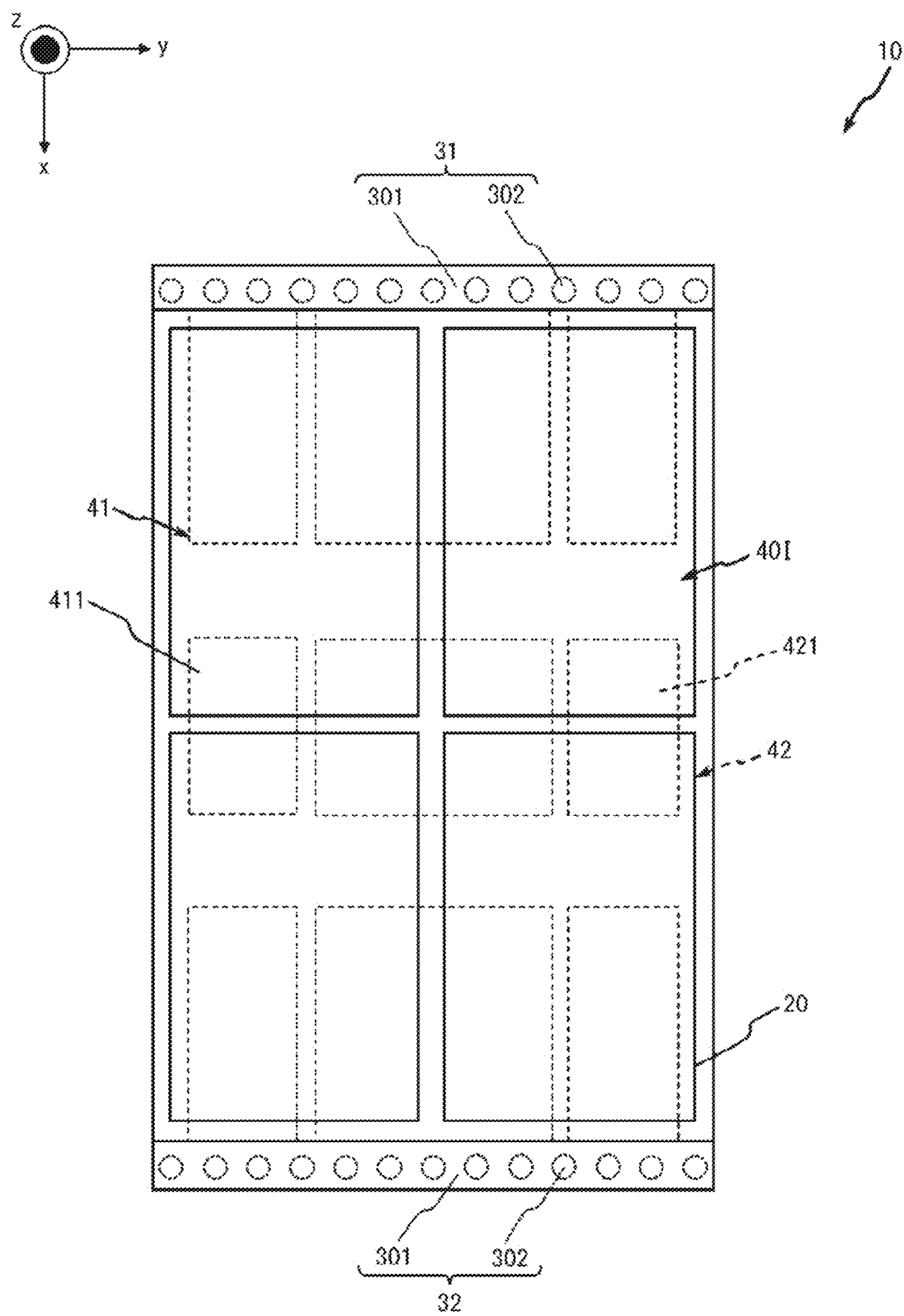
FIG. 57 is a plan view of an embodiment of the resonator.

FIG. 57 is a diagram illustrating another example of the resonator illustrated in FIG. 55. The resonator 10 of FIG. 57 is different from the resonator 10 illustrated in FIG. 55 in the size of the second conductive layer 42. In the resonator 10 illustrated in FIG. 57, the length of each second floating conductor 424 in the x-direction is smaller than the length of each second connecting conductor 423 in the x-direction.

Figure 58:
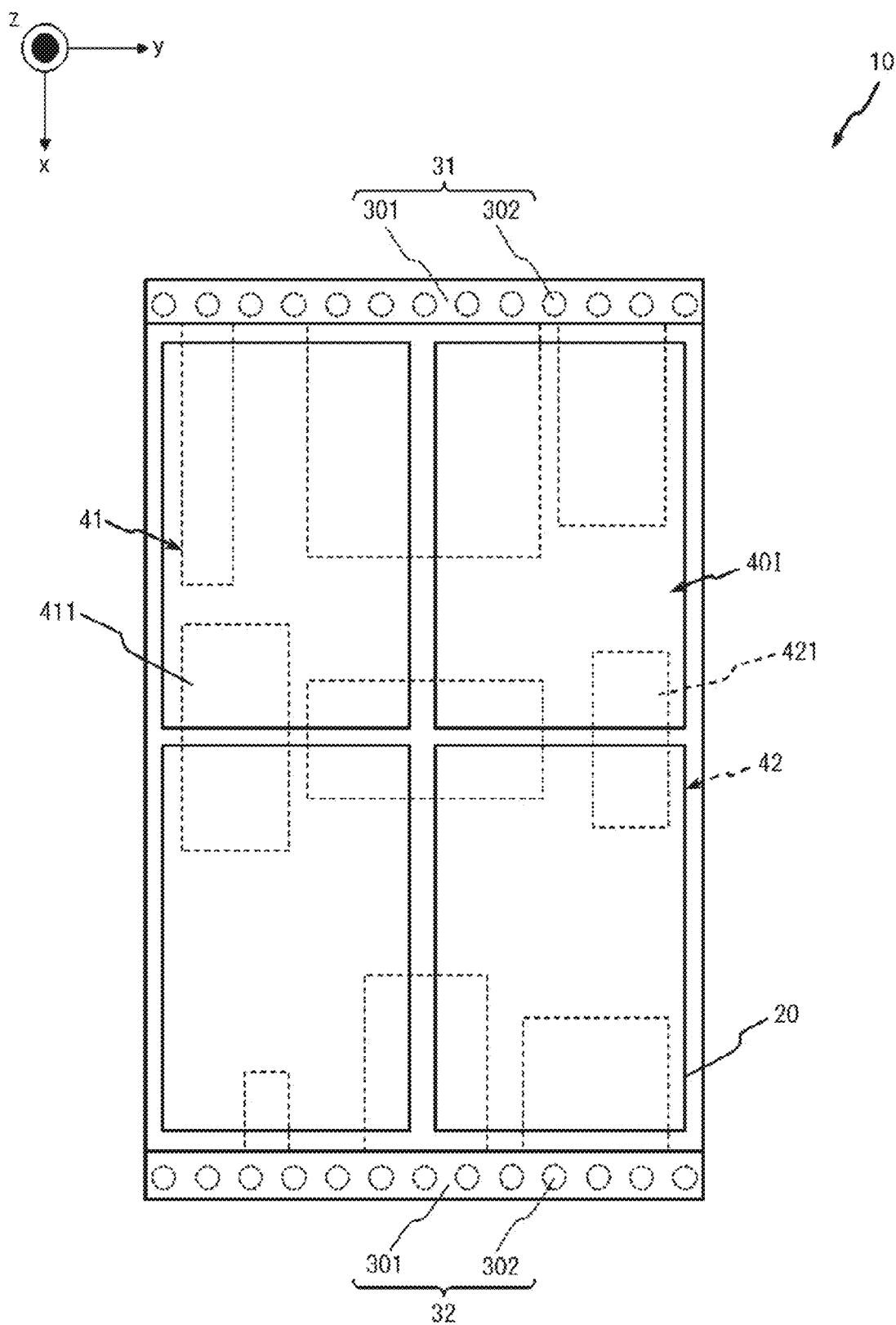
FIG. 58 is a plan view of an embodiment of the resonator.

FIG. 58 is a diagram illustrating another example of the resonator illustrated in FIG. 55. The resonator 10 of FIG. 58 is different from the resonator 10 illustrated in FIG. 55 in the size of the second conductive layer 42. In the resonator 10 illustrated in FIG. 58, the plurality of second unit conductors 421 has different first areas. In the resonator 10 illustrated in FIG. 58, the plurality of second unit conductors 421 has different lengths in x-directions. In the resonator 10 illustrated in FIG. 58, the plurality of second unit conductors 421 has different lengths in y-directions. In FIG. 58, the plurality of second unit conductors 421 has, but is not limited to, different first areas, lengths, and widths. In FIG. 58, the plurality of second unit conductors 421 can be different from each other in part of first area, length, and width. The plurality of second unit conductors 421 can match each other in part or all of first area, length, and width. The plurality of second unit conductors 421 can be different from each other in part or all of first area, length, and width. The plurality of second unit conductors 421 can match each other in part or all of first area, length, and width. Part of the plurality of second unit conductors 421 can match each other in part or all of first area, length, and width.

In the resonator 10 illustrated in FIG. 58, the plurality of second connecting conductors 423 arranged in the y-direction has different first areas. In the resonator 10 illustrated in FIG. 58, the plurality of second connecting conductors 423 arranged in the y-direction has different lengths in x-directions. In the resonator 10 illustrated in FIG. 58, the plurality of second connecting conductors 423 arranged in the y-direction has different lengths in the y-direction. In FIG. 58, the plurality of second connecting conductors 423 has, but is not limited to, different first areas, lengths, and widths. In FIG. 58, the plurality of second connecting conductors 423 can be different from each other in part of first area, length, and width. The plurality of second connecting conductors 423 can match each other in part or all of first area, length, and width. The plurality of second connecting conductors 423 can be different from each other in part or all of first area, length, and width. The plurality of second connecting conductors 423 can match each other in part or all of first area, length, and width. Part of the plurality of second connecting conductors 423 can match each other in part or all of first area, length, and width.

In the resonator 10 illustrated in FIG. 58, a plurality of second floating conductors 424 arranged in the y-direction has different first areas. In the resonator 10 illustrated in FIG. 58, the plurality of second floating conductors 424 arranged in the y-direction has different lengths in x-directions. In the resonator 10 illustrated in FIG. 58, the plurality of second floating conductors 424 arranged in the y-direction has different lengths in the y-direction. In FIG. 58, the plurality of second floating conductors 424 has, but is not limited to, different first areas, lengths, and widths. In FIG. 58, the plurality of second floating conductors 424 can be different from each other in part of first area, length, and width. The plurality of second floating conductors 424 can match each other in part or all of first area, length, and width. The plurality of second floating conductors 424 can be different from each other in part or all of first area, length, and width. The plurality of second floating conductors 424 can match each other in part or all of first area, length, and width. Part of the plurality of second floating conductors 424 can match each other in part or all of first area, length, and width.

Figure 59:
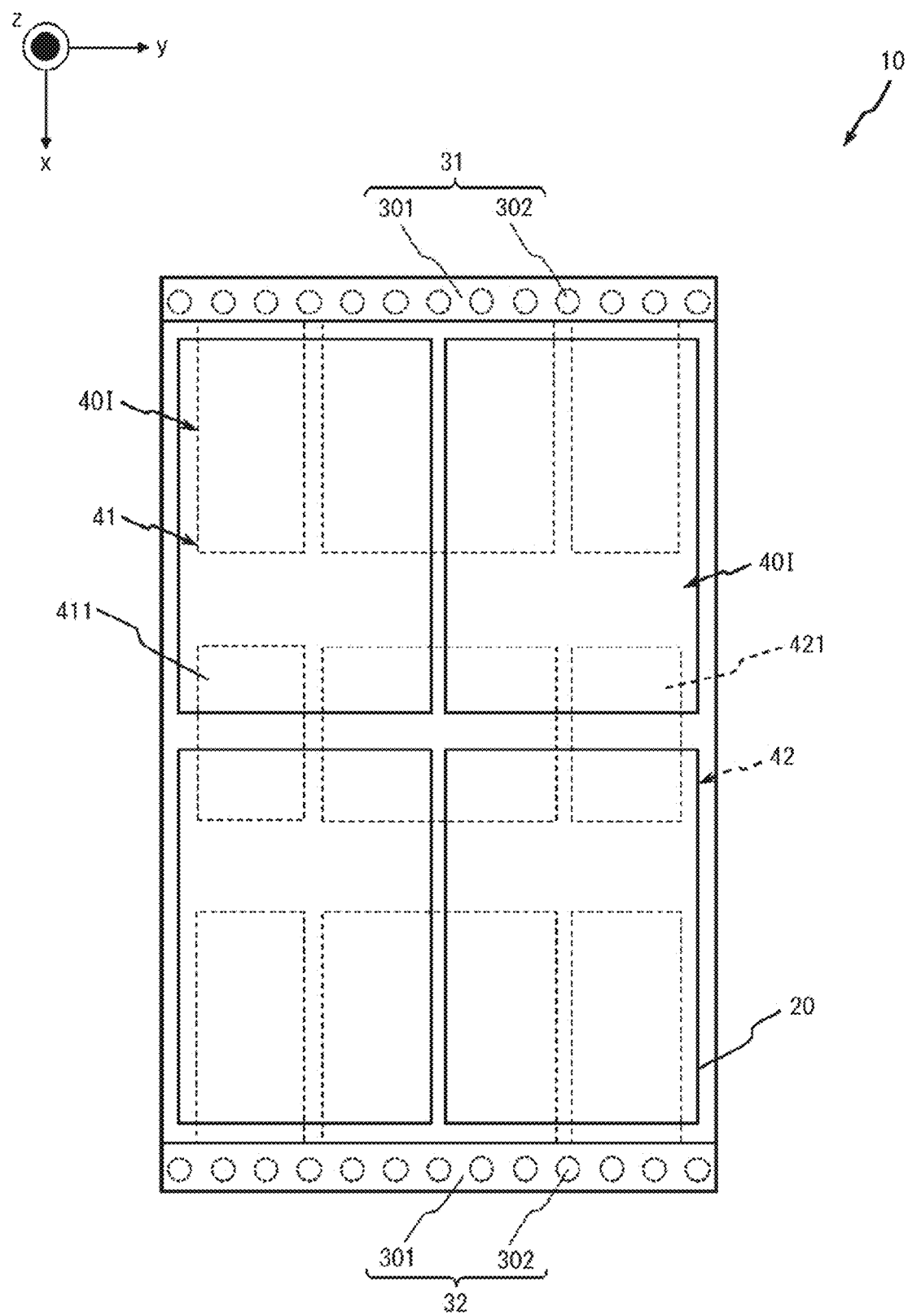
FIG. 59 is a plan view of an embodiment of the resonator.

FIG. 59 is a diagram illustrating another example of the resonator 10 illustrated in FIG. 57. The resonator 10 of FIG. 59 is different from the resonator 10 illustrated in FIG. 57 in distance between first unit conductors 411 in the y-direction. In the resonator 10 of FIG. 59, a distance between first unit conductors 411 in the y-direction is smaller than a distance between first unit conductors 411 in the x-direction. In the resonator 10, since the pair conductors 30 can function as the electric walls, current flows in the x-direction. In the resonator 10, current flowing through the third conductor 40 in the y-direction can be ignored. The distance between the first unit conductors 411 in the y-direction can be reduced relative to the distance between the first unit conductors 411 in the x-direction. The distance between the first unit conductors 411 in the y-direction can be reduced to increase the areas of the first unit conductors 411.

Figure 60:
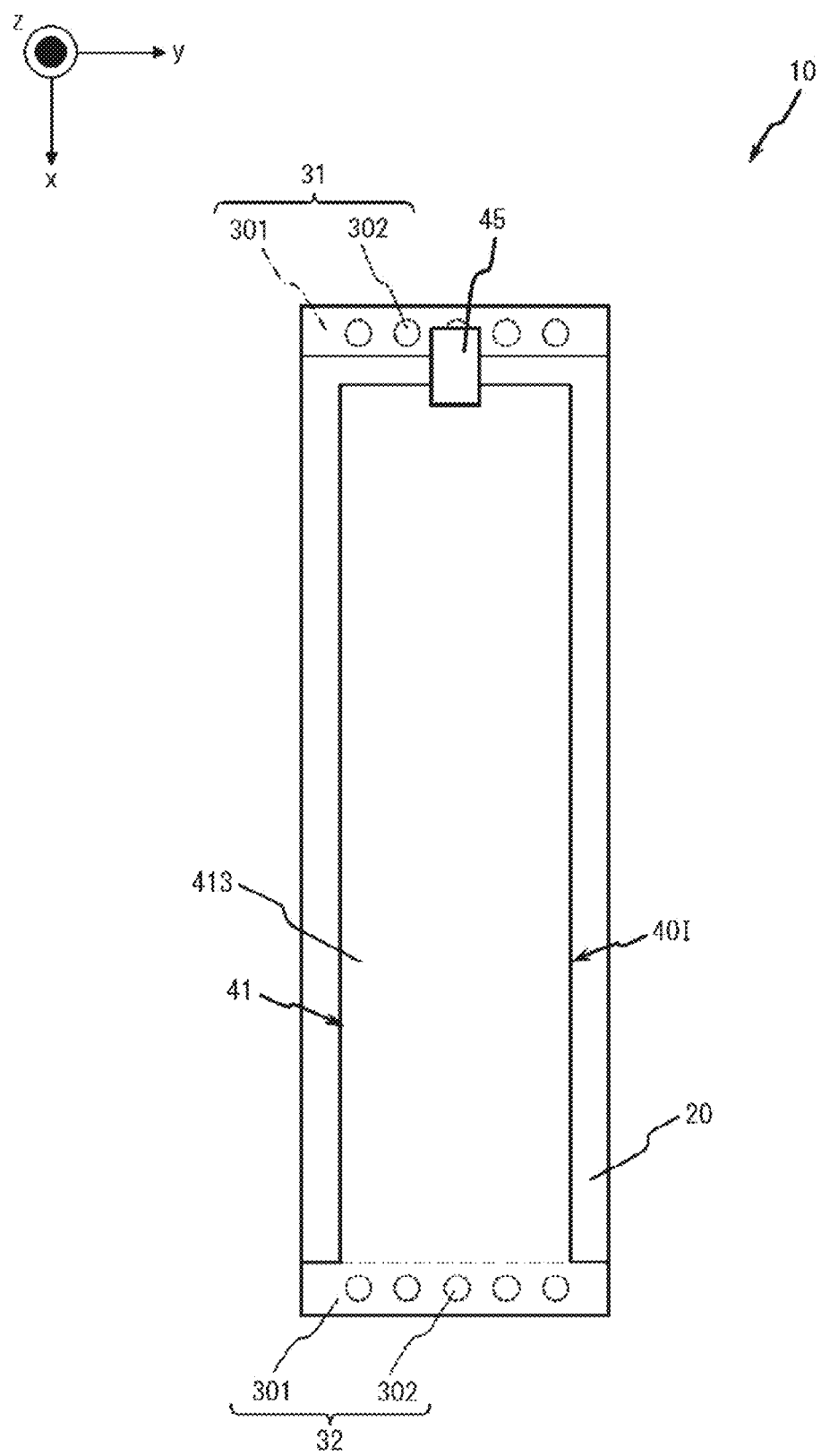
FIG. 60 is a plan view of an embodiment of the resonator.
Figure 61:
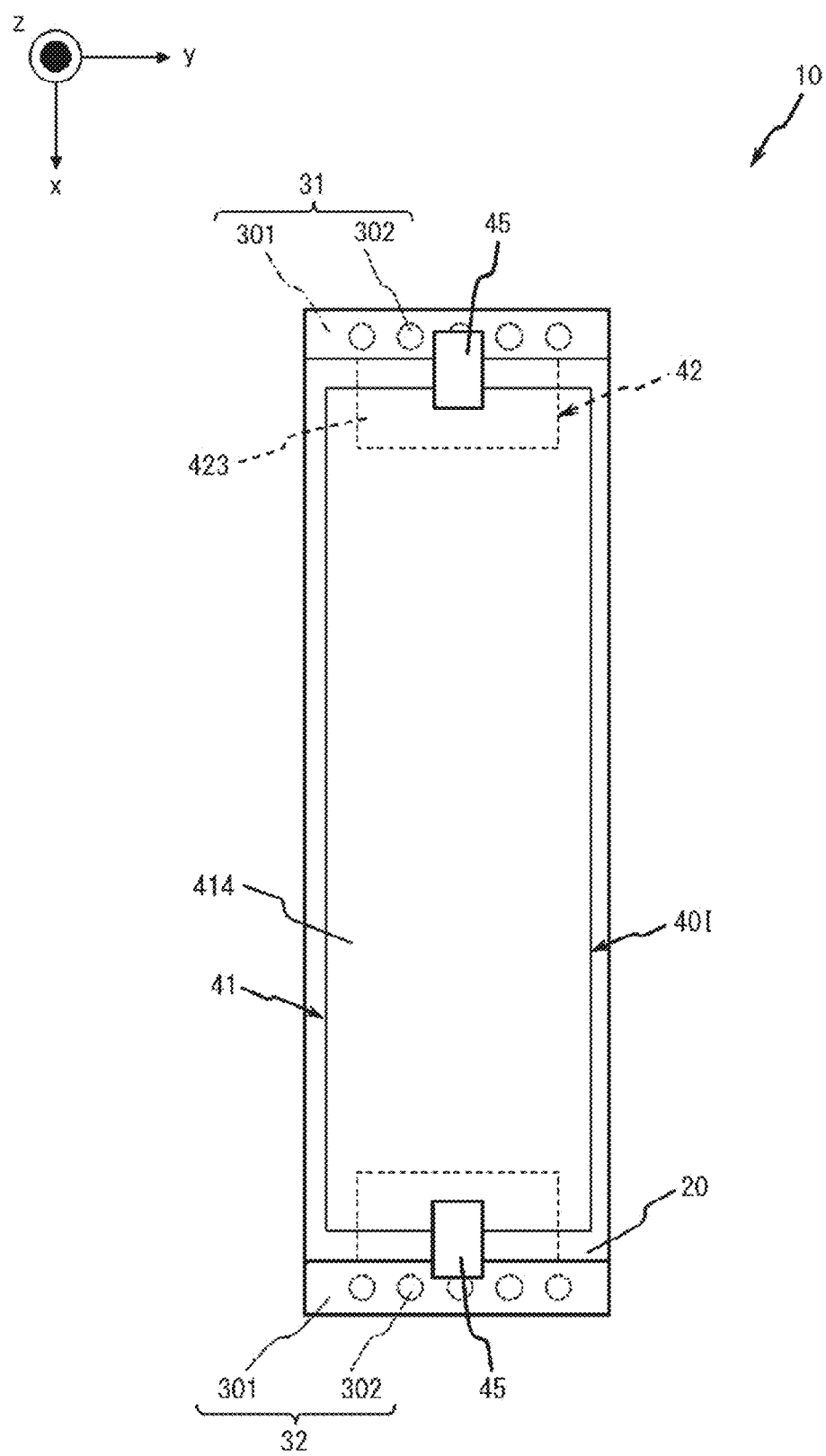
FIG. 61 is a plan view of an embodiment of the resonator.
Figure 62:
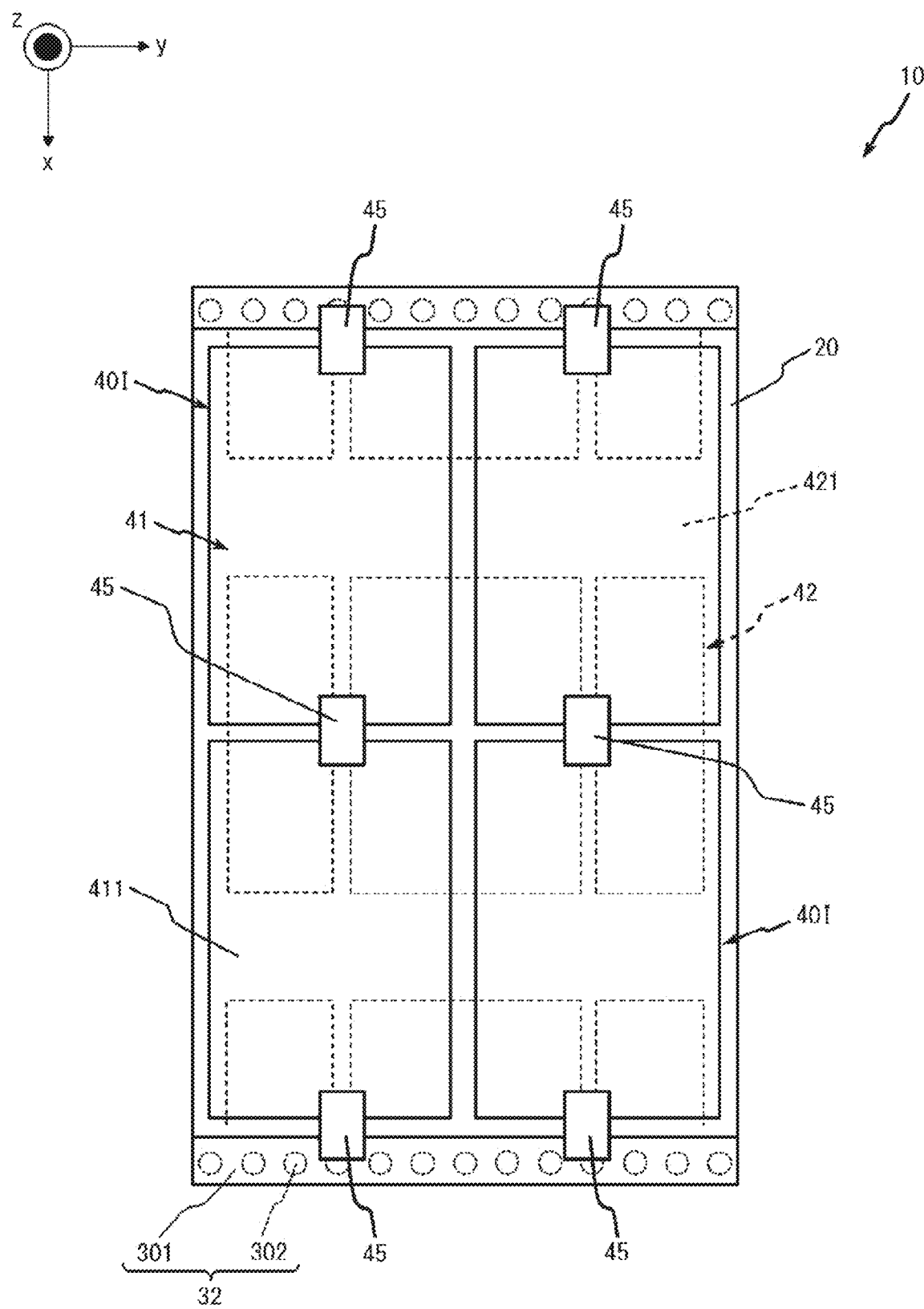
FIG. 62 is a plan view of an embodiment of the resonator.

FIGS. 60 to 62 are diagrams illustrating other examples of the resonators 10. These resonators 10 have the impedance element 45. A unit conductor to which the impedance element 45 is connected is not limited to the examples illustrated in FIGS. 60 to 62. Part of the impedance elements 45 illustrated in FIGS. 60 to 62 can be omitted. The impedance element 45 can have capacitance characteristics. The impedance element 45 can have inductance characteristics. The impedance element 45 can be a mechanical or electrical variable element. The impedance element 45 can connect two different conductors located in one layer.

An antenna has at least one of a function of radiating electromagnetic waves and a function of receiving electromagnetic waves. An antenna according to the present disclosure includes, but is not limited to, a first antenna 60 and a second antenna 70.

The first antenna 60 includes the base 20, the pair conductors 30, the third conductor 40, the fourth conductor 50, and a first feeding line 61. In an example, the first antenna 60 includes a third base 24 on the base 20. The third base 24 can have a different composition from the composition of the base 20. The third base 24 can be located above the third conductor 40. FIGS. 63 to 76 are diagrams each illustrating the first antenna 60 as an example of the plurality of embodiments.

The first feeding line 61 supplies power to at least one of resonators arranged periodically as artificial magnetic walls. In a case where power is fed to a plurality of resonators, the first antenna 60 can include a plurality of first feeding lines. The first feeding line 61 can be electromagnetically connected to any of the resonators arranged periodically as the artificial magnetic walls. The first feeding line 61 can be electromagnetically connected to any of a pair of conductors that appear as electric walls from the resonators arranged periodically as the artificial magnetic walls.

The first feeding line 61 supplies power to at least one of the first conductor 31, the second conductor 32, and the third conductor 40. In a case where power is fed to a plurality of portions of the first conductor 31, second conductor 32, and third conductor 40, the first antenna 60 can include a plurality of first feeding lines. The first feeding line 61 can be electromagnetically connected to any of the first conductor 31, second conductor 32, and third conductor 40. In a case where the first antenna 60 includes the reference potential layer 51 in addition to the fourth conductor 50, the first feeding line 61 can be electromagnetically connected to any of the first conductor 31, second conductor 32, third conductor 40, and fourth conductor 50. The first feeding line 61 is electrically connected to any of the fifth conductive layer 301 or the fifth conductor 302 of the pair conductors 30. The first feeding line 61 can be partially integrated with the fifth conductive layer 301.

The first feeding line 61 can be electromagnetically connected to the third conductor 40. For example, the first feeding line 61 is electromagnetically connected to one of first unit resonators 41X. For example, the first feeding line 61 is electromagnetically connected to one of second unit resonators 42X. The first feeding line 61 is electromagnetically connected to a unit conductor of the third conductor 40 at a point different from the center in the x-direction. In an embodiment, the first feeding line 61 supplies power to at least one resonator included in the third conductor 40. In an embodiment, the first feeding line 61 supplies power from at least one resonator included in the third conductor 40 to the outside. At least part of the first feeding line 61 can be located within the base 20. The first feeding line 61 can be exposed to the outside from any of two zx surfaces, two yz surfaces, and two xy surfaces of the base 20.

The first feeding line 61 can make contact with the third conductor 40 in a forward direction and reverse direction of the z-direction. The fourth conductor 50 can be omitted around the first feeding line 61. The first feeding line 61 can be electromagnetically connected to the third conductor 40 through the opening of the fourth conductor 50. The first conductive layer 41 can be omitted around the first feeding line 61. The first feeding line 61 can be connected to the second conductive layer 42 through the opening of the first conductive layer 41. The first feeding line 61 can make contact with the third conductor 40 along the xy plane. The pair conductors 30 can be omitted around the first feeding line 61. The first feeding line 61 can be connected to the third conductor 40 through the openings of the pair conductors 30. The first feeding line 61 is connected to a unit conductor of the third conductor 40, apart from the center of the unit conductor.

Figure 63:
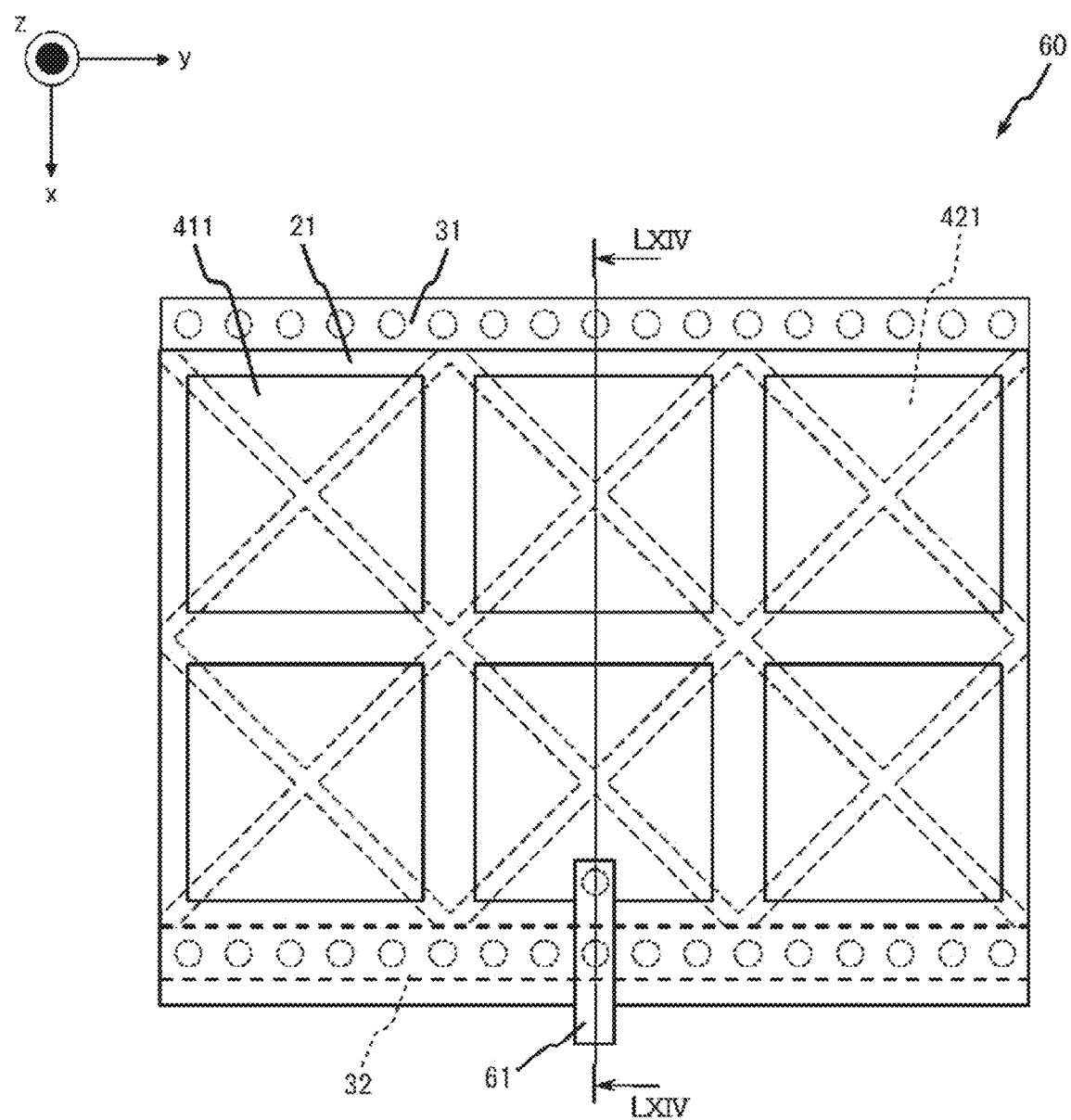
FIG. 63 is a plan view of an embodiment of an antenna.
Figure 64:
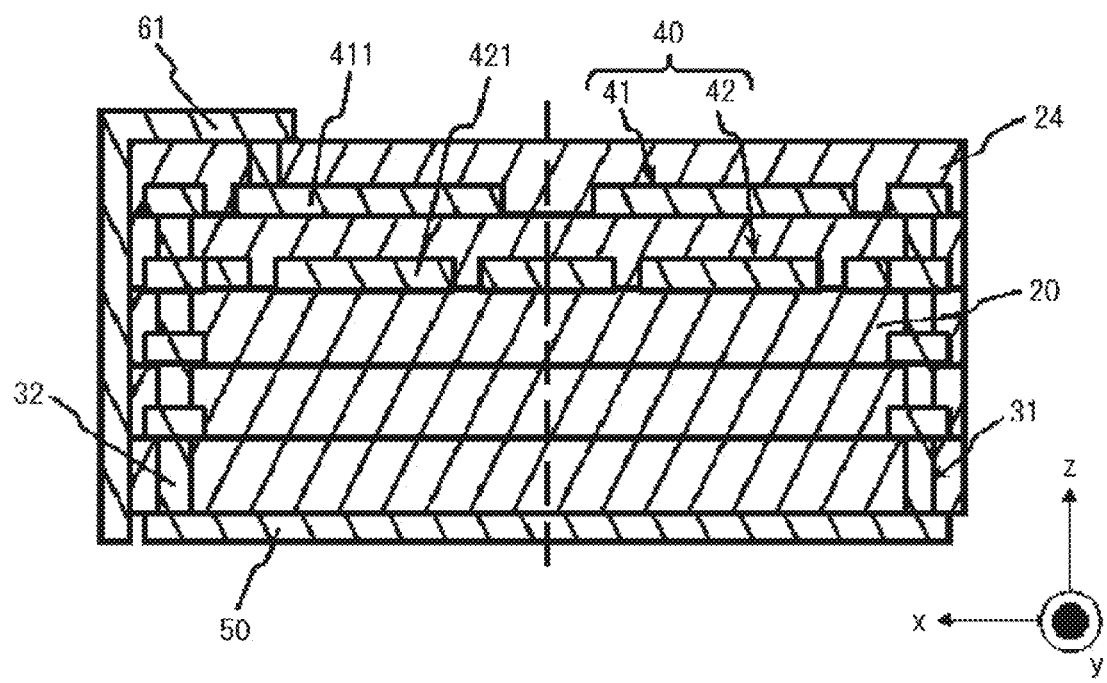
FIG. 64 is a sectional view illustrating an embodiment of the antenna.

FIG. 63 is a plan view of the first antenna 60 in the xy plane, as viewed in the z-direction. FIG. 64 is a cross-sectional view taken along line LXIV-LXIV illustrated in FIG. 63. The first antenna 60 illustrated in FIGS. 63 and 64 includes the third base 24 above the third conductor 40. The third base 24 has an opening above the first conductive layer 41. The first feeding line 61 is electrically connected to the first conductive layer 41 via the opening of the third base 24.

Figure 65:
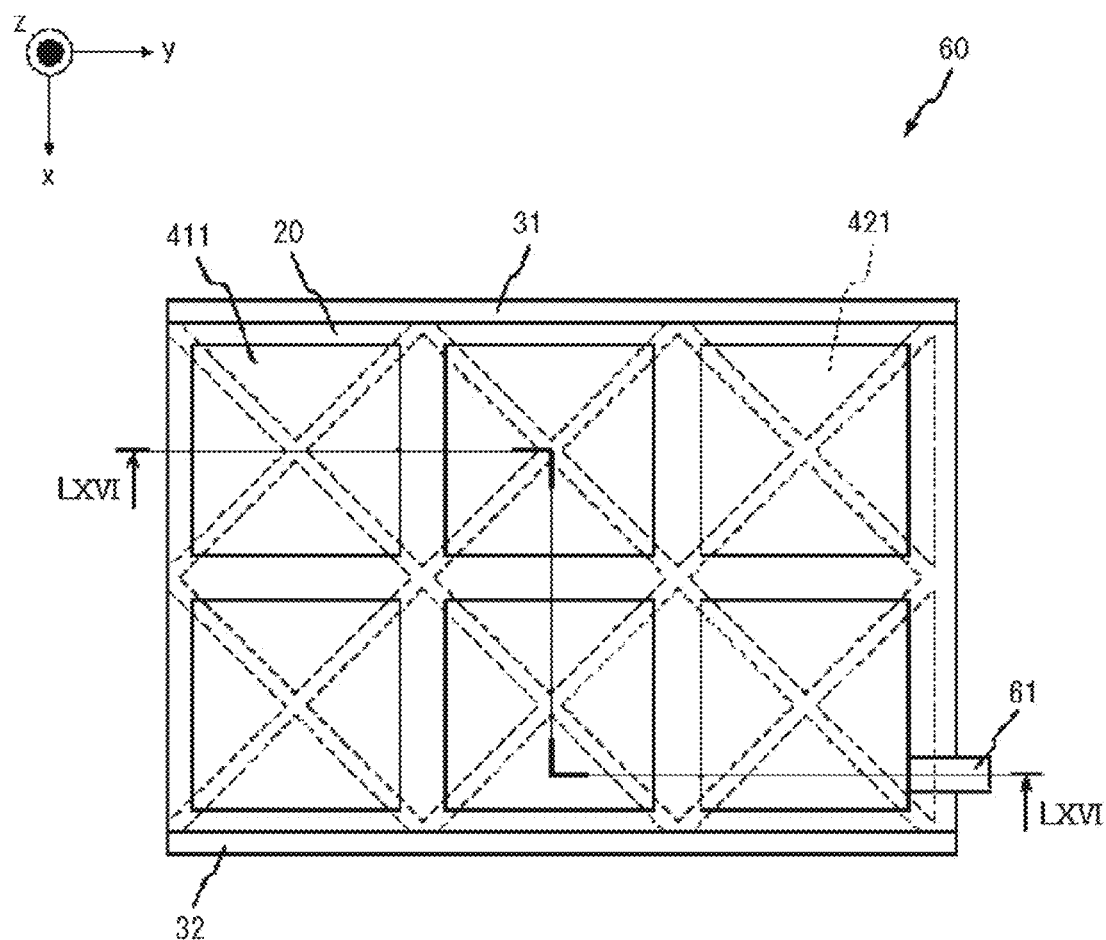
FIG. 65 is a plan view of an embodiment of the antenna.
Figure 66:
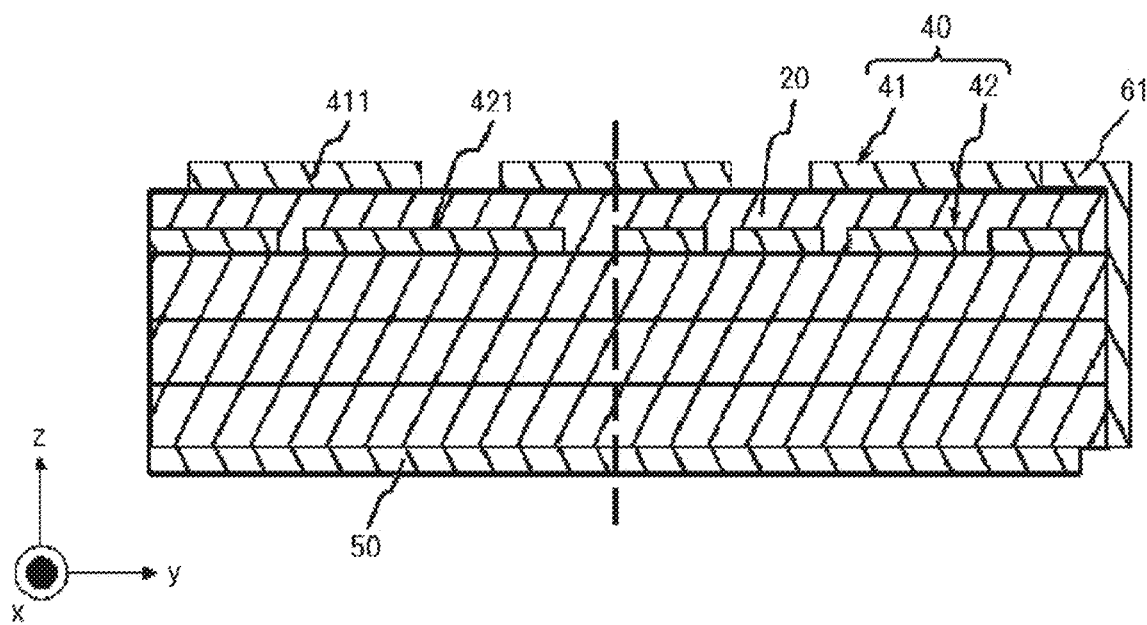
FIG. 66 is a sectional view illustrating an embodiment of the antenna.

FIG. 65 is a plan view of the first antenna 60 in the xy plane, as viewed in the z-direction. FIG. 66 is a cross-sectional view taken along line LXVI-LXVI illustrated in FIG. 65. In the first antenna 60 illustrated in FIGS. 65 and 66, the first feeding line 61 is partially located on the base 20. The first feeding line 61 can be connected to the third conductor 40 in the xy plane. The first feeding line 61 can be connected to the first conductive layer 41 in the xy plane. In an embodiment, the first feeding line 61 can be connected to the second conductive layer 42 in the xy plane.

Figure 67:
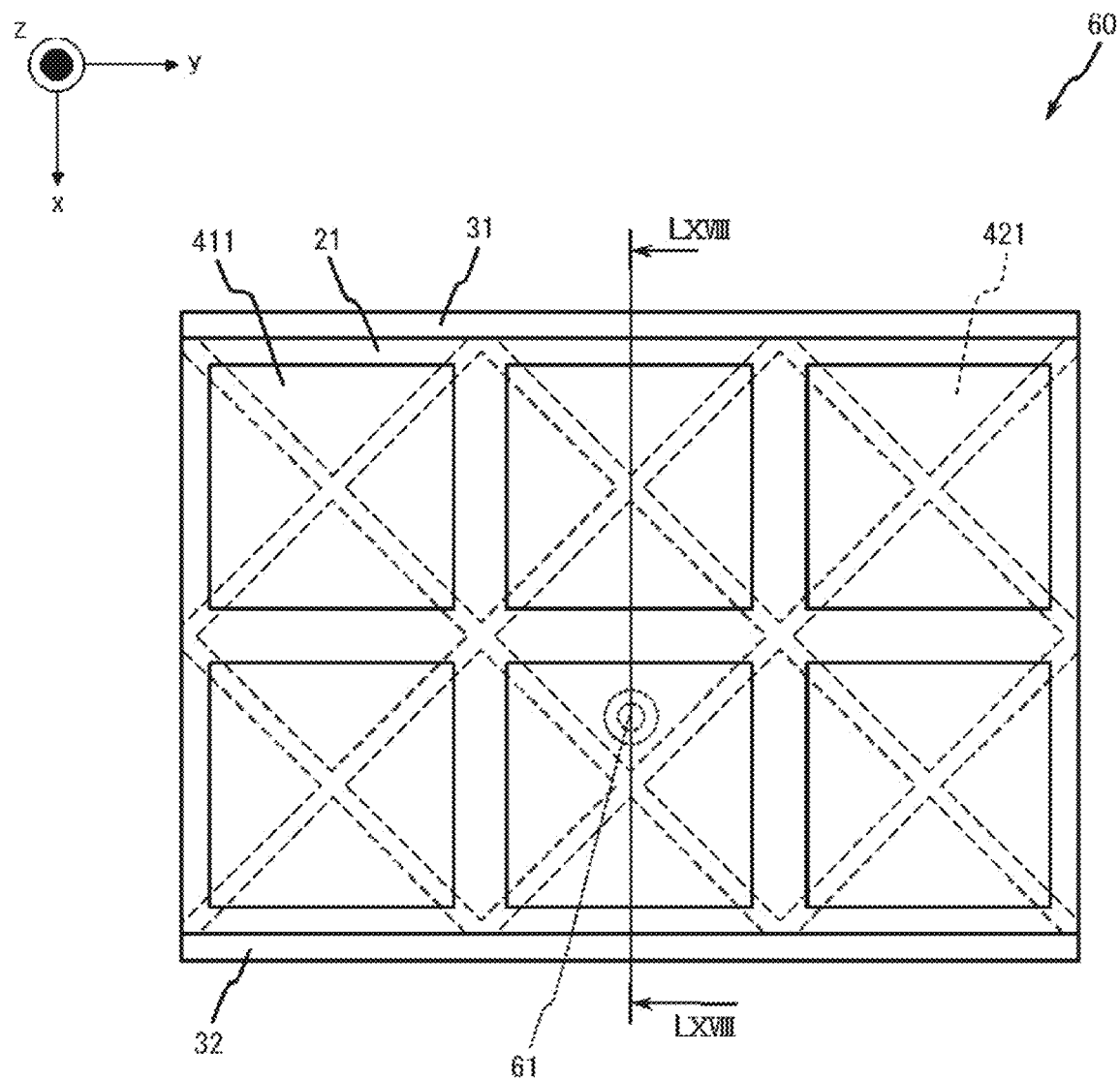
FIG. 67 is a plan view of an embodiment of the antenna.
Figure 68:
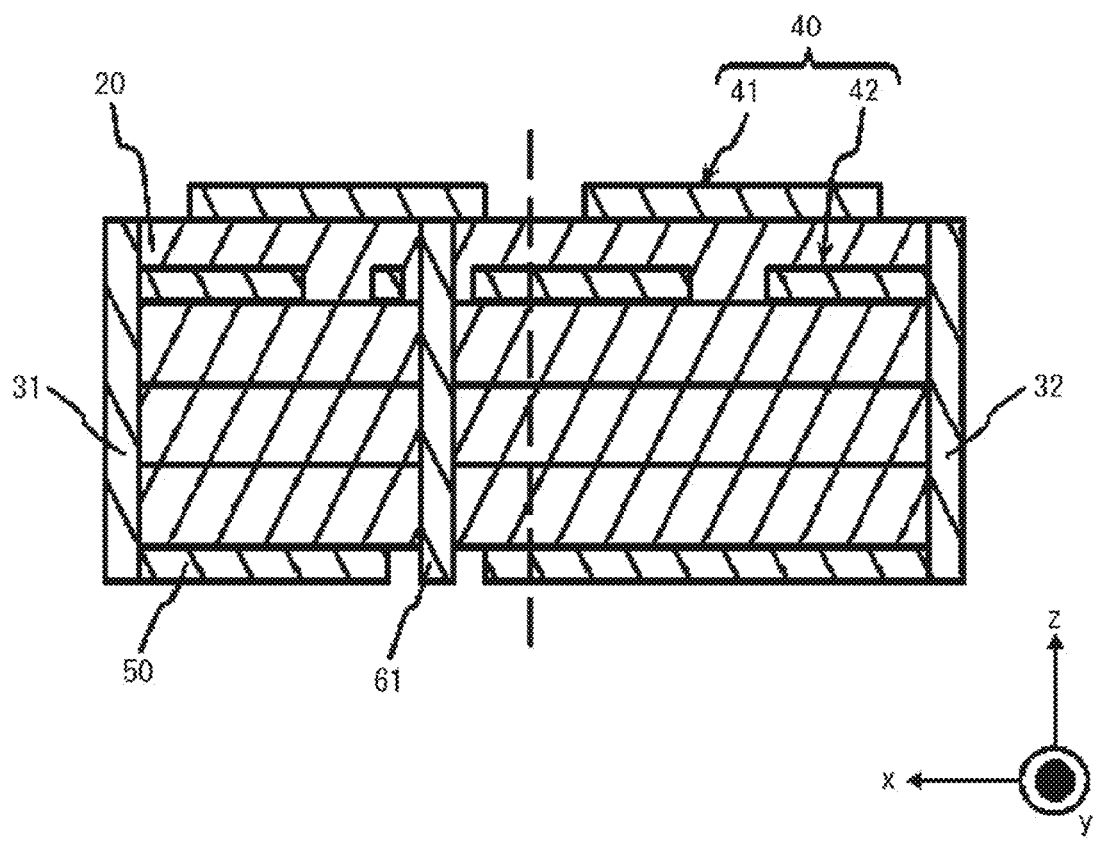
FIG. 68 is a sectional view illustrating an embodiment of the antenna.

FIG. 67 is a plan view of the first antenna 60 in the xy plane, as viewed in the z-direction. FIG. 68 is a cross-sectional view taken along line LXVIII-LXVIII illustrated in FIG. 67. In the first antenna 60 illustrated in FIGS. 67 and 68, the first feeding line 61 is located within the base 20. The first feeding line 61 can be connected to the third conductor 40 in a reverse direction of the z-direction. The fourth conductor 50 can have an opening. The fourth conductor 50 can have an opening at a position where the fourth conductor 50 overlaps the third conductor 40 in the z-direction. The first feeding line 61 can be exposed to the outside of the base 20 through the opening.

Figure 69:
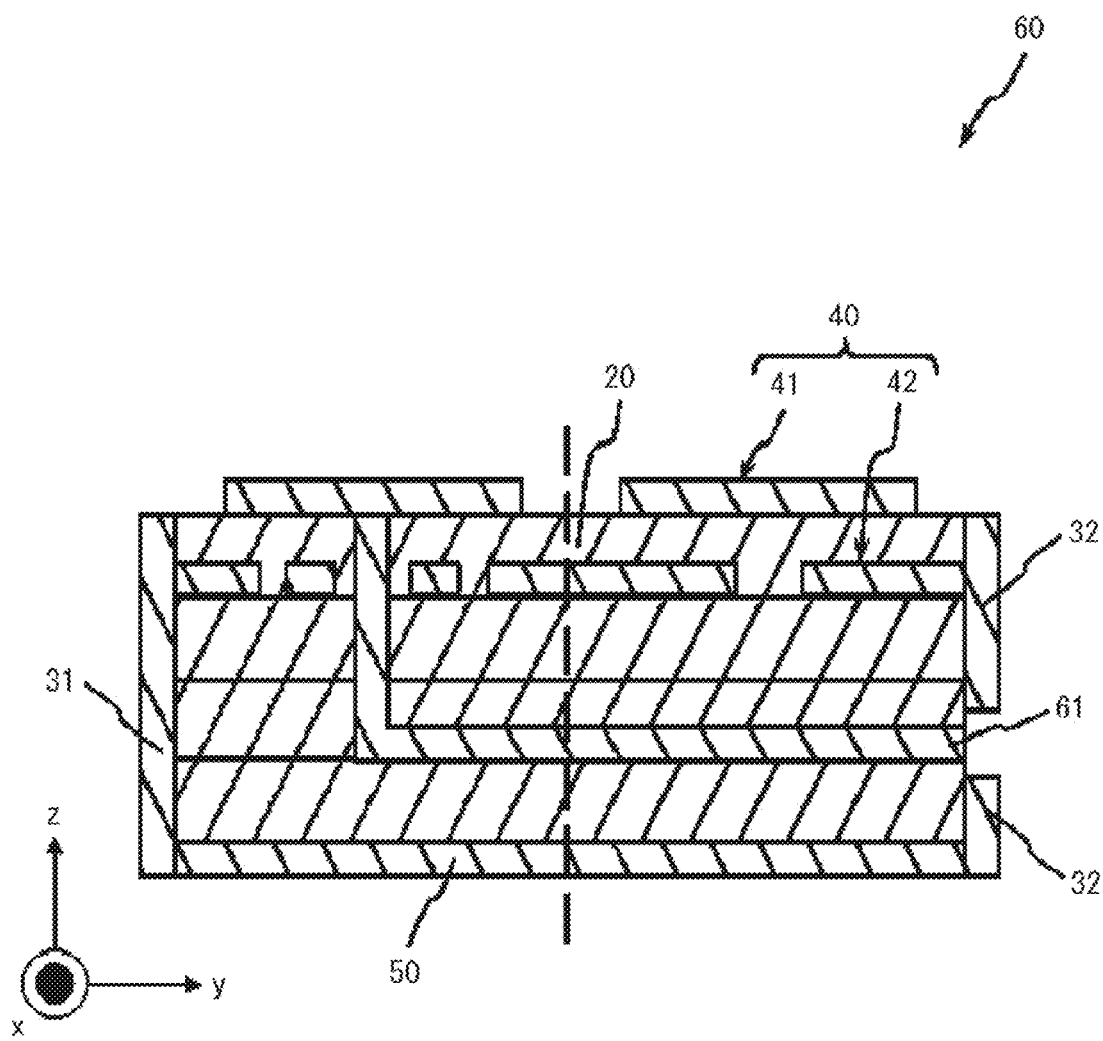
FIG. 69 is a sectional view illustrating an embodiment of the antenna.

FIG. 69 is a cross-sectional view of the first antenna 60 as viewed in the yz plane in the x-direction. The pair conductors 30 can have an opening. The first feeding line 61 can be exposed to the outside of the base 20 through the opening.

An electromagnetic wave radiated by the first antenna 60 has a polarization component in the x-direction that is larger than that in the y-direction, in the first plane. The polarization component in the x-direction has less attenuation than a horizontal polarization component when a metal plate approaches the fourth conductor 50 in the z-direction. The first antenna 60 can maintain radiation efficiency when a metal plate approaches from outside.

Figure 70:
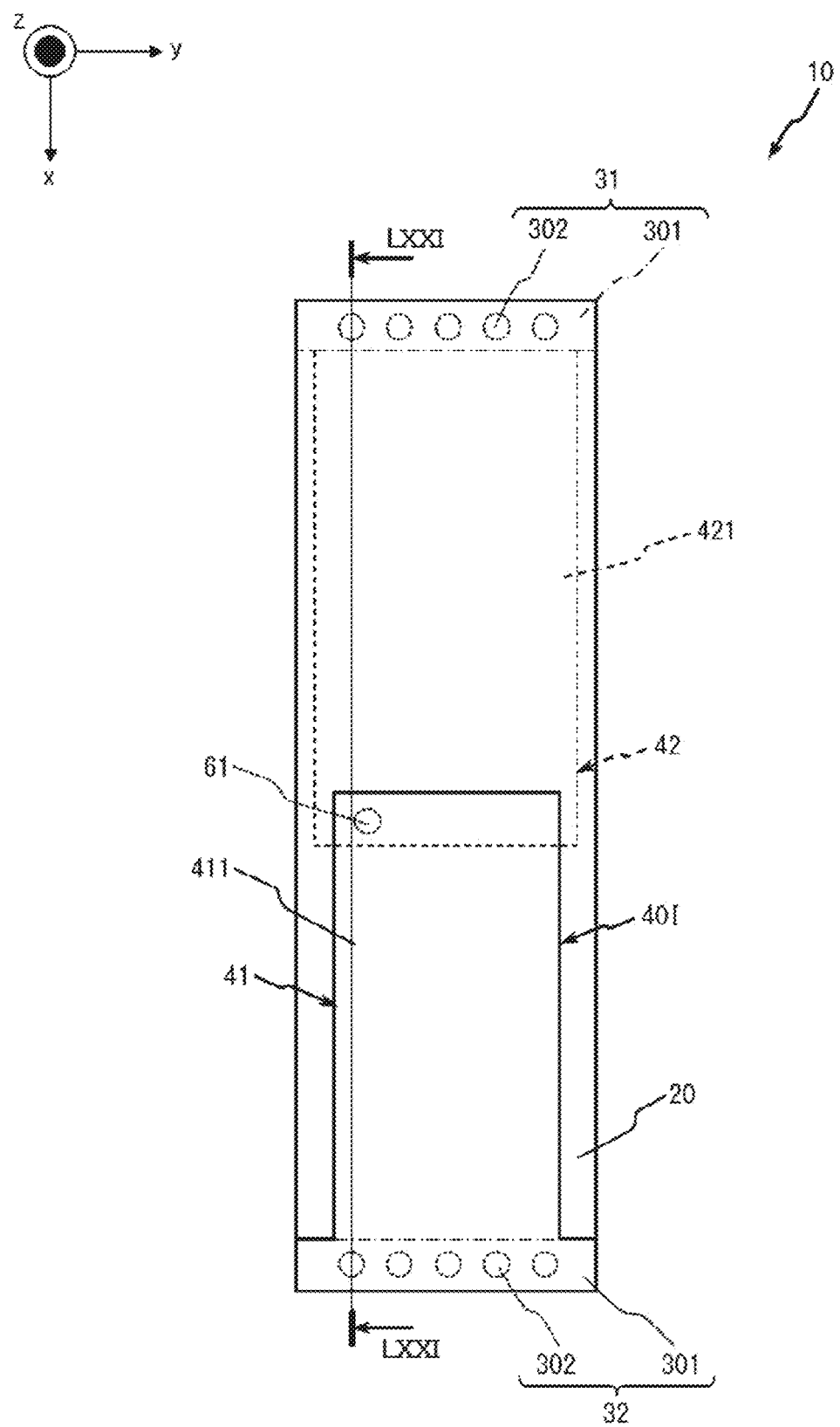
FIG. 70 is a plan view of an embodiment of the antenna.
Figure 71:
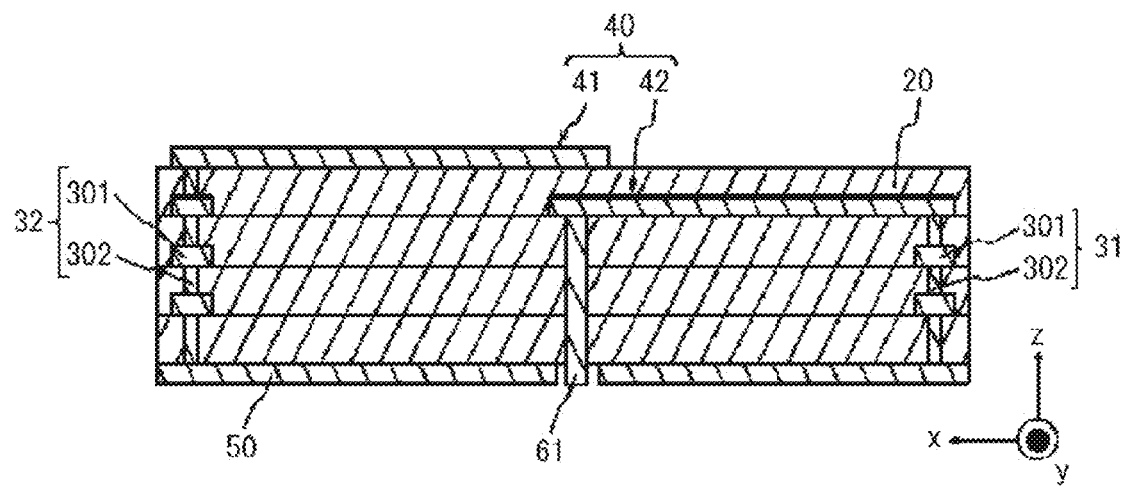
FIG. 71 is a sectional view illustrating an embodiment of the antenna.
Figure 72:
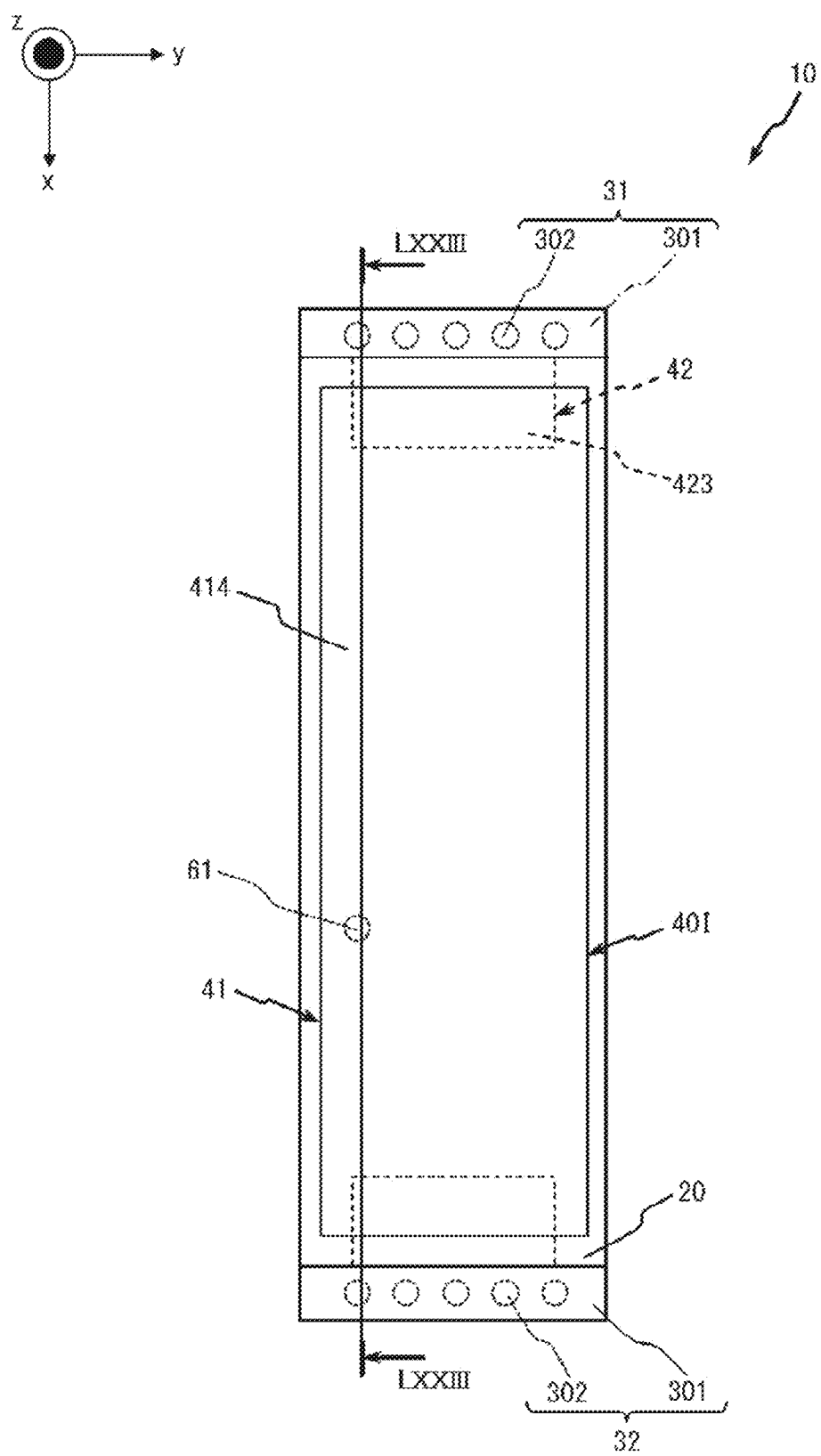
FIG. 72 is a plan view of an embodiment of the antenna.
Figure 73:
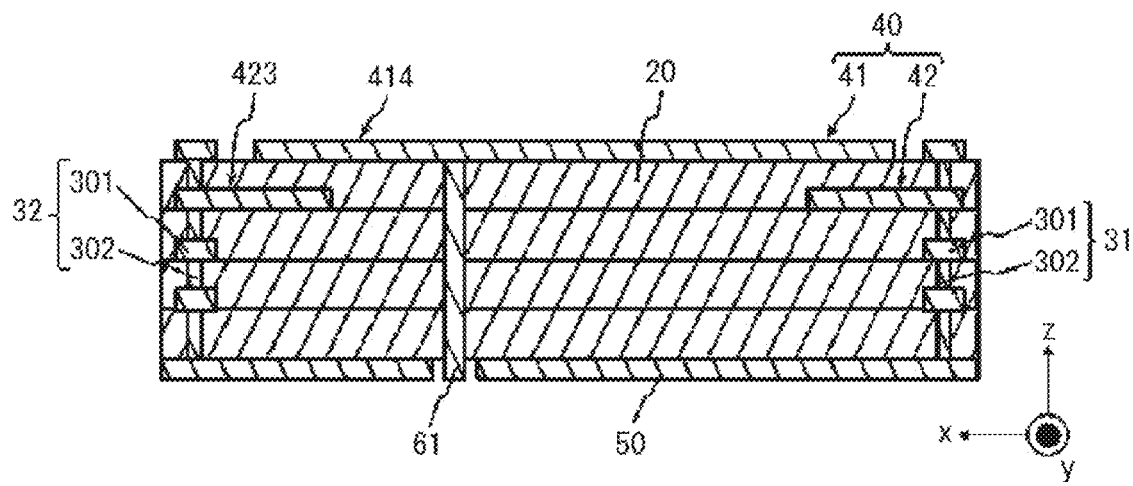
FIG. 73 is a sectional view illustrating an embodiment of the antenna.
Figure 74:
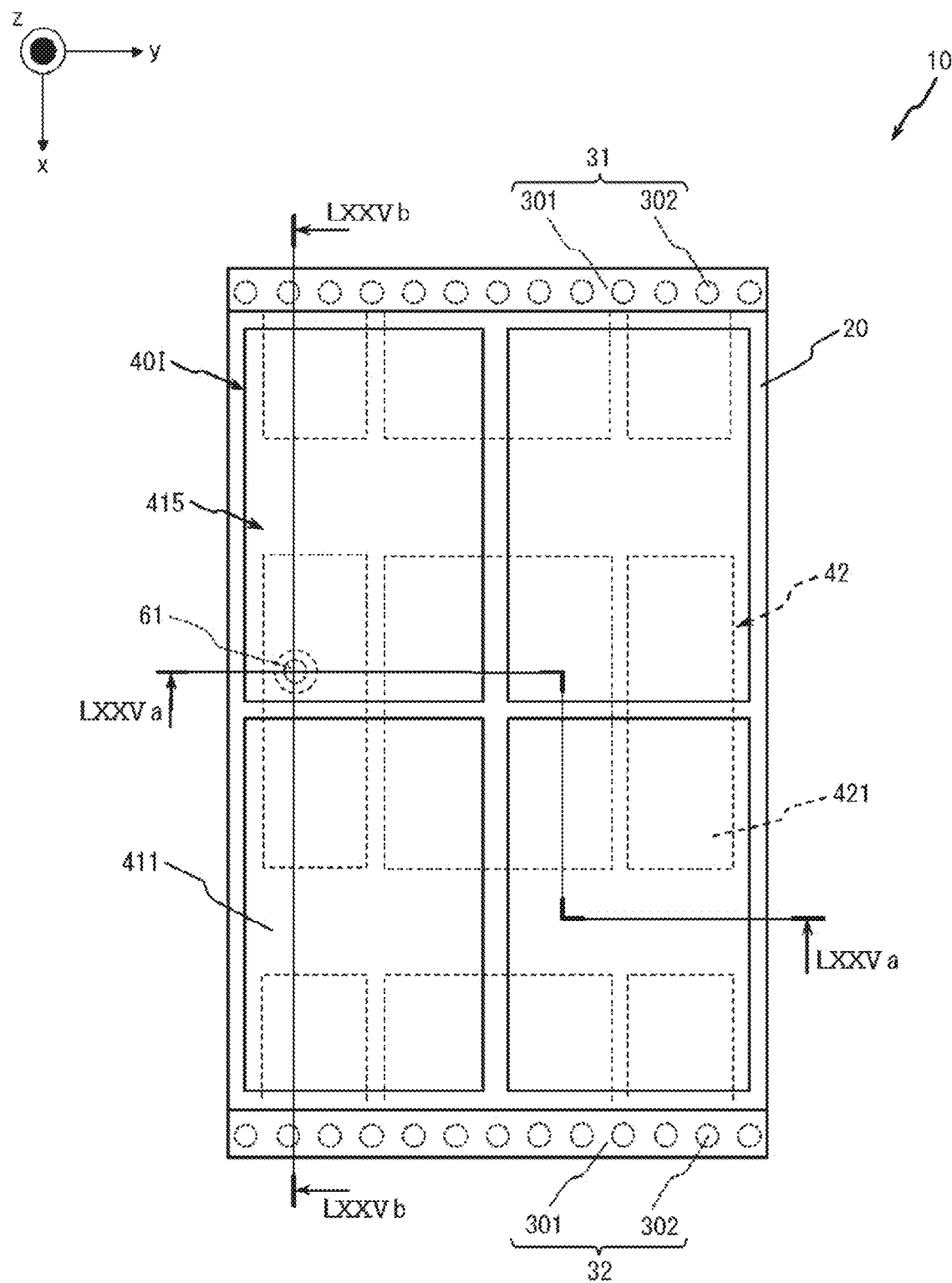
FIG. 74 is a plan view of an embodiment of the antenna.
Figure 75A:
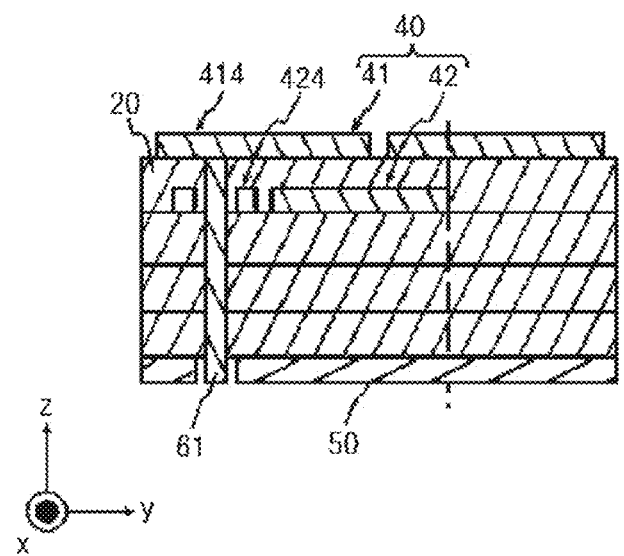
FIG. 75A is a sectional view illustrating an embodiment of the antenna.
Figure 75B:
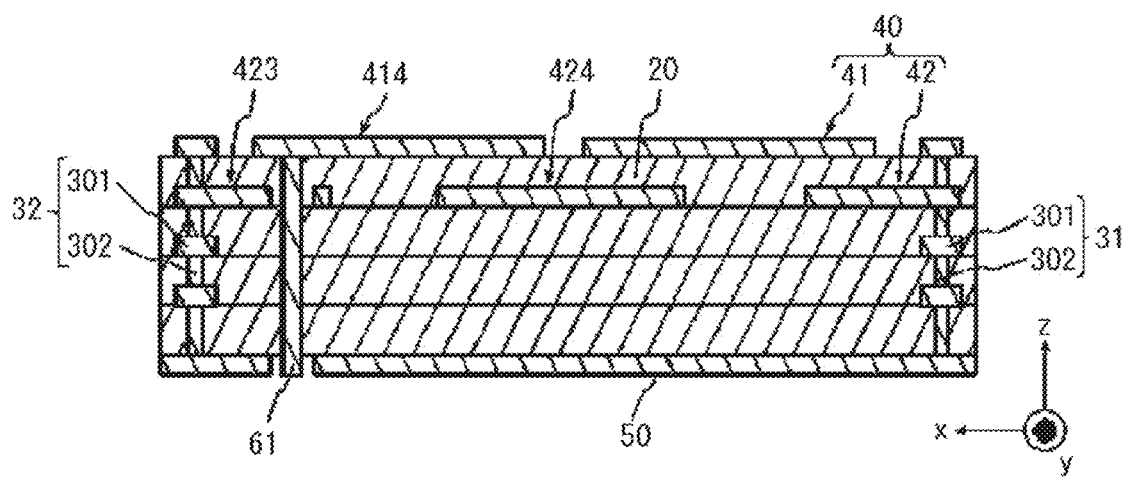
FIG. 75B is a sectional view illustrating an embodiment of the antenna.
Figure 76:
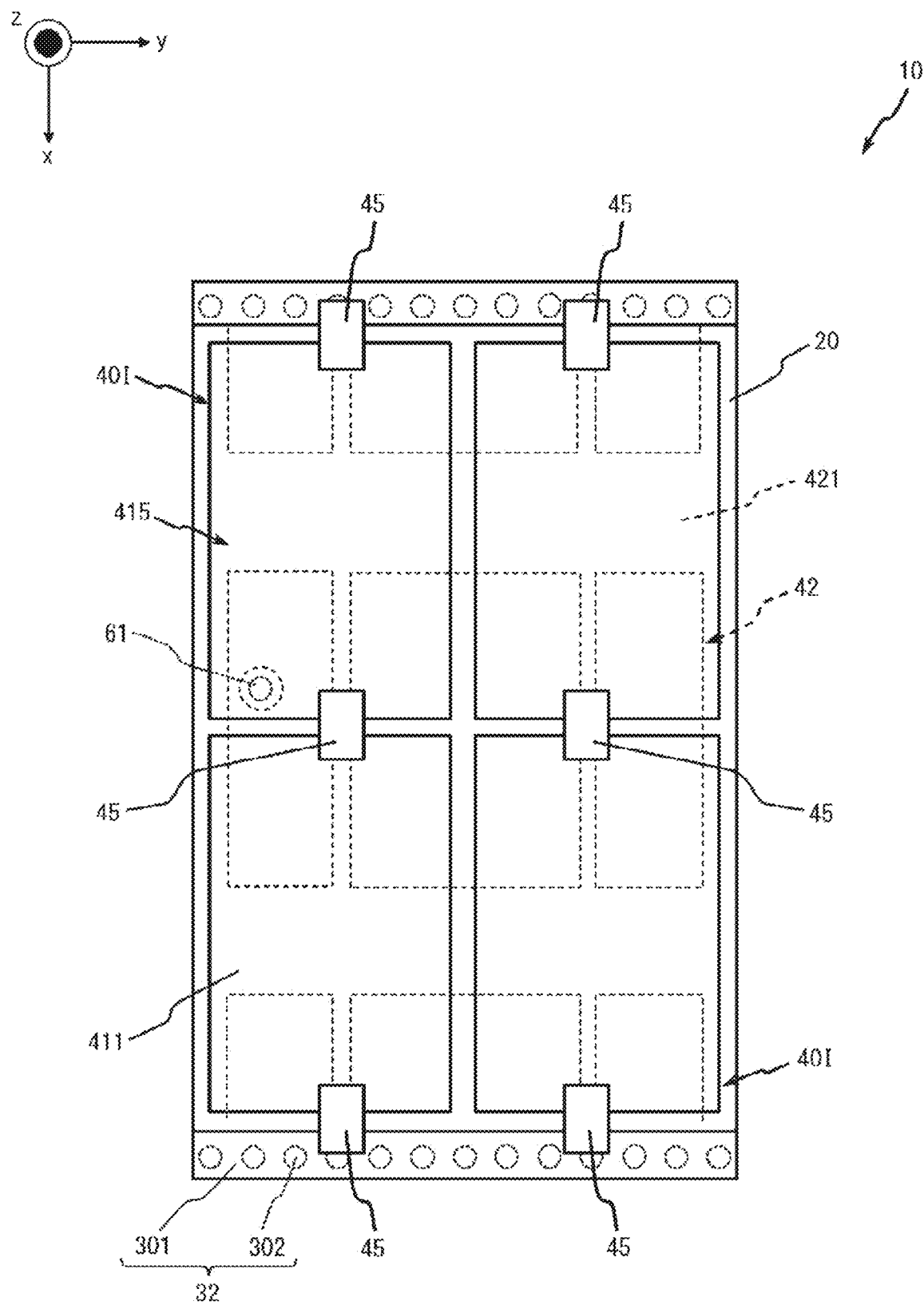
FIG. 76 is a plan view of an embodiment of the antenna.

FIG. 70 illustrates another example of the first antenna 60. FIG. 71 is a cross-sectional view taken along line LXXI-LXXI illustrated in FIG. 70. FIG. 72 illustrates another example of the first antenna 60. FIG. 73 is a cross-sectional view taken along line LXXIII-LXXIII illustrated in FIG. 72. FIG. 74 illustrates another example of the first antenna 60. FIG. 75A is a cross-sectional view taken along line LXXVa-LXXVa illustrated in FIG. 74. FIG. 75B is a cross-sectional view taken along line LXXVb-LXXVb illustrated in FIG. 74. FIG. 76 illustrates another example of the first antenna 60. The first antenna 60 illustrated in FIG. 76 has an impedance element 45.

The operating frequency of the first antenna 60 can be changed by the impedance element 45. The first antenna 60 includes a first feeding conductor 415 that is connected to the first feeding line 61 and the first unit conductor 411 that is not connected to the first feeding line 61. Impedance matching changes when the impedance element 45 is connected to the first feeding conductor 415 and another conductive member. In the first antenna 60, the impedance matching can be adjusted by connecting the first feeding conductor 415 and another conductive member by the impedance element 45. In the first antenna 60, the impedance element 45 can be inserted between the first feeding conductor 415 and the other conductive member to adjust the impedance matching. In the first antenna 60, the impedance element 45 can be inserted between two first unit conductors 411 that are not connected to the first feeding line 61 to adjust the operating frequency. In the first antenna 60, the impedance element 45 can be inserted between the first unit conductor 411 that is not connected to the first feeding line 61 and any of the pair conductors 30 to adjust the operating frequency.

The second antenna 70 includes the base 20, the pair conductors 30, the third conductor 40, the fourth conductor 50, a second feeding layer 71, and a second feeding line 72. In an example, the third conductor 40 is located within the base 20. In an example, the second antenna 70 includes the third base 24 above the base 20. The third base 24 can have a different composition from the composition of the base 20. The third base 24 can be located above the third conductor 40. The third base 24 can be located above the second feeding layer 71.

The second feeding layer 71 is spaced above the third conductor 40. The base 20 or the third base 24 can be located between the second feeding layer 71 and the third conductor 40. The second feeding layer 71 includes a line resonator, patch resonator, and slot resonator. The second feeding layer 71 can be referred to as an antenna element. In an example, the second feeding layer 71 can be electromagnetically coupled to the third conductor 40. The second feeding layer 71 has a resonant frequency that changes from a single resonant frequency due to the electromagnetic coupling to the third conductor 40. In an example, the second feeding layer 71 receives power transmitted from the second feeding line 72 and resonates with the third conductor 40. In an example, the second feeding layer 71 receives power transmitted from the second feeding line 72 and resonates with the third conductor 40 and the third conductor.

The second feeding line 72 is electrically connected to the second feeding layer 71. In an embodiment, the second feeding line 72 transmits power to the second feeding layer 71. In an embodiment, the second feeding line 72 transmits power from the second feeding layer 71 to the outside.

Figure 77:
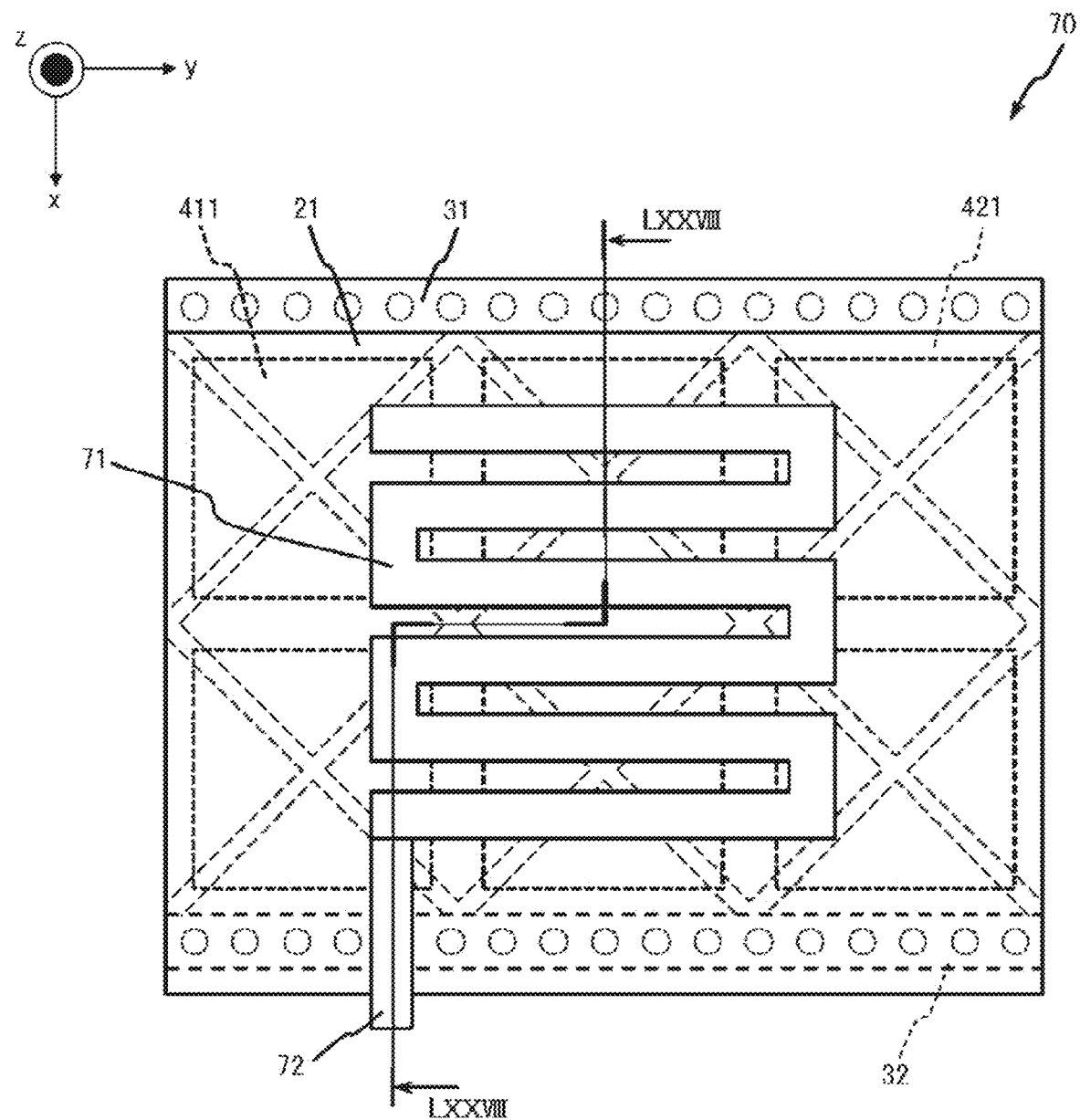
FIG. 77 is a plan view of an embodiment of the antenna.
Figure 78:
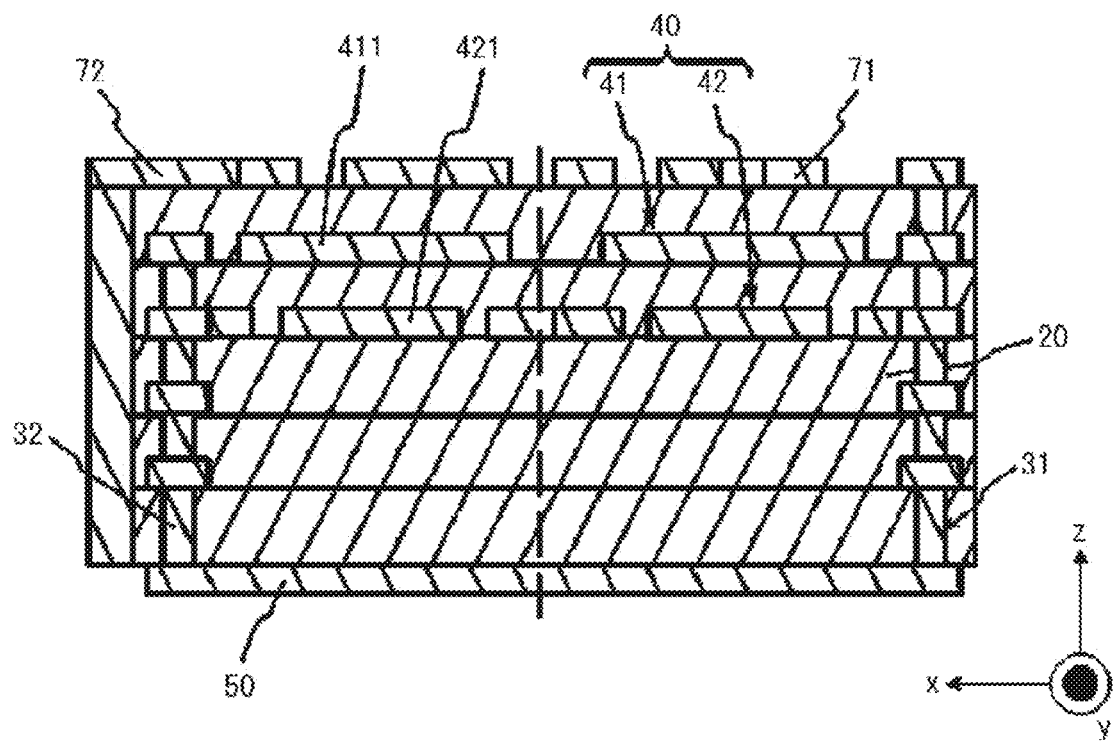
FIG. 78 is a sectional view of the antenna illustrated in FIG. 43.

FIG. 77 is a plan view of the second antenna 70 in the xy plane, as viewed in the z-direction. FIG. 78 is a cross-sectional view taken along line LXXVIII-LXXVIII illustrated in FIG. 77. In the second antenna 70 illustrated in FIGS. 77 and 78, the third conductor 40 is located within the base 20. The second feeding layer 71 is located above the base 20. The second feeding layer 71 is located so as to overlap a unit structure 10X in the z-direction. The second feeding line 72 is located on the base 20. The second feeding line 72 is electromagnetically connected to the second feeding layer 71 in the xy plane.

Figure 79:
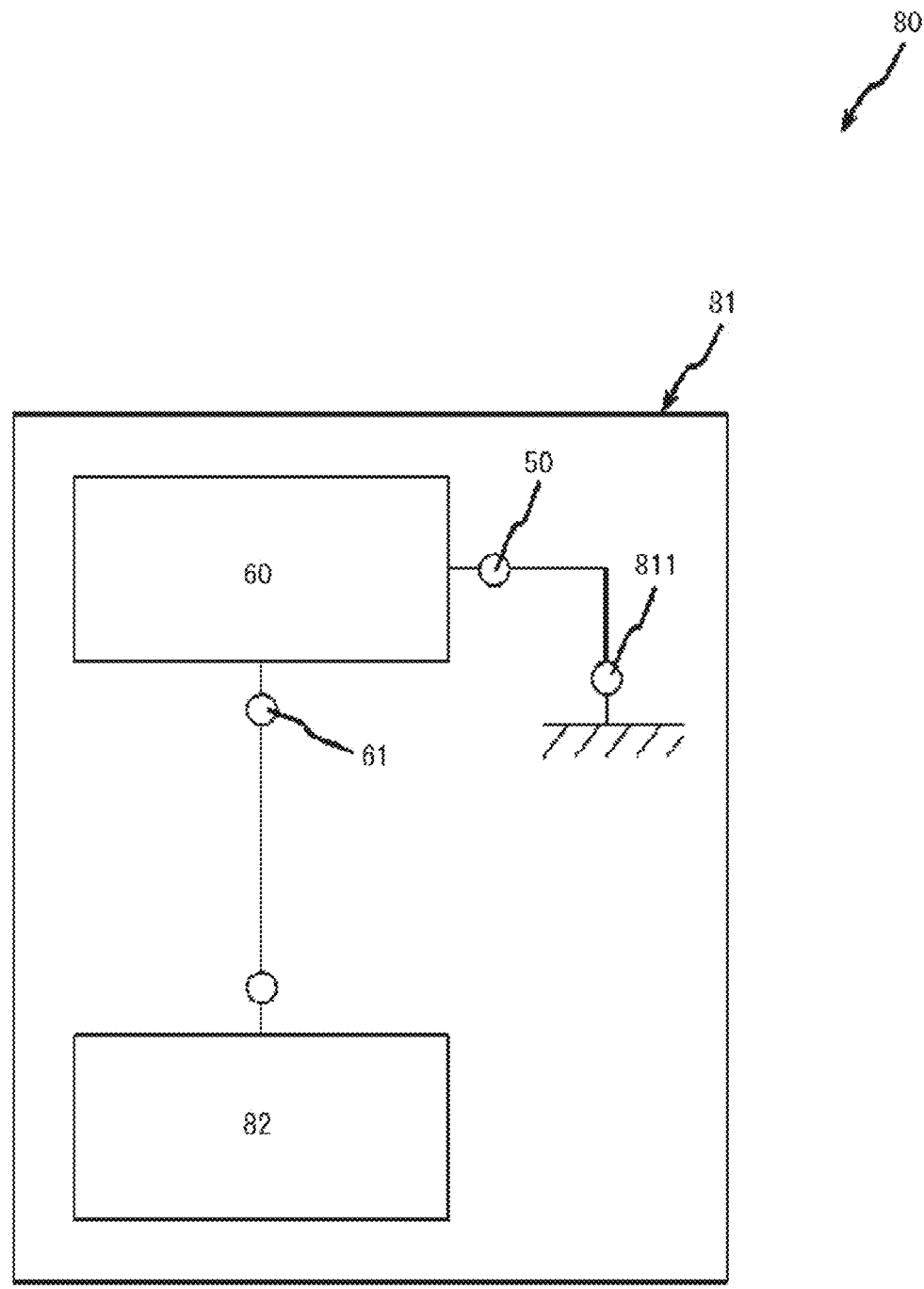
FIG. 79 is a block diagram illustrating an embodiment of a wireless communication module.
Figure 80:
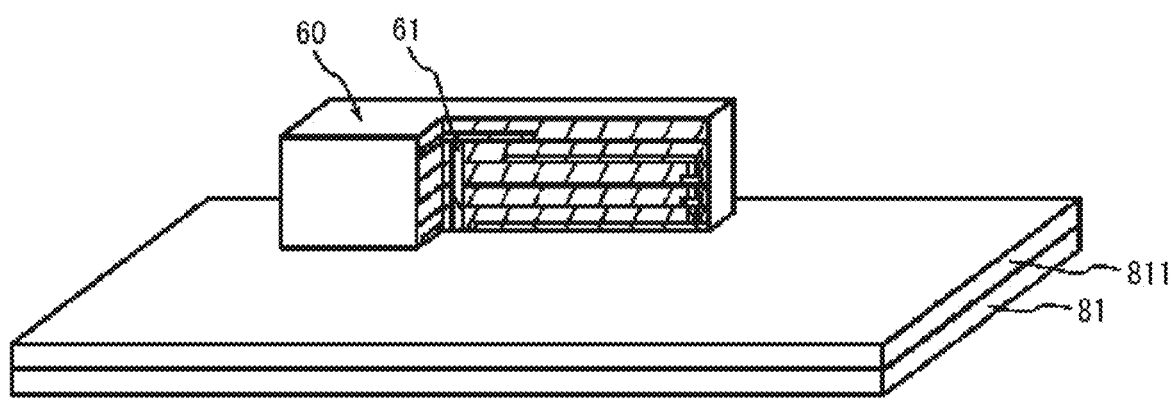
FIG. 80 is a partial sectional perspective view illustrating an embodiment of the wireless communication module.

A wireless communication module according to the present disclosure includes a wireless communication module 80 as an example of the plurality of embodiments. FIG. 79 is a block structural diagram of the wireless communication module 80. FIG. 80 is a schematic configuration diagram of the wireless communication module 80. The wireless communication module 80 includes the first antenna 60, a circuit board 81, and an RF module 82. The wireless communication module 80 can include the second antenna 70 instead of the first antenna 60.

The first antenna 60 is located on the circuit board 81. The first antenna 60 includes the first feeding line 61 that is electromagnetically connected to the RF module 82 via the circuit board 81. The first antenna 60 includes the fourth conductor 50 that is electromagnetically connected to a ground conductor 811 of the circuit board 81.

The ground conductor 811 can extend in the xy plane. The ground conductor 811 has a larger area than the fourth conductor 50, in the xy plane. The ground conductor 811 has a larger length than the fourth conductor 50, in the y-direction. The ground conductor 811 has a larger length than the fourth conductor 50, in the x-direction. The first antenna 60 can be located closer to an end side relative to the center of the ground conductor 811, in the y-direction. The center of the first antenna 60 may not coincide with the center of the ground conductor 811 in the xy plane. The center of the first antenna 60 may not coincide with the centers of a first conductive layer 41 and second conductive layer 42. A point at which the first feeding line 61 is connected to the third conductor 40 may not coincide with the center of the ground conductor 811 in the xy plane.

In the first antenna 60, first current and second current flow in a loop via the pair conductors 30. The first antenna 60 is located on the end side in the y-direction relative to the center of the ground conductor 811, and thus, the second current flowing through the ground conductor 811 becomes asymmetric. When the flow of the second current through the ground conductor 811 becomes asymmetric, the polarization component of a radiation wave in the x-direction is increased, in an antenna structure including the first antenna 60 and the ground conductor 811. The increased polarization component of the radiation wave in the x-direction can improve the total radiation efficiency of the radiation wave.

The RF module 82 can control power supplied to the first antenna 60. The RF module 82 modulates a baseband signal and supplies the baseband signal to the first antenna 60. The RF module 82 can modulate an electric signal received by the first antenna 60 into a baseband signal.

A change in the resonant frequency of the first antenna 60 is small due to a conductor of the circuit board 81 side. The first antenna 60 of the wireless communication module 80 can reduce the influence from an external environment.

The first antenna 60 can be integrated with the circuit board 81. When the first antenna 60 and the circuit board 81 are integrally configured, the fourth conductor 50 and the ground conductor 811 are integrally configured.

Figure 81:
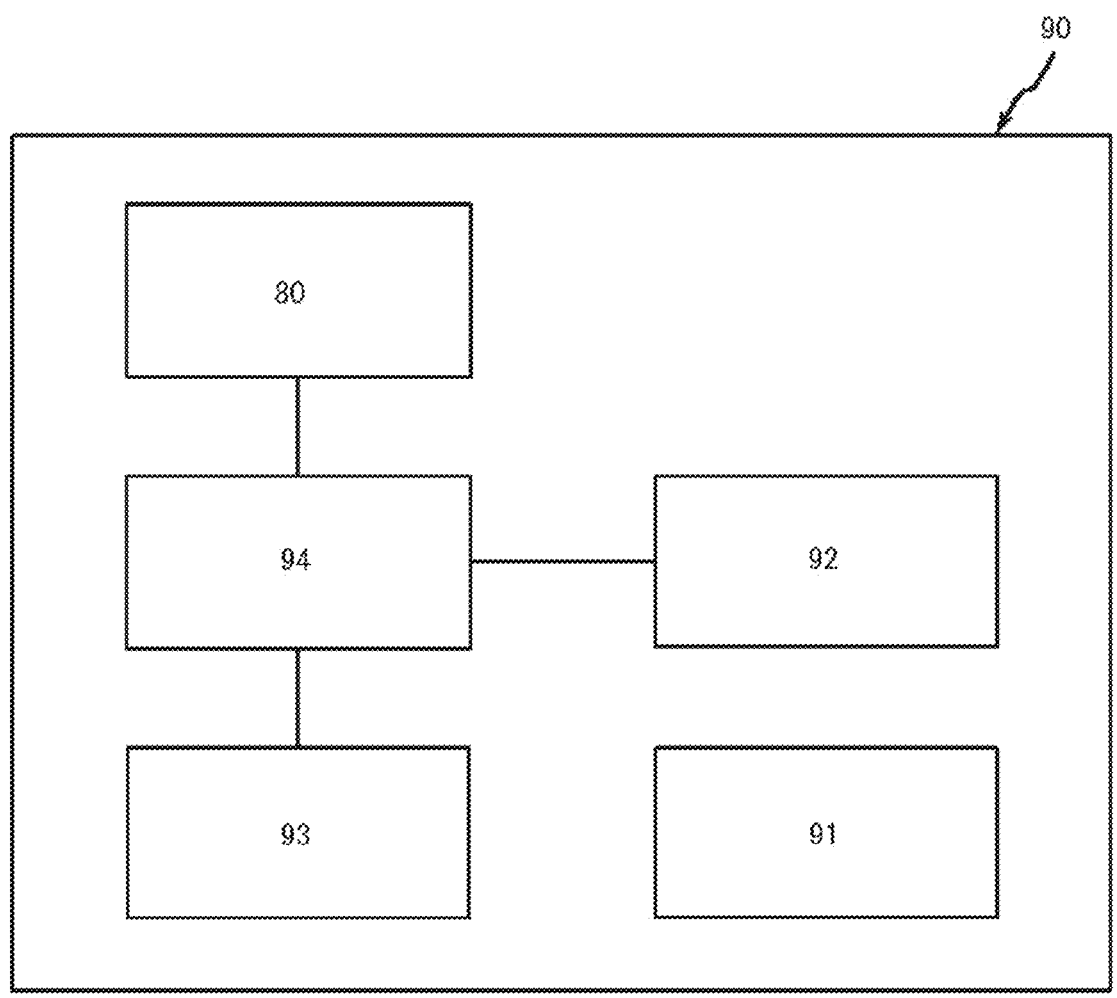
FIG. 81 is a block diagram illustrating an embodiment of a wireless communication device.
Figure 82:
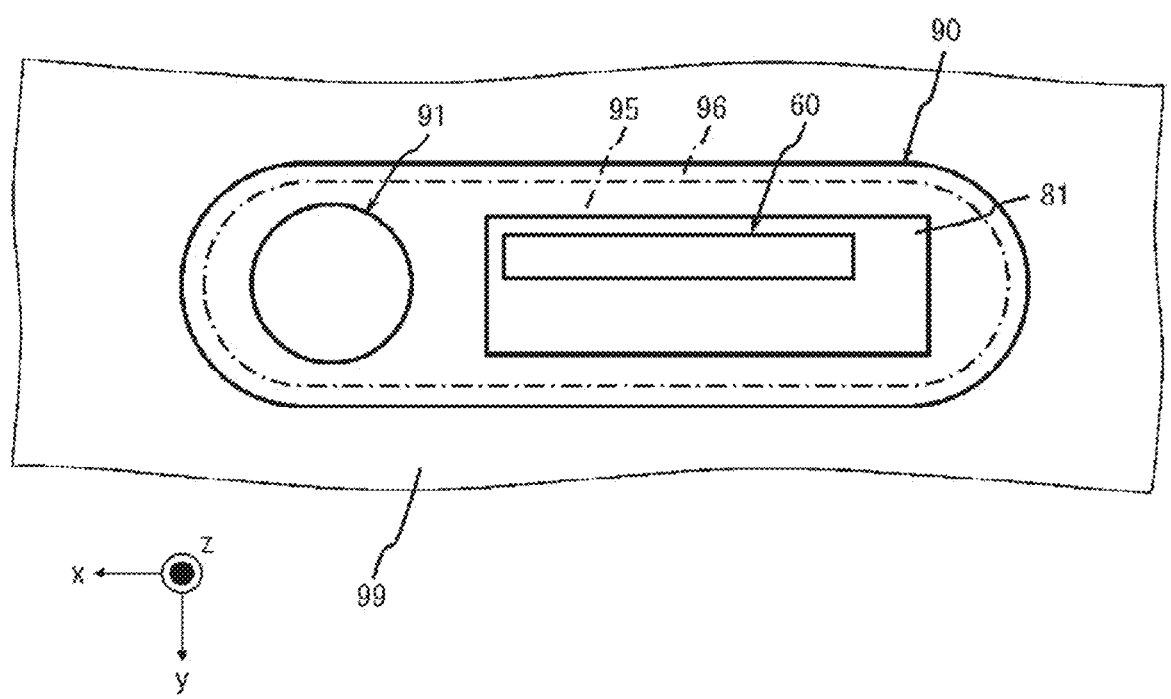
FIG. 82 is a plan view illustrating an embodiment of the wireless communication device.
Figure 83:
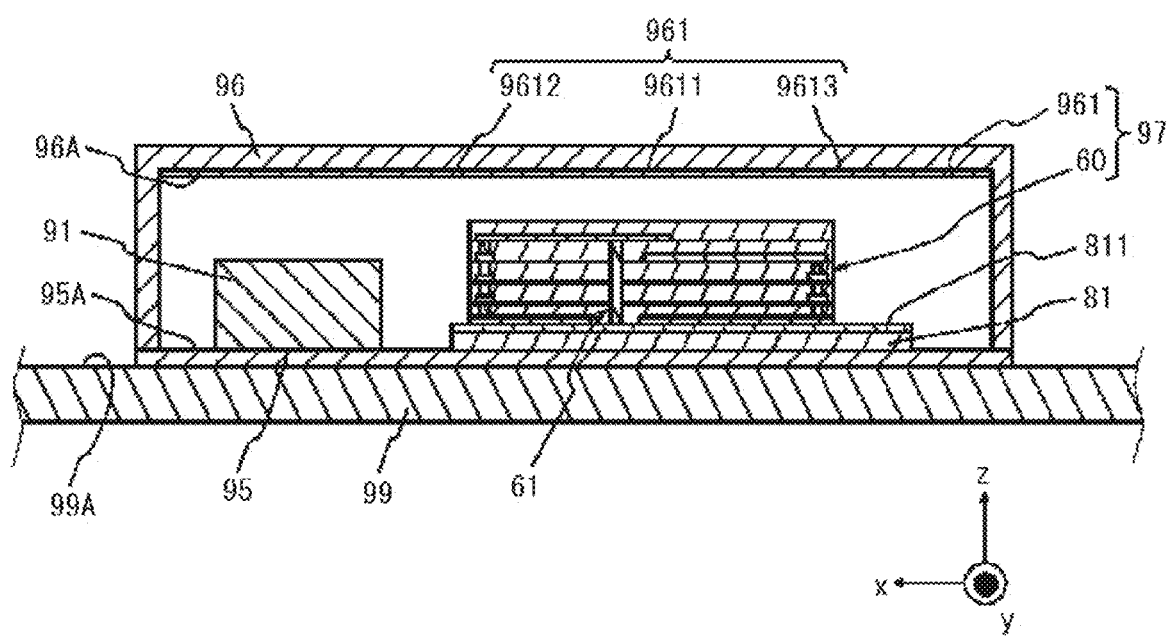
FIG. 83 is a sectional view illustrating an embodiment of the wireless communication device.
Figure 84:
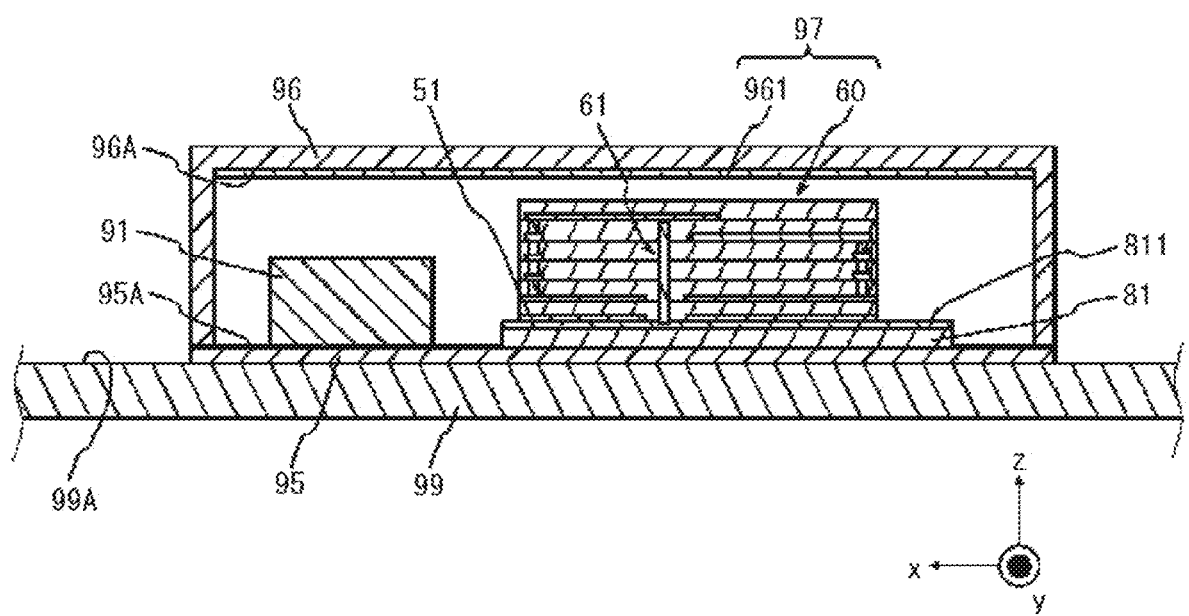
FIG. 84 is a plan view illustrating an embodiment of the wireless communication device.

A wireless communication device according to the present disclosure includes a wireless communication device 90 as an example of the plurality of embodiments. FIG. 81 is a block structural diagram of the wireless communication device 90. FIG. 82 is a plan view of the wireless communication device 90. Part of the configuration of the wireless communication device 90 illustrated in FIG. 82 is omitted. FIG. 83 is a cross-sectional view of the wireless communication device 90. Part of the configuration of the wireless communication device 90 illustrated in FIG. 83 is omitted. The wireless communication device 90 includes the wireless communication module 80, a battery 91, a sensor 92, a memory 93, a controller 94, a first case 95, and a second case 96. The wireless communication module 80 of the wireless communication device 90 includes the first antenna 60 but can include the second antenna 70. FIG. 84 illustrates one of other embodiments of the wireless communication device 90. The first antenna 60 of the wireless communication device 90 can include the reference potential layer 51.

The battery 91 supplies power to the wireless communication module 80. The battery 91 can supply power to at least one of the sensor 92, memory 93, and controller 94. The battery 91 can include at least one of a primary battery and a secondary battery. A negative electrode of the battery 91 is electrically connected to a ground terminal of a circuit board 81. The negative electrode of the battery 91 is electrically connected to a fourth conductor 50 of the first antenna 60.

The sensor 92 may include, for example, a speed sensor, vibration sensor, acceleration sensor, gyro-sensor, rotation angle sensor, angular velocity sensor, geomagnetic sensor, magnet sensor, temperature sensor, humidity sensor, atmospheric pressure sensor, optical sensor, illuminance sensor, UV sensor, gas sensor, gas concentration sensor, atmosphere sensor, level sensor, odor sensor, pressure sensor, air pressure sensor, contact sensor, wind sensor, infrared sensor, human sensor, displacement sensor, image sensor, weight sensor, smoke sensor, leak sensor, vital sensor, battery remaining amount sensor, ultrasonic sensor, a global positioning system (GPS) signal receiving device, or the like.

The memory 93 can include, for example, a semiconductor memory or the like. The memory 93 can function as a work memory for the controller 94. The memory 93 can be included in the controller 94. The memory 93 stores a program in which processing contents for achieving each function of the wireless communication device 90 is described, information used for processing in the wireless communication device 90, and the like.

The controller 94 can include, for example, a processor. The controller 94 may include one or more processors. The processor may include a general-purpose processor that is used for loading a specific program to execute a specific function and a dedicated processor that is dedicated to specific processing. The dedicated processor may include an application specific IC. The application specific IC is also referred to as ASIC. The processor may include a programmable logic device. The programmable logic device is also referred to as PLD. The PLD may include a field-programmable gate array (FPGA). The controller 94 may include any of an SoC (System-on-a-Chip) and an SiP (System In a Package) that are configured such that one or more processors cooperating with each other. The controller 94 may store a variety of information, a program for operating each component module of the wireless communication device 90, or the like in the memory 93.

The controller 94 generates a transmission signal to be transmitted from the wireless communication device 90. The controller 94 may obtain measurement data, for example, from the sensor 92. The controller 94 may generate a transmission signal according to the measurement data. The controller 94 can transmit a baseband signal to the RF module 82 of the wireless communication module 80.

The first case 95 and the second case 96 protect other devices of the wireless communication device 90. The first case 95 can extend in the xy plane. The first case 95 supports other devices. The first case 95 can support the wireless communication module 80. The wireless communication module 80 is located on an upper surface 95A of the first case 95. The first case 95 can support the battery 91. The battery 91 is located on the upper surface 95A of the first case 95. In an example of the plurality of embodiments, the wireless communication module 80 and the battery 91 are arranged in the x-direction on the upper surface 95A of the first case 95. The first conductor 31 is located between the battery 91 and the third conductor 40. The battery 91 is located behind the pair conductors 30 when viewed from the third conductor 40.

The second case 96 can cover other devices. The second case 96 includes an under surface 96A located in the z-direction from the first antenna 60. The under surface 96A extends along the xy plane. The under surface 96A is not limited to a flat shape but can include irregularities. The second case 96 can have an eighth conductor 961. The eighth conductor 961 is located at least within, on the outer side, or on the inner side of the second case 96. The eighth conductor 961 is located at least on an upper surface or lateral side surface of the second case 96.

The eighth conductor 961 faces the first antenna 60. The eighth conductor 961 includes a first body 9611 that faces the first antenna 60 in the z-direction. The eighth conductor 961 can include, in addition to the first body 9611, at least one of a second body that faces the first antenna 60 in the x-direction and a third body that faces the first antenna in the y-direction. The eighth conductor 961 partially faces the battery 91.

The eighth conductor 961 can include a first extra-body 9612 that extends outward from the first conductor 31 in the x-direction. The eighth conductor 961 can include a second extra-body 9613 that extends outward from the second conductor 32 in the x-direction. The first extra-body 9612 can be electrically connected to the first body 9611. The second extra-body 9613 can be electrically connected to the first body 9611. The first extra-body 9612 of the eighth conductor 961 faces the battery 91 in the z-direction. The eighth conductor 961 can be capacitively coupled to the battery 91. The eighth conductor 961 can have capacitance between the eighth conductor 961 and the battery 91.

The eighth conductor 961 is separated from the third conductor 40 of the first antenna 60. The eighth conductor 961 is not electrically connected to each conductor of the first antenna 60. The eighth conductor 961 can be separated from the first antenna 60. The eighth conductor 961 can be electromagnetically coupled to any conductor of the first antenna 60. The first body 9611 of the eighth conductor 961 can be electromagnetically coupled to the first antenna 60. The first body 9611 can overlap the third conductor 40 in plan view in the z-direction. Since the first body 9611 overlaps the third conductor 40, propagation due to electromagnetic coupling can be increased. The eighth conductor 961 can have a mutual inductance, due to electromagnetic coupling with the third conductor 40.

The eighth conductor 961 extends in the x-direction. The eighth conductor 961 extends along the xy plane. The length of the eighth conductor 961 is larger than the length of the first antenna 60 in the x-direction. The length of the eighth conductor 961 in the x-direction is larger than the length of the first antenna 60 in the x-direction. The length of the eighth conductor 961 can be larger than that of ½ of the operating wavelength λ of the wireless communication device 90. The eighth conductor 961 can include a portion extending along the y-direction. The eighth conductor 961 can bend in the xy plane. The eighth conductor 961 can include a portion extending in the z-direction. The eighth conductor 961 can bend from the xy plane to the yz plane or the zx plane.

Figure 85:
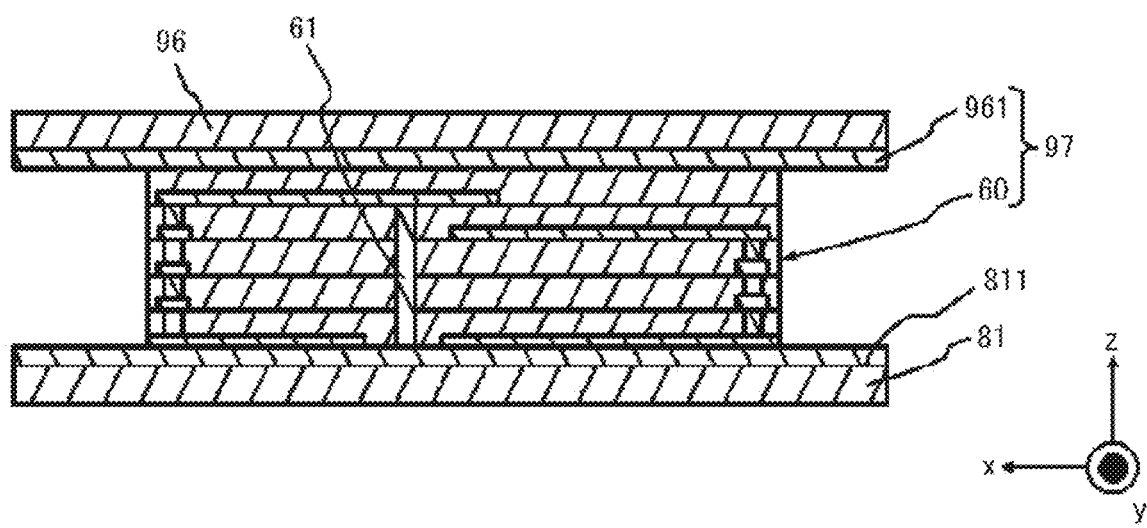
FIG. 85 is a sectional view illustrating an embodiment of the wireless communication device.

In the wireless communication device 90 including the eighth conductor 961, the first antenna 60 and the eighth conductor 961 can be electromagnetically coupled to function as a third antenna 97. The third antenna 97 may have an operating frequency $f_c$ that is different from the resonant frequency of the first antenna 60 alone. The operating frequency $f_c$ of the third antenna 97 may be closer to the resonant frequency of the first antenna 60 than the resonant frequency of the eighth conductor 961 alone. The operating frequency $f_c$ of the third antenna 97 can be within the resonant frequency band of the first antenna 60. The operating frequency $f_c$ of the third antenna 97 can be outside the resonant frequency band of the eighth conductor 961 alone. FIG. 85 illustrates another embodiment of the third antenna 97. The eighth conductor 961 can be configured integrally with the first antenna 60. In FIG. 85, part of the configuration of the wireless communication device 90 is omitted. In the example of FIG. 85, the second case 96 may not include the eighth conductor 961.

In the wireless communication device 90, the eighth conductor 961 is capacitively coupled to the third conductor 40. The eighth conductor 961 is electromagnetically coupled to the fourth conductor 50. The third antenna 97 includes the first extra-body 9612 and the second extra-body 9613 of the eighth conductor in the air, and thus, a gain is improved as compared with the first antenna 60.

Figure 86:
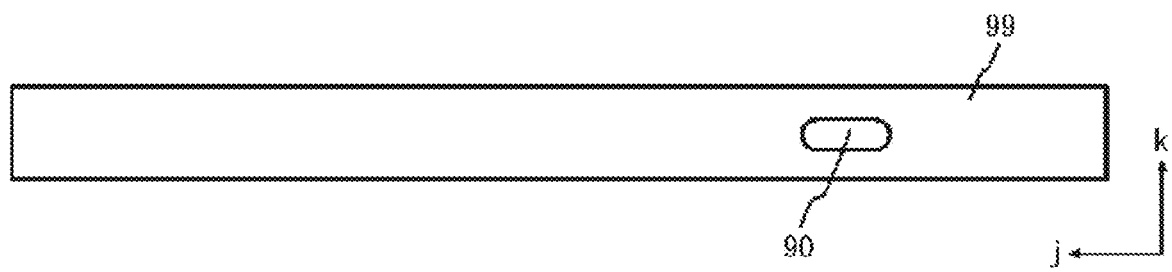
FIG. 86 is a sectional view illustrating an embodiment of the antenna.

The wireless communication device 90 can be located on various objects. The wireless communication device 90 can be located on an electrical conductive body 99. FIG. 86 is a plan view illustrating an embodiment of the wireless communication device 90. The electrical conductive body 99 is a conductor that transmits electricity. The material of the electrical conductive body 99 can include a metal, highly-doped semiconductor, conductive plastic, and liquid containing ions. The electrical conductive body 99 can include a non-conductive layer that does not transmit electricity on the surface. A portion that transmits electricity and the non-conductive layer can contain a common element. For example, the electrical conductive body 99 including aluminum can include the non-conductive layer of aluminum oxide on the surface. The portion that transmits electricity and the non-conductive layer can include different elements.

The shape of the electrical conductive body 99 is not limited to a flat plate shape but can include a three-dimensional shape such as a box shape. The three-dimensional shape of the electrical conductive body 99 includes a rectangular parallelepiped shape or a cylindrical shape. The three-dimensional shape can include a shape partially depressed, a shape partially penetrated, and a shape partially protruded. For example, the electrical conductive body 99 can be formed into a torus shape.

The electrical conductive body 99 includes an upper surface 99A on which the wireless communication device 90 can be placed. The upper surface 99A can extend over the entire surface of the electrical conductive body 99. The upper surface 99A can be part of the electrical conductive body 99. The upper surface 99A can have a larger area than the wireless communication device 90. The wireless communication device 90 can be placed on the upper surface 99A of the electrical conductive body 99. The upper surface 99A can have a smaller area than the wireless communication device 90. The wireless communication device 90 can be partially placed on the upper surface 99A of the electrical conductive body 99. The wireless communication device 90 can be placed on the upper surface 99A of the electrical conductive body 99 in various orientations. The wireless communication device 90 can have any orientation. The wireless communication device 90 can be appropriately secured on the upper surface 99A of the electrical conductive body 99 with a fastener. The fastener includes a fastener that uses a surface for securing, such as double-sided tape and adhesive. The fastener includes a fastener that uses a point for securing, such as a screw and a nail.

The upper surface 99A of the electrical conductive body 99 can include a portion extending in a j-direction. In the portion extending in the j-direction, a length extending in the j-direction is larger than a length extending in the k-direction. The j-direction and the k-direction are orthogonal to each other. The j-direction is a direction in which the electrical conductive body 99 extends long. The k-direction is a direction in which the electrical conductive body 99 has a length smaller than that in the j-direction. The wireless communication device 90 can be placed on the upper surface 99A such that the x-direction is along the j-direction. The wireless communication device 90 can be placed on the upper surface 99A of the electrical conductive body 99 so as to be aligned in the x-direction in which the first conductor 31 and the second conductor 32 are arranged. When the wireless communication device 90 is located on the electrical conductive body 99, the first antenna 60 can be electromagnetically coupled to the electrical conductive body 99. In the fourth conductor 50 of the first antenna 60, second current flows in the x-direction. In the electrical conductive body 99 electromagnetically coupled to the first antenna 60, the second current induces current. When the x-direction of the first antenna 60 and the j-direction of the electrical conductive body 99 are aligned, current flowing in the j-direction becomes large in the electrical conductive body 99. When the x-direction of the first antenna 60 and the j-direction of the electrical conductive body 99 are aligned, radiation due to the induced current becomes large in the electrical conductive body 99. The angle between the x-direction and the j-direction can be 45 degrees or less.

The ground conductor 811 of the wireless communication device 90 is separated from the electrical conductive body 99. The ground conductor 811 is separated from the electrical conductive body 99. The wireless communication device 90 can be placed on the upper surface 99A such that the direction along a long side of the upper surface 99A is aligned in the x-direction in which the first conductor 31 and the second conductor 32 are arranged. The upper surface 99A can include a diamond-shaped surface and a circular surface in addition to a rectangular surface. The electrical conductive body 99 can include a diamond-shaped surface. This diamond-shaped surface can be the upper surface 99A on which the wireless communication device 90 is placed. The wireless communication device 90 can be placed on the upper surface 99A such that a direction along a long diagonal of the upper surface 99A is aligned in the x-direction in which the first conductor 31 and the second conductor 32 are arranged. The upper surface 99A is not limited to a flat shape. The upper surface 99A can include irregularities. The upper surface 99A can include a curved surface. The curved surface includes a ruled surface. The curved surface includes a cylinder.

The electrical conductive body 99 extends in the xy plane. In the electrical conductive body 99, a length in the x-direction can be larger than a length in the y-direction. In the electrical conductive body 99, the length in the y-direction can be smaller than that one half of a wavelength $\lambda_c$ at the operating frequency $f_c$ of the third antenna 97. The wireless communication device 90 can be located on the electrical conductive body 99. The electrical conductive body 99 is located apart from the fourth conductor 50 in the z-direction. In the electrical conductive body 99, the length in the x-direction is larger than that of the fourth conductor 50. In the electrical conductive body 99, an area in the xy plane is larger than that of the fourth conductor 50. The electrical conductive body 99 is located apart from the ground conductor 811 in the z-direction. In the electrical conductive body 99, the length in the x-direction is larger than that of the ground conductor 811. In the electrical conductive body 99, an area in the xy plane is larger than that of the ground conductor 811.

The wireless communication device 90 can be placed on the electrical conductive body 99 in an orientation aligned with the x-direction in which the first conductor 31 and the second conductor 32 are arranged, in a direction in which the electrical conductive body 99 extends long. In other words, the wireless communication device 90 can be placed on the electrical conductive body 99, in an orientation in which a direction in which the current of the first antenna 60 flows is aligned with a direction in which the electrical conductive body 99 extends long, in the xy plane.

The first antenna 60 has a small change in resonant frequency due to the conductor of the circuit board 81 side. The first antenna 60 of the wireless communication device 90 can reduce the influence from an external environment.

In the wireless communication device 90, the ground conductor 811 is capacitively coupled to the electrical conductive body 99. The wireless communication device 90 includes the portion of the electrical conductive body 99 extending outward from the third antenna 97, and thus, a gain is improved as compared with the first antenna 60.

Figure 87:
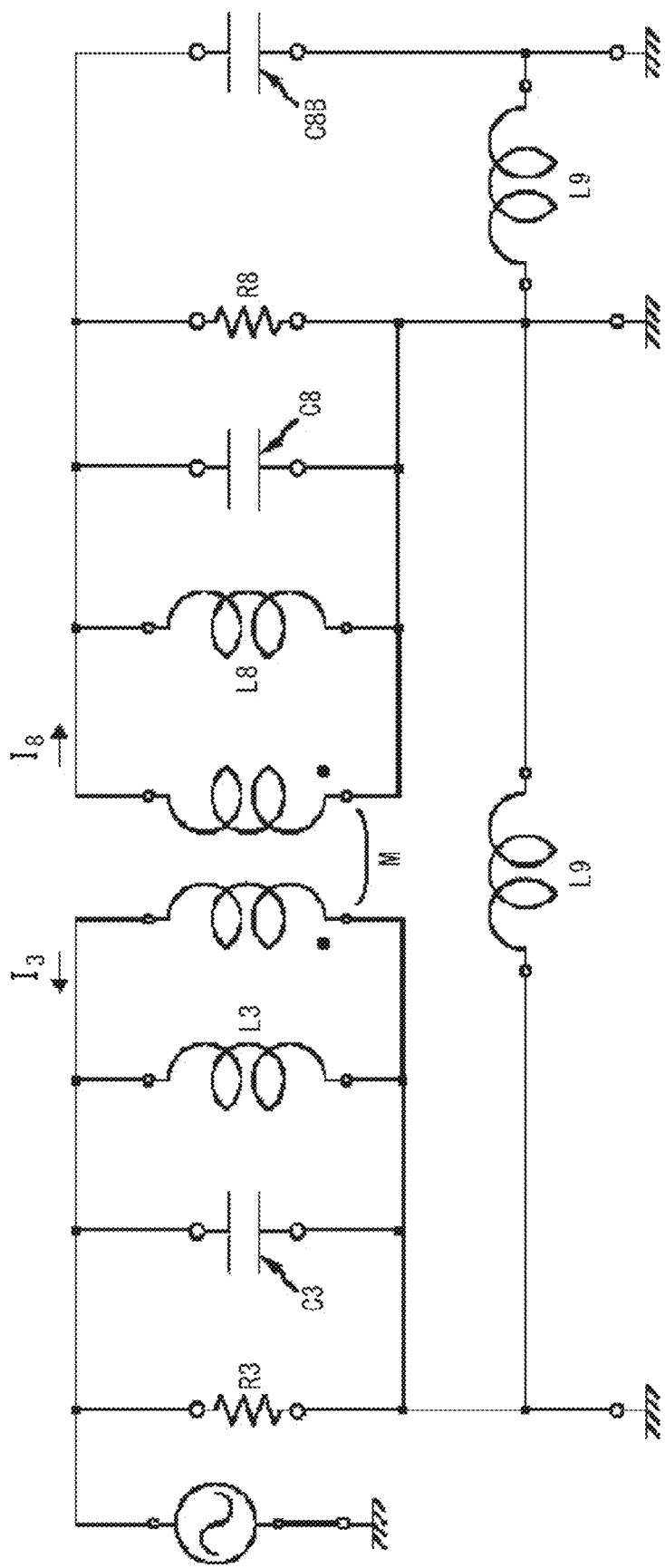
FIG. 87 is a diagram illustrating a schematic circuit of the wireless communication device.
Figure 88:
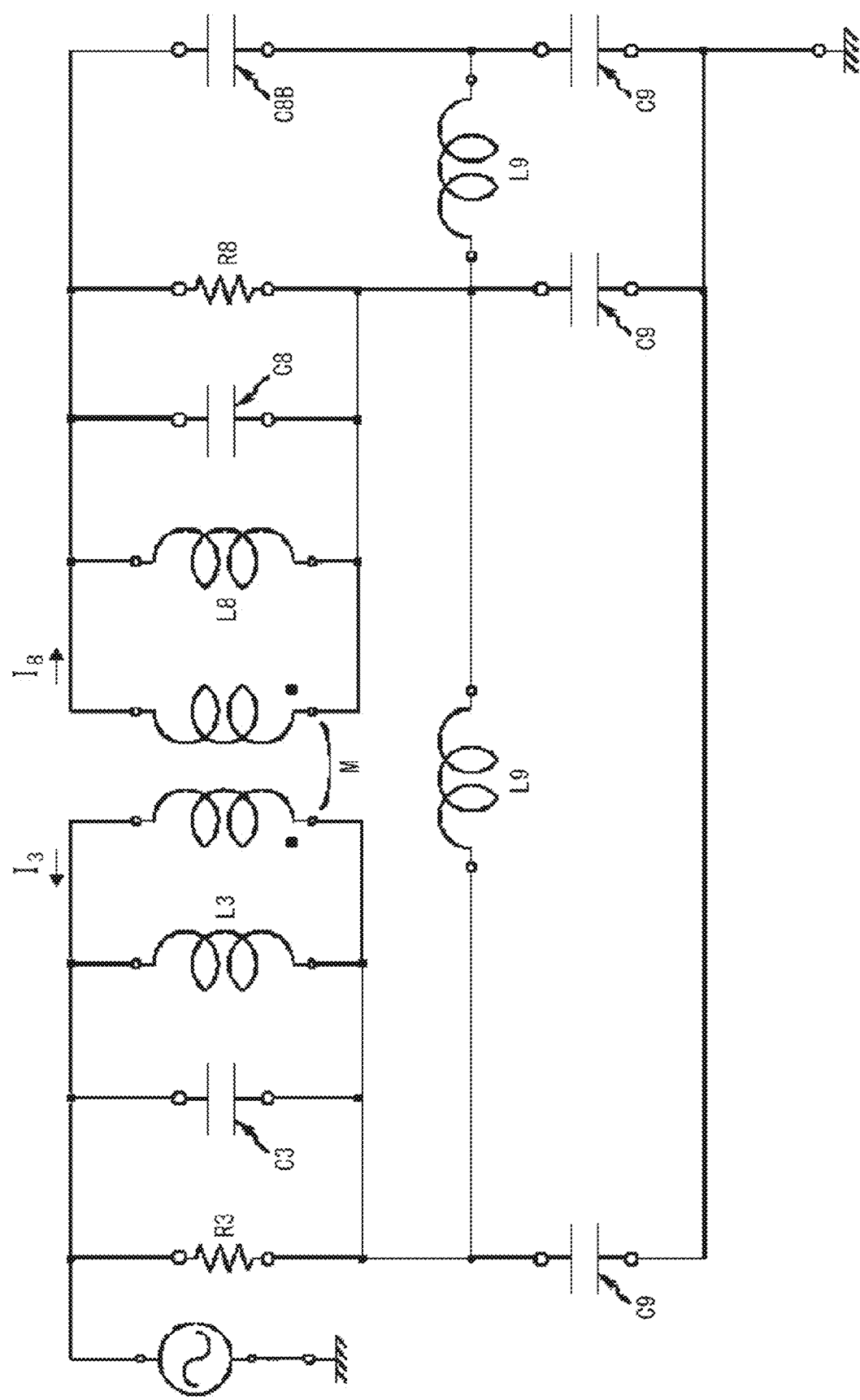
FIG. 88 is a diagram illustrating the schematic circuit of the wireless communication device.

The wireless communication device 90 can have different resonance circuits for use in the air and for use on the electrical conductive body 99. FIG. 87 illustrates a schematic circuit of a resonance structure for use in the air. FIG. 88 illustrates a schematic circuit of a resonance structure for use on the electrical conductive body 99. L3 is the inductance of the resonator 10, L8 is the inductance of the eighth conductor 961, L9 is the inductance of the electrical conductive body 99, and M is the mutual inductance between L3 and L8. C3 is the capacitance of the third conductor 40, C4 is the capacitance of the fourth conductor 50, C8 is the capacitance of the eighth conductor 961, C8B is the capacitance between the eighth conductor 961 and the battery 91, and C9 is the capacitance between the electrical conductive body 99 and the ground conductor 811. R3 is the radiation resistance of the resonator 10 and R8 is the radiation resistance of the eighth conductor 961. The operating frequency of the resonator 10 is lower than the resonant frequency of the eighth conductor. In the wireless communication device 90, the ground conductor 811 functions as a chassis ground in the air. In the wireless communication device 90, the fourth conductor 50 is capacitively coupled to the electrical conductive body 99. In the wireless communication device 90 on the electrical conductive body 99, the electrical conductive body 99 substantially functions as the chassis ground.

In the plurality of embodiments, the wireless communication device 90 includes the eighth conductor 961. The eighth conductor 961 is electromagnetically coupled to the first antenna 60 and capacitively coupled to the fourth conductor 50. The wireless communication device 90 has capacitance C8B increased due to the capacitive coupling, and when the wireless communication device 90 is put on the electrical conductive body 99 from the air, the operating frequency thereof can be increased. The wireless communication device 90 has mutual inductance M increased due to the electromagnetic coupling, and when the wireless communication device 90 is put on the electrical conductive body 99 from the air, the operating frequency can be reduced. In the wireless communication device 90, changing the balance between the capacitance C8B and the mutual inductance M can adjust the change in operating frequency when the wireless communication device 90 is placed on the electrical conductive body 99 from the air. In the wireless communication device 90, changing the balance between the capacitance C8B and the mutual inductance M can reduce the change in operating frequency when the wireless communication device 90 is placed on the electrical conductive body 99 from the air.

The wireless communication device 90 includes the eighth conductor 961 that is electromagnetically coupled to the third conductor 40 and capacitively coupled to the fourth conductor 50. The wireless communication device 90 including the eighth conductor 961 can adjust the change in operating frequency when the wireless communication device 90 is placed on the electrical conductive body 99 from the air. The wireless communication device 90 including such an eighth conductor 961 can reduce the change in operating frequency when the wireless communication device 90 is placed on the electrical conductive body 99 from the air.

Likewise, in the wireless communication device 90 that does not include the eighth conductor 961, the ground conductor 811 functions as the chassis ground in the air. Likewise, in the wireless communication device 90 that does not include the eighth conductor 961, the electrical conductive body 99 functions as a substantial chassis ground, on the electrical conductive body 99. The resonant structure including the resonator 10 can oscillate even if the chassis ground changes. This configuration corresponds to that the resonator 10 including the reference potential layer 51 and the resonator 10 not including the reference potential layer 51 can oscillate.

Configuration Example of a Bicycle

Figure 89:
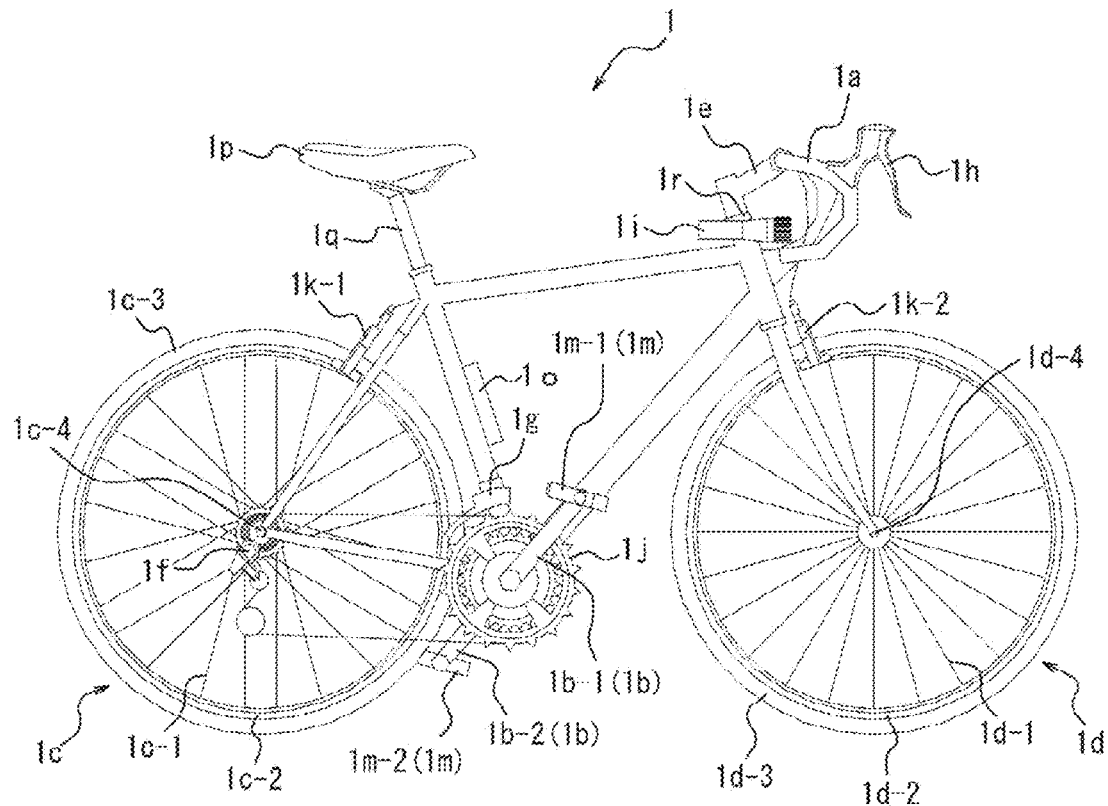
FIG. 89 is an exterior view illustrating an embodiment of a bicycle.
Figure 90:
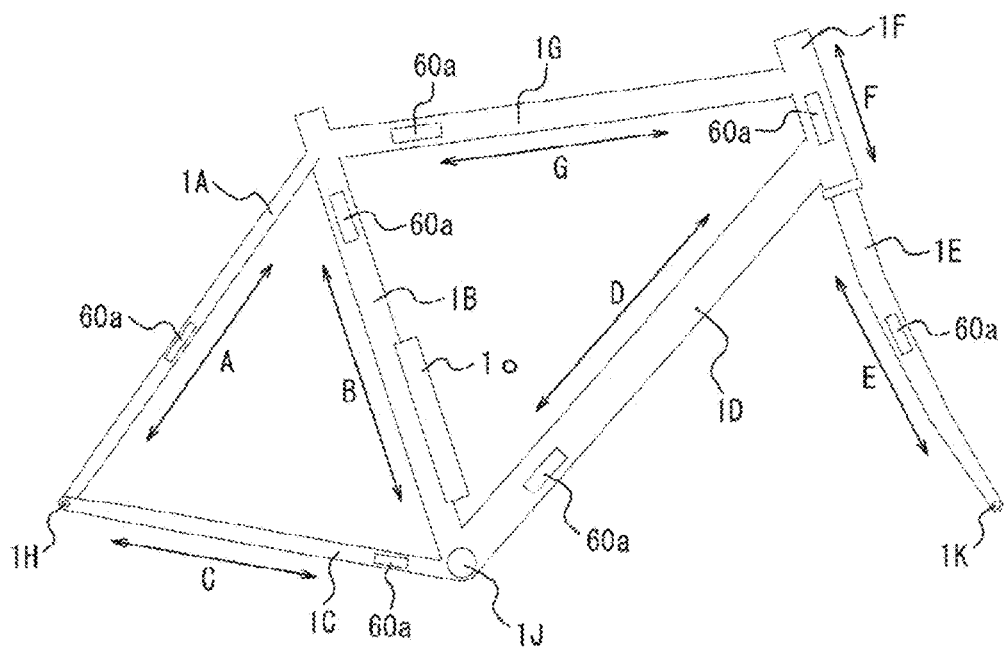
FIG. 90 is a view illustrating frames of the bicycle illustrated in FIG. 89.
Figure 91:
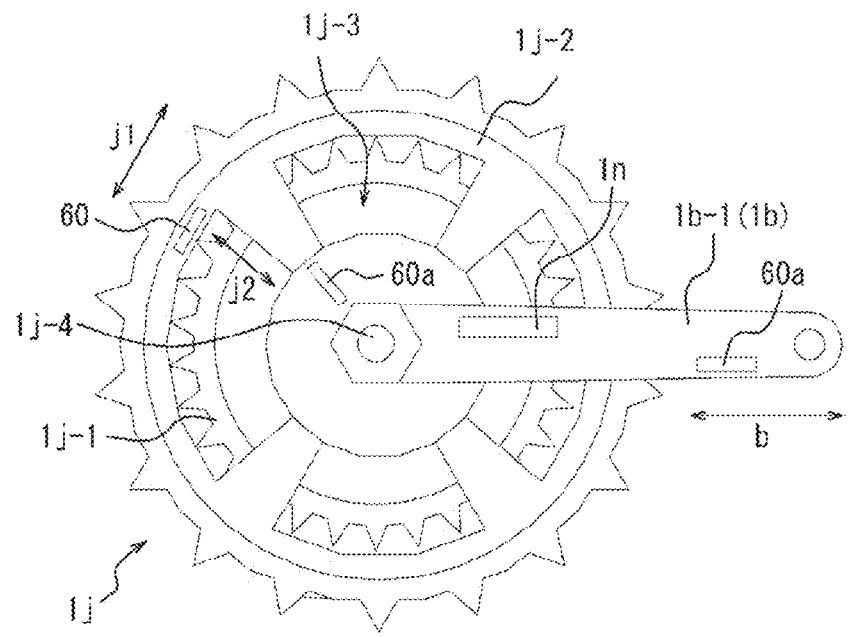
FIG. 91 is a view illustrating a crank and a chain wheel of the bicycle illustrated in FIG. 89.
Figure 92:
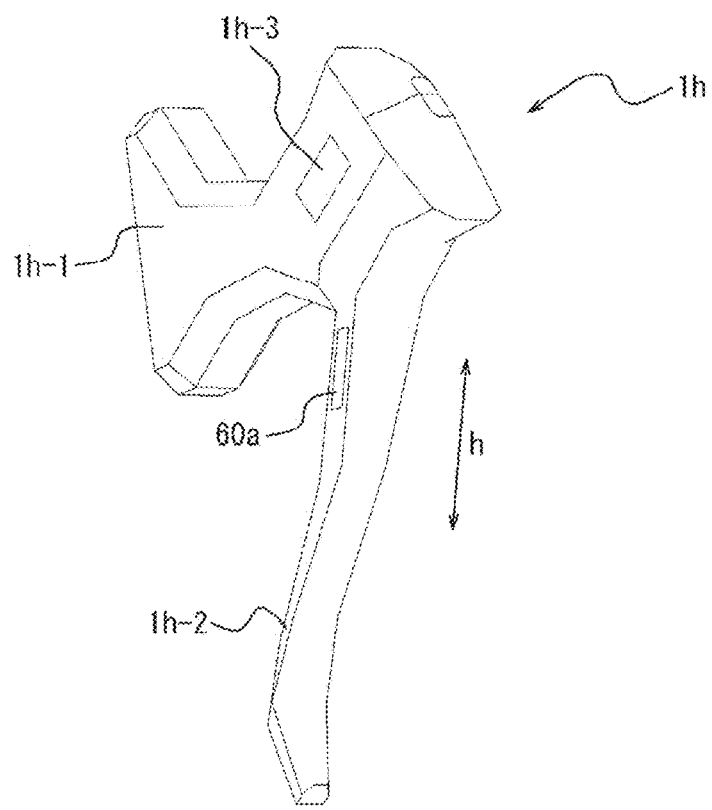
FIG. 92 is a view illustrating a dual control lever of the bicycle illustrated in FIG. 89.

FIG. 89 is an exterior view illustrating an embodiment of a bicycle 1. FIG. 90 is a view illustrating frames of the bicycle 1 illustrated in FIG. 89. FIG. 91 is a view illustrating a crank 1b-1 and a chain wheel 1j of the bicycle 1 illustrated in FIG. 89. FIG. 92 is a view illustrating a dual control lever 1h of the bicycle 1 illustrated in FIG. 89.

The bicycle 1 travels with human power. The "bicycle" of the present disclosure is not limited to a bicycle that travels with only human power. For example, the "bicycle" may include an electric powered bicycle, an electric bicycle, and a two-wheel drive bicycle. The "bicycle" of the present disclosure is not limited to a two-wheel vehicle. For example, the "bicycle" may include a unicycle, a tricycle, and a four-wheel vehicle. Classifications of the bicycle are not limited to the above description. For example, the "bicycle" may include a tandem bicycle.

The bicycle 1 may be a bicycle owned by an individual. The bicycle 1 may be a bicycle owned by a company that provides bicycle lending service. The bicycle 1 may be a bicycle owned by a company that provides a home delivery service for foods and the like. In the following explanation, a person having authority of using the bicycle 1 is referred to as "user". A person currently operating the bicycle 1 is referred to as "driver".

The bicycle 1 includes frames and bicycle components. The frames of the bicycle 1 may be any conductive material. The conductive material may include metal and carbon fiber reinforced plastic. The bicycle components may be configured by any members according to uses of the components.

The frames of the bicycle 1 may include, as illustrated in FIG. 90, a seat stay 1A, a seat tube 1B, a chain stay 1C, a down tube 1D, a front fork 1E, a head tube 1F, and a top tube 1G. The frames of the bicycle 1 may include a rear fork end 1H, a bottom bracket shell 1J, and a front fork end 1K. The shape of the frames of the bicycle 1 is not limited to the shape illustrated in FIG. 90 and may be any shape.

The seat stay 1A extends along an extending direction A from the rear fork end 1H to one end of the seat tube 1B.

The seat tube 1B extends along an extending direction B from the bottom bracket shell 1J to one end of the seat stay 1A.

The chain stay 1C extends along an extending direction C extending from the rear fork end 1H to the bottom bracket shell 1J.

The down tube 1D extends along an extending direction D from the bottom bracket shell 1J to the head tube 1F.

The front fork 1E extends along an extending direction E from one end of the head tube 1F to the front fork end 1K.

The head tube 1F extends along an extending direction F from one end of the front fork 1E to one end of the top tube 1G.

The top tube 1G extends along an extending direction F from one end of the seat stay 1A to the other end of the head tube 1F.

The bicycle components of the bicycle 1 may include, as illustrated in FIG. 89, a handlebar 1a, a crank 1b, a rear wheel 1c, a wheel 1d, a stem 1e, a rear derailleur 1f, a front derailleur 1g, the dual control lever 1h, a light 1i, the chain wheel 1j, a brake 1k-1, a brake 1k-2, and a pedal 1m. The bicycle components of the bicycle 1 may include a power meter 1n as illustrated in FIG. 91. The bicycle components of the bicycle 1 may include a battery 1o as illustrated in FIG. 89. The bicycle components of the bicycle 1 may include, as illustrated in FIG. 89, a saddle 1p, a seat post 1q, and a head part 1r.

As illustrated in FIG. 91, the crank 1b extends along an extending direction b from the bottom bracket shell 1J to the pedal 1m. The crank 1b may include a crank 1b-1 that receives power from the right foot of the driver and a crank 1b-2 that receives power from the left foot of the driver.

The rear wheel 1c may include a spoke 1c-1, a rim 1c-2, a tire 1c-3, and a hub 1c-4. The hub 1c-4 is attached to the rear fork end 1H illustrated in FIG. 90. The hub 1c-4 functions as a rotating shaft of the rear wheel 1c.

The wheel 1d may include a spoke 1d-1, a rim 1d-2, a tire 1d-3, and a hub 1d-4. The hub 1d-4 is attached to the front fork end 1K illustrated in FIG. 90. The hub 1d-4 functions as a rotating shaft of the wheel 1d.

Each of the brake 1k-1 and the brake 1k-2 may include a brake caliper. The brake caliper of the brake 1k-1 may be configured to be capable of holding the rear wheel 1c. The brake caliper of the brake 1k-2 may be configured to be capable of holding the wheel 1d.

The chain wheel 1j extends along a circumferential direction j1. The chain wheel 1j may include a plurality of chain wheels. For example, the chain wheel 1j may include, as illustrated in FIG. 91, a chain wheel 1j-1 and a chain wheel 1j-2. The chain wheel 1j may include a part that connects the chain wheel 1j-1 and the chain wheel 1j-2. The part may extend along a radial direction j2 of the chain wheel 1j.

The chain wheel 1j may include a hole portion 1j-3 and a bottom bracket 1j-4. The bottom bracket 1j-4 is attached to the bottom bracket shell 1J illustrated in FIG. 90. The chain wheel 1j is attached to the bottom bracket 1j-4. The bottom bracket 1j-4 functions as a rotating shaft of the chain wheel 1j.

The pedal 1m may include a pedal 1m-1 on which the right foot of the driver is placed and a pedal 1m-2 on which the left foot of the driver is placed.

The dual control lever 1h may include, as illustrated in FIG. 92, a shift lever 1h-1 and a brake lever 1h-2. A switch 1h-3 may be provided in the shift lever 1h-1. The brake lever 1h-2 may extend along an extending direction h. The bicycle components may include an independent shift lever and an independent brake lever instead of the dual control lever 1h.

The power meter 1n may be disposed in the hole portion 1j-3 of the chain wheel 1j illustrated in FIG. 91.

The "bicycle components" of the present disclosure are not limited to the components described above. The "bicycle components" of the present disclosure may include any components according to a use of the bicycle. For example, the "bicycle components" may include a shadow and a cycle computer.

The bicycle 1 includes at least one first antenna 60a. The first antenna 60a has the same structure as the structure of the first antenna 60 explained above. The bicycle 1 may include the second antenna 70 in addition to the first antenna 60a or instead of the first antenna 60a.

The first antenna 60a may be disposed in any one of the frames of the bicycle 1. The first antenna 60a may be disposed in a frame of the bicycle 1 such that the fourth conductor 50 included in the first antenna 60a faces the frame. Since the fourth conductor 50 of the first antenna 60a faces the frame of the bicycle 1, a direction in which the frame is located with respect to the fourth conductor 50 can be set in the opposite direction of a direction in which the third conductor 40 is located with respect to the fourth conductor 50. An effective traveling direction of an electromagnetic wave radiated by the first antenna 60a can be a direction in which the third conductor 40 is located with respect to the fourth conductor 50. Since the fourth conductor 50 of the first antenna 60a faces the frame of the bicycle 1, the frame of the bicycle 1 can be located in the opposite direction of the effective traveling direction of the electromagnetic wave radiated by the first antenna 60a. Since the frame of the bicycle 1 is located in the opposite direction of the effective traveling direction of the electromagnetic wave radiated from the first antenna 60a, radiation efficiency of the first antenna 60a can be maintained.

When the frame of the bicycle 1 includes a conductive long portion, the first antenna 60a may be disposed in the long portion. The first antenna 60a may be disposed in the long portion such that the first direction is along the conductive long portion. The long portion may include the seat stay 1A, the seat tube 1B, the chain stay 1C, the down tube 1D, the front fork 1E, the head tube 1F, and the top tube 1G. Since the first antenna 60a is disposed in the conductive long portion included in the frame of the bicycle 1, the first antenna 60a and the long portion can be electromagnetically coupled. Since the fourth conductor 50 of the first antenna 60a and the long portion are capacitively coupled, when the first antenna 60a radiates the electromagnetic wave, an electric current can be induced in the long portion. The long portion can radiate the electromagnetic wave with the electric current induced in the long portion. Since the long portion radiates, as the electromagnetic wave, the electric current induced in the long portion, when the first antenna 60a radiates the electromagnetic wave, overall radiation efficiency of the first antenna 60a can be improved. The electromagnetic wave radiated from the long portion can be isotropically radiated from the long portion.

For example, when the first antenna 60a is disposed in the seat stay 1A functioning as the long portion, the first antenna 60a may be disposed in the seat stay 1A such that the first direction is along the extending direction A.

For example, when the first antenna 60a is disposed in the seat tube 1B functioning as the long portion, the first antenna 60a may be disposed in the seat tube 1B such that the first direction is along the extending direction B.

For example, when the first antenna 60a is disposed in the chain stay 1C functioning as the long portion, the first antenna 60a is disposed in the chain stay 1C such that the first direction is along the extending direction C.

For example, when the first antenna 60a is disposed in the down tube 1D functioning as the long portion, the first antenna 60a may be disposed in the down tube 1D such that the first direction is along the extending direction D.

For example, when the first antenna 60a is disposed in the front fork 1E functioning as the long portion, the first antenna 60a may be disposed in the front fork 1E such that the first direction is along the extending direction E.

For example, the first antenna 60a is disposed in the head tube 1F functioning as the long portion, the first antenna 60a may be disposed in the head tube 1F such that the first direction is along the extending direction F.

For example, when the first antenna 60a is disposed in the top tube 1G functioning as the long portion, the first antenna 60a may be disposed in the top tube 1G such that the first direction is along the extend direction G.

The first antenna 60a may be disposed in any one of the bicycle components of the bicycle 1. The first antenna 60a may be disposed in a bicycle component of the bicycle 1 such that the fourth conductor 50 included in the first antenna 60a faces the bicycle component. Since the fourth conductor 50 of the first antenna 60a faces the bicycle component, as explained above, the radiation efficiency of the first antenna 60a can be maintained.

When the bicycle component includes a conductive long portion, the first antenna 60a may be disposed in the long portion. The first antenna 60a may be disposed in a conductive long portion of the bicycle component such that the first direction is along the long portion. Since the first antenna 60a is disposed in the long portion, as explained above, the overall radiation efficiency of the first antenna 60a can be improved. As an example, the bicycle component including the conductive long portion may include the brake lever 1h-2, the chain wheel 1j, and the crank 1b.

For example, when the first antenna 60a is disposed in the crank 1b functioning as the long portion, the first antenna 60a may be disposed in the crank 1b such that the first direction is along the extending direction b.

For example, when the first antenna 60a is disposed in the chain wheel 1j functioning as the long portion, the first antenna 60a may be disposed in the chain wheel 1j such that the first direction is along the circumferential direction j1. The first antenna 60a may be disposed in the chain wheel 1j such that the first direction is along the radial direction j2.

For example, when the first antenna 60a is disposed in the brake lever 1h-2 functioning as the long portion, the first antenna 60a may be disposed in the brake lever 1h-2 such that the first direction is along the extending direction h.

The first antenna 60a may be disposed in a bicycle component that can come into contact with the driver. The first antenna 60a may be disposed in a portion with less contact with the driver among portions included in the bicycle component that can come into contact with the driver. As an example, the bicycle component that can come into contact with the driver may include the handlebar 1a, the shift lever 1h-1, and the brake lever 1h-2

For example, when the first antenna 60a is disposed in the handlebar 1a, the first antenna 60a may be disposed in a part not often gripped by the driver with a hand among parts included in the handlebar 1a. The part may be a root portion of the handlebar 1a or may be a terminal end portion of the handlebar 1a.

For example, when the first antenna 60a is disposed in the brake lever 1h-2, the first antenna 60a may be disposed in a part not often gripped by the driver with a hand among parts included in the brake lever 1h-2. The part may be a root portion of the brake lever 1h-2 illustrated in FIG. 92.

Example of Functions of the Bicycle

Figure 93:
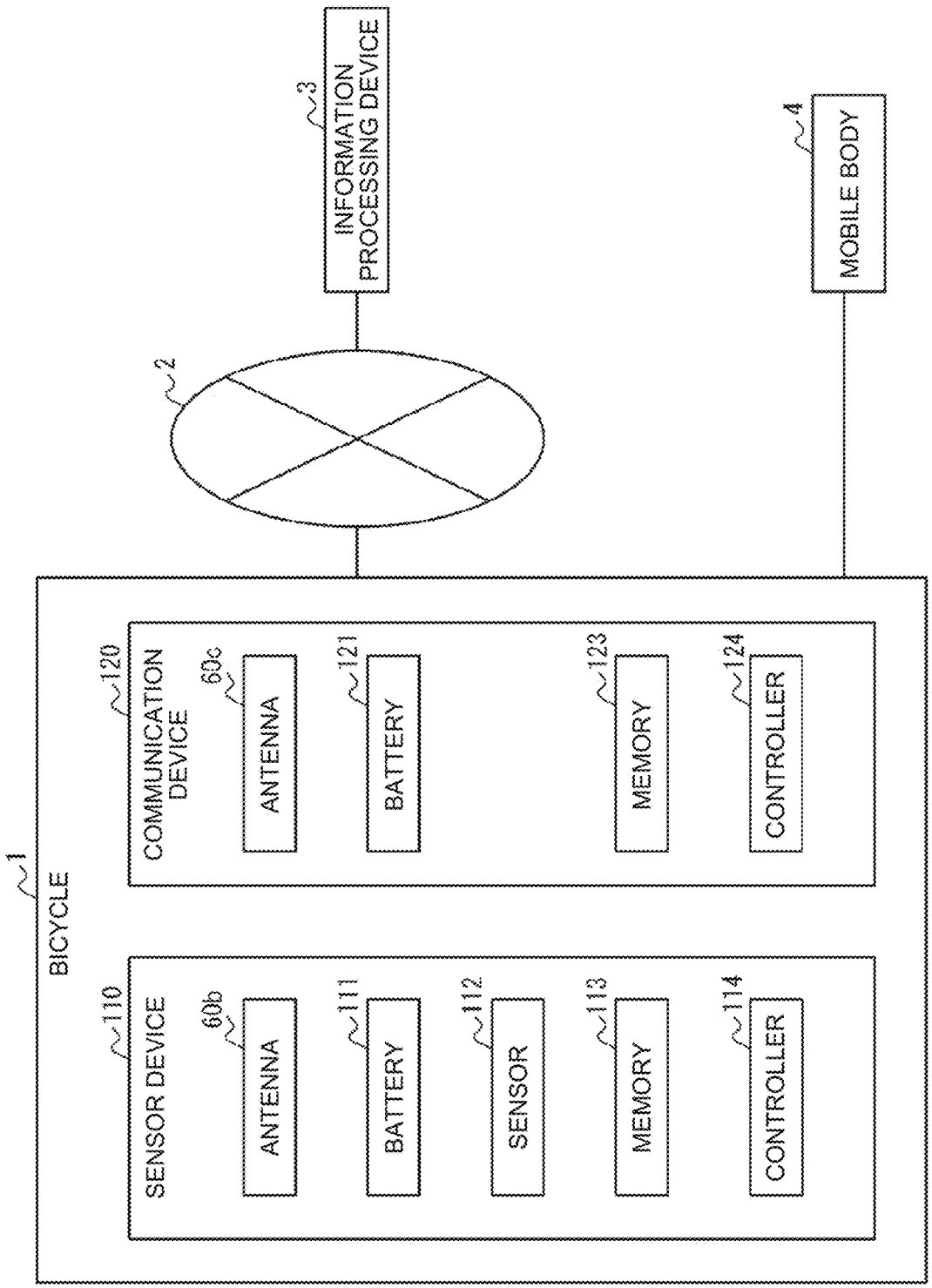
FIG. 93 is a functional block diagram of an example of the bicycle illustrated in FIG. 89.

FIG. 93 is a functional block diagram of an example of the bicycle 1 illustrated in FIG. 89. The bicycle 1 can communicate with an information processing device 3 via a network 2. The bicycle 1 can directly communicate with a mobile body 4. The network 2 may include a wireless network. A part of the network 2 may include a wired network. The bicycle 1 and the information processing device 3 can configure an information integration system. The information processing device 3 can communicate with a plurality of bicycles 1.

The bicycle 1 includes a sensor device 110 and a communication device 120. The sensor device 110 and the communication device 120 may be integrally configured. For example, the sensor device 110 and the communication device 120 may be integrally configured by integrating a sensor 112 of the sensor device 110 with the communication device 120.

The information processing device 3 may be managed by any company or the like. For example, when a company that provides a bicycle lending service owns the bicycle 1, the information processing device 3 may be managed by the company that provides the lending service. For example, when a company that provides a home delivery service owns the bicycle 1, the information processing device 3 may be managed by the company that provides the home delivery service. For example, when an owner of the bicycle 1 has a contract with an insurance company, the information processing device 3 may be managed by the insurance company.

The information processing device 3 may be configured by a computer system and other hardware capable of executing a program command. The computer system and the other hardware may include a general-purpose computer, a PC (personal computer), a dedicated computer, a work station, a personal communications system (PCS), a mobile (cellular) phone, a mobile phone including a data processing function, a radio frequency identification (RFID) receiver, a game machine, an electronic notepad, a laptop computer, a global positioning system (GPS) receiver, or other programmable data processing devices.

The mobile body 4 is a mobile body present within a communication zone of the bicycle 1 among mobile bodies. Examples of the mobile body 4 include, but are not limited to, a vehicle, a ship, and an airplane. For example, the mobile body 4 may be a vehicle that travels within the communication zone of the bicycle 1. The "vehicle" of the present disclosure includes an automobile, a railway vehicle, an industrial vehicle, and a life vehicle but is not limited to these vehicles. For example, the vehicle may include an airplane that travels on a runway. The automobile includes a passenger car, a truck, a bus, a motorbike, and a trolley bus but is not limited to these vehicles and may include other vehicles that travel on a road. The railway vehicle includes a locomotive, a freight car, a passenger car, a streetcar, a guide track railway, a ropeway, a cable car, a linear motor car, and a monorail but is not limited to these vehicles and may include other vehicles that move along a track. Examples of the industrial vehicle include, but are not limited to, industrial vehicles for agriculture and construction. The industrial vehicle includes a forklift and a golf cart but is not limited to these vehicles. The industrial vehicle for agriculture include a tractor, a cultivator, a transplanting machine, a binder, a combine, and a lawn mower but is not limited to these vehicles. The industrial vehicle for construction includes a bulldozer, a scraper, a shovel car, a crane car, a dump car, and a road roller but is not limited to these vehicles. The life vehicle includes a bicycle, a wheelchair, a baby carriage, a hand craft, and an electric standing motorcycle but is not limited to these vehicles. A power engine of a vehicle includes an internal combustion engine including a diesel engine, a gasoline engine, and a hydrogen engine and an electric engine including a motor but is not limited to these engines. The vehicle includes a vehicle that runs with human power. Classifications of the vehicle are not limited to the above. For example, the automobile may include an industrial vehicle capable of traveling on a road. The same vehicle may be included in a plurality of classifications.

The sensor device 110 can directly communicate with the communication device 120. The sensor device 110 and the communication device 120 may perform wired communication or may perform wireless communication. The wireless communication may be based on a short-range communication standard. The short-range communication standard may include WiFi (registered trademark), Bluetooth (registered trademark), and wireless local area network (LAN).

The sensor device 110 includes the sensor 112, a memory 113, and a controller 114. For example, when the sensor device 110 and the communication device 120 perform the wireless communication, the sensor device 110 may include at least one first antenna 60_b_. The sensor device 110 may include the first antenna 60_b_ on the outside or the outer surface of the sensor device 110. The sensor device 110 may include a battery 111. When the sensor device 110 does not include the battery 111, the sensor device 110 may operate with electric power supplied from the battery 10 illustrated in FIG. 90. When the sensor device 110 receives the supply of the electric power from the battery 10, the sensor device 110 and the battery 1_o_ may be electrically connected by a power line or the like.

The first antenna 60_b_ may be the first antenna 60_a_ independent from a first antenna 60_c_ of the communication device 120.

The first antenna 60_b_ is configured as appropriate according to a frequency band used in communication between the sensor device 110 and other devices. In other words, each of the first conductor 31, the second conductor 32, the third conductor 40, and the fourth conductor 50 included in the first antenna 60_b_ may be configured as appropriate according to the frequency band used in the communication between the sensor device 110 and the other devices. For example, the first antenna 60_b_ may be configured according to a frequency band used in short-range communication between the sensor device 110 and the communication device 120. For example, the first antenna 60_b_ may be configured according to a frequency band used in communication between the sensor device 110 and a GPS satellite.

A disposition position of the first antenna 60_b_ may be selected as appropriate out of the disposition positions explained above with reference to FIG. 89 to FIG. 92 according to a communication partner of the sensor device 110 or according to data acquired by the sensor 112.

For example, when the communication partner of the sensor device 110 is a GPS satellite, the disposition position of the first antenna 60_b_ may be the top tube 1G illustrated in FIG. 90 or the stem 1_e_ illustrate in FIG. 89. Since the first antenna 60_b_ is disposed in the top tube 1G or the like illustrated in FIG. 90, the first antenna 60_b_ easily receives an electromagnetic wave from the GPS satellite.

The first antenna 60_b_ can receive an electromagnetic wave from another device as a reception signal. The reception signal received by the first antenna 60_b_ is transmitted to the controller 114 through the first feeding line 61 of the first antenna 60_b_. Electric power is supplied to the first feeding line 61 of the first antenna 60_b_, whereby the first antenna 60_b_ can radiate an electromagnetic wave to another device as a transmission signal.

The battery 111 can supply electric power to at least one of the first antenna 60_b_, the sensor 112, the memory 113, and the controller 114. The battery 111 can include, for example, at least one of a primary battery and a secondary battery. A negative pole of the battery 111 is electrically connected to the fourth conductor 50 of the first antenna 60*b*.

The sensor 112 may be configured as appropriate according to a use of the sensor device 110. The sensor 112 may include at least one of a speed sensor, an acceleration sensor, a gyro sensor, a rotation angle sensor, a distortion sensor, a terrestrial magnetism sensor, a temperature sensor, a humidity sensor, an atmospheric pressure sensor, an illuminance sensor, a camera, and a biological sensor. As explained above, the disposition position of the first antenna 60*b* may be selected as appropriate out of the disposition positions explained above with reference to FIG. 89 to FIG. 92 according to data measured by the sensor 112.

For example, when the sensor 112 includes the speed sensor, the sensor 112 can measure the speed of the bicycle 1. The sensor 112 outputs the measured speed of the bicycle 1 to the controller 114. In this example, the sensor device 110 including the sensor 112 can be disposed in the seat stay 1A or the chain stay 1C illustrated in FIG. 90. In this example, the disposition position of the first antenna 60*b* may be the seat stay 1A or the chain stay 1C.

For example, when the sensor 112 includes the acceleration sensor, the sensor 112 can measure acceleration acting on the bicycle 1. The sensor 112 outputs the measured acceleration to the controller 114. In this example, the sensor device 110 including the sensor 112 can be disposed in the seat stay 1A or the chain stay 1C illustrated in FIG. 90. In this example, the disposition position of the first antenna 60*b* may be the seat stay 1A or the chain stay 1C.

For example, when the sensor 112 includes the gyro sensor, the sensor 112 can measure the angular velocity of the bicycle 1. The sensor 112 outputs the measured angular velocity to the controller 114. In this example, the sensor device 110 including the sensor 112 can be disposed in the seat stay 1A or the chain stay 1C illustrated in FIG. 90. In this example, the disposition position of the first antenna 60*b* may be the seat stay 1A or the chain stay 1C.

For example, when the sensor 112 includes the rotation angle sensor, the sensor 112 can measure the rotation speed of the crank 1*b* of the bicycle 1. In this example, the sensor device 110 including the sensor 112 can be the power meter 1*n* disposed in the hole portion 1*j*-3 of the chain wheel 1*j* illustrated in FIG. 91. The sensor 112 outputs the measured rotation speed to the controller 114. In this example, the disposition position of the first antenna 60*b* may be the chain wheel 1*j*-1 or the chain wheel 1*j*-2 illustrated in FIG. 91.

For example, when the sensor 112 includes the distortion sensor, the sensor 112 can measure a load applied to the crank 1*b*. The sensor 112 outputs data of the measured load to the controller 114. In this example, the sensor device 110 including the sensor 112 can be the power meter 1*n* disposed in the crank 1*b* illustrated in FIG. 91. In this example, the disposition position of the first antenna 60*b* may be the power meter 1*n* illustrated in FIG. 91 or may be the crank 1*b*.

For example, when the sensor 112 includes the terrestrial magnetism sensor, the sensor 112 can measure the magnitude and the direction of magnetism around the bicycle 1. The sensor 112 outputs the measured magnitude and the measured direction of the magnetism to the controller 114. In this example, the sensor device 110 including the sensor 112 can be disposed in any one of the frames of the bicycle 1 or any one of the bicycle components. In this example, the disposition position of the first antenna 60*b* may be any one of the frames of the bicycle 1 or any one of the bicycle components in which the sensor device 110 is disposed or that is near the sensor device 110.

For example, when the sensor 112 includes the temperature sensor, the sensor 112 can measure the temperature around the bicycle 1. The sensor 112 outputs the measured temperature to the controller 114. In this example, the sensor device 110 including the sensor 112 can be disposed in any one of the frames of the bicycle 1 or any one of the bicycle components. In this example, the disposition position of the first antenna 60*b* may be any one of the frames of the bicycle 1 or any one of the bicycle components in which the sensor device 110 is disposed or that is near the sensor device 110.

For example, when the sensor 112 includes the humidity sensor, the sensor 112 can measure the humidity around the bicycle 1. The sensor 112 outputs the measured humidity to the controller 114. In this example, the sensor device 110 including the sensor 112 can be disposed in any one of the frames of the bicycle 1 or any one of the bicycle components. In this example, the disposition position of the first antenna 60*b* may be any one of the frames of the bicycle 1 or any one of the bicycle components in which the sensor device 110 is disposed or that is near the sensor device 110.

For example, when the sensor 112 includes the atmospheric pressure sensor, the sensor 112 can measure the atmospheric pressure around the bicycle 1. The sensor 112 outputs the measured atmospheric pressure to the controller 114. In this example, the sensor device 110 including the sensor 112 can be disposed in any one of the frames of the bicycle 1 or any one of the bicycle components. In this example, the disposition position of the first antenna 60*b* may be any one of the frames of the bicycle 1 or any one of the bicycle components in which the sensor device 110 is disposed or that is near the sensor device 110.

For example, when the sensor 112 includes the illuminance sensor, the sensor 112 can measure the illuminance around the bicycle 1. The sensor 112 outputs the measured illuminance to the controller 114. In this example, the sensor device 110 including the sensor 112 can be disposed in any one of the frames of the bicycle 1 or any one of the bicycle components. In this example, the disposition position of the first antenna 60*b* may be any one of the frames of the bicycle 1 or any one of the bicycle components in which the sensor device 110 is disposed or that is near the sensor device 110.

For example, when the sensor 112 includes the camera, the sensor 112 can photograph (measure) a face image of the driver. The sensor 112 outputs the measured face image of the driver to the controller 114. In this example, the sensor device 110 including the sensor 112 is disposed in the handlebar 1*a* or the stem 1*e* illustrated in FIG. 89. In this example, the disposition position of the first antenna 60*b* may be the handlebar 1*a* or the stem 1*e* illustrated in FIG. 89.

For example, when the sensor 112 includes the biological sensor, the sensor 112 can measure at least one of a heart rate or a pulse rate of the driver. The biological sensor may be a microwave sensor. The sensor 112 outputs the measured heart rate and the measured pulse rate to the controller 114. In this example, the sensor device 110 including the sensor 112 is disposed in the top tube 1G illustrated in FIG. 90 or the handlebar 1*a* or the stem 1*e* illustrated in FIG. 89. In this example, the disposition position of the first antenna 60*b* may be the top tube 1G, the handlebar 1*a*, or the stem 1*e*.

The memory 113 may be configured by, for example, a semiconductor memory. The memory 113 may function as a work memory of the controller 114. The memory 113 may be included in the controller 114.

The controller 114 can include, for example, a processor. The controller 114 may include one or more processors. The processor may include a general-purpose processor that reads a specific program and executes a specific function and a dedicated processor specialized for specific processing. The dedicated processor may include an IC for specific use. The processor may include a programmable logic device. The PLD may include an FPGA. The controller 114 may be one of an SoC and an SiP in which one or a plurality of processors cooperate. The controller 114 may store, in the memory 113, various kinds of information, a program for operating constituent modules of the sensor device 110, or the like.

The controller 114 acquires data of the bicycle 1 from the sensor 112. The data of the bicycle 1 may include the speed of the bicycle 1, the acceleration acting on the bicycle 1, the angular velocity of the bicycle 1, the magnetism around the bicycle 1, the temperature around the bicycle 1, the humidity around the bicycle 1, the atmospheric pressure around the bicycle 1, and the illuminance around the bicycle 1. The data of the bicycle 1 may include the rotating speed of the crank 1b and the load applied to the crank 1b.

The controller 114 may acquire biological data of the driver from the sensor 112. The biological data of the driver may include a face image, a heart rate, and a pulse rate.

When the first antenna 60b is configured to be capable of communicating with a GPS satellite, the controller 114 may acquire position information of the bicycle 1 based on a GPS signal received by the first antenna 60b.

The controller 114 may generate a transmission signal to be transmitted from the sensor device 110 to the communication device 120. The controller 114 may generate a transmission signal corresponding to at least one of the data of the bicycle 1, the biological data of the driver, and the position information of the bicycle 1. The controller 114 may generate a transmission signal according to a communication standard between the sensor device 110 and the communication device 120. The controller 114 supplies electric power corresponding to the generated transmission signal to the first feeding line 61 of the first antenna 60b. The controller 114 supplies the electric power corresponding to the transmission signal to the first feeding line 61 of the first antenna 60b to transmit the transmission signal to the communication device 120 as an electromagnetic wave.

The communication device 120 can communicate with the information processing device 3 via the network 2. A communication standard between a communication device 120 and the information processing device 3 may be a telecommunication standard. The telecommunication standard may include 2nd generation (2G), 3rd generation (3G), 4th generation (4G), long term evolution (LTE), worldwide interoperability for microwave access (WiMAX), and personal handy-phone system (PHS). The communication device 120 can directly communicate with the mobile body 4. A communication standard between the communication device 120 and the mobile body 4 may be a short-range communication standard. The short-range communication standard may include WiFi (registered trademark), Bluetooth (registered trademark), and wireless LAN.

The communication device 120 includes at least one first antenna 60c, a memory 123, and a controller 124. The communication device 120 may include the first antenna 60c on the outside or the outer surface of the communication device 120. The communication device 120 may include a battery 121. When the communication device 120 does not include the battery 121, the communication device 120 may operate with electric power supplied from the battery 10 illustrated in FIG. 90. When the communication device 120 receives the supply of the electric power from the battery 1o, the communication device 120 and the battery 10 may be electrically connected by a power line or the like.

The first antenna 60c may be the first antenna 60a independent from the first antenna 60b of the sensor device 110.

The first antenna 60c may be configured as appropriate according to a frequency band used in communication between the communication device 120 and other devices. In other words, each of the first conductor 31, the second conductor 32, the third conductor 40, and the fourth conductor 50 included in the first antenna 60c may be configured as appropriate according to the frequency band used in the communication between the communication device 120 and the other devices.

The disposition position of the first antenna 60c may be selected as appropriate out of the disposition positions explained above with reference to FIG. 89 to FIG. 92 according to a communication partner of the communication device 120.

For example, when the communication partner is the information processing device 3 and the mobile body 4, the disposition position of the first antenna 60c may be the seat stay 1A, the front fork 1E, or the head tube 1F illustrated in FIG. 90. When the first antenna 60c is disposed in the seat stay 1A, an electromagnetic wave from the first antenna 60c is easily radiated to the rear of the bicycle 1. When the first antenna 60c is disposed in the front fork 1E or the head tube 1F, the electromagnetic wave from the first antenna 60c is easily radiated to the front of the bicycle 1. Since the electromagnetic wave from the first antenna 60c is easily radiated to the front or the rear of the bicycle 1, communication between the communication device 120 and the information processing device 3 and the mobile body 4 is stabilized.

For example, when the communication partner is a GPS satellite, the disposition position of the first antenna 60c may be the top tube 1G illustrated in FIG. 90 or the stem 1e illustrated in FIG. 89. When the first antenna 60c is disposed in the top tube 1G or the like illustrated in FIG. 90, the first antenna 60c easily receives an electromagnetic wave from the GPS satellite.

The first antenna 60c can receive an electromagnetic wave from another device as a reception signal. The reception signal received by the first antenna 60c is transmitted to the controller 124 through the first feeding line 61 of the first antenna 60c. Electric power is supplied to the first feeding line 61 of the first antenna 60c, whereby the first antenna 60c can radiate an electromagnetic wave serving as a transmission signal to the other device.

The battery 121 can supply electric power to at least one of the first antenna 60c, the memory 123, and the controller 124. The battery 121 can include, for example, at least one of a primary battery and a secondary battery. A negative pole of the battery 121 is electrically connected to the fourth conductor 50 of the first antenna 60c.

The memory 123 may be configured by, for example, a semiconductor memory. The memory 123 may function as a work memory of the controller 124. The memory 123 may be included in the controller 124. The memory 123 may store identification information of the bicycle 1 and biological data of the user. The identification information of the bicycle 1 may be information specific to the bicycle 1. The identification information of the bicycle 1 may be formed by a combination of numbers and/or characters.

The controller 124 can include, for example, a processor. The processor may include a general-purpose processor that reads a specific program and executes a specific function and a dedicated processor specialized for specific processing. The dedicated processor may include an IC for specific use. The processor may include a programmable logic device. The PLD may include an FPGA. The controller 124 may include one or more processors. The controller 124 may be one of an SoC and an SiP in which one or a plurality of processors cooperate. The controller 124 may store, in the memory 123, various kinds of information, a program for operating constituent modules of the communication device 120, or the like. The controller 124 may store, in the memory 123, identification information of the bicycle 1 acquired from the information processing device 3 or the like on the outside. The controller 124 may store, in the memory 123, biological data of the user acquired from the information processing device 3 or the like on the outside.

The controller 124 acquires a reception signal from the sensor device 110 through, for example, the first feeding line 61 of the first antenna 60c. The reception signal can include data of the bicycle 1 and biological data of the driver measured by the sensor device 110. When the sensor device 110 is configured to be capable of measuring position information of the bicycle 1, the reception signal can include the position information of bicycle 1.

The controller 124 may detect a driving state of the bicycle 1 based on the data of the bicycle 1. The driving state of the bicycle 1 may include a traveling distance of the bicycle 1, a turning direction of the bicycle 1, tumble during traveling of the bicycle 1, and a temporary stop during driving of the bicycle 1.

For example, the controller 124 may calculate a traveling distance of the bicycle 1 based on the acceleration included in the data of the bicycle 1.

For example, the controller 124 may detect a turning direction of the bicycle 1 based on the speed and the angular velocity of the bicycle 1 included in the data of the bicycle 1.

For example, the controller 124 may detect tumble during traveling of the bicycle 1 based on the speed and the angular velocity of the bicycle 1 included in the data of the bicycle 1. When the bicycle 1 tumbles during traveling, since the bicycle 1 tilts, angular velocity equal to or larger than a predetermined value can be measured.

For example, the controller 124 may detect a temporary stop during driving of the bicycle 1 based on the speed and the angular velocity of the bicycle included in the data of the bicycle 1. When temporarily stopping the bicycle 1 during the driving of the bicycle 1, the driver can tilt the bicycle 1 and touch the ground with the foot of the driver. When the driver tilts the bicycle 1 and touches the ground with the foot of the driver, speed lower than predetermined speed is measured and angular velocity equal to or larger than a predetermined value is measured.

When the first antenna 60c is configured to be capable of communicating with a GPS satellite, the controller 124 may acquire position information of the bicycle 1 based on a GPS signal received by the first antenna 60c.

The controller 124 may generate a transmission signal from the communication device 120 to the information processing device 3. The controller 124 may generate a transmission signal corresponding to at least one of the data of the bicycle 1, the driving state of the bicycle 1, and the position information of the bicycle 1. The controller 124 may generate a transmission signal such that the identification information of the bicycle 1 stored in the memory 123 is included in the transmission signal. The controller 124 may generate a transmission signal according to the communication standard between the communication device 120 and the information processing device 3. The controller 124 supplies electric power corresponding to the generated transmission signal to the first feeding line 61 of the first antenna 60c. The controller 124 supplies the electric power corresponding to the transmission signal to the first feeding line 61 of the first antenna 60c to transmit the transmission signal from the communication device 120 to the information processing device 3 as an electromagnetic wave.

For example, the controller 124 may generate, as the transmission signal from the communication device 120 to the information processing device 3, a transmission signal corresponding to the traveling distance of the bicycle 1 included in the driving state of the bicycle 1. The controller 124 may generate the transmission signal such that the identification information of the bicycle 1 is included in the transmission signal. Since the communication device 120 transmits the transmission signal to the information processing device 3, the information processing device 3 can acquire the transmission signal from the communication device 120 through the network 2. The information processing device 3 can acquire the traveling distance of the bicycle 1 and the identification information of the bicycle 1 by acquiring the transmission signal. By viewing the traveling distance of the bicycle 1 acquired by the information processing device 3, the user can grasp a distance that the user travels with the bicycle 1.

For example, the controller 124 may generate a transmission signal corresponding to the position information of the bicycle 1 as the transmission signal from the communication device 120 to the information processing device 3. The controller 124 may generate the transmission signal such that the identification information of the bicycle 1 is included in the transmission signal. Since the communication device 120 transmits the transmission signal to the information processing device 3, the information processing device 3 can acquire the transmission signal from the communication device 120 through the network 2. The information processing device 3 can acquire the position information of the bicycle 1 and the identification information of the bicycle 1 by acquiring the transmission signal. For example, when a company that provides a home delivery service owns the bicycle 1, the company can grasp the position of the bicycle 1 in delivery by viewing identification information and position information of the bicycle 1 acquired by the information processing device 3. For example, when the bicycle 1 is stolen, an owner of the bicycle 1 can grasp the position of the stolen bicycle 1 by viewing identification information and the position information of the bicycle 1 acquired by the information processing device 3.

The controller 124 may generate a transmission signal from the communication device 120 to the mobile body 4 around the bicycle 1. The controller 124 may generate a transmission signal corresponding to at least one of the data of the bicycle 1 and the driving state of the bicycle 1. The controller 124 may generate a transmission signal according to the short-range communication standard. The controller 124 supplies electric power corresponding to the generated transmission signal to the first feeding line 61 of the first antenna 60c. The controller 124 supplies the electric power corresponding to the transmission signal to the first feeding line 61 of the first antenna 60c to transmit the transmission signal from the communication device 120 to the mobile body 4 as an electromagnetic wave.

For example, the controller 124 may generate a transmission signal corresponding to the turning direction of the bicycle 1 included in the driving state of the bicycle 1 as the transmission signal from the communication device 120 to the mobile body 4 around the communication device 120. When detecting the turning direction of the bicycle 1, the controller 124 may generate the transmission signal. The mobile body 4 can acquire information concerning the turning direction of the bicycle 1 by acquiring the transmission signal from the communication device 120. For example, when the mobile body 4 is an automobile, a driver of the automobile can grasp the turning direction of the bicycle 1. Since the driver of the automobile grasps the turning direction of the bicycle 1, an accident of the mobile body 4 and the bicycle 1 can be avoided.

For example, the controller 124 may generate a transmission signal corresponding to the tumble during traveling of the bicycle 1 included in the driving state of the bicycle 1 as the transmission signal from the communication device 120 to the mobile body 4 around the communication device 120. When detecting tumble during traveling of the bicycle 1, the controller 124 may generate a transmission signal. The mobile body 4 can acquire information concerning the tumble during traveling of the bicycle 1 by acquiring the transmission signal from the communication device 120. For example, when the mobile body 4 is an automobile, by grasping tumble of the bicycle 1, a driver of the automobile can quickly stop the automobile in order to avoid collision with the bicycle 1.

The controller 124 may determine, based on the biological data of the driver of the bicycle 1 and the biological data of the user stored in the memory 123, whether the driver and the user are the same person. When determining that the driver of the bicycle 1 and the user of the bicycle 1 are not the same person, the controller 124 may generate a transmission signal indicating warning. The transmission signal may be transmitted from the communication device 120 to the information processing device 3. The controller 124 may generate the transmission signal such that the position information of the bicycle 1 stored in the memory 123 is included in the transmission signal. The information processing device 3 can acquire the signal indicating the warning and the position information of the bicycle 1 by acquiring the transmission signal. For example, from the signal indicating the warning acquired by the information processing device 3, the user of the bicycle 1 can learn that the bicycle 1 is stolen. The user learning the theft of the bicycle 1 can learn the location of the bicycle 1 from the position information of the bicycle 1 acquired by the information processing device 3.

Another Example of the Functions of the Bicycle

Figure 94:
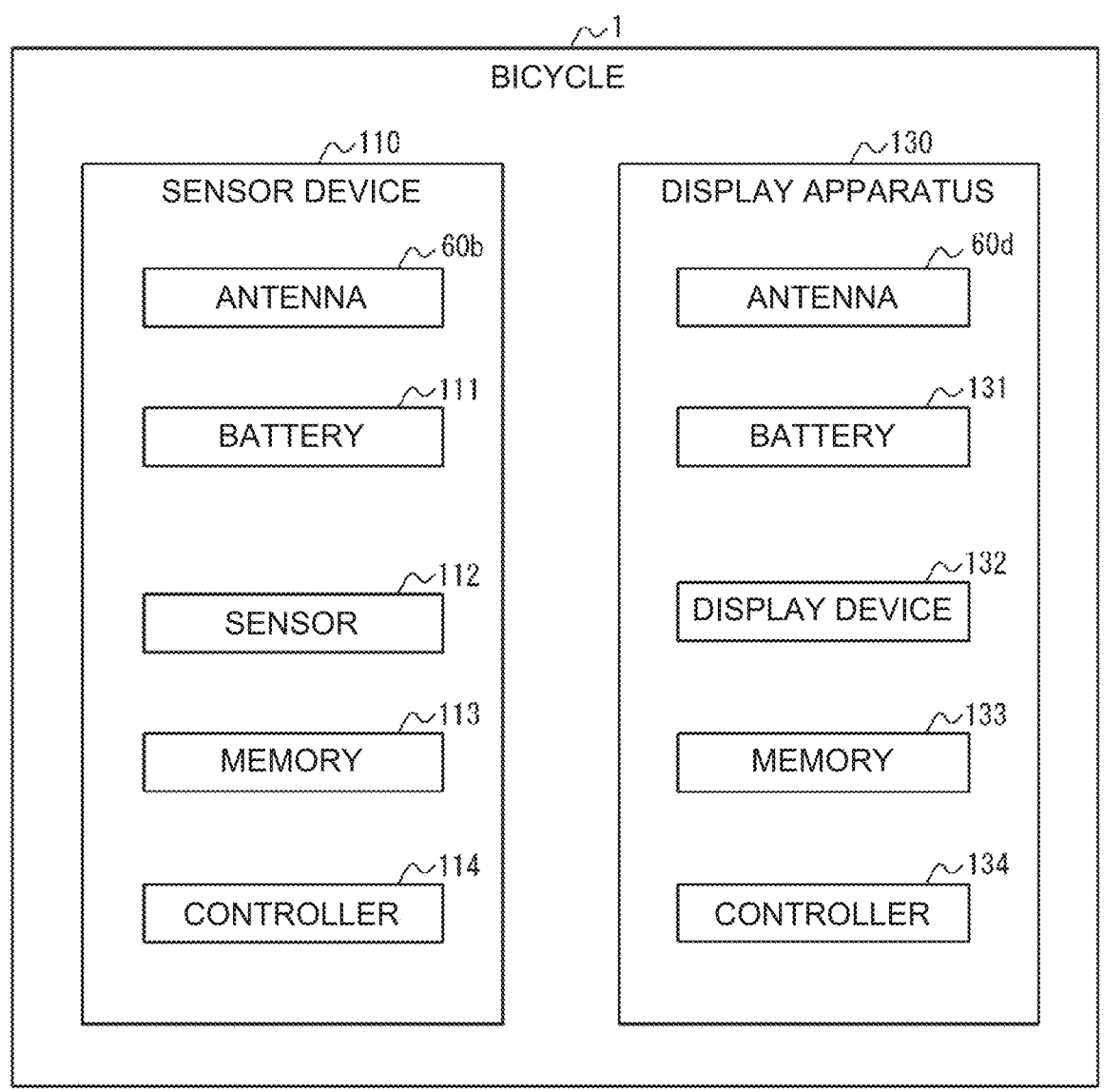
FIG. 94 is a functional block diagram of another example of the bicycle illustrated in FIG. 89.

FIG. 94 is a functional block diagram of another example of the bicycle 1 illustrated in FIG. 89. The bicycle 1 includes the sensor device 110 and a display apparatus 130. The sensor device 110 and the display apparatus 130 can perform wireless communication with each other. The wireless communication may be based on a short-range communication standard. The short-range communication standard may include WiFi (registered trademark), Bluetooth (registered trademark), and wireless LAN.

The sensor device 110 can transmit the data of the bicycle 1 to the display apparatus 130. The sensor device 110 can transmit the biological data of the driver to the display apparatus 130. The sensor device 110 can transmit the position information of the bicycle 1 to the display apparatus 130. The same configuration as the configuration of the sensor device 110 illustrated in FIG. 93 may be adopted as the sensor device 110.

The display apparatus 130 presents various data to the driver. The display apparatus 130 may be a cycle computer. The display apparatus 130 may be disposed as appropriate in any one of the frames of the bicycle 1 illustrated in FIG. 90 or any one of the bicycle components illustrated in FIG. 89 and the like. As an example, the display apparatus 130 may be disposed in the top tube 1G illustrated in FIG. 90, the handlebar 1a illustrated in FIG. 89, or the stem 1e illustrated in FIG. 89. A disposition place of the display apparatus 130 is not limited to the frame of the bicycle 1 and the bicycle component. For example, the display apparatus 130 may be attached to the user of the bicycle 1.

The display apparatus 130 includes at least one first antenna 60d, a display device 132, a memory 133, and a controller 134. The display apparatus 130 may include the first antenna 60d on the outside or the outer surface of the display apparatus 130. The display apparatus 130 may include a battery 131. When the display apparatus 130 does not include the battery 131, the display apparatus 130 may operate with electric power supplied from the battery 10 illustrated in FIG. 90. When the display apparatus 130 receives the supply of the electric power from the battery 1o, the display apparatus 130 and the battery 10 may be electrically connected by a power line or the like.

The first antenna 60d may be the first antenna 60a independent from the first antenna 60b of the sensor device 110.

The first antenna 60d may be configured as appropriate according to a frequency band in use used in the communication between the display apparatus 130 and the other devices. In other words, each of the first conductor 31, the second conductor 32, the third conductor 40, and the fourth conductor 50 included in the first antenna 60d may be configured as appropriate according to the frequency band used in the communication between the display apparatus 130 and the other devices. For example, the first antenna 60d may be configured as appropriate according to a frequency band in use used in short-range communication between the display apparatus 130 and the sensor device 110. For example, the first antenna 60d may be configured according to a frequency band used in the communication between the display apparatus 130 and a GPS satellite.

The first antenna 60d can receive an electromagnetic wave from another device as a reception signal. The reception signal received by the first antenna 60d is transmitted to the controller 134 through the first feeding line 61 of the first antenna 60d. Electric power is supplied to the first feeding line 61 of the first antenna 60d, whereby the first antenna 60d can radiate, on the other device, an electromagnetic wave serving as a transmission signal.

A disposition position of the first antenna 60d may be selected as appropriate from the disposition positions explained above with reference to FIG. 89 to FIG. 92 according to a disposition position of the display apparatus 130 or a communication partner of the display apparatus 130.

For example, when the disposition position of the display apparatus 130 is the top tube 1G illustrated in FIG. 90, the disposition position of the first antenna 60d may be the top tube 1G. For example, when the disposition position of the display apparatus 130 is the handlebar 1a or the stem 1e illustrated in FIG. 89, a disposition place of the first antenna 60d may be the handlebar 1a or the stem 1e.

For example, when the communication partner of the display apparatus 130 is a GPS satellite, the disposition position of the first antenna 60*d* may be the top tube 1G illustrated in FIG. 90 or the stem 1*e* illustrated in FIG. 89. Since the first antenna 60*d* is disposed in the top tube 1G or the stem 1*e*, the first antenna 60*d* easily receives an electromagnetic wave from the GPS satellite.

The battery 131 can supply electric power to at least one of the first antenna 60*d*, the display device 132, the memory 133, and the controller 134. The battery 131 can include, for example, at least one of a primary battery and a secondary battery. A negative pole of the battery 131 is electrically connected to the fourth conductor 50 of the first antenna 60*d*.

The display device 132 may include an liquid crystal display (LCD), organic electro luminescence (EL), or an inorganic EL. The display device 132 displays a character, an image, an object for operation, a pointer, and the like based on control by the controller 134.

The memory 133 may be configured by, for example, a semiconductor memory. The memory 133 may function as a work memory of the controller 134. The memory 133 may be included in the controller 134. The memory 133 may store the weight of the user and the weight of the bicycle 1.

The controller 134 can include, for example, a processor. The processor may include a general-purpose processor that reads a specific program and executes a specific function and a dedicated processor specialized for specific processing. The dedicated processor may include an IC for specific use. The processor may include a programmable logic device. The PLD may include an FPGA. The controller 134 may include one or more processors. The controller 134 may be one of an SoC or an SiP in which one or a plurality of processors cooperate. The controller 134 may store, in the memory 133, various kinds of information, a program for operating constituent modules of the display apparatus 130, and the like.

The controller 134 acquires a reception signal from the sensor device 110 through, for example, the first feeding line 61 of the first antenna 60*d*. The reception signal can include data of the bicycle 1 and biological data of the driver measured by the sensor device 110. When the sensor device 110 is configured to be capable of measuring position information of the bicycle 1, the reception signal can include the position information of bicycle 1.

When the first antenna 60*d* is configured to be capable of communicating with a GPS satellite, the controller 134 may acquire the position information of the bicycle 1 based on a GPS signal received by the first antenna 60*d*.

The controller 134 may calculate a traveling distance of the bicycle 1 based on the acceleration included in the data of the bicycle 1. The controller 134 may calculate, based on the traveling distance of the bicycle 1, the weight of the user, and the weight of the bicycle 1, a consumed calorie consumed by the user by driving the bicycle 1.

The controller 134 may cause the display device 132 to display various kinds of information. For example, the controller 134 may cause the display device 132 to display the speed of the bicycle 1 included in the data of the bicycle 1. For example, the controller 134 may cause the display device 132 to display the position information of the bicycle 1. For example, the controller 134 may cause the display device 132 to display the rotating speed of the crank 1*b* included in the data of the bicycle 1. For example, the controller 134 may cause the display device 132 to display the load applied to the crank 1*b* included in the data of the bicycle 1. For example, the controller 134 may cause the display device 132 to display the calculated traveling distance of the bicycle 1 and the calculated consumed calorie of the user. For example, the controller 134 may cause the display device 132 to display residual power of the battery 1*o* illustrated in FIG. 90. For example, the controller 134 may cause the display device 132 to display the heart rate and the pulse rate included in the biological data of the driver.

The controller 134 may generate a transmission signal from the display apparatus 130 to the sensor device 110. The controller 134 may generate a transmission signal according to a short-range communication standard between the display apparatus 130 and the sensor device 110. The controller 134 supplies electric power corresponding to the generated transmission signal to the first feeding line 61 of the first antenna 60*d*. The controller 134 supplies the electric power corresponding to the transmission signal to the first feeding line 61 of the first antenna 60*d* to transmit the transmission signal from the display apparatus 130 to the sensor device 110.

In this way, the sensor device 110 and the display apparatus 130 respectively include the first antenna 60*b* and the first antenna 60*d* independent from each other. Therefore, the sensor device 110 and the display apparatus 130 can perform wireless communication each other. Since the sensor device 110 and the display apparatus 130 perform the wireless communication, wires such as cables attached to the bicycle 1 can be reduced. The bicycle 1 can be reduced in weight by reducing the wires attached to the bicycle 1. Since the bicycle 1 can be reduced in weight, convenience of the bicycle 1 can be improved.

Still Another Example of the Functions of the Bicycle

Figure 95:
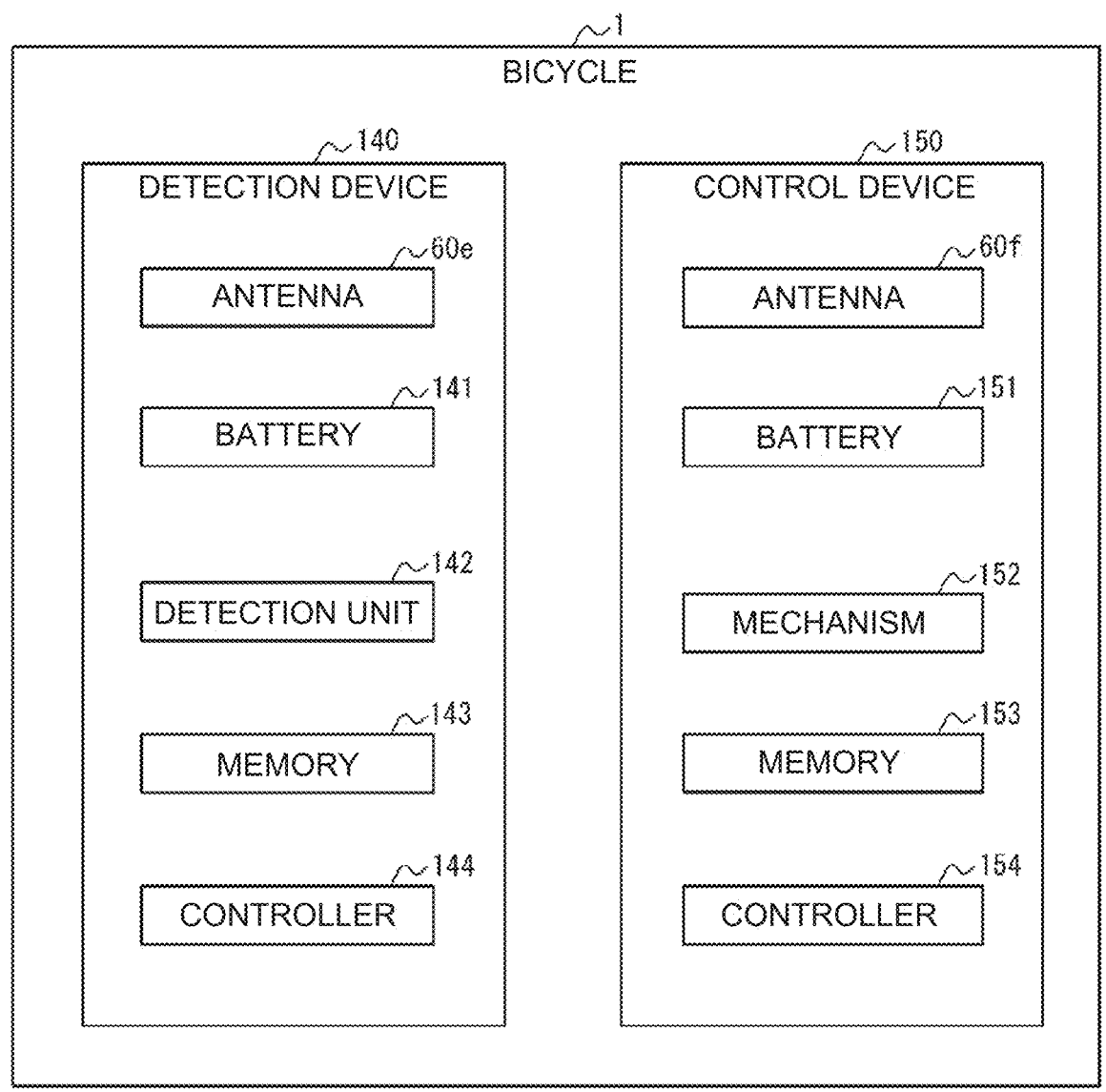
FIG. 95 is a functional block diagram of still another example of the bicycle illustrated in FIG. 89.

FIG. 95 is a functional block diagram of still another example of the bicycle 1 illustrated in FIG. 89. The bicycle 1 includes a detection device 140 and a control device 150. The detection device 140 and the control device 150 can perform wireless communication with each other. The wireless communication may be based on a short-range communication standard. The short-range communication standard may include WiFi (registered trademark), Bluetooth (registered trademark), and wireless LAN.

The detection device 140 detects operation by the driver. The detection device 140 may be a bicycle component. For example, the detection device 140 may be the dual control lever 1*h* illustrated in FIG. 92. In this example, the detection device 140 may detect operation by the driver on the shift lever 1*h*-1 or may detect operation by the driver on the brake lever 1*h*-2.

The detection device 140 may detect an environment around the bicycle 1. For example, the detection device 140 may detect illuminance around the bicycle 1.

The detection device 140 includes at least one first antenna 60*e*, a detection unit 142, a memory 143, and a controller 144. The detection device 140 may include a first antenna 60*e* on the outside or the outer surface of the detection device 140. The detection device 140 may include a battery 141. When the detection device 140 does not include the battery 141, the detection device 140 may operate with electric power supplied from the battery 10 illustrated in FIG. 90. When the detection device 140 receives the supply of the electric power from the battery 1*o*, the detection device 140 and the battery 10 may be electrically connected via a power line or the like.

The first antenna 60e may be the first antenna 60a independent from a first antenna 60f of the control device 150.

A disposition position of the first antenna 60e may be selected as appropriate from the disposition positions explained above with reference to FIG. 89 to FIG. 92 according to a bicycle component that could be the detection device 140.

For example, the detection device 140 could be the dual control lever 1h illustrated in FIG. 89. In this example, the disposition position of the first antenna 60e may be the dual control lever 1h or may be the head tube 1F near the dual control lever 1h illustrated in FIG. 90.

The first antenna 60e may be configured as appropriate according to a frequency band used in communication between the detection device 140 and other devices. In other words, each of the first conductor 31, the second conductor 32, the third conductor 40, and the fourth conductor 50 included in the first antenna 60e may be configured as appropriate according to the frequency band used in the communication between the detection device 140 and the other devices.

The first antenna 60e can receive an electromagnetic wave from another device as a reception signal. The reception signal received by the first antenna 60e is transmitted to the controller 144 through the first feeding line 61 of the first antenna 60e. Electric power is supplied to the first feeding line 61 of the first antenna 60e, whereby the first antenna 60e can radiate, on the other device, an electromagnetic wave serving as a transmission signal.

The battery 141 can supply electric power to at least one of the first antenna 60e, the detection unit 142, the memory 143, and the controller 144. The battery 141 can include, for example, at least one of a primary battery and a secondary battery. A negative pole of the battery 141 is electrically connected to the fourth conductor 50 of the first antenna 60e.

The detection unit 142 detects operation by the driver. The detection unit 142 may be configured as appropriate according to the specifications and the like of the bicycle component that could be the detection device 140.

For example, the detection device 140 can be the dual control lever 1h illustrated in FIG. 92. The specification of the dual control lever 1h can be changing a speed gear ratio according to left and right rotations of the shift lever 1h-1. The speed gear ratio is the number of revolutions of the rear wheel 1c per one rotation of the chain wheel 1j. In this example, the detection unit 142 may include a rotation sensor. The detection unit 142 detects, with the rotation sensor, the left and right rotations of the shift lever 1h-1. The detection unit 142 outputs the detected left and right rotations to the controller 144.

For example, the detection device 140 can be the dual control lever 1h illustrated in FIG. 92. The specification of the dual control lever 1h can be changing a speed gear ratio according to operation by the driver on the switch 1h-3. In this example, the detection unit 142 may include a pressure sensor. The detection unit 142 detects operation by the driver on the switch 1h-3. The detection unit 142 outputs the operation by the driver on the switch 1h-3 to the controller 144.

For example, the detection device 140 can be the dual control lever 1h illustrated in FIG. 92. The specification of the dual control lever 1h can be exerting a brake function according to pressure applied to the brake lever 1h-2 by, for example, grasping power of the driver. The brake function is a function of stopping the rear wheel 1c and the wheel 1d illustrated in FIG. 89. In this example, the detection unit 142 may include a pressure sensor. The detection unit 142 detects, with the pressure sensor, the pressure applied to the brake lever 1h-2. The detection unit 142 outputs the detected pressure to the controller 144.

The detection unit 142 may detect an environment around the bicycle 1. The detection unit 142 may be configured as appropriate according to the environment around the bicycle 1 detected by the detection device 140.

For example, when the detection device 140 detects illuminance around the bicycle 1, the detection unit 142 may include an illuminance sensor. The detection unit 142 detects, with the illuminance sensor, the illuminance around the bicycle 1. The detection unit 142 outputs the detected illuminance to the controller 144.

The memory 143 may be configured by, for example, a semiconductor memory. The memory 143 may function as a work memory of the controller 144. The memory 143 may be included in the controller 144.

The controller 144 can include a processor. The processor may include a general-purpose processor that reads a specific program and executes a specific function and a dedicated processor specialized for specific processing. The dedicated processor may include an IC for specific use. The processor may include a programmable logic device. The PLD may include an FPGA. The controller 144 may include one or more processors. The controller 144 may be one of an SoC and an SiP in which one or a plurality of processors cooperate. The controller 144 may store, in the memory 143, various kinds of information, a program for operating constituent modules of the detection device 140, or the like. The controller 144 may acquire a reception signal from the control device 150 through the first feeding line 61 of the first antenna 60e.

The controller 144 acquires a detection result of the detection unit 142. The controller 144 generates a control signal based on the detection result of the detection unit 142.

For example, the controller 144 determines a speed gear ratio according to left and right rotations of the shift lever 1h-1 detected by the detection unit 142. The controller 114 generates, as a control signal, a signal indicating the determined speed gear ratio.

For example, the controller 144 determines a speed gear ratio according to operation on the switch 1h-3 detected by the detection unit 142. The controller 144 generates, as a control signal, a signal indicating the determined speed gear ratio.

For example, the controller 114 acquires, from the detection unit 142, pressure applied to the brake lever 1h-2. The controller 114 generates, according to the pressure applied to the brake lever 1h-2, as a control signal, a signal indicating execution of the brake function.

For example, the controller 114 generates, based on illuminance around the bicycle 1 detected by the detection unit 142, as a control signal, a signal indicating lighting of the light 1i or a signal indicating extinction of the light 1i. For example, when the illuminance detected by the detection unit 142 is smaller than a predetermined value, the controller 144 generates, as a control signal, a signal indicating lighting of the light 1i. For example, when the illuminance detected by the detection unit 142 increases to the predetermined value or more after the signal indicating the lighting of the light 1i is generated, the controller 144 generates, as a control signal, a signal indicating extinction of the light 1i.

The controller 144 generates a transmission signal corresponding to the generated control signal as a transmission signal from the detection device 140 to the control device 150. The controller 144 may generate a transmission signal according to a short-range communication standard between the detection device 140 and the control device 150. The controller 144 supplies electric power corresponding to the generated transmission signal to the first feeding line 61 of the first antenna 60e.

The controller 144 may acquire a reception signal from the control device 150 through the first feeding line 61 of the first antenna 60e.

The control device 150 controls a function of the bicycle 1 based on operation by the driver detected by the detection device 140. The control device 150 may control a function of the bicycle 1 based on an environment around the bicycle 1 detected by the detection device 140. The control device 150 may be a bicycle component corresponding to the function of the bicycle 1 controlled by the control device 150.

For example, the control device 150 may control a speed gear ratio of the bicycle 1 as the function of the bicycle 1. In this example, the control device 150 may be the rear derailleur 1f or the front derailleur 1g.

For example, the control device 150 may control a brake function of the bicycle 1 as the function of the bicycle 1. In this example, the control device 150 may be the brake 1k-1 or the brake 1k-2.

For example, the control device 150 may perform lighting around the bicycle 1 as the function of the bicycle 1. In this example, the control device 150 may be the light 1i.

The control device 150 includes at least one first antenna 60f, a mechanism 152, a memory 153, and a controller 154. The control device 150 may include the first antenna 60f on the outside or the outer surface of the control device 150. The control device 150 may include a battery 151. When the control device 150 does not include the battery 151, the control device 150 may operate with electric power supplied from the battery 10 illustrated in FIG. 90. When the control device 150 receives the supply of the electric power from the battery 1o, the control device 150 and the battery 10 may be electrically connected by a power line or the like.

The first antenna 60f may be the first antenna 60a independent from the first antenna 60e of the detection device 140.

The first antenna 60f may be configured as appropriate according to a frequency band used in communication between the control device 150 and other devices. In other words, each of the first conductor 31, the second conductor 32, the third conductor 40, and the fourth conductor 50 included in the first antenna 60f may be configured as appropriate according to the frequency band used in the communication between the control device 150 and the other devices.

The first antenna 60f can receive an electromagnetic wave from another device as a reception signal. The reception signal received by the first antenna 60f is transmitted to the controller 154 through the first feeding line 61 of the first antenna 60f. Electric power is supplied to the first feeding line 61 of the first antenna 60f, whereby the first antenna 60f can radiate, on the other device, an electromagnetic wave serving as a transmission signal.

A disposition position of the first antenna 60f may be selected as appropriate out of the disposition positions explained above with reference to FIG. 89 to FIG. 92 according to a bicycle component that could be the control device 150.

For example, the control device 150 could be the rear derailleur 1f illustrated in FIG. 89. In this example, the disposition position of the first antenna 60f may be the rear derailleur 1f or may be the seat stay 1A illustrated in FIG. 90 near the rear derailleur 1f.

For example, the control device 150 could be the front derailleur 1g illustrated in FIG. 89. In this example, the disposition position of the first antenna 60f may be the front derailleur 1g or may be the seat tube 1B illustrated in FIG. 90 near the front derailleur 1g.

For example, the control device 150 could be the brake 1k-1 illustrated in FIG. 89. In this example, the disposition position of the first antenna 60f may be the brake 1k-1. The disposition position of the first antenna 60f may be the seat stay 1A illustrated in FIG. 90 near the brake 1k-1.

For example, the control device 150 could be the brake 1k-2 illustrated in FIG. 89. In this example, the disposition position of the first antenna 60f may be the brake 1k-2. The disposition position of the first antenna 60f may be the head tube 1F illustrated in FIG. 90 near the brake 1k-2.

For example, the control device 150 could be the light 1i illustrated in FIG. 89. In this example, the disposition position of the first antenna 60f may be the light 1i. The disposition position of the first antenna 60f may be the head tube 1F illustrated in FIG. 90 near the light 1i.

The battery 151 can supply electric power to at least one of the first antenna 60f, the mechanism 152, the memory 153, and the controller 154. The battery 151 can include, for example, at least one of a primary battery and a secondary battery. A negative pole of the battery 151 is electrically connected to the fourth conductor 50 of the first antenna 60f.

The mechanism 152 may include any member according to, for example, a bicycle component that could be the control device 150.

For example, the control device 150 could be the front derailleur 1g illustrated in FIG. 89. In this example, the mechanism 152 may include a chain guide and a motor that drives the chain guide. The chain guide guides a chain laid on the chain wheel 1j illustrated in FIG. 91 to the chain wheel 1j-1 or the chain wheel 1j-2.

For example, the control device 150 could be the rear derailleur 1f illustrated in FIG. 89. In this example, the mechanism 152 may include a chain guide and a motor that drives the chain guide. The chain guide guides a chain of the bicycle 1 to any one of a plurality of chain wheels attached to the rear wheel 1c illustrated in FIG. 91.

For example, the control device 150 can be the brake 1k-1 or the brake 1k-2 illustrated in FIG. 89. In this example, the mechanism 152 may be a brake caliper that can be included in the brake 1k-1 or a brake caliper that can be included in the brake 1k-2.

For example, the control device 150 could be the light 1i illustrated in FIG. 89. In this example, the mechanism 152 may include an LED.

The memory 153 may be configured by, for example, a semiconductor memory. The memory 153 may function as a work memory of the controller 154. The memory 153 may be included in the controller 154.

The controller 154 can include, for example, a processor. The processor may include a general-purpose processor that reads a specific program and executes a specific function and a dedicated processor specialized for specific processing. The dedicated processor may include an IC for specific use. The processor may include a programmable logic device. The PLD may include an FPGA. The controller 154 may include one or more processors. The controller 154 may be one of an SoC and an SiP in which one or a plurality of processors cooperate. The controller 154 may store, in the memory 153, various kinds of information, a program for operating constituent modules of the control device 150, or the like.

The controller 154 acquires a reception signal from the detection device 140 through a feeding line of the first antenna 60f. The reception signal can include a control signal. The control signal may include a signal indicating a speed gear ratio, a signal indicating execution of a brake function, a signal indicating lighting of the light 1i, and a signal indicating extinction of the light 1i. The controller 154 controls the mechanism 152 according to the control signal.

For example, when the control device 150 is the rear derailleur 1f or the front derailleur 1g illustrated in FIG. 89, the controller 154 controls the mechanism 152 according to the signal indicating the speed gear ratio.

For example, when the control device 150 is the brake 1k-1 or the brake 1k-2 illustrated in FIG. 89, the controller 154 controls the mechanism 152 according to the signal indicating the execution of the brake function.

For example, when the control device 150 is the light 1i illustrated in FIG. 89, the controller 154 lights the LED of the mechanism 152 according to the signal indicating the lighting of the light 1i. The controller 154 extinguishes the LED of the mechanism 152 according to the signal indicating the extinction of the light 1i.

The controller 154 may generate a transmission signal transmitted from the control device 150 to the detection device 140. The controller 154 may generate a transmission signal according to the short-range communication standard between the detection device 140 and the control device 150. The controller 154 supplies electric power corresponding to the generated transmission signal to the first feeding line 61 of the first antenna 60f. The controller 154 supplies the electric power corresponding to the transmission signal to the first feeding line 61 of the first antenna 60f to transmit the transmission signal from the control device 150 to the detection device 140 as an electromagnetic wave.

In this way, the detection device 140 and the control device 150 respectively include the first antenna 60e and the first antenna 60f independent from each other. Therefore, the detection device 140 and the control device 150 can perform wireless communication each other. Since the detection device 140 and the control device 150 performs the wireless communication, wires such as cables attached to the bicycle 1 can be reduced. The bicycle 1 can be reduced in weight by reducing the wires attached to the bicycle 1. Since the bicycle 1 can be reduced in weight, convenience of the bicycle 1 can be improved.

The configuration according to the present disclosure is not limited to only the embodiments explained above. Many modifications and changes of the configuration are possible. For example, the functions and the like included in the constituent modules and the like can be rearranged not to logically contradict. A plurality of constituent modules or the like can be combined into one or can be divided.

For example, when the bicycle 1 is an electric powered bicycle, the control device 150 illustrated in FIG. 95 may be a motor that drives the rear wheel 1c and the like illustrate in FIG. 89. In this example, the detection device 140 may be a device that detects a load applied to the crank 1b illustrated in FIG. 91.

Configuration Example of an Unmanned Aircraft

Figure 96:
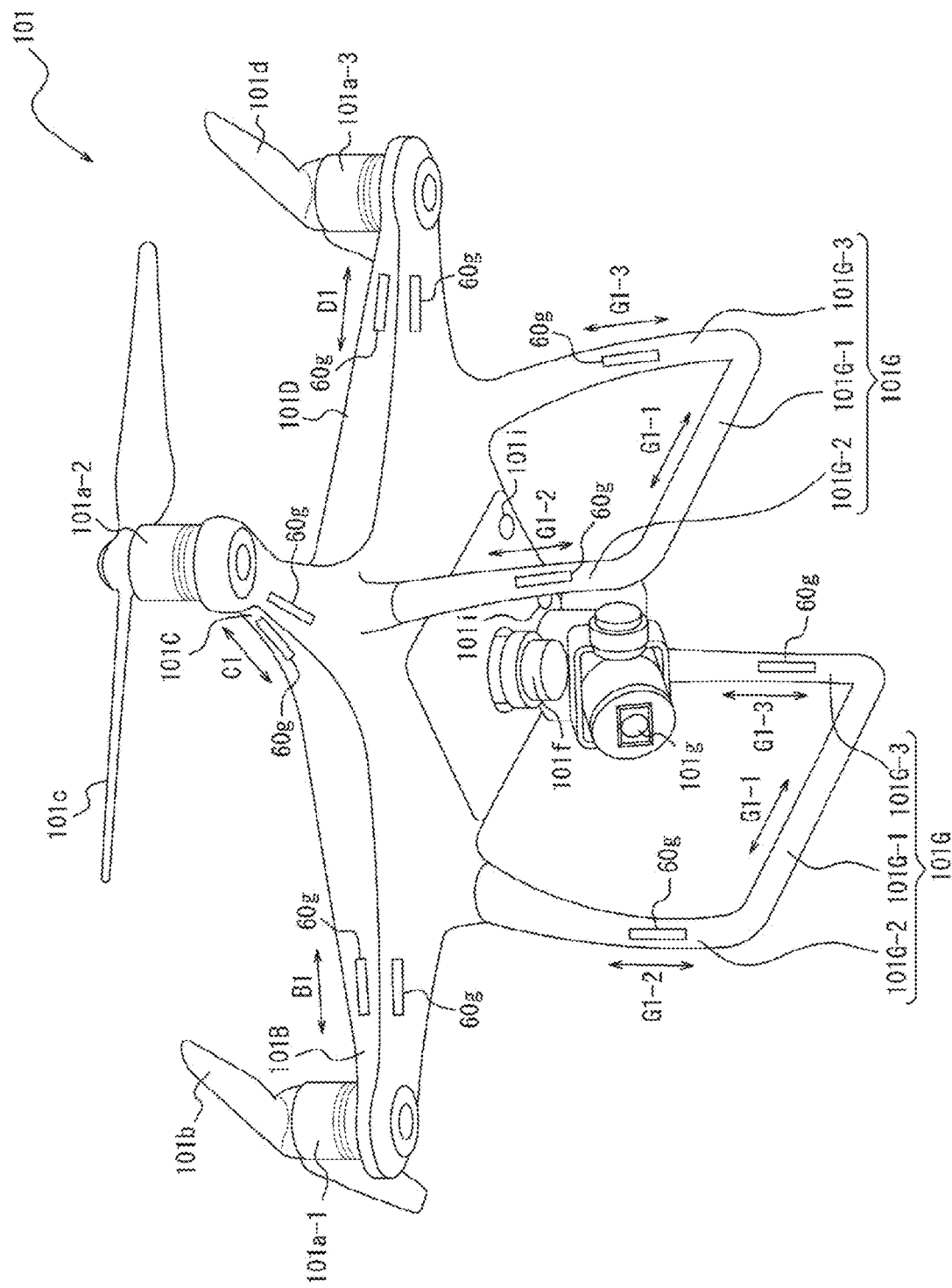
FIG. 96 is a perspective view of an embodiment of an unmanned aircraft.
Figure 97:
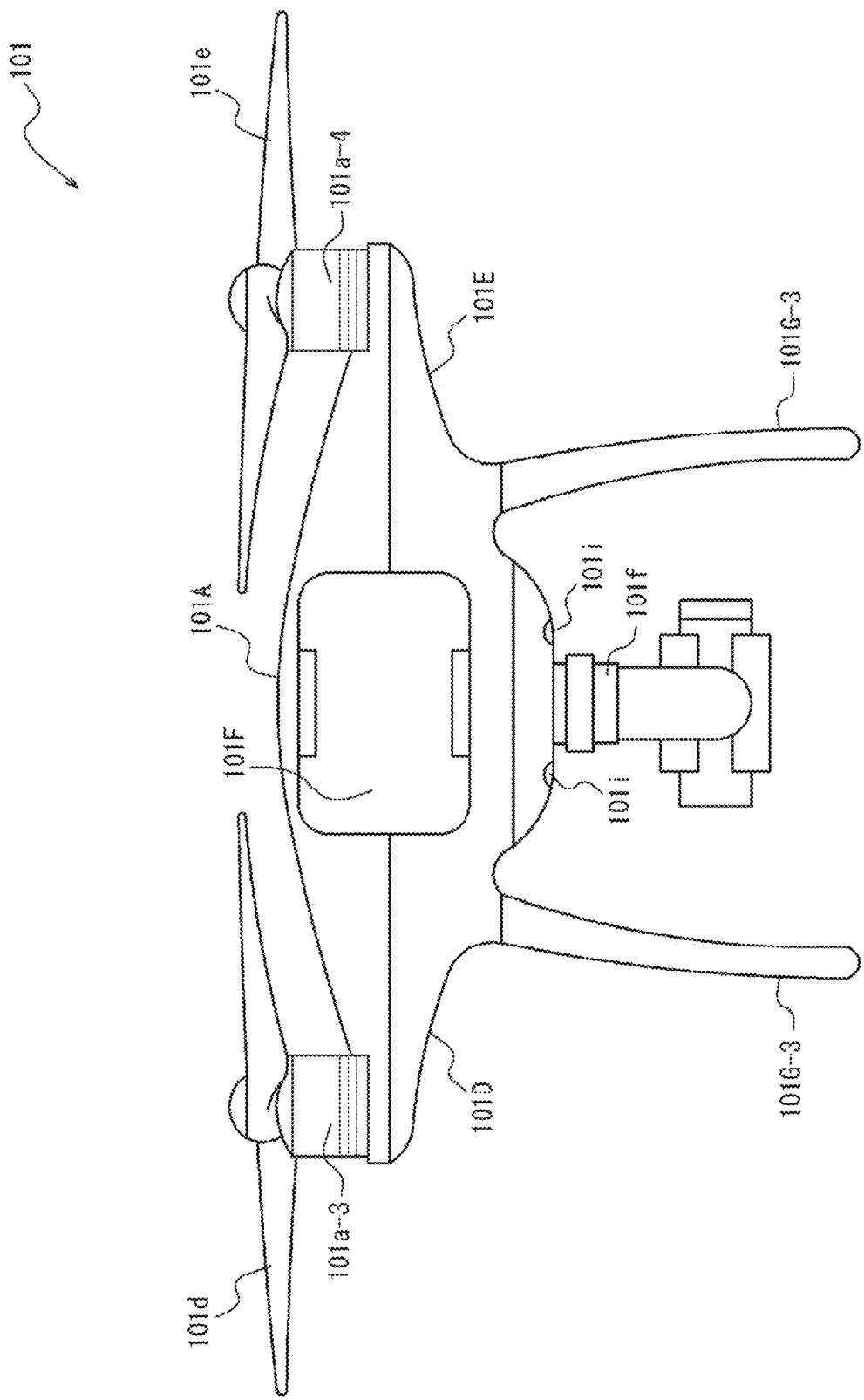
FIG. 97 is a rear view of the unmanned aircraft illustrated in FIG. 96.
Figure 98:
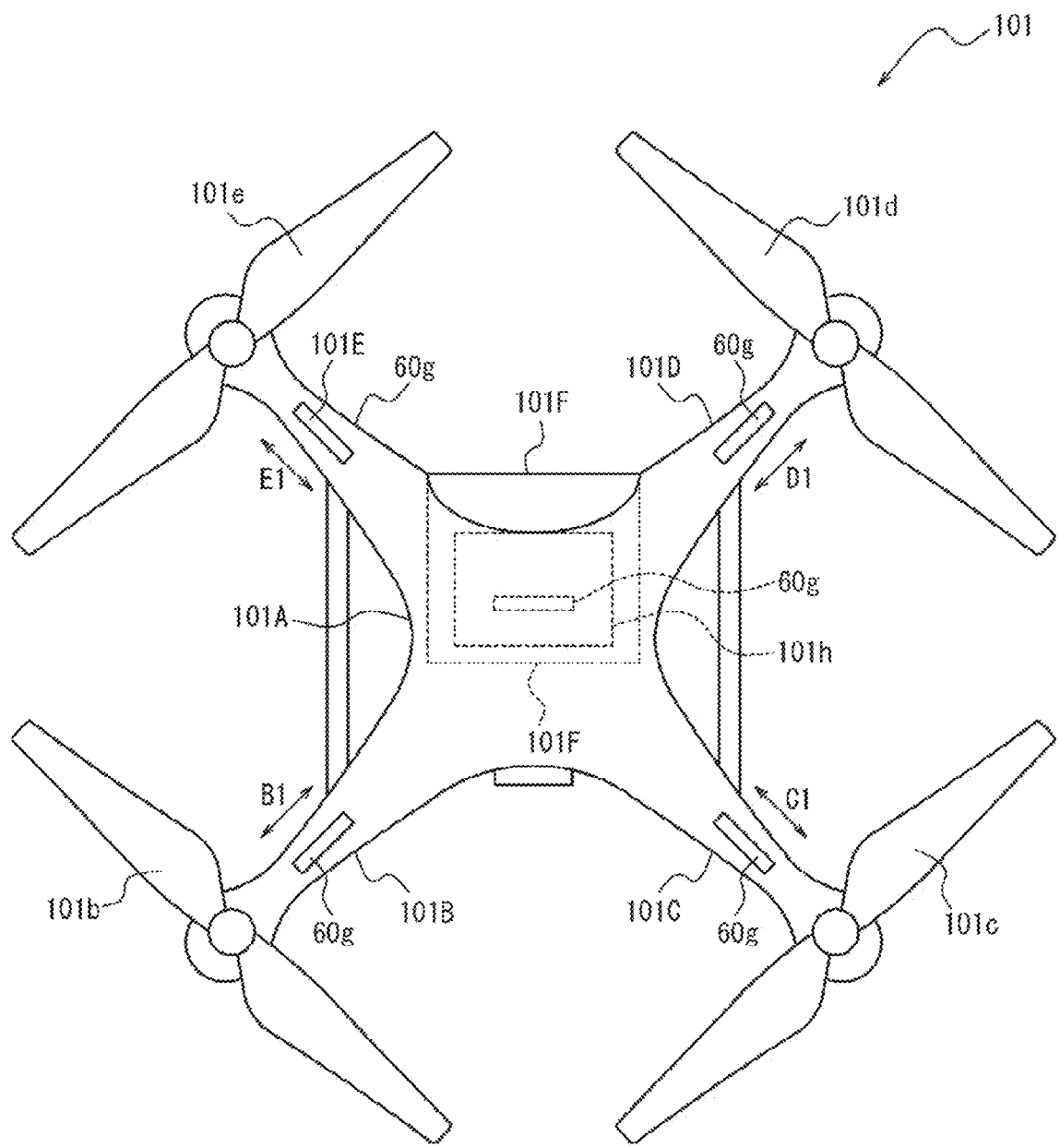
FIG. 98 is a top view of the unmanned aircraft illustrated in FIG. 96.

FIG. 96 is a perspective view of an embodiment of an unmanned aircraft 101. FIG. 97 is a rear view of the unmanned aircraft 101 illustrated in FIG. 96. FIG. 98 is a top view of the unmanned aircraft 101 illustrated in FIG. 96.

The unmanned aircraft" of the present disclosure is an aircraft that can be flown by remote operation or automatic operation among aircrafts, airframes of which a person cannot get on in terms of structure. The "unmanned aircraft" of the present disclosure may include a fixed wing aircraft and a rotary wing aircraft. The rotary wing aircraft may include a multi-copter and a mono-copter.

The unmanned aircraft 101 includes components and frames. The components of the unmanned aircraft 101 may be configured by any member according to a use of the components. The frames of the unmanned aircraft 101 may be formed of any material. As an example, any material may include metal and carbon fiber reinforced plastic. The carbon fiber reinforced plastic may have electric conductivity.

The components of the unmanned aircraft 101 may include, as illustrated in FIG. 96 and FIG. 97, motors 101a-1, 101a-2, 101a-3, and 101a-4 and propellers 101b, 101c, 101d, and 101e. The components of the unmanned aircraft 101 may include, as illustrated in FIG. 96, a gimbal 101f and a camera 101g. The components of the unmanned aircraft 101 may include, as illustrate in FIG. 98, a battery 101h housed in a battery holder 101F. The components of the unmanned aircraft 101 may include an ultrasonic sensor 101i as illustrated in FIG. 97.

The propeller 101b is attached to the motor 101a-1. The propeller 101c is attached to the motor 101a-2. The propeller 101d is attached to the motor 101a-3. The propeller 101e is attached to the motor 101a-4.

Disposition positions of the propellers 101b, 101c, 101d, and 101e may be determined as appropriate considering balance and the like of the unmanned aircraft 101 during flight. The propellers 101b, 101c, 101d, and 101e may be disposed on the same circumference that can center on the center of gravity of the unmanned aircraft 101. The propellers 101b, 101c, 101d, and 101e may be disposed in positions that equally divide the circumference into four.

The frames of the unmanned aircraft 101 may include, as illustrated in FIG. 98, a main body portion 101A and arms 101B, 101C, 101D, and 101E. The frames of the unmanned aircraft 101 may include a battery holder 101F as illustrated in FIG. 97 and FIG. 98. The frames of the unmanned aircraft 101 may include two legs 101G as illustrated in FIG. 96.

The arm 101B extends along an extending direction B1 from the main body portion 101A to a disposition position of the motor 101a-1. The arm 101C extends along an extending direction C1 from the main body portion 101A to a disposition position of the motor 101a-2. The extending direction C1 can be substantially orthogonal to the extending direction B1. The arm 101D extends along an extending direction D1 from the main body portion 101A to a disposition position of the motor 101a-3. The extending direction D1 can be substantially parallel to the extending direction B1 and is the opposite orientation of the extending direction B1. The arm 101E extends along an extending direction E1 from the main body portion 101A to a disposition position of the motor 101a-4. The extending direction E1 can be substantially parallel to the extending direction C1 and is the opposite orientation of the extending direction C1.

The legs 101G may include, as illustrated in FIG. 96, a bottom portion 101G-1 and side portions 101G-2 and 101G-3.

The bottom portion 101G-1 comes into contact with the ground when the unmanned aircraft 101 lands and when the unmanned aircraft 101 stands on the ground. The length of the bottom portion 101G-1 and an extending direction G1-1 in which the bottom portion 101G-1 extends may be determined as appropriate considering balance and the like of the unmanned aircraft 101 standing on the ground.

The side portion 101G-2 may extend along an extending direction G1-2 from one end of the bottom portion 101G-1 to the main body portion 101A. The side portion 101G-3 may extend along an extending direction G1-3 from the other end of the bottom portion 101G-1 to the main body portion 101A. The extending direction G1-2 and the extending direction G1-3 can be substantially parallel. The extending direction G1-2 and the extending direction G1-3 are further separated from each other toward the bottom portion 101G-1. The interval between the extending direction G1-2 and the extending direction G1-3 can be wide on the bottom portion 101G-1 side compared with the main body portion 101A side. Safety of the unmanned aircraft 101 during landing can be improved by forming the bottom portion 101G-1 long compared with the main body portion 101A.

The unmanned aircraft 101 includes at least one first antenna 60g. The first antenna 60g has the same structure as the structure of the first antenna 60. The first antenna 60g is an antenna independent from the first antenna 60. The unmanned aircraft 101 may include a plurality of first antennas 60g. The plurality of first antennas 60g may be disposed such that the unmanned aircraft 101 is adapted to diversity and a communication method of multi input multi output (MIMO). The first antenna 60g may be disposed to form a circularly polarized wave or a vertically polarized wave according to a communication use. The unmanned aircraft 101 may include the second antenna 70 in addition to the first antenna 60g or instead of the first antenna 60g.

The first antenna 60g may be disposed in any one of the components of the unmanned aircraft 101. The first antenna 60g may be disposed in a component of the unmanned aircraft 101 such that the fourth conductor 50 included in the first antenna 60g faces the component. Since the fourth conductor 50 of the first antenna 60g faces the component of the unmanned aircraft 101, a direction in which the component is located with respect to the fourth conductor 50 can be the opposite direction of a direction in which the third conductor 40 is located with respect to the fourth conductor 50. An effective traveling direction of an electromagnetic wave radiated by the first antenna 60g can be the direction in which the third conductor 40 is located with respect to the fourth conductor 50. Since the fourth conductor 50 of the first antenna 60g faces the component of the unmanned aircraft 101, the component of the unmanned aircraft 101 can be located in the opposite direction of the effective traveling direction of the electromagnetic wave radiated by the first antenna 60g. Since the component of the unmanned aircraft 101 is located in the opposite direction of the effective traveling direction of the electromagnetic wave from the first antenna 60g, radiation efficiency of the first antenna 60g can be maintained.

For example, the first antenna 60g may be disposed in the battery 101h such that the fourth conductor 50 faces the battery 101h. In this example, the fourth conductor 50 may face a surface that can be located on the sky side during the flight of the unmanned aircraft 101, for example, a surface facing the opposite side of the legs 101G among surfaces included in the battery 101h.

The first antenna 60g may be disposed in any one of the frames of the unmanned aircraft 101. The first antenna 60g may be disposed in a frame of the unmanned aircraft 101 such that the fourth conductor 50 included in the first antenna 60g faces the frame of the unmanned aircraft 101. Since the fourth conductor 50 of the first antenna 60g faces the frame of the unmanned aircraft 101, as explained above, the radiation efficiency of the first antenna 60g can be maintained.

When the frame of the unmanned aircraft 101 includes a conductive long portion, the first antenna 60g may be disposed in the long portion. The first antenna 60g may be disposed in the conductive long portion such that the first direction is along the long portion. The long portion may include the arms 101B, 101C, 101D, and 101E illustrated in FIG. 98. The long portion may include the bottom portion 101G-1 and the side portions 101G-2 and 101G-3 illustrated in FIG. 96. Since the first antenna 60g is disposed in the conductive long portion of the frame of the unmanned aircraft 101, the first antenna 60g and the long portion can be electromagnetically coupled. Since the first antenna 60g and the long portion are electromagnetically coupled, when the first antenna 60g radiates an electromagnetic wave, an electric current is induced in the long portion. The long portion can radiate an electromagnetic wave with the electric current induced in the long portion. Since the long portion radiates the electromagnetic wave with the electric current induced in the long portion, when the first antenna 60g radiates the electromagnetic wave, overall radiation efficiency of the first antenna 60g can be improved.

For example, when the first antenna 60g is disposed in the arm 101B functioning as the long portion, the first antenna 60g may be disposed in the arm 101B such that the first direction is along the extending direction B1. The first antenna 60g may be disposed on a surface that can be located on the sky side during the flight of the unmanned aircraft 101, for example, a surface facing the opposite side of the legs 101G among surfaces included in the arm 101B. The first antenna 60g may be disposed on a surface that can be located on the ground side during the flight of the unmanned aircraft 101, for example, a surface facing the legs 101G side among the surfaces included in the arm 101B. The first antenna 60g may be disposed on a side surface of the arm 101B.

For example, when the first antenna 60g is disposed in the arm 101C functioning as the long portion, the first antenna 60g may be disposed in the arm 101C such that the first direction is along the extending direction C1. The first antenna 60g may be disposed on a surface that can be located on the sky side during the flight of the unmanned aircraft 101, for example, a surface facing the opposite side of the legs 101G among surfaces included in the arm 101C. The first antenna 60g may be disposed on a surface that can be located on the ground side during the flight of the unmanned aircraft 101, for example, a surface facing the legs 101G side among the surfaces included in the arm 101C. The first antenna 60g may be disposed on a side surface of the arm 101C.

For example, when the first antenna 60g is disposed in the arm 101D functioning as the long portion, the first antenna 60g may be disposed in the arm 101D such that the first direction is along the extending direction D1. The first antenna 60g may be disposed on a surface that can be located on the sky side during the flight of the unmanned aircraft 101, for example, a surface facing the opposite side of the legs 101G among surfaces included in the arm 101D. The first antenna 60g may be disposed on a surface that can be located on the ground side during the flight of the unmanned aircraft 101, for example, a surface facing the legs 101G side among the surfaces included in the arm 101D. The first antenna 60g may be disposed on a side surface of the arm 101D.

For example, when the first antenna 60g is disposed in the arm 101E functioning as the long portion, the first antenna 60g may be disposed in the arm 101E such that the first direction is along the extending direction E1. The first antenna 60g may be disposed on a surface that can be located on the sky side during the flight of the unmanned aircraft 101, for example, a surface facing the opposite side of the legs 101G among surfaces included in the arm 101E. The first antenna 60g may be disposed on a surface that can be located on the ground side during the flight of the unmanned aircraft 101, for example, a surface facing the legs 101G side among the surfaces included in the arm 101E. The first antenna 60g may be disposed on a side surface of the arm 101E.

For example, when the first antenna 60g is disposed in the bottom portion 101G-1 functioning as the long portion, the first antenna 60g may be disposed in the bottom portion 101G-1 such that the first direction is along the extending direction G1-1. The first antenna 60g may be disposed on a surface facing the main body portion 101A among surfaces included in the bottom portion 101G-1. Since the first antenna 60g is disposed on the surface facing the main body portion 101A of the bottom portion 101G-1, for example, when the unmanned aircraft 101 lands, contact of the first antenna 60g with the ground can be reduced. Since the first antenna 60g is disposed on the surface facing the main body portion 101A of the bottom portion 101G-1, the unmanned aircraft 101 can enable wireless communication from the landing time.

For example, when the first antenna 60g is disposed in the side portion 101G-2 functioning as the long portion, the first antenna 60g may be disposed in the side portion 101G-2 to extend along the extending direction G1-2. For example, when the first antenna 60g is disposed in the side portion 101G-3 functioning as the long portion, the first antenna 60g may be disposed in the side portion 101G-3 to extend along the extending direction G1-3.

Function Example of the Unmanned Aircraft

FIG. 99 is a functional block diagram of the unmanned aircraft 101 illustrated in FIG. 96. The unmanned aircraft 101 may be connected to a network 103 by performing wireless communication with a communication base station 102. The unmanned aircraft 101 may communicate with an information processing device 104 via the network 103. The unmanned aircraft 101 may directly communicate with a transmitter 105. The unmanned aircraft 101 may directly communicate with an airplane 106 around the unmanned aircraft 101. The unmanned aircraft 101 may directly communicate with a land base station 107.

A communication standard between the unmanned aircraft 101 and the information processing device 104 may be the telecommunication standard. The telecommunication standard may include 2nd generation (2G), 3rd generation (3G), 4th generation (4G), long term evolution (LTE), worldwide interoperability for microwave access (WiMAX), and personal handy-phone system (PHS). A communication standard between the unmanned aircraft 101 and the transmitter 105, the airplane 106, and the land base station 107 may be the short-range communication standard. The short-range communication standard may include WiFi (registered trademark), Bluetooth(registered trademark), or wireless LAN.

The unmanned aircraft 101 can fly based on control by a controller 180 of the unmanned aircraft 101. The unmanned aircraft 101 may be an unmanned aircraft owned by an individual or may be an unmanned aircraft owned by any company. The any company may include a home delivery company that delivers baggage using the unmanned aircraft 101 and a monitoring company that monitors a predetermined region using the unmanned aircraft 101.

The communication base station 102 is a communication facility present within a communication zone of the unmanned aircraft 101 among communication facilities disposed in various places on the ground. The communication facility is managed by a communication company. The communication company provides a communication service for connecting a general-purpose mobile phone and the like to the network 103 with the communication facilities disposed in the various places on the ground. The network 103 may include a wireless network. A part of the network 103 may include a wired network.

The information processing device 104 may be managed by any company or the like. For example, when a delivery company owns the unmanned aircraft 101, the information processing device 104 may be managed by the delivery company. For example, when a monitoring company owns the unmanned aircraft 101, the information processing device 104 may be managed by the monitoring company.

The information processing device 104 may be configured by a computer system and other hardware capable of executing a program command. The computer system and the other hardware may include a general-purpose computer, a PC (personal computer), a dedicated computer, a work station, a PCS, a mobile (cellular) phone, a mobile phone including a data processing function, an RFID receiver, a game machine, an electronic notepad, a laptop computer, a GPS receiver, or other programmable data processing devices.

The transmitter 105 is used by an operator to remotely operate the unmanned aircraft 101. The transmitter 105 detects an input by the operator. The transmitter 105 transmits a control signal corresponding to the detected input by the operator to the unmanned aircraft 101.

The transmitter 105 may be configured by a computer system and other hardware capable of executing a program command. The computer system and the other hardware may include a general-purpose computer, a PC, a dedicated computer, a work station, a PCS, a mobile phone, a mobile phone including a data processing function, an RFID receiver, a game machine, an electronic notepad, a laptop computer, a GPS receiver, or other programmable data processing devices.

The airplane 106 is an airplane that flies within the communication zone of the unmanned aircraft 101 among a variety of airplanes. The airplane 106 may be an unmanned aircraft or may be a manned aircraft.

The land base station 107 is a communication facility set in a predetermined land base. The predetermined land base may be a base in which the unmanned aircraft 101 can land. The predetermined land base may be a place predetermined by an administrator or the like of the unmanned aircraft 101. The unmanned aircraft 101 may land in the predetermined land base according to a situation. The unmanned aircraft 101 may land in any place on the ground according to a situation.

The unmanned aircraft 101 includes, as a control unit 100, at least one first antenna 60g, the battery 101h, a sensor 160, a memory 170, and the controller 180. The unmanned aircraft 101 may include the wireless communication device 90.

The wireless communication device 90 can perform wireless communication with the control unit. A communication standard between the control unit and the wireless communication device 90 may be the short-range communication standard.

The wireless communication device 90 generates a transmission signal corresponding to measurement data measured by the sensor 92 of the wireless communication device 90. The wireless communication device 90 transmits the generated transmission signal to the first antenna 60g of the control unit 100. A disposition position of the wireless communication device 90 may be determined as appropriate according to the measurement data acquired by the sensor 92. For example, when any one of illuminance, temperature, and humidity around the unmanned aircraft 101 is acquired by the sensor 92, the wireless communication device 90 may be disposed in the side portion 101G-3 illustrated in FIG. 96.

The first antenna 60g may be configured as appropriate according to a frequency band used in communication between the unmanned aircraft 101 and other devices. In other words, each of the first conductor 31, the second conductor 32, the third conductor 40, and the fourth conductor 50 included in the first antenna 60g may be configured as appropriate according to the frequency band used in the communication between the unmanned aircraft 101 and the other devices. A disposition position of the first antenna 60g may be determined as appropriate according to a communication partner.

For example, when the communication partner is the information processing device 104, the disposition position of the first antenna 60g may be a side surface of the arm 101B or the like illustrated in FIG. 96 or may be a surface on the sky side of the arm 101B or the like illustrated in FIG. 98 Since the first antenna 60g is disposed on the side surface or the like and the surface on the sky side of the arm 101B, radiation strength of the first antenna 60g can increase in the direction on the sky side from the unmanned aircraft 101 and the lateral direction of the unmanned aircraft 101 during the flight of the unmanned aircraft 101. Since the radiation strength of the first antenna 60g increases in the direction on the sky side and the lateral direction, communication between the unmanned aircraft 101 and the information processing device 104 through the communication base station 102 can be stabilized.

For example, when the communication partner is the transmitter 105, the disposition position of the first antenna 60g may be a surface on the ground side of the arm 101B or the like illustrated in FIG. 96 or may be the side portion 101G-2 or the like illustrated in FIG. 96. Since the first antenna 60g is disposed on the surface on the ground side of the arm 101B or the like and in the side portion 101G-2 or the like, the radiation strength of the first antenna 60g can increase in the direction on the ground side from the unmanned aircraft 101 during the flight of the unmanned aircraft 101. Since the radiation strength of the first antenna 60g increases in the direction on the ground side, communication between the unmanned aircraft 101 and the transmitter 105 on the ground can be stabilized.

For example, when the communication partner is the airplane 106, the disposition position of the first antenna 60g may be a side surface and a surface on the sky side of the arm 101B or the like illustrated in FIG. 96 or may be the side portion 101G-2 or the like illustrated in FIG. 96. Since the first antenna 60g is disposed on the side surface and the surface on the sky side of the arm 101B or the like and in the side portion 101G-2 or the like, the radiation strength of the first antenna 60g can increase in the direction on the sky side from the unmanned aircraft 101 and the lateral direction of the unmanned aircraft 101 during the flight of the unmanned aircraft 101. Since the radiation strength of the first antenna 60g increases in the direction on the sky side and the lateral direction of the unmanned aircraft 101, communication between the unmanned aircraft 101 and the airplane 106 around the unmanned aircraft 101 can be stabilized.

For example, when the communication partner is the land base station 107, the disposition position of the first antenna 60g may be a surface on the ground side of the arm 101B or the like illustrated in FIG. 96 or may be the side portion 101G-2 or the like illustrate in FIG. 96. Since the first antenna 60g is disposed on the surface on the ground side of the arm 101B or the like and in the side portion 101G-2 or the like, the radiation strength of the first antenna 60g can increase in the direction on the ground side from the unmanned aircraft 101 during the flight of the unmanned aircraft 101. Since the radiation strength of the first antenna 60g increases in the direction on the ground side, communication between the unmanned aircraft 101 and the land base station 107 on the ground can be stabilized.

For example, when the communication partner is a GPS satellite, the disposition position of the first antenna 60g may be a surface on the sky side of the arm 101B or the like illustrated in FIG. 98 or may be the battery 101h illustrated in FIG. 98. Since the first antenna 60g is disposed on the surface on the sky side of the arm 101B or the like and in the battery 101h, the first antenna 60g easily receives an electromagnetic wave from the GPS satellite.

The first antenna 60g can receive an electromagnetic wave from another device as a reception signal. The reception signal received by the first antenna 60g is output to the controller 180 through the first feeding line 61 of the first antenna 60g. Electric power is supplied to the first feeding line 61, whereby the first antenna 60g can radiate an electromagnetic wave on the other device as a transmission signal.

The battery 101h can be housed in the battery holder 101F illustrated in FIG. 97. The battery 101h can supply electric power to at least one of the first antenna 60g, the sensor 160, the memory 170, and the controller 180. The battery 101h can include, for example, at least one of a primary battery and a secondary battery. A negative pole of the battery 101h is electrically connected to the fourth conductor 50 of the first antenna 60g.

The sensor 160 measures various data. The sensor 160 may include at least one of the camera 101g illustrated in FIG. 96 and the ultrasonic sensor 101i illustrated in FIG. 97. The sensor 160 may include at least one of an acceleration sensor, an angular velocity sensor, a terrestrial magnetism sensor, a temperature sensor, a humidity sensor, an atmospheric pressure sensor, and an illuminance sensor.

For example, the camera 101g included in the sensor 160 measures (photographs) an image of the periphery of the unmanned aircraft 101. The camera 101g outputs the measured image to the controller 180.

For example, the ultrasonic sensor 101i included in the sensor 160 measures a relative positional relation between the unmanned aircraft 101 and an object around the unmanned aircraft 101. The object around the unmanned aircraft 101 may include an obstacle and the airplane 106 around the unmanned aircraft 101. The ultrasonic sensor 101i outputs the measured relative positional relation to the controller 180.

For example, the acceleration sensor included in the sensor 160 measures acceleration acting on the unmanned aircraft 101. The acceleration sensor outputs the measured acceleration to the controller 180.

For example, the angular velocity sensor included in the sensor 160 measures the angular velocity of the unmanned aircraft 101. The angular velocity sensor outputs the measured angular velocity to the controller 180.

For example, the terrestrial magnetism sensor included in the sensor 160 measures the magnitude and the direction of terrestrial magnetism around the unmanned aircraft 101. The terrestrial magnetism sensor outputs the measured magnitude and the measured direction of the terrestrial magnetism to the controller 180.

For example, the temperature sensor included in the sensor 160 measures the temperature around the unmanned aircraft 101. The temperature sensor outputs the measured temperature to the controller 180.

For example, the humidity sensor included in the sensor 160 measures the humidity around the unmanned aircraft 101. The humidity sensor outputs the measured humidity to the controller 180.

For example, the atmospheric pressure sensor included in the sensor 160 measures the atmospheric pressure around the unmanned aircraft 101. The atmospheric pressure sensor outputs the measured atmospheric pressure to the controller 180.

For example, the illuminance sensor included in the sensor 160 measures the illuminance around the unmanned aircraft 101. The illuminance sensor outputs the measured illuminance to the controller 180.

The memory 170 may be configured by, for example, a semiconductor memory. The memory 170 may function as a work memory of the controller 180. The memory 170 may be included in the controller 180. The memory 170 may store identification information of the unmanned aircraft 101. The identification information of the unmanned aircraft 101 may be information specific to the unmanned aircraft 101. The identification information of the unmanned aircraft 101 may be formed by a combination of numbers and/or characters. The memory 170 may store information concerning a flyable area of the unmanned aircraft 101. The flyable area may be an area where flight of the unmanned aircraft 101 is permitted by a law or the like.

The controller 180 can include, for example, a processor. The controller 180 may include one or more processors. The processor may include a general-purpose processor that reads a specific program and executes a specific function and a dedicated processor specialized for specific processing. The dedicated processor may include an IC for specific use. The processor may include a programmable logic device. The PLD may include an FPGA. The controller 180 may be one of an SoC or an SiP in which one or a plurality of processors cooperate. The controller 180 may store, in the memory 170, various kinds of information, a program for operating constituent modules of the unmanned aircraft 101, or the like.

The controller 180 can acquire a reception signal from the transmitter 105 through the first feeding line 61 of the first antenna 60g. The controller 180 flies the unmanned aircraft 101 based on a control signal included in the reception signal. The controller 180 may fly the unmanned aircraft 101 according to automatic control based on a predetermined program stored in the memory 170.

The controller 180 may acquire various data from the sensor 160. When the unmanned aircraft 101 includes the wireless communication device 90, the controller 180 may acquire various data from the sensor 92 of the wireless communication device 90. When acquiring the various data from the sensor 92, the controller 180 may acquire a reception signal from the wireless communication device 90 through the first feeding line 61 of the first antenna 60g. The measurement data measured by the sensor 92 can be included in the reception signal.

The controller 180 may acquire environment data around the unmanned aircraft 101. The environment data may include an image, temperature, humidity, atmospheric pressure, and illuminance around the unmanned aircraft 101.

The controller 180 may acquire or calculate flight data of the unmanned aircraft 101. The flight data may include speed, a flying distance, a flyable time of the unmanned aircraft 101. For example, the controller 180 may acquire the speed of the unmanned aircraft 101 with the sensor 160 or the sensor 92 of the wireless communication device 90. For example, the controller 180 may calculate a flying distance of the unmanned aircraft 101 based on acceleration acquired by the sensor 160 or the sensor 92. For example, the controller 180 may calculate a flyable time of the unmanned aircraft 101 based on residual power of the battery 101h.

The controller 180 may acquire position information of the unmanned aircraft 101. For example, the controller 180 may acquire position information of the unmanned aircraft 101 based on a GPS signal acquired by the first antenna 60g. For example, the controller 180 may acquire position information of the unmanned aircraft 101 based on a signal from the communication base station 102 around the unmanned aircraft 101 acquired by the first antenna 60g. The controller 180 may control the flyable area based on the acquired position information and the information concerning the flyable area stored the memory 170.

The controller 180 may generate a transmission signal transmitted from the unmanned aircraft 101 to the information processing device 104. The controller 180 may generate a transmission signal according to the telecommunication standard. The controller 180 may supply electric power corresponding to the generated transmission signal to the first feeding line 61 of the first antenna 60g. The controller 180 can transmit the transmission signal to the information processing device 104 as an electromagnetic wave by the electric power corresponding to the transmission signal to the first feeding line 61 of the first antenna 60g.

The controller 180 may generate, as the transmission signal from the unmanned aircraft 101 to the information processing device 104, a transmission signal corresponding to at least one of the environment data, the flight data of the unmanned aircraft 101, and the position information of the unmanned aircraft 101. The controller 180 may generate a transmission signal such that the identification information of the unmanned aircraft 101 stored the memory 170 is included in the transmission signal. The information processing device 104 can acquire at least one of the environment data, the flight data of the unmanned aircraft 101, and the position information of the unmanned aircraft 101 together with the identification information of the unmanned aircraft 101 by acquiring the transmission signal.

For example, when a monitoring company uses the unmanned aircraft 101, the monitoring company can monitor a predetermined region with an image of the predetermined region included in environment data acquired by the information processing device 104. For example, when the unmanned aircraft 101 is flying by automatic control, an owner of the unmanned aircraft 101 can grasp a state of the unmanned aircraft 101 from flight data acquired by the unmanned aircraft 101. For example, a home delivery company uses the unmanned aircraft 101, the home delivery company can grasp the position of the unmanned aircraft 101 in delivery from identification information and position information of the unmanned aircraft 101 acquired by the information processing device 104. For example, when the unmanned aircraft 101 is stolen, an owner of the unmanned aircraft 101 can grasp the position of the unmanned aircraft 101 from identification information and the position information of the unmanned aircraft 101 acquired by the information processing device 104.

The controller 180 may generate a transmission signal transmitted from the unmanned aircraft 101 to the transmitter 105. The controller 180 may generate a transmission signal according to the short-range communication standard. The controller 180 may supply electric power corresponding to the generated transmission signal to the first feeding line 61 of the first antenna 60g. The controller 180 can transmit the transmission signal to the transmitter 105 as an electromagnetic wave by supplying the electric power corresponding to the transmission signal to the first feeding line 61 of the first antenna 60g.

The controller 180 may generate, as the transmission signal from the unmanned aircraft 101 to the transmitter 105, a transmission signal corresponding to at least one of environment data around the unmanned aircraft 101, flight data of the unmanned aircraft 101, and position information of the unmanned aircraft 101. The controller 180 may generate a transmission signal such that the identification information of the unmanned aircraft 101 stored the memory 170 is included in the transmission signal. The transmitter 105 can acquire at least one of the environment data around the unmanned aircraft 101, the flight data of the unmanned aircraft 101, and the position information of the unmanned aircraft 101 together with the identification information of the unmanned aircraft 101 by acquiring the transmission signal.

The controller 180 may generate, as the transmission signal from the unmanned aircraft 101 to the transmitter 105, a transmission signal corresponding to a relative positional relation between the unmanned aircraft 101 and the transmitter 105. The controller 180 may acquire the relative positional relation between the unmanned aircraft 101 and the transmitter 105 based on communication between the unmanned aircraft 101 and the transmitter 105. When acquiring the relative positional relation, the controller 180 may control an attitude of the unmanned aircraft 101 such that radiation strength of the first antenna 60g increases in the direction of the transmitter 105. The controller 180 may generate a transmission signal such that the identification information of the unmanned aircraft 101 stored the memory 170 is included in the transmission signal. The controller 180 may generate a transmission signal while the unmanned aircraft 101 returns to the base. The transmitter 105 can acquire the relative positional relation between the unmanned aircraft 101 and the transmitter 105 together with the identification information of the unmanned aircraft 101 by acquiring the transmission signal. The operator can grasp the relative positional relation between the unmanned aircraft 101 and the transmitter 105 from the information acquired by the transmitter 105. The operator can safely land the unmanned aircraft 101 by grasping the relative positional relation between the unmanned aircraft 101 and the transmitter 105.

The controller 180 may generate a transmission signal transmitted from the unmanned aircraft 101 to the airplane 106 around the unmanned aircraft 101. The controller 180 may generate a transmission signal according to the short-range communication standard. The controller 180 may supply electric power corresponding to the generated transmission signal to the first feeding line 61 of the first antenna 60g. The controller 180 can transmit the transmission signal to the airplane 106 around the unmanned aircraft 101 as an electromagnetic wave by supplying the electric power corresponding to the transmission signal to the first feeding line 61 of the first antenna 60g.

The controller 180 may generate, as the transmission signal from the unmanned aircraft 101 to the airplane 106 around the unmanned aircraft 101, a transmission signal corresponding to a relative positional relation between the unmanned aircraft 101 and the airplane 106. The controller 180 may acquire, with the ultrasonic sensor 101i, the relative positional relation between the unmanned aircraft 101 and the airplane 106. The controller 180 may acquire the relative positional relation between the unmanned aircraft 101 and the airplane 106 based on communication between the unmanned aircraft 101 and the airplane 106. When acquiring the relative positional relation, the controller 180 may control the attitude of the unmanned aircraft 101 such that radiation strength of the first antenna 60g increases in the direction of the airplane 106. The controller 180 may generate a transmission signal such that the identification information of the unmanned aircraft 101 stored the memory 170 is included in the transmission signal. The airplane 106 can acquire the relative positional relation between the unmanned aircraft 101 and the airplane 106 by acquiring the transmission signal. Since the airplane 106 acquires the relative positional relation, collision of the unmanned aircraft 101 and the airplane 106 can be avoided.

The controller 180 may generate a transmission signal transmitted from the unmanned aircraft 101 to the land base station 107. The controller 180 may generate a transmission signal according to the short-range communication standard. The controller 180 may supply electric power corresponding to the generated transmission signal to the first feeding line 61 of the first antenna 60g. The controller 180 supplies the electric power corresponding to the transmission signal to the first feeding line 61 of the first antenna 60g to transmit the transmission signal to the land base station 107 as an electromagnetic wave.

The controller 180 may generate as the transmission signal from the unmanned aircraft 101 to the land base station 107, a transmission signal corresponding to a relative positional relation between the unmanned aircraft 101 and the land base station 107. The controller 180 may acquire the relative positional relation between the unmanned aircraft 101 and the land base station 107 based on the communication between the unmanned aircraft 101 and the land base station 107. When acquiring the relative positional relation, the controller 180 may control the attitude of the unmanned aircraft 101 such that radiation strength of the first antenna 60g increases in the direction of the land base station 107. The controller 180 may generate a transmission signal such that the identification information of the unmanned aircraft 101 stored the memory 170 is included in the transmission signal. The controller 180 may generate a transmission signal while the unmanned aircraft 101 returns to the base. The land base station 107 can acquire the relative positional relation between the unmanned aircraft 101 and the land base station 107 together with the identification information of the unmanned aircraft 101 by acquiring the transmission signal. Since the land base station 107 acquires the relative positional relation between the unmanned aircraft 101 and the land base station 107, the unmanned aircraft 101 can be safely landed.

Usually, a rod antenna is disposed in an unmanned aircraft. The rod antenna is attached to the outer surface of the unmanned aircraft in order to maintain radiation efficiency of the rod antenna. When a frame of the unmanned aircraft has electric conductivity, the radiation efficiency of the rod antenna is sometimes deteriorated by the conductive frame. Accordingly, when the frame of the unmanned aircraft has electric conductivity, the rod antenna is attached to the outer surface of the unmanned aircraft to project from the frame of the unmanned aircraft.

However, when the rod antenna is attached to the outer surface of the unmanned aircraft, air resistance against the unmanned aircraft can increase during flight of the unmanned aircraft. When the rod antenna is attached to project from the frame of the unmanned aircraft, the air resistance against the unmanned aircraft can further increase. When the air resistance against the unmanned aircraft increases, stability during the flight of the unmanned aircraft is sometimes deteriorated.

In order to maintain the stability during the flight of the unmanned aircraft, it is conceived to dispose an antenna such as a patch antenna on the inside of the unmanned aircraft. However, in the unmanned aircraft, a space for disposing the antenna is sometimes limited in terms of structure.

On the other hand, in this embodiment, the first antenna 60g is disposed in the unmanned aircraft 101 instead of the rod antenna. The first antenna 60g can be smaller than the rod antenna. In this embodiment, since the first antenna 60g smaller than the rod antenna is used, even if the first antenna 60g is disposed on the outer surface of the unmanned aircraft 101, the unmanned aircraft 101 can stably fly.

Further, since the fourth conductor 50 of the first antenna 60g faces the unmanned aircraft 101, even if the first antenna 60g is disposed near the frame of the unmanned aircraft 101, the radiation efficiency of the first antenna 60g can be maintained. Since the first antenna 60g is disposed near the frame of the unmanned aircraft 101, the unmanned aircraft 101 can stably fly.

The first antenna 60g is smaller than the rod antenna. Therefore, the first antenna 60g can be easily disposed on the inside of the unmanned aircraft 101.

The configuration according to the present disclosure is not limited to only the embodiments explained above. Many modifications and changes of the configuration are possible. For example, the functions and the like included in the constituent modules and the like can be rearranged not to logically contradict. A plurality of constituent modules or the like can be combined into one or can be divided.

The figures for explaining the components according to the present disclosure are schematic. Dimension ratios and the like on the drawings do not always coincide with real ones.

In the present disclosure, the description such as "first", "second", and "third" are examples of identifiers for distinguishing the components. The numbers of the components distinguished by the descriptions such as "first" and "second" in the present disclosure can be interchanged. For example, "first" and "second", which are identifiers of a first frequency and a second frequency, can be interchanged. The interchange of the identifiers is simultaneously performed. The components can be distinguished even after the interchange of the identifiers. The identifiers may be deleted. The components, the identifiers of which are deleted, are distinguished by signs. For example, the first conductor 31 can be referred to as conductor 31. Only the description of the identifiers such as "first" and "second" in the present disclosure must not be used for interpretation of the order of the components, a ground for present of identifiers having small numbers, and a ground for presence of identifiers having large numbers. The present disclosure includes a configuration in which the second conductive layer 42 includes the second unit slot 422 but the first conductive layer 41 does not include a first unit slot.

The invention claimed is:

1. An antenna comprising:
   a first conductor;
   a second conductor that faces the first conductor in a first direction;
   a third conductor that is located between the first conductor and the second conductor, apart from the first conductor and the second conductor, and extends in the first direction;
   a fourth conductor that is connected to the first conductor and the second conductor and extends in the first direction; and
   a feeding line that is electromagnetically connected to the third conductor,
   wherein
   the first conductor and the second conductor are capacitively connected via the third conductor,
   the antenna is disposed in a bicycle component of a bicycle such that the fourth conductor faces the bicycle component,
   the first conductor, the third conductor, and the second conductor are arranged in a row, and
   the third conductor between the first and second conductors includes
      first and second surfaces that define electric walls and face the first and second conductors, respectively, and
      third and fourth surfaces that define high impedance surfaces and do not face the first and second conductors.

2. The antenna according to claim 1, wherein
   the bicycle component includes a long portion having electric conductivity, and
   the antenna is disposed in the long portion such that the first direction is along the long portion.

3. The antenna according to claim 2, wherein the bicycle component includes at least one of a brake lever or a chain wheel.

4. The antenna according to claim 1, wherein the antenna is configured in accordance with a frequency band used in telecommunication.

5. The antenna according to claim 1, wherein the antenna is configured in accordance with a frequency band used in short-range communication.

6. A bicycle comprising:
   an antenna; and
   a bicycle component,
   wherein
   the antenna includes:
      a first conductor;
      a second conductor that faces the first conductor in a first direction;
      a third conductor that is located between the first conductor and the second conductor, apart from the first conductor and the second conductor, and extends in the first direction;
      a fourth conductor that is connected to the first conductor and the second conductor and extends in the first direction; and
      a feeding line that is electromagnetically connected to the third conductor,
   the first conductor and the second conductor are capacitively connected via the third conductor, the antenna is disposed in the bicycle component of the bicycle such that the fourth conductor faces the bicycle component, the first conductor, the third conductor, and the second conductor are arranged in a row, and the third conductor between the first and second conductors includes first and second surfaces that define electric walls and face the first and second conductors, respectively, and third and fourth surfaces that define high impedance surfaces and do not face the first and second conductors.

7. The bicycle according to claim 6, further comprising a sensor device configured to measure either data of the bicycle or biological data of a driver, wherein the sensor device is configured to communicate with another device with the antenna.

8. The bicycle according to claim 6, further comprising:

a detection device configured to detect an operation by a driver or an environment around the bicycle; and a control device configured to control a function of the bicycle based on the operation by the driver or the environment around the bicycle detected by the detection device, wherein the detection device and the control device each include the antenna independent from each other and are capable of communicating each other.

9. A display apparatus comprising:

an antenna; and a display device, wherein the antenna includes:

a first conductor;

a second conductor that faces the first conductor in a first direction;

a third conductor that is located between the first conductor and the second conductor, apart from the first conductor and the second conductor, and extends in the first direction;

a fourth conductor that is connected to the first conductor and the second conductor and extends in the first direction; and a feeding line that is electromagnetically connected to the third conductor, the first conductor and the second conductor are capacitively connected via the third conductor, the antenna is disposed in a bicycle component of a bicycle such that the fourth conductor faces the bicycle component or disposed in a conductive long portion included in a frame of the bicycle such that the first direction is along the long portion, the first conductor, the third conductor, and the second conductor are arranged in a row, and the third conductor between the first and second conductors includes first and second surfaces that define electric walls and face the first and second conductors, respectively, and third and fourth surfaces that define high impedance surfaces and do not face the first and second conductors.

10. The display apparatus according to claim 9, wherein the bicycle includes a sensor device configured to measure at least one of data of the bicycle or biological data of a driver, and the display apparatus is configured to acquire, with the antenna, at least one of the data of the bicycle or the biological data of the driver from the sensor device, and display the at least one of the data or the biological data on the display device.

11. The display apparatus according to claim 9, wherein the antenna is configured in accordance with a frequency band used in communication between the display apparatus and the sensor device.

\* \* \* \* \*